US010894033B2

(12) United States Patent
Shao et al.

(10) Patent No.: US 10,894,033 B2
(45) Date of Patent: Jan. 19, 2021

(54) MULTICYCLIC COMPOUNDS AND METHODS OF USE THEREOF

(71) Applicants: Sunovion Pharmaceuticals Inc., Marlborough, MA (US); PGI Drug Discovery LLC, Paramus, NJ (US)

(72) Inventors: Liming Shao, Lincoln, MA (US); John Emmerson Campbell, Cambridge, MA (US); Michael Charles Hewitt, Somerville, MA (US); Una Campbell, Marlborough, MA (US); Taleen G. Hanania, Valhalla, NY (US)

(73) Assignees: Sunovion Pharmaceuticals Inc., Marlborough, MA (US); PGI Drug Discovery LLC, Paramus, NJ (US)

( * ) Notice: Subject to any disclaimer, the term of this patent is extended or adjusted under 35 U.S.C. 154(b) by 0 days.

(21) Appl. No.: 16/791,118

(22) Filed: Feb. 14, 2020

(65) Prior Publication Data

US 2020/0323819 A1     Oct. 15, 2020

Related U.S. Application Data

(63) Continuation of application No. 16/117,450, filed on Aug. 30, 2018, now abandoned, which is a continuation of application No. 14/950,834, filed on Nov. 24, 2015, now Pat. No. 10,085,968, which is a continuation of application No. 14/205,859, filed on Mar. 12, 2014, now Pat. No. 9,351,954, which is a continuation of application No. 13/513,176, filed as application No. PCT/US2010/058884 on Dec. 3, 2010, now Pat. No. 8,710,245.

(60) Provisional application No. 61/266,880, filed on Dec. 4, 2009.

(51) Int. Cl.
| | |
|---|---|
| A61K 31/381 | (2006.01) |
| C07D 277/60 | (2006.01) |
| C07D 333/54 | (2006.01) |
| C07D 333/76 | (2006.01) |
| A61K 45/06 | (2006.01) |
| C07D 495/04 | (2006.01) |
| C07D 495/20 | (2006.01) |
| A61K 31/435 | (2006.01) |
| A61K 31/55 | (2006.01) |
| C07D 333/78 | (2006.01) |

(52) U.S. Cl.
CPC .......... *A61K 31/381* (2013.01); *A61K 31/435* (2013.01); *A61K 31/55* (2013.01); *A61K 45/06* (2013.01); *C07D 277/60* (2013.01); *C07D 333/54* (2013.01); *C07D 333/76* (2013.01); *C07D 333/78* (2013.01); *C07D 495/04* (2013.01); *C07D 495/20* (2013.01)

(58) Field of Classification Search
CPC .................................................. A61K 31/381

USPC ......................................................... 548/203
See application file for complete search history.

(56) References Cited

U.S. PATENT DOCUMENTS

| | | | |
|---|---|---|---|
| 4,021,451 A | 5/1977 | Dobson et al. | |
| 4,021,452 A | 5/1977 | Floyd, Jr. | |
| 4,036,842 A | 7/1977 | Dobson et al. | |
| 4,127,665 A | 11/1978 | Sarges et al. | |
| 4,337,343 A | 6/1982 | Maillard et al. | |
| 5,532,233 A | 7/1996 | Weber et al. | |
| 6,262,044 B1 | 7/2001 | M.o Slashed.ller et al. | |
| 6,313,309 B1 | 11/2001 | Baxter et al. | |
| 7,019,026 B1 | 3/2006 | Andersen et al. | |
| 8,710,245 B2 | 4/2014 | Shao | |
| 2004/0180883 A1 | 9/2004 | Gilmore | |
| 2004/0220402 A1 | 11/2004 | Chow et al. | |
| 2005/0075366 A1 | 4/2005 | Heidelbaugh et al. | |
| 2005/0187281 A1 | 8/2005 | Hinze et al. | |
| 2006/0047127 A1 | 3/2006 | Arjona | |
| 2006/0148872 A1 | 7/2006 | Chow et al. | |
| 2007/0072926 A1 | 3/2007 | Chow et al. | |
| 2008/0081910 A1 | 4/2008 | Sabb et al. | |
| 2008/0113961 A1 | 5/2008 | Nishi et al. | |
| 2008/0255239 A1 | 10/2008 | Chow et al. | |
| 2009/0318690 A1 | 12/2009 | Sasaki et al. | |
| 2010/0035887 A1 | 2/2010 | Ricciardi | |
| 2012/0295881 A1 | 11/2012 | Lange et al. | |
| 2019/0256525 A1 | 8/2019 | Bauer et al. | |
| 2020/0129477 A1 | 4/2020 | Hopkins et al. | |
| 2020/0179336 A1 | 6/2020 | Hopkins | |

FOREIGN PATENT DOCUMENTS

| | | |
|---|---|---|
| AU | 2010325925 A1 | 6/2011 |
| AU | 2016200448 A1 | 2/2016 |
| CA | 2031684 A1 | 6/1991 |
| CA | 2781716 A1 | 6/2011 |
| CN | 1300291 A | 6/2001 |

(Continued)

OTHER PUBLICATIONS

Koblan et al., "A Non-D2-Receptor-Binding Drug for the Treatment of Schizophrenia", The New England Journal of Medicine, vol. 382, No. 16, pp. 1497-1506. Apr. 16, 2020.

Jones et al. "SEP-0363856, A Novel Psychotropic Agent With A Unique, Non-D2 Mechanism of Action", European College of Neuropsychopharmacology Congress, Poster. Sep. 2019.

Koblan et al. "Efficacy and Safety of SEP-363856, A Novel Non-D2 Agent, In the Treatment of Schizophrenia: A 4-Week, Randomized, Placebo-Controlled Trial", European College of Neuropsychopharmacology Congress, Poster. Sep. 2019.

(Continued)

*Primary Examiner* — Taofiq A Solola
(74) *Attorney, Agent, or Firm* — Heslin Rothenberg Farley & Mesiti P.C.

(57) ABSTRACT

Provided herein are multicyclic compounds, methods of their synthesis, pharmaceutical compositions comprising the compounds, and methods of their use. The compounds provided herein are useful for the treatment, prevention, and/or management of various neurological disorders, including but not limited to, psychosis and schizophrenia.

21 Claims, No Drawings

(56) References Cited

FOREIGN PATENT DOCUMENTS

| | | | |
|---|---|---|---|
| CN | 101759710 | A | 6/2010 |
| CN | 102731574 | A | 10/2012 |
| CN | 104193761 | A | 12/2014 |
| DE | 3827727 | A1 | 2/1990 |
| DE | 4104257 | A1 | 8/1992 |
| EP | 333427 | A1 | 9/1989 |
| EP | 366327 | A1 | 5/1990 |
| EP | 0368175 | A1 | 5/1990 |
| EP | 370732 | A2 | 5/1990 |
| EP | 416740 | A2 | 3/1991 |
| EP | 431945 | A2 | 6/1991 |
| EP | 483647 | A1 | 5/1992 |
| EP | 0518805 | A1 | 12/1992 |
| EP | 555824 | A1 | 8/1993 |
| EP | 574313 | A1 | 12/1993 |
| EP | 600836 | A2 | 6/1994 |
| EP | 745598 | A1 | 12/1996 |
| EP | 1634873 | A1 | 3/2006 |
| EP | 1829869 | A1 | 9/2007 |
| EP | 1982714 | A1 | 10/2008 |
| EP | 1982987 | A1 | 10/2008 |
| EP | 2377850 | A1 | 10/2011 |
| FR | 2875230 | A1 | 3/2017 |
| JP | 54109975 | A | 8/1979 |
| JP | S567772 | A | 1/1981 |
| JP | 2243691 | A | 9/1990 |
| JP | 4009367 | A | 1/1992 |
| JP | 03163068 | B2 | 5/2001 |
| JP | 03223277 | B2 | 10/2001 |
| JP | 2003261566 | A | 9/2003 |
| JP | 2004269449 | A | 9/2004 |
| JP | 2005145859 | A | 6/2005 |
| JP | 2005523925 | A | 8/2005 |
| JP | 2006117568 | A | 5/2006 |
| JP | 2008530229 | A | 8/2008 |
| JP | 2009505948 | A | 2/2009 |
| JP | 2015227348 | A | 12/2015 |
| JP | 6333382 | B2 | 5/2018 |
| MX | 2012006326 | A | 10/2012 |
| RU | 2128649 | C1 | 4/1999 |
| SG | 181498 | A1 | 7/2012 |
| WO | 9108205 | A1 | 6/1991 |
| WO | 9203434 | A1 | 3/1992 |
| WO | 9215592 | A1 | 9/1992 |
| WO | 9400441 | A1 | 1/1994 |
| WO | 9604287 | A1 | 2/1996 |
| WO | 9946237 | A1 | 9/1999 |
| WO | 9946267 | A1 | 9/1999 |
| WO | 0023445 | A1 | 4/2000 |
| WO | 2000023445 | | 4/2000 |
| WO | 0035915 | A1 | 6/2000 |
| WO | 2000035915 | | 6/2000 |
| WO | 0043397 | A1 | 7/2000 |
| WO | 2000043397 | | 7/2000 |
| WO | 0068230 | A1 | 11/2000 |
| WO | 2000068230 | | 11/2000 |
| WO | 0117516 | A2 | 3/2001 |
| WO | 0119831 | A1 | 3/2001 |
| WO | 2001017516 | | 3/2001 |
| WO | 2001019831 | | 3/2001 |
| WO | 0132610 | A1 | 5/2001 |
| WO | 0132655 | A2 | 5/2001 |
| WO | 2001032610 | | 5/2001 |
| WO | 0212189 | A1 | 2/2002 |
| WO | 2002012189 | | 2/2002 |
| WO | 0222614 | A1 | 3/2002 |
| WO | 2002022614 | | 3/2002 |
| WO | 02102387 | A1 | 12/2002 |
| WO | 03006455 | A1 | 1/2003 |
| WO | 03035065 | A1 | 5/2003 |
| WO | 03092374 | A2 | 11/2003 |
| WO | 2004004726 | A1 | 1/2004 |
| WO | 2004035812 | A2 | 4/2004 |
| WO | 2004066912 | A2 | 8/2004 |
| WO | 2004078723 | A1 | 9/2004 |
| WO | 2004082687 | A1 | 9/2004 |
| WO | 2004087680 | A1 | 10/2004 |
| WO | 2005072412 | A2 | 8/2005 |
| WO | 2005073236 | A2 | 8/2005 |
| WO | 2005087779 | A1 | 9/2005 |
| WO | 2006014135 | A1 | 2/2006 |
| WO | 2006014136 | A1 | 2/2006 |
| WO | 2006015259 | A2 | 2/2006 |
| WO | 2006053274 | A2 | 5/2006 |
| WO | 2006089053 | A2 | 8/2006 |
| WO | 2007001939 | A1 | 1/2007 |
| WO | 2007002681 | A2 | 1/2007 |
| WO | 2007006546 | A1 | 1/2007 |
| WO | 2007095586 | A2 | 8/2007 |
| WO | 2007102999 | A2 | 9/2007 |
| WO | 2007126041 | A1 | 11/2007 |
| WO | 2008042422 | A2 | 4/2008 |
| WO | 2008048981 | A2 | 4/2008 |
| WO | 2008058342 | A1 | 5/2008 |
| WO | 2008155132 | A1 | 12/2008 |
| WO | 2009009550 | A1 | 1/2009 |
| WO | 2009067202 | A1 | 5/2009 |
| WO | 2009068467 | A1 | 6/2009 |
| WO | 2009072621 | A1 | 6/2009 |
| WO | 2009085256 | A1 | 7/2009 |
| WO | 2010053583 | A2 | 5/2010 |
| WO | 2010092180 | A1 | 8/2010 |
| WO | 2010092181 | A1 | 8/2010 |
| WO | 2011036889 | A1 | 3/2011 |
| WO | 2011060035 | A1 | 5/2011 |
| WO | 2011060217 | A1 | 5/2011 |
| WO | 2011069063 | A2 | 6/2011 |
| WO | 2011081205 | A1 | 7/2011 |
| WO | 2011133729 | A2 | 10/2011 |
| WO | 2012020133 | A1 | 2/2012 |
| WO | 2012122340 | A1 | 9/2012 |
| WO | 2013010453 | A1 | 1/2013 |
| WO | 2018151861 | A1 | 8/2018 |
| WO | 2019161236 | A1 | 8/2019 |
| WO | 2019161238 | A1 | 8/2019 |
| WO | 2020118032 | A1 | 6/2020 |
| ZA | 9102744 | A | 2/1992 |

OTHER PUBLICATIONS

Koblan et al. "Efficacy and Safety of SEP-363856, A Novel Psychotropic Agent With a Non-D2 Mechanism of Action, in the Treatment of Schizophrenia: A 4-Week, Randomized, Placebo-Controlled Trial", US Psychiatric and Mental Health Congress, Poster. May 2019.

Koblan et al. "Efficacy and Safety of SEP-363856, A Novel Psychotropic Agent With a Non-D2 Mechanism of Action, In the Treatment of Schizophrenia: A Randomized, Placebo-Controlled Trial", Neuroscience Education Institute, Poster. Nov. 2019.

Correll et al. "Safety and Effectiveness of SEP-363856 in Schizophrenia: Results of a 6-Month, Open-Label Extension Study", American College of Neuropsychopharmacology, Poster. Dec. 2019.

Hopkins et al. "Effects of SEP-363856 on Negative Symptoms in Schizophrenia: Analysis of an Acute, Placebo-Controlled Trial of a Novel Psychotropic Agent With No Dopamine-D2/5-Ht2a Antagonist Activity", American College of Neuropsychopharmacology, Poster. Dec. 2019.

Dedic et al. "The Novel, Non-D2 Psychotropic Agent SEP-363856 Modulates Presynaptic Dopamine Function in Mice", American College of Neuropsychopharmacology, Poster Dec. 9, 2019.

Dedic et al. "SEP-363856, A Novel Psychotropic Agent With a Unique, Non-D2 Receptor Mechanism of Action", The Journal of Pharmacology and Experimental Therapeutics, vol. 371, pp. 1-14. Oct. 2019.

Deakin et al. "A Phase 1 Functional Neuroimaging Study of SEP 363856 in Healthy Volunteers With High or Low Schizotypy", 55th Annual Meeting of the American College of Neuropsychopharmacology (ANCP) Congress, Poster. Dec. 2016.

Koblan et al. "A Phase 1 Open Label Safety and Tolerability Study of SEP-363856, A Novel Non-D2 Mechanism of Action Molecule,

(56) References Cited

OTHER PUBLICATIONS

In Patients With Schizophrenia", American College of Neuropsychopharmacology, Poster. Dec. 2016.
Poola et al. "Pharmacokinetics, Safety, and Tolerability of SEP-363856 in Healthy Adult Male Subjects and in Adult Patients With Schizophrenia Following Oral Administration", American College of Clinical Pharmacology, Poster. Sep. 2018.
Koblan et al. "Efficacy and Safety of SEP-363856 in the Treatment of Schizophrenia: A 4-Week, Randomized, Placebo-Controlled Trial of a Novel Compound With a Non-D2 Mechanism of Action", American College of Neuropsychopharmacology Annual Meeting, Poster. Dec. 2018.
Koblan, "SEP-363856, A Candidate Antipsychotic and Antidepressant Compound With a Novel Non-D2 Mechanism of Action", 6th Biennial Schizophrenia International Research Society Conference, Oral Presentation. 31 pages. Apr. 2018.
Koblan et al. "SEP-363856, A Novel Psychotropic Agent With a Non-D2 Mechanism of Action, for the Treatment of Schizophrenia", The 2019 Congress of the Schizophrenia International Research Society, Oral Presentation. 20 pages. Apr. 2019.
Koblan et al. "Efficacy and Safety of SEP-363856, A Novel Psychotropic Agent With a Non-D2 Mechanism of Action, In the Treatment of Schizophrenia: A 4-Week, Randomized, Placebo-Controlled Trial", American Psychiatric Association, Poster. May 2019.
Koblan et al. "Efficacy and Safety of SEP-363856, A Novel Psychotropic Agent With a Non-D2 Mechanism of Action, In the Treatment of Schizophrenia: A 4-Week, Randomized, Placebo-Controlled Trial", American Society of Clinical Psychopharmacology, Poster. May 2019.
Written Opinion in International Application No. PCT/US2019/064646. dated Mar. 9, 2020.
International Search Report in International Application No. PCT/US2019/064646. dated Mar. 9, 2020.
Unpublished U.S. Appl. No. 16/486,257 to Hopkins et al. dated Aug. 15, 2019.
Unpublished U.S. Appl. No. 16/704,202 to Hopkins. dated Dec. 5, 2019.
Unpublished International Application No. PCT/US2019/064646 to Hopkins. dated Dec. 5, 2019.
Karran et al. "The Amyloid Cascade Hypothesis for Alzheimer's Disease: An Appraisal for the Development of Therapeutics", Nature, vol. 10, p. 698. 2011.
Schmitz et al. "Hippocampal Neuron Loss Exceeds Amyloid Plaque Load in a Transgenic Mouse Model of Alzheimer's Disease", American Journal of Pathology, vol. 164, p. 1495. 2004.
Hejl et al. "Prepulse Inhibition in Patients with Alzheimer's Disease", Neurobiology of Aging, vol. 25, p. 1045. 2004.
Trehan "A New Synthesis of 13-aza-18-nor-17-oxo-A-nor-3-thiaestra-1,5(10), 9(11)-triene", retrieved from STN Database Accession No. 1986:225089 and Indian Journal of Chemistry, Section 6: Organic Chemistry Including Medicinal Chemistry, vol. 24B(6), pp. 659-661. 1985
Trehan "Synthesis of 2, 3, 13-Triaza-18-nor-17-oxo-3-phenyl-A-nor-estra-1,5(10), 9(11)-triene & 2, 3, 13-Triaza-7,7-dimethyl-18-nor-17-oxo-3-phenyl-A-nor=estra-1,5(10), 9(11)-triene", Indian Journal of Chemistry, vol. 19B, pp. 243-245. 1980.
Office Action in CN Application No. 201410333332.1 with translation. dated Nov. 2, 2015.
Mashkovskiy "Drugs", Moscow, New Wave, LLC, vol. 1, p. 11 with translation. 2002.
Berardi et al. "A Multireceptorial Binding Reinvestigation on an Extended Class of s Ligands: N-[w-(Indan-1-yl and Tetralin-1-yl)alkyl] Derivatives of 3,3-Dimethylpiperidine Reveal High Affinities Towards s1 and EBP Sites", Bioorganic & Medicinial Chemistry, vol. 9, No. 5, pp. 1325-1335. 2001.
Lowry et al. "Protein Measurement with the Folin Phenol Reagent", Journal Bio. Chem., vol. 193, p. 265. 1951.

Maier et al., "Novel Spiropiperidines as Highly Potent and Subtype Selective σ-Receptor Ligands. Part 1", Journal Med. Chem., vol. 45, pp. 438-448. 2002.
Maier et al., "Novel σ Receptor Ligands. Part 2. SAR of Spiro[[2]benzopyran-1,4'-piperidines] and Spiro [[2] benzofuran-1,4'-piperidines] with Carbon Substituents in Position 3", Journal Med. Chem., vol. 45, pp. 4923-4930. 2002.
Quirion et al. "A Proposal for the Classification of Sigma Binding Sites", Trends Pharmacol. Sci., vol. 13, pp. 86-86. Mar. 1992.
Radesca "Synthesis adn Receptor Binding EnantiomericN-Substitutedcis-N-[2-(3,4-Dichloroph-enyl)ethyl]-2-(1-pyrrolidiny) Cyclohexylamines as High-Affinity O' Receptor Ligands", Journal Med. Chem., vol. 34, pp. 3065-3074. 1991.
Schow "Novel Sigma Receptor Ligands 2", Bioorganic and Medicinal Chemistry Letters, No. 2, pp. 221-224. 1993.
Snyder et al. "Receptor Mechanisms in Antipsychotic Drug Action: Focus on Sigma Receptors", Journal Neuropsychiatry, vol. 1, pp. 7-15. 1989.
Vecchietti et al. "(1 S)-1-(Aminomethyl)-2-(Arylacetyl)-1,2,3,4-tetrahydroisoquinoline and Heterocycle-Condensed Tetrahydropyridine Derivatives: Members of a Novel Class of Very Potent K Opioid Analgesics", Journal of Medicinal Chemistry, vol. 34, No. 8, pp. 2624-2633. 1991.
Jacobs et al. "1-Imidazolyl(alkyl)-Substituted Di- and Tetrahydroquinolines and Analogues: Syntheses and Evaluation of Dual Inhibitors of Thromboxane A2 Synthase and Aromatase", Journal of Medicinal Chemistry, vol. 43, No. 9, pp. 1841-1851. Apr. 12, 2000.
Japanese Office Action issued by the Japanese Patent Office for Application No. 2012-542219, 9 pages, with translation. dated Nov. 21, 2014.
Jentsch et al., "The Neuropsychopharmacology of Phencyclidine: From NMDA Receptor Hypofunction to the Dopamine Hypothesis of Schizophrenia", Neuropsychopharmacology, vol. 20, No. 3, pp. 201-225. 1999.
Jobson et al. "Pyrano Heterocycles. I. The Syntheses of Isochromans and the Novel thieno[3,2-c]pyran, benzothieno[3,2-c]pyran, benzothieno[2,3-c]pyran, and pyrano[4,3-b] benzofuran Systems", Journal of Heterocyclic Chemistry, 12(3), pp. 591-594. Jan. 1, 1975.
Kapur et al. "NMDA Receptor Antagonist Ketamine and PCP Have Direct Effects on the Dopamine D2 adn Serotonin 5-HT2 Receptors—Implications for Models of Schizophrenia", Molecular Psychiatry, vol. 7, pp. 837-844. 2002.
Katsuki et al., "Excitotoxic Degeneration of Hypothalamic Orexin Neurons in Slice Culture", Neurobiology of Disease, vol. 15, pp. 61-69. 2004.
Kostin et al. "Lack of Hypocretin Attenuates Behavioral Changes Produced by Glutamatergic Activation of the Perifornical-Lateral Hypothalamic Area", Sleep, vol. 37, No. 5, pp. 1011-1020. 2014.
Marcus et al. "The Efficacy and Safety of Aripiprazole as Adjunctive Therapy in Major Depressive Disorder. A second Multicenterm Randomized, Double-Blind, Pacebo-Controlled Study", Journal of Clinical Psychopharmacology, vol. 28, No. 2, pp. 15-165. Apr. 2008.
Singapore Written Opinion issued in Singapore Application No. 201204089-5, 12 pages. dated Sep. 20, 2013.
Swerdlow et al. "Seroquel Restores Sensorimotor Gating in Phencyclidine-Treated Rats", Journal of Pharmacology and Experimental Therapeutics, vol. 279, No. 3, pp. 1290-1299. Dec. 1996.
Torrado et al. "Novel Selective and Potent 5-HT Reuptake Inhibitors with 5-HT1D Antagonist Activity: Chemistry and Pharmacological Evaluation of a Series of Thienopyran Derivatives", Bioorganic & Medicinial Chemistry, 12(20), pp. 5277-5295. Oct. 15, 2004.
Official Action in Japanese Application No. 2018-028819, with translation. dated Mar. 5, 2019.
PubChem CID 4878038 (search date Feb. 22, 2019). Sep. 17, 2005.
PubChem CID 4878041 (search date Feb. 22, 2019). Sep. 17, 2005.
Ross et al., "α2 Adrenoceptor Agonists as Potential Analgesic Agents. 2. Discovery of 4-(4-Imidazo)-1,3-dimethyl-6,7-dihydro-thianaphthene as a High-Affinity Ligand for the α2D Adrenergic Receptor", J. Med. Chem., vol. 43, pp. 1423-1426. 2000.

(56) References Cited

OTHER PUBLICATIONS

Berardi et al. "Novel Potent s1 Ligands: N-[w-(Tetralin-1-yl)alkyl] piperidine Derivatives" Journal of Medicinal Chemistry, American Chemical Society, vol. 39, No. 21, pp. 4255-4260. 1996.

Berardi et al. "4-(Tetralin-1-yl)-and 4-(Naphthalen-1-yl) alkyl Derivatives Ligands with Agonist s2 Activity", Journal of Medicinal Chemistry, American Chemical Society, vol. 47, No. 9, pp. 2308-2317. 2004.

Chihara et al. "Preparation of Benzothiophene Derivatives as Blood Platelet Aggregation Inhibitors", Retrieved from STN Database Accession No. 1992:128652 and JP03223277A, Yoshitomi Pharmaceutical Industries Ltd. Oct. 2, 1991.

Corbera et al. "A Medicinal-Chemistry-Guided Approach to Selective and Druglike Sigma 1 Ligands", Chemmedchem, vol. 1, No. 1, pp. 140-154. Jan. 2006.

Dehaven-Hudkins et al. "Characterization of the Binding of [3H](+)pentazocine to O'Recognition Sites in Guinea Pig Brain" Eur. Journal Pharmacol., vol. 277, pp. 371-378. 1992.

Hanner et al. "Purification, Molecular Cloning, and Expression of the Mammalian Sigma1-Binding Site", Proc. Natl. Aca. Sci, vol. 93, pp. 8072-8077. 1996.

Krogsgaard-Larsen et al. "Textbook of Drug Design and Discovery", Taylor & Francis. Apr. 2002.

Langa et al. "Generation and Phenotypic Analysis of Sigma Receptor Type 1 (Sigma1) Knockout Mice", European Journal of Neuroscience, vol. 18, pp. 2188-2196. 2003.

Extended European Search Report for EP Application No. 10835185.9, pp. 1-15. dated Apr. 4, 2013.

Walker: Pharmacological Reviews, "Sigma Receptors: Biology and Function", vol. 42, No. 4, pp. 355-402. 1990.

Bakshi et al. "Antagonism of Phencyclidine-Induced Deficits in Prepulse Inhibition by the Putative Aytpical Antipsychotic Olanzapine", Psychopharmacology, vol. 122, No. 2, pp. 198-201. Nov. 1995.

First Examination Report Issued in New Zealand Application No. 600008, 3 pages. dated Mar. 11, 2013.

Ghaemi et al. "Does Olanzapine have Antidepressant Properties? A Retrospective Preliminary Study", Bipolar Disorders, vol. 2, pp. 196-199. 2000.

Ghasemi et al. "The Role of NMDA Receptors in teh Pathophysiology and Treatment of Mood Disorders", Neuroscience and Biobehavioral Reviews, vol. 47, pp. 336-358. Sep. 16, 2014.

Gleason et al. "Blockade of Phencyclidine-Induced Hyperlocomotion by Olanzapine, Clozapine adn Serotonin Receptor Subtype Selective Antagonists in Mice", Psyhopharmacology, vol. 129, pp. 79-84. 1997.

International Search Report and Written Opinion issued in PCT/US2010/05884, 10 pages. dated Aug. 25, 2011.

Mexican Examination Report issued in Mexican Application No. MX/a/2012/006326, with English translation, 6 pages. dated Jul. 7, 2013.

Moreno et al. "Preclinical Models of Antipsychotic Drug Action", International Journal of Neuropsychopharmacology, vol. 16, pp. 2131-2144. Jun. 10, 2013.

New Zealand Examination Report in Application No. NZ 626068, 3 pages. dated Oct. 8, 2015.

New Zealand Examination Report in Application No. NZ 711802, 5 pages. dated Oct. 8, 2015.

Nordquist et al. "Effects of Aripiprazole/OPC-14597 on Motor Activity, Pharmacological Models of Psychosis, and Brain Activity in Rats", Neuropharmacology, vol. 54, pp. 405-416. 2008.

Pittenger et al. "The NMDA Receptor as a Therapeutic Target in Major Depressive Disorder", CNS & Neurological Disorders—Drug Targets, vol. 6, No. 2, pp. 101-115. Feb. 19, 2007.

Registry (STN) [online] CAS Registry No. 933704-21-3, 1 page. Apr. 30, 2007.

Singapore Search Report and Written Opinion issued in Singapore Application No. 10201401661, 10 pages. dated Jun. 15, 2015.

Frohlich et al., "A Novel Synthesis of 3,3-(Spiro)Substituted Azetidines", Heterocycles, vol. 37, No. 3, pp. 1897-1891. 1994.

Datta et al., "Studies in Sulphur Heterocycles. Part 5. Further Use of 6,7-Dihydribenzo[b]thiphen-4[5H]-one in the Synthesis of Substitited Benzo[b]thiophene Derivatives", J. Chem. Research (S), pp. 72-73. 1988.

Stanetty et al., "Heterocyclische Spiroverbindungen Spiroverbindungen: Spiro [benzo[b]thiophen-4(5H),3'-pyrrolidine]", Arch. Pharm. vol. 317, pp. 168-176. 1984.

Devani et al., "Synthesis of 2-Aminothiophenes & Thieno[2,3-d]pyrimidines", Indian Journal of Chemistry, vol. 14B, pp. 357-360. May 1976.

Caira "Crystalline Polymorphism of Organic Compounds" Topics in Current Chemistry, vol. 198. Jan. 1, 1998.

Fujima et al. "Synthesis of (S)-3-(N-Methylamino)-1-(2-thienyl)propan-1-ol: Revisiting Eli Lilly's Resolution-Racemization-Recycle Synthesis of Duloxetine for its Robust Processes", Organic Process Research and Development, vol. 10, No. 5. Jan. 1, 2006.

International Search Report in International Application No. PCT/US2019/018265. dated May 29, 2019.

International Search Report in International Application No. PCT/US2019/018263 dated Apr. 2, 2019.

Written Opinion in International Application No. PCT/US2019/018263. dated Apr. 2, 2019.

International Search Report in International Application No. PCT/US2018/000078. dated May 25, 2018.

Written Opinion in International Application No. PCT/US2018/000078. dated May 25, 2018.

MULTICYCLIC COMPOUNDS AND METHODS OF USE THEREOF

I. CROSS REFERENCE TO RELATED APPLICATION

This application is a continuation of U.S. patent application Ser. No. 16/117,450, filed Aug. 30, 2018, which is a continuation of U.S. patent application Ser. No. 14/950,834, filed Nov. 24, 2015, now U.S. Pat. No. 10,085,968, which is a continuation of U.S. patent application Ser. No. 14/205,859, filed Mar. 12, 2014, now U.S. Pat. No. 9,351,954, which is a continuation of U.S. patent application Ser. No. 13/513,176, filed Jan. 8, 2013, now U.S. Pat. No. 8,710,245, which is a § 371 national phase application of International Patent Application No. PCT/US2010/058884, filed Dec. 3, 2010, which claims priority to U.S. Provisional Patent Application No. 61/266,880, filed Dec. 4, 2009, the contents of which are hereby incorporated by reference herein in their entirety.

II. FIELD

Provided herein are multicyclic compounds useful for treating various neurological disorders, including but not limited to, psychosis and schizophrenia, compositions comprising the compounds, and methods of use thereof.

III. BACKGROUND

Central nervous system disorders affect a wide range of the population with differing severity. Generally, the major feature of this class of disorders includes the significant impairment of cognition or memory that represents a marked deterioration from a previous level of functioning.

Schizophrenia is a psychopathic disorder of unknown origin, which usually appears for the first time in early adulthood and is marked by characteristics such as, psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. See, e.g., *Diagnostic and Statistical Manual of Mental Disorders*, 4Ed., American Psychiatric Association (1997) (DSM-V™).

Schizophrenia is classified into subgroups. The paranoid type is characterized by delusions and hallucinations and absence of thought disorder, disorganized behavior, and affective flattening. The disorganized type, which is also named "hebephrenic schizophrenia," in which thought disorder and flat affect are present together. The cataconic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e., positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics may be successful in treating the positive symptoms but fare less well for the negative and cognitive symptoms.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

Agitation is a well-recognized behavioral disorder with a range of symptoms, including hostility, extreme excitement, poor impulse control, tension and/or uncooperativeness. Agitation is common in the elderly and often associated with dementia such as those caused by Alzheimer's disease, Parkinson's disease, and Huntington's disease, and by diseases that affect blood vessels, such as stroke or multi-infaret dementia, which is caused by multiple strokes in the brain. An estimated five percent of people aged 65 and older and up to 20 percent of those aged 80 and older are affected by dementia; of these sufferers, nearly half exhibit behavioral disturbances, such as agitation, wandering, and violent outbursts. Agitated behaviors can also be manifested in cognitively intact elderly people and by those with psychiatric disorders other than dementia.

Dementia is characterized by several cognitive impairments including significant memory deficit and can stand alone, or be an underlying characteristic feature of a variety of diseases, including but not limited to, Alzheimer's disease, Parkinson's disease, Huntington's disease, and multiple sclerosis.

Therefore, there is a great need for effective treatments of various neurological disorders, including but not limited to, psychosis and schizophrenia.

IV. SUMMARY

Provided herein are compounds of formula (I), or pharmaceutically acceptable salts or stereoisomers thereof:

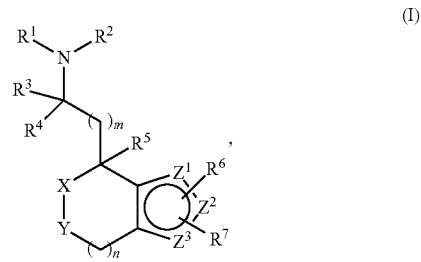

wherein $R^1$, $R^2$, $R^3$, $R^4$, $R^5$, $R^6$, $R^7$, X, Y, $Z^1$, $Z^2$, $Z^3$, m, and n are defined herein elsewhere. The compounds are useful for treating various disorders, such as neurological disorders including, but not limited to, psychosis and schizophrenia.

Also provided herein are compositions and dosage forms, comprising a compound provided herein, and one or more pharmaceutically acceptable excipients. Compositions and dosage forms provided herein may further comprise one or more additional active ingredients.

Also provided herein are methods for the treatment, prevention, and/or management of various neurological disorders, including those of the central nervous system (CNS) using the compounds and compositions provided herein. In one embodiment, provided herein is a method of treating or managing one or more symptoms of a neurological disorder provided herein. Such neurological disorders include, but are not limited to, schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., bipolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, Huntington's chorea, and premenstrual dysphoria.

In one embodiment, provided herein is a method of treating, preventing, and/or managing psychosis or schizophrenia. In one embodiment, provided herein is a method of treating or managing one or more symptoms of psychosis or schizophrenia. In one embodiment, provided herein is a method of treating, preventing, and/or managing psychosis or schizophrenia in a subject, such as a mammal, such as, e.g., human, rodent (such as, e.g., mice and rats), cat, dog, non-human primate, among others. In one embodiment, the method comprises contacting a compound provided herein with one or more receptors of the central nervous system. In one embodiment, the method comprises contacting a cell with a compound provided herein. In an exemplary embodiment, the cell is a brain cell, such as, e.g., a neuronal cell or a glial cell.

V. DETAILED DESCRIPTION

Unless defined otherwise, all technical and scientific terms used herein have the same meaning as those commonly understood by one of ordinary skill in the art. In certain embodiments, abbreviations are as defined in J. Org. Chem. 2007, 72, 23A. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may optionally be substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g, n-butyl, isobutyl, and t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere.

As used herein, and unless otherwise specified, the term "heteroalkyl" refers to a stable straight or branched chain, or cyclic hydrocarbon radical, or combinations thereof, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O, N and S can be placed at any interior position of the heteroalkyl group. In one embodiment, the heteroatom Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NHO—$CH_3$ and —$CH_2$—Si($CH_3$)$_3$. In certain embodiments, the heteroalkyl is optionally substituted as described herein elsewhere.

As used herein, and unless otherwise specified, the term "alkoxyl" refers to a stable straight or branched chain, or cyclic hydrocarbon radical, or combinations thereof, consisting of the stated number of carbon atoms and from one or more, in one embodiment, one to three, O atoms. Examples of alkoxyl include, but are not limited to, —O—$CH_3$, —O—$CF_3$, —O—$CH_2$—$CH_3$, —O—$CH_2$—$CH_2$—$CH_3$, —O—CH—($CH_3$)$_2$, and —O—$CH_2$—$CH_2$—O—$CH_3$. In one embodiment, the alkoxyl is optionally substituted as described herein elsewhere.

As used herein, and unless otherwise specified, the term "aminoalkyl" refers to a stable straight or branched chain, or cyclic hydrocarbon radical, or combinations thereof, consisting of the stated number of carbon atoms and from one or more, in one embodiment, one to three, N atoms. Examples of aminoalkyl include, but are not limited to, —NH—$CH_3$, —N($CH_3$)$_2$, —NH—$CH_2$—$CH_3$, —N($CH_3$)—$CH_2$—$CH_3$, —NH—CH—($CH_3$)$_2$, —$CH_2$—$CH_2$—NH—$CH_3$, and —$CH_2$—$CH_2$—N($CH_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. Example of aralkyl includes, but is not limited to, benzyl. In certain embodiments, both alkyl and aryl may be optionally substituted with one or more substituents as described herein elsewhere.

As used herein, and unless otherwise specified, the term "cycloalkylalkyl" refers to a monovalent alkyl group substituted with cycloalkyl. In certain embodiments, both the alkyl and cycloalkyl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N, and the remaining ring atoms are carbon atoms. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "eycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the term "optionally substituted" is intended to mean that a group, such as an alkyl, alkenyl, alkynyl, cycloalkyl, heteroalkyl, aryl, aralkyl, cycloalkylalkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR)NR$_b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O) NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents Qt. As used herein, all groups that can be substituted are "optionally substituted," unless otherwise specified.

In one embodiment, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, C(O)ONR$^f$R$^g$, —C(NR$^e$)NR$^f$R$^g$, —OR$^e$, —OC(O)R$^e$, —C(O)OR$^e$, —OC(O)NR$^f$R$^g$, —OC (=NR$^e$)NR$^f$R$^g$, —OS(O)R$^e$, —OS(O)$_2$R$^e$, —OS(O)NR$^f$R$^g$, —S(O)$_2$NR$^f$R$^g$, NR$^e$ C(O)R$^h$, —NR$^e$C(O)OR$^h$, —NR$^e$C(O) NR$^f$R$^g$, —NR$^e$C(=NR$^h$)NR$^f$R$^g$, —NR$^e$S(O)R$^h$, —NR$^e$S (O)$_2$R$^h$, NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids, such as, including but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/diastereomerically/stereomerically pure and enantiomerically/diastereomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess or diastereomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer or diastereomer and about 5% or less of the less preferred enantiomer or diastereomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In one embodiment, such symptoms are those known to a person of skill in the art to be associated with the disease or disorder being treated. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms associated with the disease or disorder. In one embodiment, such symptoms are those known to a person of skill in the art to be associated with the disease or disorder being prevented. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms associated with the disease or disorder. In one embodiment, such symptoms are those known to a person of skill in the art to be associated with the disease or disorder being managed. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression, bipolar disorder, manic conditions, and attention deficit disorder). Exemplary neurological disorders include, but are not limited to, MLS (cerebellar ataxia), Huntington's disease, Down syndrome, multi-infarct dementia, status epilecticus, contusive injuries (e.g., spinal cord injury and head injury), viral infection induced neurodegeneration, (e.g., AIDS, encephalopathies), epilepsy, benign forgetfulness, closed head injury, sleep disorders, major depressive disorder, dysthymia, seasonal affective disorder, dementias, movement disorders, psychosis, alcoholism, post-traumatic stress disorder, and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

As used herein, and unless otherwise specified, the terms "psychosis," "schizophrenia," "obsessive-compulsive disorder," "substance abuse," "anxiety," "eating disorders," "migraine," and other CNS or neurological disorders described herein elsewhere are used herein in a manner consistent with their accepted meanings in the art. See, e.g., *Diagnostic and Statistical Manual of Mental Disorders*, 4th Ed., American Psychiatric Association (1997) (DSM-IV™).

As used herein, and unless otherwise specified, the term "seizure" refers to a neurological disorder and may be used interchangeably with "convulsion," although there are many types of seizure, some of which have subtle or mild symptoms instead of convulsions. In one embodiment, the term "seizure" as used herein is intended to encompass "convulsion." In some embodiments, seizures may be caused by disorganized and sudden electrical activity in the brain. In some embodiments, convulsions are a rapid and uncontrollable shaking during which the muscles contract and relax repeatedly. Unless otherwise specified, the terms "convulsion" and "seizure" are used herein in accordance with the accepted meanings as found in the *Diagnostic and Statistical Manual of Mental Disorders*, 4th Ed., American Psychiatric Association (1997) (DSM-IV™).

As used herein, and unless otherwise specified, the term "affective disorder" includes depression, attention deficit disorder, attention deficit disorder with hyperactivity, bipolar disorder, and manic disorder, and the like.

As used herein, and unless otherwise specified, the term "depression" includes all forms of depression, including, but not limited to, major depressive disorder (MDD) or unipolar depressive disorder, dysthymia, seasonal affective disorder (SAD), and bipolar depressive disorder. "Major depressive disorder" is used herein interchangeably with "unipolar depression", "unipolar depressive disorder", and "major depression." "Depression" may also include any condition commonly associated with depression, such as all forms of fatigue (e.g., chronic fatigue syndrome) and cognitive deficits.

Unless otherwise specified, the terms "bipolar disorder" and "manic disorder" are used herein in accordance with the accepted meanings as found in the *Diagnostic and Statistical Manual of Mental Disorders*, 4th Ed., American Psychiatric Association (1997) (DSM-IV™).

Unless otherwise specified, the terms "attention deficit disorder" (ADD), and "attention deficit disorder with hyperactivity" (ADDH) or "attention deficit hyperactivity disorder" (ADHD), are used herein in accordance with the accepted meanings as found in the *Diagnostic and Statistical Manual of Mental Disorders*, 4th Ed., American Psychiatric Association (1997) (DSM-IV™).

As used herein, and unless otherwise specified, the term "pain" refers to an unpleasant sensory and emotional experience. Unless otherwise specified, the term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In one embodiment, the term "pain" includes pain resulting from dysfunction of the nervous system: organic pain states that share clinical features of neuropathic pain and possible common pathophysiology mechanisms, but are not initiated by an identifiable lesion in any part of the nervous system.

Unless otherwise specified, the term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

Unless otherwise specified, the term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, neuropathic cancer pain, HIV/AIDS induced pain, phantom limb pain, and complex regional pain syndrome. Unless otherwise specified, the term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes. As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "diabetic peripheral neuropathic pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "post-herpetic neuralgia", also called "postherpetic neuralgia" (PHN), refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "phantom limb pain" refers to pain appearing to come from where an amputated limb used to be. Phantom limb pain can also occur in limbs following paralysis (e.g., following spinal cord injury). "Phantom limb pain" is usually chronic in nature.

As used herein, and unless otherwise specified, the term "trigeminal neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "complex regional pain syndrome" (CRPS), formerly known as "reflex sympathetic dystrophy" (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

B. Compounds

In one embodiment, provided herein is a compound of formula (I):

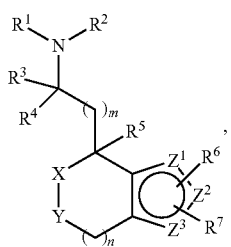

(I)

or a pharmaceutically acceptable salt or stereoisomer thereof, wherein one of X and Y is O, and the other is $CH_2$; or both X and Y are $CH_2$;

one of $Z^1$, $Z^2$, and $Z^3$ is S; and (i) two of $Z^1$, $Z^2$, and $Z^3$ are C; or (ii) one of $Z^1$, $Z^2$, and $Z^3$ is C and one of $Z^1$, $Z^2$, and $Z^3$ is N;

$R^1$ and $R^2$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^8$, wherein $R^8$ is $SO_2$alkyl or $SO_2$aryl, each of which is optionally substituted; or (iii) $R^1$ and $R^2$ together with the nitrogen atom to which they are attached form an optionally substituted heterocyclyl or heteroaryl;

$R^3$ and $R^4$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with $R^1$ and/or $R^2$ and the atoms to which they are attached form an optionally substituted heteroaryl (e.g., imidazolyl or thiazolyl);

$R^5$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{10}$, wherein $R^{10}$ is $CF_3$, CN, nitro, amino, hydroxyl, or cycloalkoxyl, each of which is optionally substituted; or (iii) $R^5$ and $R^1$ together with the atoms to which they are attached form an optionally substituted heterocyclyl;

$R^6$ and $R^7$ are each independently (i) hydrogen, halo, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^{11}$, wherein $R^{11}$ is $CF_3$, CN, nitro, amino, hydroxyl, cycloalkoxyl, heteroaryl, or heterocyclyl, each of which is optionally substituted; or (iii) $R^6$ and $R^7$ together with the atoms to which they are attached form an optionally substituted aryl, heteroaryl, cycloalkyl or heterocyclyl ring; with the proviso that when one of $Z^1$, $Z^2$, and $Z^3$ is N, $R^7$ is absent;

m is 0, 1, or 2;

n is 0, 1, or 2; and each occurrence of p is independently 0, 1, or 2.

In one embodiment, provided herein is a compound of formula (I), as defined herein elsewhere, or a pharmaceutically acceptable salt or stereoisomer thereof, wherein:

one of X and Y is O, and the other is $CH_2$; or both X and Y are $CH_2$;

two of $Z^1$, $Z^2$, and $Z^3$ are C, and one of $Z^1$, $Z^2$, and $Z^3$ is S;

$R^1$ and $R^2$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^8$, wherein $R^8$ is $SO_2$alkyl or $SO_2$aryl, each of which is optionally substituted; or (iii) $R^1$ and $R^2$ together with the nitrogen atom to which they are attached form an optionally substituted heterocyclyl or heteroaryl;

$R^3$ and $R^4$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with $R^1$ and/or $R^2$ and the atoms to which they are attached form an optionally substituted heteroaryl (e.g., imidazolyl or thiazolyl);

$R^5$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —(CH$_2$)$_p$—R$^{10}$, wherein $R^{10}$ is CF$_3$, CN, nitro, amino, hydroxyl, or cycloalkoxyl, each of which is optionally substituted; or (iii) $R^5$ and $R^1$ together with the atoms to which they are attached form an optionally substituted heterocyclyl;

$R^6$ and $R^7$ are each independently (i) hydrogen, halo, alkyl, alkoxyl, aminoalkyl, alkenyl, alkynyl, cycloalkyl, cycloalkylalkyl, aryl, or aralkyl, each of which is optionally substituted; or (ii) —(CH$_2$)$_p$—R$^{11}$, wherein $R^{11}$ is CF$_3$, CN, nitro, amino, hydroxyl, cycloalkoxyl, heteroaryl, or heterocyclyl, each of which is optionally substituted; or (iii) $R^6$ and $R^7$ together with the atoms to which they are attached form an optionally substituted aryl, heteroaryl, cycloalkyl or heterocyclyl ring;

m is 0, 1, or 2;

n is 0, 1, or 2; and each occurrence of p is independently 0, 1, or 2.

In one embodiment, X is O and Y is CH$_2$. In one embodiment, X is CH$_2$ and Y is O. In one embodiment, both X and Y are CH$_2$.

In one embodiment, $Z^1$ is S. In one embodiment, $Z^2$ is S. In one embodiment, $Z^3$ is S. In one embodiment, $Z^1$ and $Z^2$ are C, and $Z^3$ is S. In one embodiment, $Z^1$ and $Z^3$ are C, and $Z^2$ is S. In one embodiment, $Z^2$ and $Z^3$ are C, and $Z^1$ is S. In one embodiment, Z is N, $Z^2$ is C, and $Z^3$ is S. In one embodiment, $Z^1$ is C, $Z^2$ is N, and $Z^3$ is S. In one embodiment, $Z^1$ is N, $Z^2$ is S, and $Z^3$ is C. In one embodiment, $Z^1$ is C, $Z^2$ is S, and $Z^3$ is N. In one embodiment, $Z^1$ is S, $Z^2$ is N, and $Z^3$ is C. In one embodiment, $Z^1$ is S, $Z^2$ is C, and $Z^3$ is N. In one embodiment, when one of $Z^1$, $Z^2$, and $Z^3$ is N, $R^1$ is absent and R substitutes a carbon ring atom.

In one embodiment, $R^1$ is hydrogen. In one embodiment, $R^1$ is optionally substituted alkyl. In one embodiment, $R^1$ is alkyl. In one embodiment, $R^1$ is optionally substituted alkoxyl. In one embodiment, $R^1$ is alkoxyl. In one embodiment, $R^1$ is optionally substituted aminoalkyl. In one embodiment, $R^1$ is aminoalkyl. In one embodiment, $R^1$ is optionally substituted alkenyl. In one embodiment, $R^1$ is alkenyl. In one embodiment, R is optionally substituted alkynyl. In one embodiment, $R^1$ is alkynyl. In one embodiment, R is optionally substituted cycloalkyl. In one embodiment, $R^1$ is cycloalkyl. In one embodiment, $R^1$ is optionally substituted cycloalkylalkyl. In one embodiment, $R^1$ is cycloalkylalkyl. In one embodiment, $R^1$ is optionally substituted aryl. In one embodiment, $R^1$ is aryl. In one embodiment, $R^1$ is optionally substituted aralkyl. In one embodiment, $R^1$ is aralkyl. In one embodiment, $R^1$ is —(CH$_2$)$_p$—SO$_2$alkyl, wherein the alkyl is optionally substituted. In one embodiment, $R^1$ is —(CH$_2$)$_p$—SO$_2$alkyl. In one embodiment, $R^1$ is —(CH$_2$)$_p$—SO$_2$aryl, wherein the aryl is optionally substituted. In one embodiment, $R^1$ is —(CH$_2$)$_p$—SO$_2$aryl. In one embodiment, $R^1$ is C$_1$-C$_4$ alkyl optionally substituted with —SO$_2$alkyl or —SO$_2$aryl, each of which is further optionally substituted. In one embodiment, $R^1$ is C$_1$-C$_4$ alkyl optionally substituted with —SO$_2$alkyl or —SO$_2$aryl. In one embodiment, the alkyl, alkoxyl, aminoalkyl, alkenyl, alkynyl, and cycloalkyl are optionally substituted with one or more halo.

In one embodiment, $R^2$ is hydrogen. In one embodiment, $R^2$ is optionally substituted alkyl. In one embodiment, $R^2$ is alkyl. In one embodiment, $R^2$ is optionally substituted alkoxyl. In one embodiment, $R^2$ is alkoxyl. In one embodiment, $R^2$ is optionally substituted aminoalkyl. In one embodiment, $R^2$ is aminoalkyl. In one embodiment, $R^2$ is optionally substituted alkenyl. In one embodiment, $R^2$ is alkenyl. In one embodiment, $R^2$ is optionally substituted alkynyl. In one embodiment, $R^2$ is alkynyl. In one embodiment, $R^2$ is optionally substituted cycloalkyl. In one embodiment, $R^2$ is cycloalkyl. In one embodiment, $R^2$ is optionally substituted cycloalkylalkyl. In one embodiment, $R^2$ is cycloalkylalkyl. In one embodiment, $R^2$ is optionally substituted aryl. In one embodiment, $R^2$ is aryl. In one embodiment, $R^2$ is optionally substituted aralkyl. In one embodiment, $R^2$ is aralkyl. In one embodiment, $R^2$ is —(CH$_2$)$_p$—SO$_2$alkyl, wherein the alkyl is optionally substituted. In one embodiment, $R^2$ is —(CH$_2$)$_p$—SO$_2$alkyl. In one embodiment, $R^2$ is —(CH$_2$)$_p$—SO$_2$aryl, wherein the aryl is optionally substituted. In one embodiment, $R^2$ is —(CH$_2$)$_p$—SO$_2$aryl. In one embodiment, $R^2$ is C$_1$-C$_4$ alkyl optionally substituted with —SO$_2$alkyl or —SO$_2$aryl, each of which is further optionally substituted. In one embodiment, $R^2$ is C$_1$-C$_4$ alkyl optionally substituted with —SO$_2$alkyl or —SO$_2$aryl. In one embodiment, the alkyl, alkoxyl, aminoalkyl, alkenyl, alkynyl, and cycloalkyl are optionally substituted with one or more halo.

In one embodiment, $R^1$ and $R^2$ together with the nitrogen atom to which they are attached form an optionally substituted heterocyclyl. In one embodiment, $R^1$ and $R^2$ together with the nitrogen atom to which they are attached form a heterocyclyl. In one embodiment, R and $R^2$ together with the nitrogen atom to which they are attached form an optionally substituted heteroaryl. In one embodiment, R and $R^2$ together with the nitrogen atom to which they are attached form a heteroaryl.

In one embodiment, $R^3$ and $R^4$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —(CH$_2$)$_p$—R$^9$, wherein $R^9$ is CF$_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with $R^1$ and the atoms to which they are attached form an optionally substituted heteroaryl (e.g., imidazolyl).

In one embodiment, $R^3$ is hydrogen. In one embodiment, $R^3$ is optionally substituted alkyl. In one embodiment, $R^3$ is alkyl. In one embodiment, $R^3$ is optionally substituted alkoxyl. In one embodiment, $R^3$ is alkoxyl. In one embodiment, $R^3$ is optionally substituted aminoalkyl. In one embodiment, $R^3$ is aminoalkyl. In one embodiment, $R^3$ is optionally substituted alkenyl. In one embodiment, $R^3$ is alkenyl. In one embodiment, $R^3$ is optionally substituted alkynyl. In one embodiment, $R^3$ is alkynyl. In one embodiment, $R^3$ is optionally substituted cycloalkyl. In one embodiment, $R^3$ is cycloalkyl. In one embodiment, $R^3$ is optionally substituted cycloalkylalkyl. In one embodiment, $R^3$ is cycloalkylalkyl. In one embodiment, $R^3$ is optionally substituted aryl. In one embodiment, $R^3$ is aryl. In one embodiment, $R^3$ is optionally substituted aralkyl. In one embodiment, $R^3$ is aralkyl. In one embodiment, $R^3$ is —(CH$_2$)$_p$—CF$_3$. In one embodiment, $R^3$ is —(CH$_2$)$_p$—CN. In one embodiment, $R^3$ is —(CH$_2$)$_p$-nitro. In one embodiment, $R^3$ is —(CH$_2$)$_p$-amino, wherein the amino is optionally substituted. In one embodiment, $R^3$ is —(CH$_2$)$_p$-amino. In one embodiment, $R^3$ is —(CH$_2$)$_p$-hydroxyl, wherein the hydroxyl is optionally substituted. In one embodiment, $R^3$ is —(CH$_2$)$_p$-hydroxyl. In one embodiment, $R^3$ is —(CH$_2$)$_p$-cycloalkoxyl, wherein the cycloalkoxyl is optionally substituted. In one embodiment, $R^3$ is —$(CH_2)_p$-cycloalkoxyl. In one embodiment, $R^3$ is $C_1$-$C_4$ alkyl optionally substituted with $CF_3$, CN, nitro, amino, hydroxyl, or cycloalkoxyl, each of which is further optionally substituted. In one embodiment, $R^3$ is $C_1$-$C_4$ alkyl optionally substituted with $CF_3$, CN, nitro, amino, hydroxyl, or cycloalkoxyl. In one embodiment, the alkyl, alkoxyl, aminoalkyl, alkenyl, alkynyl, and cycloalkyl are optionally substituted with one or more halo.

In one embodiment, $R^4$ is hydrogen. In one embodiment, $R^4$ is optionally substituted alkyl. In one embodiment, $R^4$ is alkyl. In one embodiment, $R^4$ is optionally substituted alkoxyl. In one embodiment, $R^4$ is alkoxyl. In one embodiment, $R^4$ is optionally substituted aminoalkyl. In one embodiment, $R^4$ is aminoalkyl. In one embodiment, $R^4$ is optionally substituted alkenyl. In one embodiment, $R^4$ is alkenyl. In one embodiment, $R^4$ is optionally substituted alkynyl. In one embodiment, $R^4$ is alkynyl. In one embodiment, $R^4$ is optionally substituted cycloalkyl. In one embodiment, $R^4$ is cycloalkyl. In one embodiment, $R^4$ is optionally substituted cycloalkylalkyl. In one embodiment, $R^4$ is cycloalkylalkyl. In one embodiment, $R^4$ is optionally substituted aryl. In one embodiment, $R^4$ is aryl. In one embodiment, $R^4$ is optionally substituted aralkyl. In one embodiment, $R^4$ is aralkyl. In one embodiment, $R^4$ is —$(CH_2)_p$—$CF_3$. In one embodiment, $R^4$ is —$(CH_2)_p$—CN. In one embodiment, $R^4$ is —$(CH_2)_p$-nitro. In one embodiment, $R^4$ is —$(CH_2)_p$-amino, wherein the amino is optionally substituted. In one embodiment, $R^4$ is —$(CH_2)_p$-amino. In one embodiment, $R^4$ is —$(CH_2)_p$-hydroxyl, wherein the hydroxyl is optionally substituted. In one embodiment, $R^4$ is —$(CH_2)_p$-hydroxyl. In one embodiment, $R^4$ is —$(CH_2)_p$-cycloalkoxyl, wherein the cycloalkoxyl is optionally substituted. In one embodiment, $R^4$ is —$(CH_2)_p$-cycloalkoxyl. In one embodiment, $R^4$ is $C_1$-$C_4$ alkyl optionally substituted with $CF_3$, CN, nitro, amino, hydroxyl, or cycloalkoxyl, each of which is further optionally substituted. In one embodiment, $R^4$ is $C_1$-$C_4$ alkyl optionally substituted with $CF_3$, CN, nitro, amino, hydroxyl, or cycloalkoxyl. In one embodiment, the alkyl, alkoxyl, aminoalkyl, alkenyl, alkynyl, and cycloalkyl are optionally substituted with one or more halo.

In one embodiment, $R^3$ and $R^4$ together with the carbon atom to which they are attached form an optionally substituted cycloalkyl. In one embodiment, $R^1$ and $R^4$ together with the carbon atom to which they are attached form a cycloalkyl. In one embodiment, $R^3$ and $R^4$ together with the carbon atom to which they are attached form an optionally substituted heterocyclyl. In one embodiment, $R^3$ and $R^4$ together with the carbon atom to which they are attached form a heterocyclyl.

In one embodiment, $R^3$ and $R^1$ together with the atoms to which they are attached form an optionally substituted heterocyclyl, and $R^4$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —$(CH_2)_p$—$R^9$, wherein $R^9$ is $CF_3$, CN, nitro, amino, hydroxyl, or cycloalkoxyl, each of which is optionally substituted. In one embodiment, $R^3$ and $R^1$ together with the atoms to which they are attached form a heterocyclyl, and $R^4$ is (i) hydrogen, alkyl, alkoxyl, aminoalkyl, alkenyl, alkynyl, cycloalkyl, cycloalkylalkyl, aryl, or aralkyl; or (ii) —$(CH_2)_p$—$R^9$, wherein $R^9$ is $CF_3$, CN, nitro, amino, hydroxyl, or cycloalkoxyl.

In one embodiment, $R^3$ and $R^4$ are combined together to form a double bond and together with $R^1$ and the atoms to which they are attached form an optionally substituted heteroaryl (e.g., imidazole). A skilled person will understand that when $R^3$ and $R^4$ are combined together to form a double bond and together with $R^1$ and the atoms to which they are attached form an optionally substituted heteroaryl, this embodiment could also be described as: one of $R^3$ and $R^4$ is absent and the other of $R^3$ and $R^4$ together with $R^1$ and the atoms to which they are attached form an optionally substituted heteroaryl (e.g., imidazole), which is substituted by $R^2$ (e.g., substituent on ring nitrogen atom). In one embodiment, $R^3$ and $R^4$ are combined together to form a double bond and together with $R^1$ and the atoms to which they are attached form a heteroaryl. Examples of the heteroaryl include, but are not limited to, imidazolyl, pyrrolyl, benzimidazolyl, or indazolyl. In some embodiments, $R^1$ and $R^2$ are also combined to form a double bond and together with $R^3$ and $R^4$ and the atoms to which they are attached form an optionally substituted heteroaryl (e.g., thiazole). A skilled person will understand that when $R^1$ and $R^2$ are also combined together to form a double bond and together with $R^3$ and $R^4$ and the atoms to which they are attached form an optionally substituted heteroaryl, this embodiment could also be described as: one of $R^3$ and $R^4$ is absent and one of $R^1$ and $R^2$ is absent, and the other of $R^3$ and $R^4$ together with the other of $R^1$ and $R^2$ and the atoms to which they are attached form an optionally substituted heteroaryl (e.g., thiazole). In some embodiments, $R^1$ and $R^2$ are also combined to form a double bond and together with $R^3$ and $R^4$ and the atoms to which they are attached form a heteroaryl. Examples of the heteroaryl include, but are not limited to, oxazolyl, isoxazolyl, thiazolyl, pyridyl, or benzoxazolyl. In one embodiment, $R^1$, $R^2$, $R^3$, and $R^4$ are combined together with the atoms to which they are attached form an optionally substituted heteroaryl (e.g., imidazole or thiazole).

In one embodiment, $R^1$ is hydrogen. In one embodiment, $R^1$ is optionally substituted alkyl. In one embodiment, $R^5$ is alkyl. In one embodiment, $R^5$ is optionally substituted alkoxyl. In one embodiment, $R^5$ is alkoxyl. In one embodiment, $R^5$ is optionally substituted aminoalkyl. In one embodiment, $R^5$ is aminoalkyl. In one embodiment, $R^5$ is optionally substituted alkenyl. In one embodiment, $R^5$ is alkenyl. In one embodiment, $R^5$ is optionally substituted alkynyl. In one embodiment, $R^5$ is alkynyl. In one embodiment, $R^5$ is optionally substituted cycloalkyl. In one embodiment, $R^5$ is cycloalkyl. In one embodiment, $R^5$ is optionally substituted cycloalkylalkyl. In one embodiment, $R^5$ is cycloalkylalkyl. In one embodiment, $R^5$ is optionally substituted aryl. In one embodiment, $R^5$ is aryl. In one embodiment, $R^5$ is optionally substituted aralkyl. In one embodiment, $R^5$ is aralkyl. In one embodiment, $R^5$ is —$(CH_2)_p$—$CF_3$. In one embodiment, $R^5$ is —$(CH_2)_p$—CN. In one embodiment, $R^5$ is —$(CH_2)_p$-nitro. In one embodiment, $R^5$ is —$(CH_2)_p$-amino, wherein the amino is optionally substituted. In one embodiment, $R^5$ is —$(CH_2)_p$-amino. In one embodiment, $R^5$ is —$(CH_2)_p$-hydroxyl, wherein the hydroxyl is optionally substituted. In one embodiment, $R^5$ is —$(CH_2)_p$-hydroxyl. In one embodiment, $R^5$ is —$(CH_2)_p$-cycloalkoxyl, wherein the cycloalkoxyl is optionally substituted. In one embodiment, $R^5$ is —$(CH_2)_p$-cycloalkoxyl. In one embodiment, $R^5$ is $C_1$-$C_4$ alkyl optionally substituted with $CF_3$, CN, nitro, amino, hydroxyl, or cycloalkoxyl, each of which is further optionally substituted. In one embodiment, $R^5$ is $C_1$-$C_4$ alkyl optionally substituted with $CF_3$, CN, nitro, amino, hydroxyl, or cycloalkoxyl. In one embodiment, the alkyl, alkoxyl, aminoalkyl, alkenyl, alkynyl, and cycloalkyl are optionally substituted with one or more halo.

In one embodiment, $R^5$ and $R^1$ together with the atoms to which they are attached form an optionally substituted heterocyclyl. In one embodiment, $R^5$ and R together with the atoms to which they are attached form a heterocyclyl.

In one embodiment, $R^6$ is hydrogen. In one embodiment, $R^6$ is halo. In one embodiment, $R^6$ is optionally substituted alkyl. In one embodiment, $R^6$ is alkyl. In one embodiment, $R^6$ is optionally substituted alkoxyl. In one embodiment, $R^6$ is alkoxyl. In one embodiment, $R^6$ is optionally substituted aminoalkyl. In one embodiment, $R^6$ is aminoalkyl. In one embodiment, $R^6$ is optionally substituted alkenyl. In one embodiment, $R^6$ is alkenyl. In one embodiment, $R^6$ is optionally substituted alkynyl. In one embodiment, $R^6$ is alkynyl. In one embodiment, $R^6$ is optionally substituted cycloalkyl. In one embodiment, $R^6$ is cycloalkyl. In one embodiment, $R^6$ is optionally substituted cycloalkylalkyl. In one embodiment, R is cycloalkylalkyl. In one embodiment, $R^6$ is optionally substituted aryl. In one embodiment, R is aryl. In one embodiment, $R^6$ is optionally substituted aralkyl. In one embodiment, $R^6$ is aralkyl. In one embodiment, $R^6$ is $-(CH_2)_p-CF_3$. In one embodiment, $R^6$ is $-(CH_2)_p-CN$. In one embodiment, $R^6$ is $-(CH_2)_p$-nitro. In one embodiment, $R^6$ is $-(CH_2)_p$-amino, wherein the amino is optionally substituted. In one embodiment, $R^6$ is $-(CH_2)_p$-amino. In one embodiment, $R^6$ is $-(CH_2)_p$-hydroxyl, wherein the hydroxyl is optionally substituted. In one embodiment, $R^6$ is $-(CH_2)_p$-hydroxyl. In one embodiment, $R^6$ is $-(CH_2)_p$-cycloalkoxyl, wherein the cycloalkoxyl is optionally substituted. In one embodiment, $R^6$ is $-(CH_2)_p$-cycloalkoxyl. In one embodiment, $R^6$ is $-(CH_2)_p$-heteroaryl, wherein the heteroaryl is optionally substituted. In one embodiment, $R^6$ is $-(CH_2)_p$-heteroaryl. In one embodiment, $R^6$ is $-(CH_2)_p$-heterocyclyl, wherein the heterocyclyl is optionally substituted. In one embodiment, $R^6$ is $-(CH_2)_p$-heterocyclyl. In one embodiment, the alkyl, alkoxyl, aminoalkyl, alkenyl, alkynyl, and cycloalkyl are optionally substituted with one or more halo.

In one embodiment, $R^7$ is hydrogen. In one embodiment, $R^7$ is halo. In one embodiment, $R^7$ is optionally substituted alkyl. In one embodiment, $R^7$ is alkyl. In one embodiment, $R^7$ is optionally substituted alkoxyl. In one embodiment, $R^7$ is alkoxyl. In one embodiment, $R^7$ is optionally substituted aminoalkyl. In one embodiment, $R^7$ is aminoalkyl. In one embodiment, $R^7$ is optionally substituted alkenyl. In one embodiment, $R^7$ is alkenyl. In one embodiment, $R^7$ is optionally substituted alkynyl. In one embodiment, $R^7$ is alkynyl. In one embodiment, $R^7$ is optionally substituted cycloalkyl. In one embodiment, $R^7$ is cycloalkyl. In one embodiment, $R^7$ is optionally substituted cycloalkylalkyl. In one embodiment, R is cycloalkylalkyl. In one embodiment, $R^7$ is optionally substituted aryl. In one embodiment, $R^7$ is aryl. In one embodiment, $R^7$ is optionally substituted aralkyl. In one embodiment, $R^7$ is aralkyl. In one embodiment, $R^7$ is $-(CH_2)_p-CF_3$. In one embodiment, $R^7$ is $-(CH_2)_p-CN$. In one embodiment, $R^7$ is $-(CH_2)_p$-nitro. In one embodiment, $R^7$ is $-(CH_2)_p$-amino, wherein the amino is optionally substituted. In one embodiment, $R^7$ is $-(CH_2)_p$-amino. In one embodiment, R is $-(CH_2)_p$-hydroxyl, wherein the hydroxyl is optionally substituted. In one embodiment, R is $-(CH_2)_p$-hydroxyl. In one embodiment, $R^7$ is $-(CH_2)_p$-cycloalkoxyl, wherein the cycloalkoxyl is optionally substituted. In one embodiment, $R^7$ is $-(CH_2)_p$-cycloalkoxyl. In one embodiment, R is $-(CH_2)_p$-heteroaryl, wherein the heteroaryl is optionally substituted. In one embodiment, $R^7$ is $-(CH_2)_p$-heteroaryl. In one embodiment, $R^7$ is $-(CH_2)_p$-heterocyclyl, wherein the heterocyclyl is optionally substituted. In one embodiment, $R^7$ is $-(CH_2)_p$-heterocyclyl. In one embodiment, the alkyl, alkoxyl, aminoalkyl, alkenyl, alkynyl, and cycloalkyl are optionally substituted with one or more halo.

In one embodiment, $R^6$ and $R^7$ together with the atoms to which they are attached form an optionally substituted aryl. In one embodiment, $R^6$ and $R^7$ together with the atoms to which they are attached form an aryl. In one embodiment, $R^6$ and $R^7$ together with the atoms to which they are attached form an optionally substituted heteroaryl. In one embodiment, $R^6$ and $R^7$ together with the atoms to which they are attached form a heteroaryl. In one embodiment, $R^6$ and $R^7$ together with the atoms to which they are attached form a partially saturated optionally substituted cycloalkyl. In one embodiment, $R^6$ and $R^7$ together with the atoms to which they are attached form a partially saturated cycloalkyl. In one embodiment, $R^6$ and $R^7$ together with the atoms to which they are attached form an optionally substituted heterocyclyl. In one embodiment, $R^6$ and $R^7$ together with the atoms to which they are attached form a heterocyclyl.

In one embodiment, m is 0. In one embodiment, m is 1. In one embodiment, m is 2.

In one embodiment, n is 0. In one embodiment, n is 1. In one embodiment, n is 2.

In one embodiment, p is 0. In one embodiment, p is 1. In one embodiment, p is 2.

In one embodiment, at least one of $R^1$, $R^2$, $R^3$, $R^4$, $R^5$, $R^6$, and $R^7$ is not hydrogen. In one embodiment, at least one of $R^1$, $R^2$, $R^3$, $R^4$, $R^5$, and $R^6$ is not hydrogen (e.g., when $R^7$ is absent). In one embodiment, at least one of $R^1$, $R^2$, $R^3$, $R^4$, $R^6$, and $R^7$ is not hydrogen. In one embodiment, at least one of $R^1$, $R^2$, $R^3$, $R^4$, and $R^6$ is not hydrogen (e.g., when $R^7$ is absent). In one embodiment, at least one of $R^1$ and $R^2$ is not hydrogen. In one embodiment, at least one of $R^3$ and $R^4$ is not hydrogen. In one embodiment, at least one of $R^6$ and $R^7$ is not hydrogen. In one embodiment, when $R^5$ is not hydrogen, at least one of $R^1$, $R^2$, $R^3$, $R^4$, $R^6$, and $R^7$ is not hydrogen. In one embodiment, when $R^5$ is not hydrogen, at least one of $R^1$, $R^2$, $R^3$, $R^4$, and $R^6$ is not hydrogen (e.g., when $R^7$ is absent). In one embodiment, $R^5$ is not hydroxyl. In one embodiment, $R^5$ is not substituted hydroxyl (e.g., alkoxyl). In one embodiment, $R^5$ is not alkyl. In one embodiment, $R^5$ is not methyl.

In one embodiment, $R^1$ and $R^2$ are not optionally substituted acyl. In one embodiment, $R^6$ and $R^7$ are not optionally substituted amide. In one embodiment, $R^{11}$ is not optionally substituted amide. In one embodiment, $R^6$ and $R^7$ are not optionally substituted acyl. In one embodiment, $R^{11}$ is not optionally substituted acyl.

In one embodiment, when X and Y are $CH_2$, $R^3$ and $R^4$ are not combined together with $R^1$ or $R^2$ and the atoms to which they are attached to form a ring (e.g., imidazole or imidazoline). In one embodiment, when X and Y are $CH_2$, $R^3$ and $R^4$ are not combined together with $R^1$ and $R^2$ and the atoms to which they are attached to form a ring (e.g., thiazole).

In one embodiment, when X and Y are $CH_2$, $R^1$ (or $R^2$) and $R^5$ are not combined together with the atoms to which they are attached form a ring (e.g., pyrrolidine or azetidine).

In one embodiment, when any one of $R^1$, $R^2$, $R^3$, $R^4$, $R^5$, $R^6$, or $R^7$ is alkyl or cycloalkyl, the alkyl or cycloalkyl is optionally substituted with one or more halo (e.g., fluoro).

Any of the combinations of X, Y, $Z^1$, $Z^2$, $Z^3$, $R^1$, $R^2 R^3$, $R^4$, $R^5$, $R^6$, $R^7$, m, n, and p are encompassed by this disclosure and specifically provided herein.

In one embodiment, provided herein is a compound of formula (IIa):

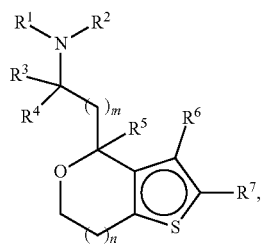

(IIa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, m is 0 or 1. In one embodiment, n is 1 or 2. In one embodiment, m is 0 and n is 1. In one embodiment, n is 0 or 1. In one embodiment, n is 0.

In one embodiment, $R^5$ is hydrogen.

In one embodiment, $R^1$ and $R^2$ are each independently hydrogen, $C_1$-$C_4$ alkyl (e.g., methyl, ethyl, or propyl (e.g., n-propyl or i-propyl)), or $C_3$-$C_6$ cycloalkyl (e.g., cyclopropyl). In one embodiment, $R^1$ and $R^2$ are each independently hydrogen or $C_1$-$C_4$ alkyl (e.g., methyl, ethyl, or propyl (e.g., n-propyl or i-propyl)). In one embodiment, R and $R^2$ are each independently $C_1$-$C_4$ alkyl, wherein one or more hydrogen(s) in the alkyl are replaced with deuterium (e.g., $CD_3$).

In one embodiment, $R^3$ and $R^4$ are hydrogen or $C_1$-$C_4$ alkyl (e.g., methyl, ethyl, or propyl (e.g., n-propyl or i-propyl)). In one embodiment, $R^3$ and $R^4$ are hydrogen.

In one embodiment, $R^6$ and $R^7$ are each independently hydrogen, halo (e.g., F or Cl), $C_1$-$C_4$ alkyl (e.g., methyl, ethyl, propyl, or $CF_3$), aryl (e.g., phenyl), heteroaryl (e.g., pyridyl), heterocyclyl (e.g., pyrrolidinyl, piperidinyl, or morpholinyl), alkoxyl (e.g., OMe), or aminoalkyl (e.g., NMe), each of which is optionally substituted. In one embodiment, $R^6$ and $R^7$ are each independently hydrogen, halo, $C_1$-$C_4$ alkyl, aryl, heteroaryl, heterocyclyl, alkoxyl, or aminoalkyl. In one embodiment, the $C_1$-$C_4$ alkyl is optionally substituted with one or more fluoro. In one embodiment, $R^6$ and $R^7$ are each independently hydrogen, fluoro, chloro, methyl, $CF_3$, ethyl, propyl, isopropyl, phenyl, pyridyl, pyrrolidinyl, piperidinyl, morpholinyl, methoxyl, or dimethylamino.

Specific examples include, but are not limited to, the following compounds:

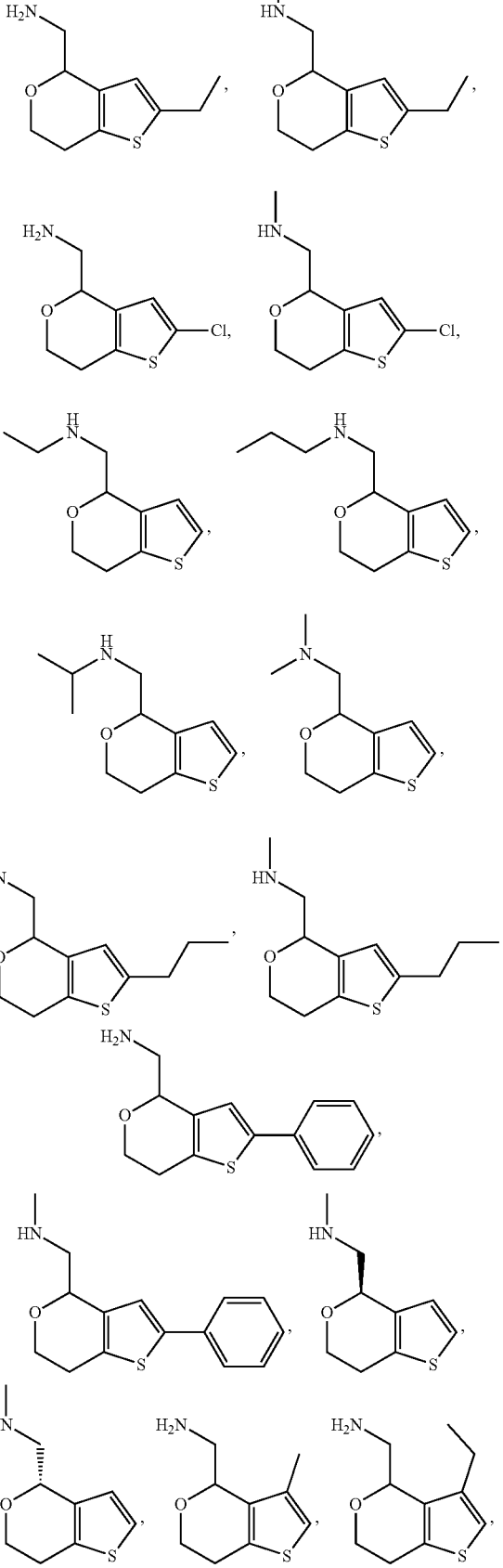

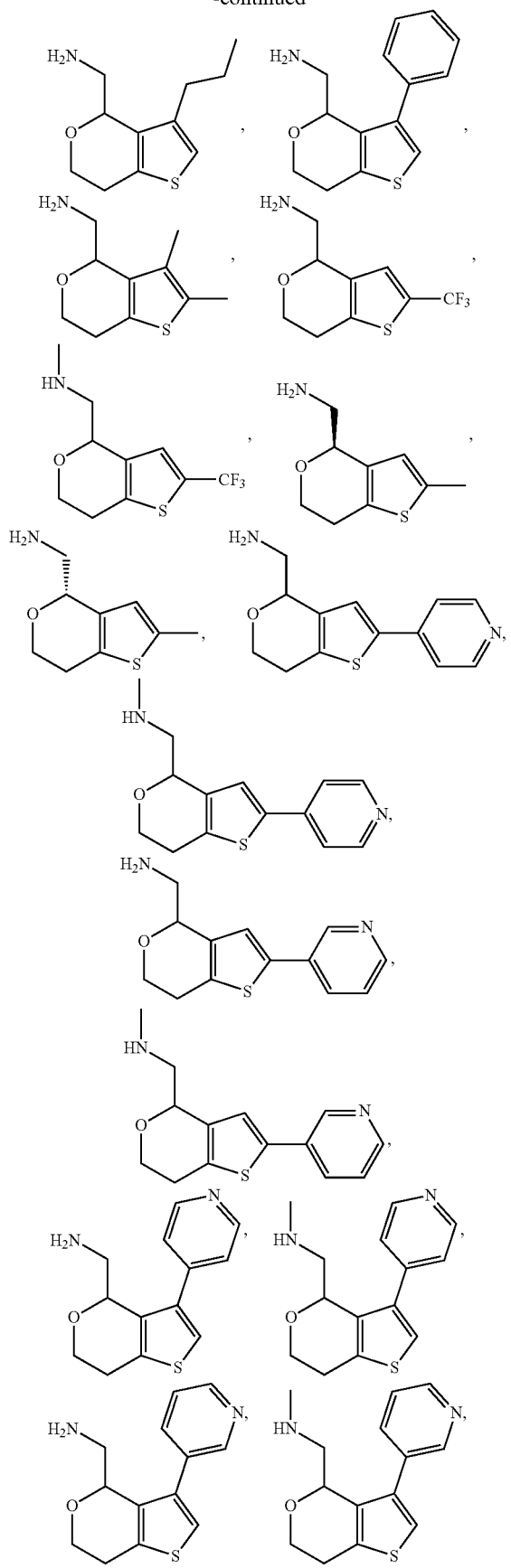
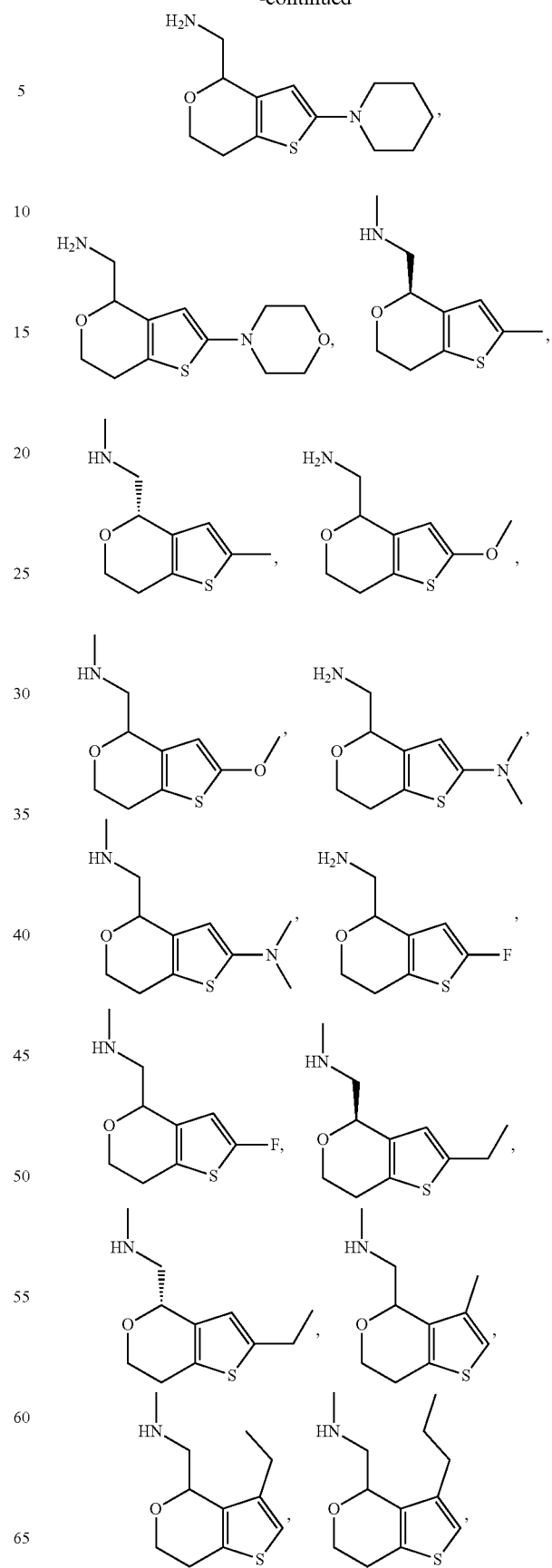

-continued
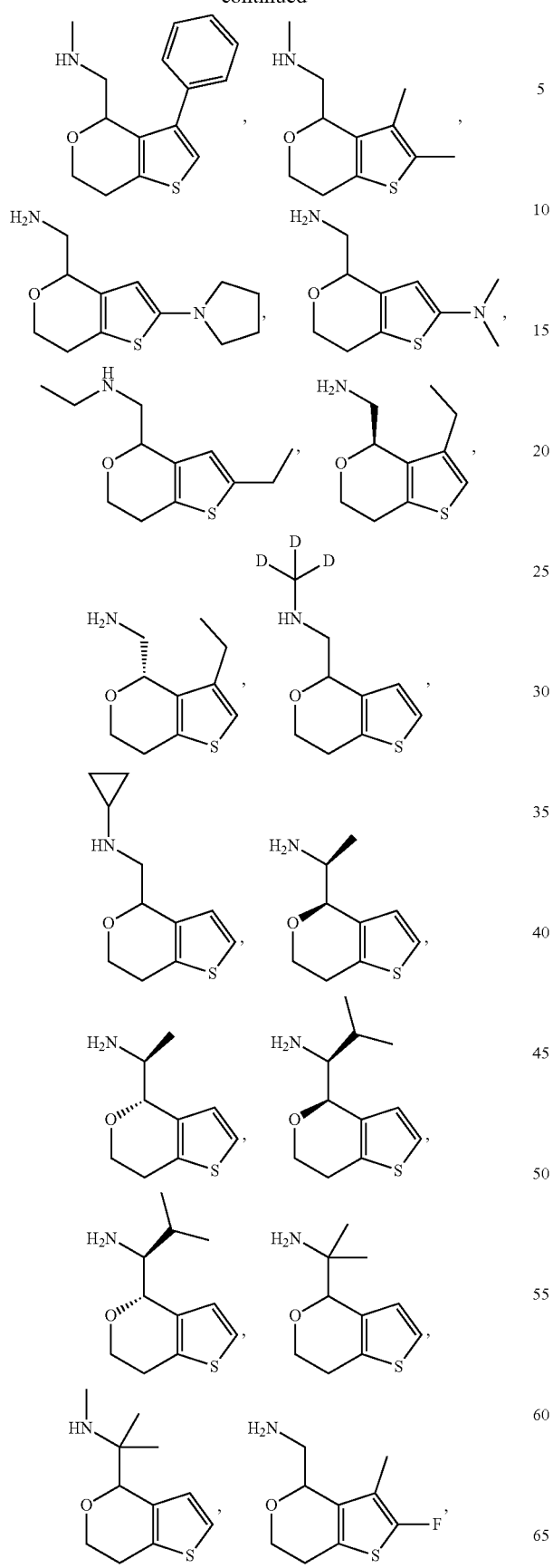
-continued
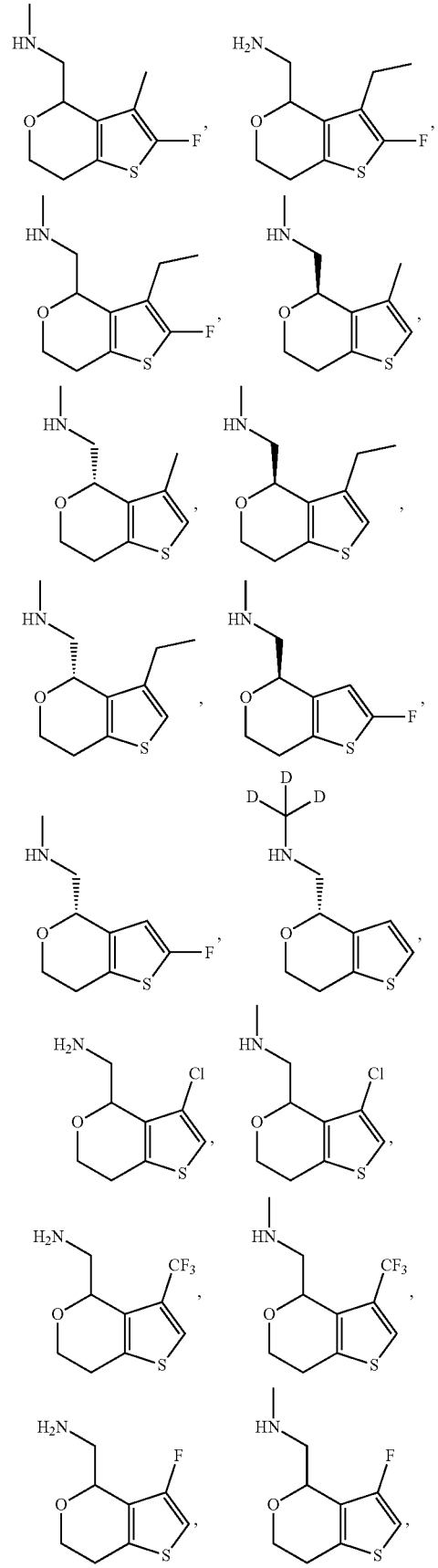

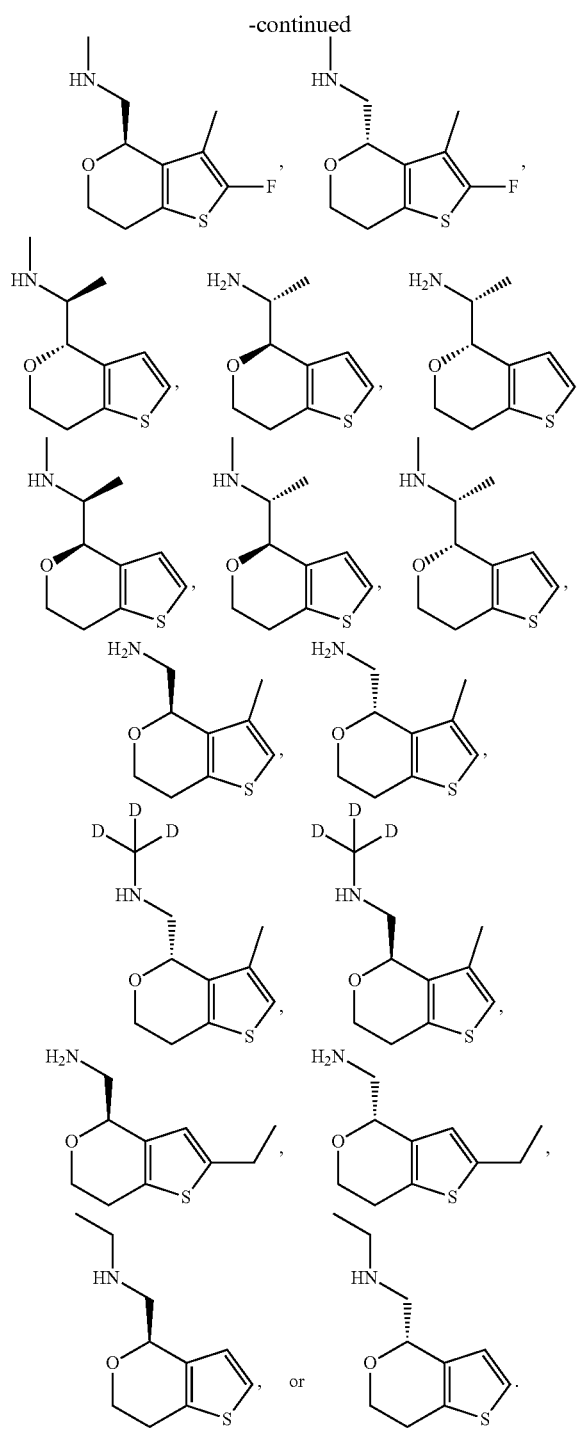

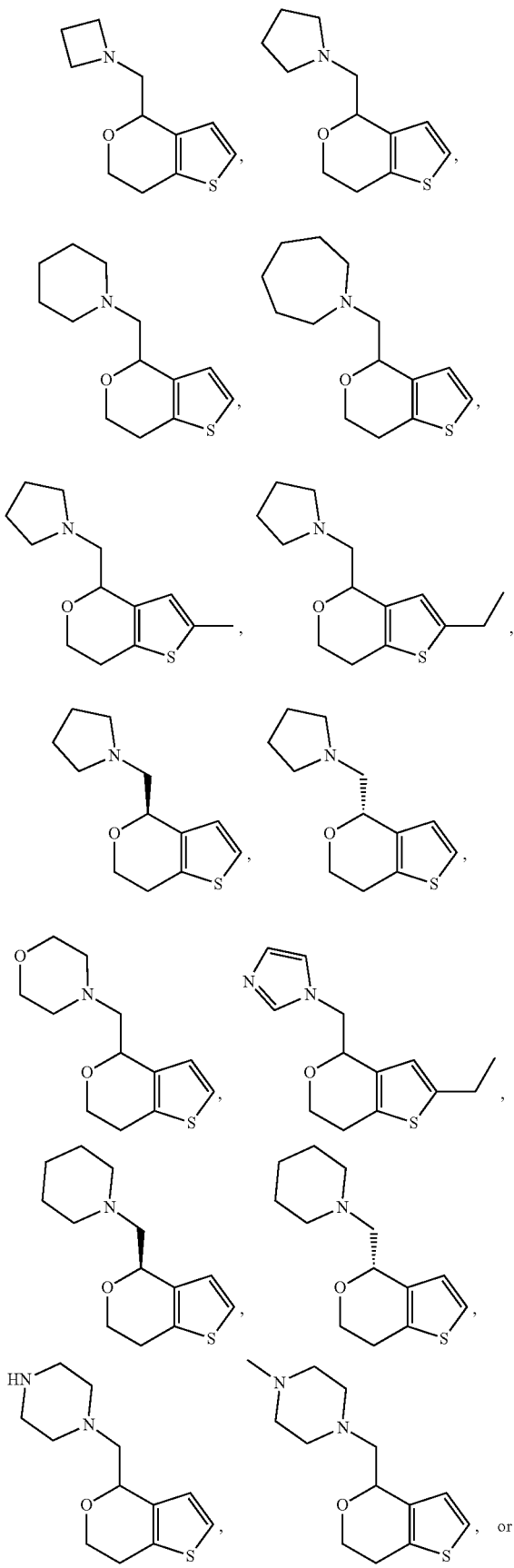

In one embodiment, R[1] and R[2] together with the nitrogen atom to which they are attached form a heteroaryl or heterocyclyl, each of which is optionally substituted. In one embodiment, R[1] and R[2] together with the nitrogen atom to which they are attached form an optionally substituted heterocyclyl. In one embodiment, R[1] and R[2] together with the nitrogen atom to which they are attached form a heteroaryl or heterocyclyl. Examples include, but are not limited to, azetidinyl, pyrrolidinyl, piperidinyl, azepanyl, morpholinyl, imidazolyl, piperazinyl, and N-methylpiperazinyl. Specific examples include, but are not limited to, the following compounds:

-continued

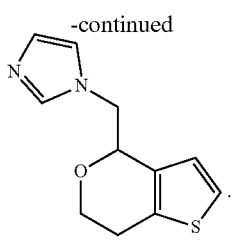

In one embodiment, R and $R^3$ together with the atoms to which they are attached form an optionally substituted heterocyclyl ring (e.g., pyrrolidine, including, e.g., unsubstituted pyrrolidine and N-methyl-pyrrolidine). Specific examples include, but are not limited to, the following compounds:

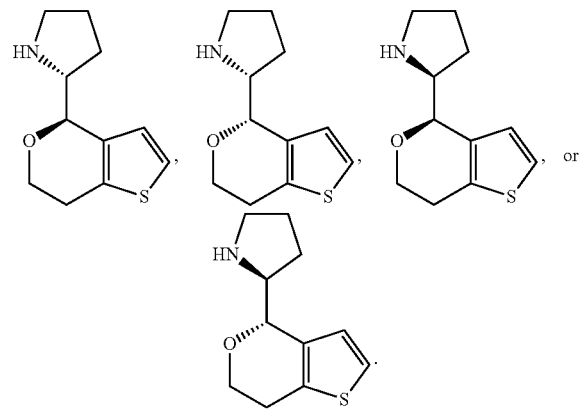

In one embodiment, $R^3$ and $R^4$ together with the atom to which they are attached form a cycloalkyl (e.g., cyclopropyl, cyclobutyl, cyclopentyl, or cyclohexyl) or heterocyclyl (e.g., tetrahydrofuranyl) ring, each of which is optionally substituted. Specific examples include, but are not limited to, the following compounds:

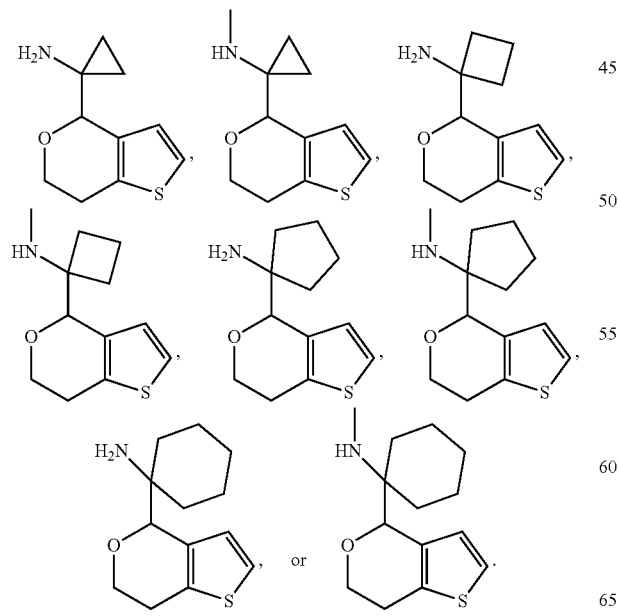

In one embodiment, $R^6$ and $R^7$ together with the atoms to which they are attached form an aryl (e.g., phenyl) or cycloalkyl (e.g., 5-, 6-, or 7-membered) ring, each of which is optionally substituted (e.g., by one or more halo or phenyl). In one embodiment, $R^6$ and $R^7$ together with the atoms to which they are attached form an optionally substituted aryl. In one embodiment, $R^6$ and $R^7$ together with the atoms to which they are attached form an aryl. Examples include, but are not limited to, phenyl, cyclopentenyl, cyclohexenyl, and cycloheptenyl. Specific examples include, but are not limited to, the following compounds:

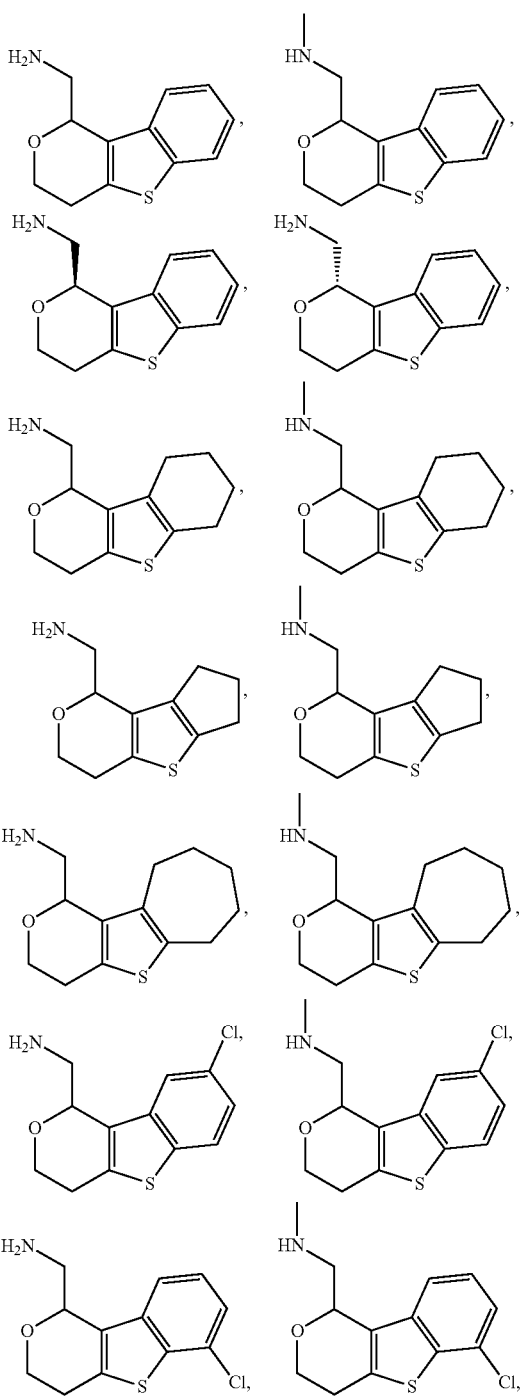

-continued

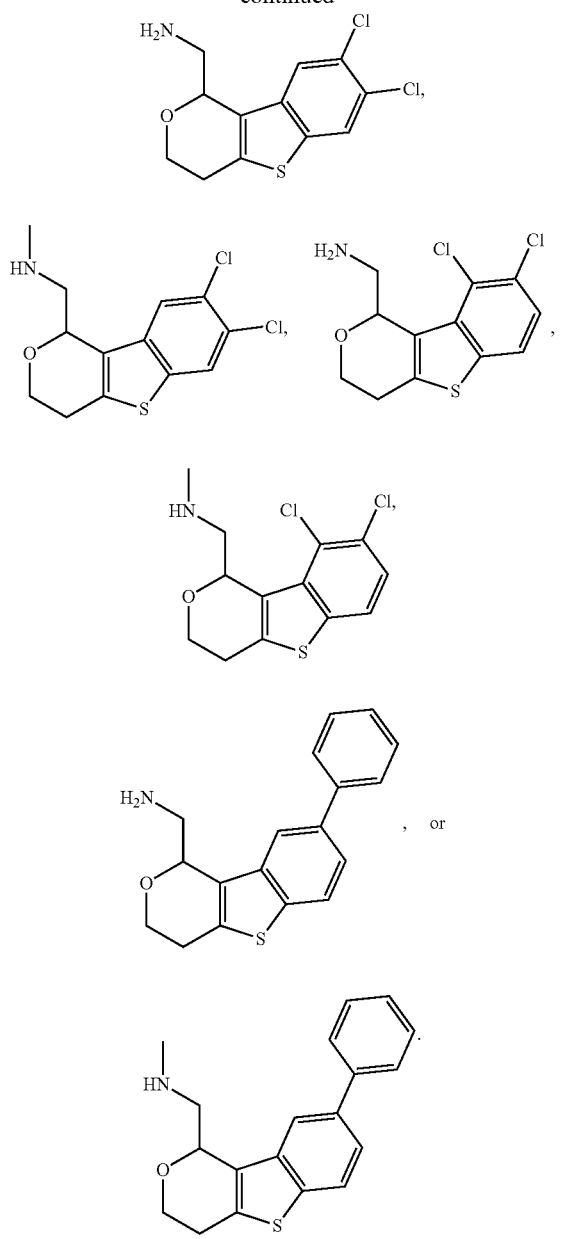

In one embodiment, $R^1$ and $R^5$ together with the atoms to which they are attached form an optionally substituted heterocyclyl. In one embodiment, $R^1$ and $R^5$ together with the atoms to which they are attached form a heterocyclyl. Examples include, but are not limited to, pyrrolidinyl and piperidinyl. Specific examples include, but are not limited to, the following compounds:

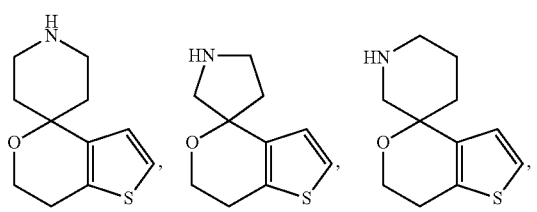

-continued

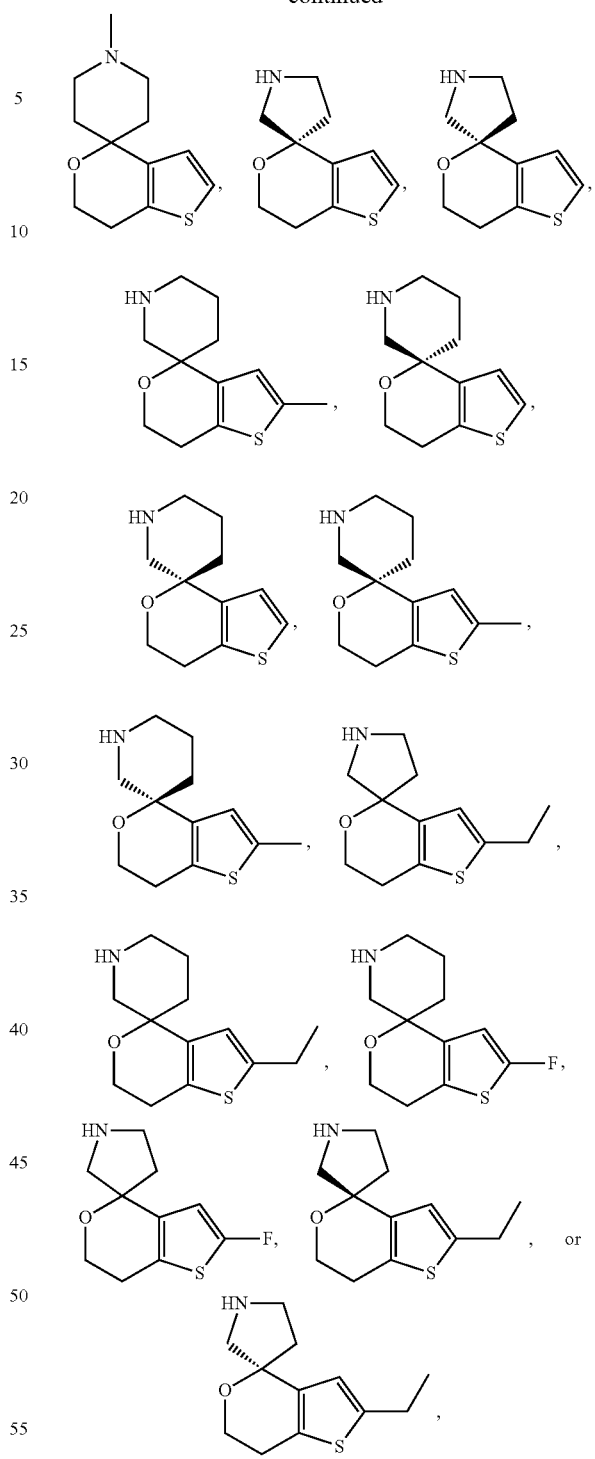

In one embodiment, $R^1$ and $R^5$ together with the atoms to which they are attached form an optionally substituted heterocyclyl (e.g., piperidinyl) and $R^6$ and $R^7$ together with the atoms to which they are attached form an optionally substituted aryl (e.g., phenyl). In one embodiment, $R^1$ and $R^5$ together with the atoms to which they are attached form a heterocyclyl and $R^6$ and $R^7$ together with the atoms to which they are attached form an aryl. Specific examples include, but are not limited to, the following compound:

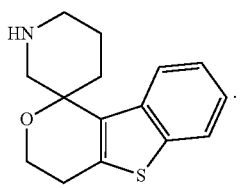 [SMILES: c1ccc2c3c(sc2c1)CCOC31CCCNC1]

In one embodiment, m is 0 and $R^3$ and $R^4$ are combined together to form a double bond and together with $R^1$ and/or $R^2$ and the atoms to which they are attached form an optionally substituted heteroaryl. In one embodiment, the heteroaryl contains one or more heteroatoms selected from N, O, and S. Examples include, but are not limited to, imidazolyl, pyrazolyl, or thiazolyl. Specific examples include, but are not limited to, the following compounds:

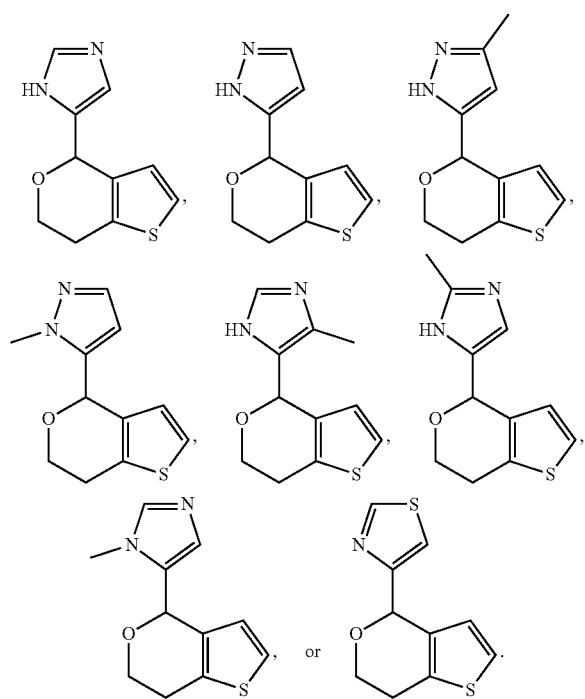

In one embodiment, m is 1. Specific examples include, but are not limited to, the following compound:

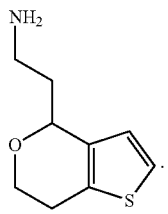 [SMILES: NCCC1OCCc2sccc21 ; "."]

In one embodiment, n is 2. In one embodiment, $R^1$, $R^2$, $R^6$, and $R^7$ are each independently hydrogen or optionally substituted $C_1$-$C_4$ alkyl (e.g., methyl or ethyl). Specific examples include, but are not limited to, the following compounds:

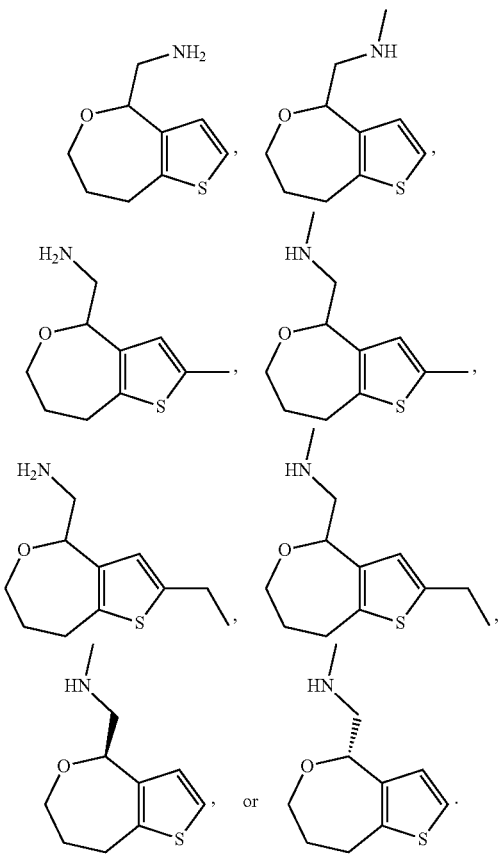

In one embodiment, $R^5$ is alkyl. In one embodiment, $R^5$ is $C_1$-$C_4$ alkyl. In one embodiment, $R^5$ is methyl. Specific examples include, but are not limited to, the following compound:

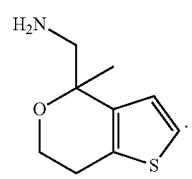

In one embodiment, provided herein is a compound of formula (Ib):

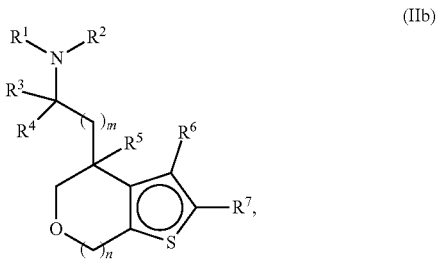

(IIb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, provided herein is a compound of formula (IIc):

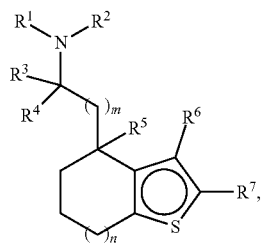

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, $R^5$ is OH. Specific examples include, but are not limited to, the following compound:

In one embodiment, $R^5$ is hydrogen.

In one embodiment, n is 0. In one embodiment, $R^1$ and $R^2$ are each independently hydrogen or optionally substituted $C_1$-$C_4$ alkyl (e.g., methyl or ethyl). In one embodiment, $R^6$ and $R^1$ are each independently hydrogen, halo (e.g., F or Cl), or optionally substituted $C_1$-$C_4$ alkyl (e.g., methyl or ethyl). Specific examples include, but are not limited to, the following compounds:

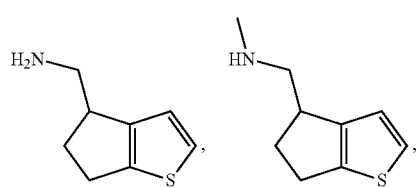

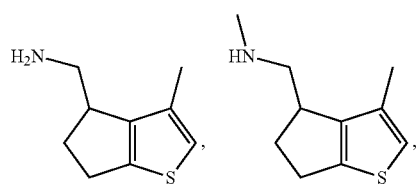

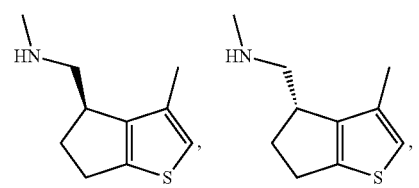

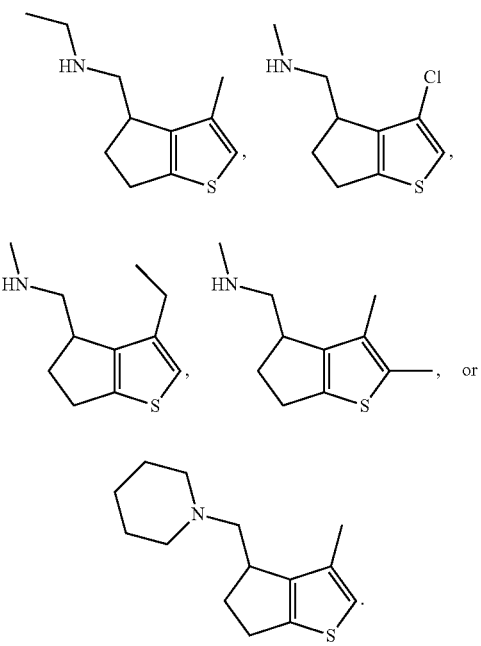

In one embodiment, n is 1. In one embodiment, $R^1$ and $R^2$ are each independently hydrogen or optionally substituted $C_1$-$C_4$ alkyl (e.g., methyl or ethyl). In one embodiment, $R^1$ and $R^2$ together with the atom to which they are attached form an optionally substituted heterocyclyl (e.g., piperidinyl). In one embodiment, $R^6$ and $R^7$ are each independently hydrogen or optionally substituted $C_1$-$C_4$ alkyl (e.g., methyl or ethyl). Specific examples include, but are not limited to, the following compounds:

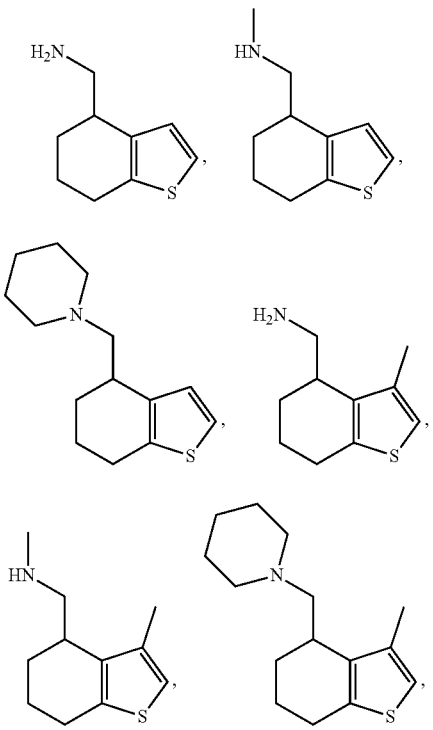

-continued

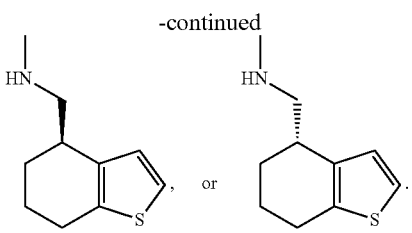

In one embodiment, provided herein is a compound of formula (IIIa):

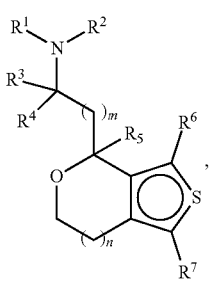
(IIIa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, $R^1$, $R^2$, $R^6$, and $R^7$ are each independently hydrogen or optionally substituted $C_1$-$C_4$ alkyl (e.g., methyl or ethyl). Specific examples include, but are not limited to, the following compounds:

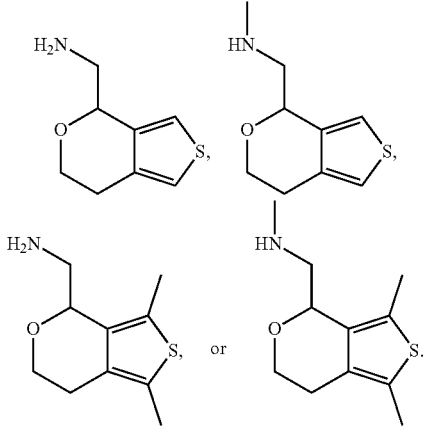

In one embodiment, provided herein is a compound of formula (IIIb):

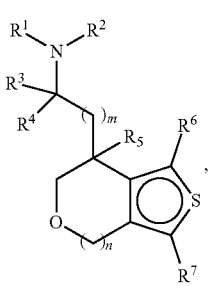
(IIIb)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, provided herein is a compound of formula (IIIc):

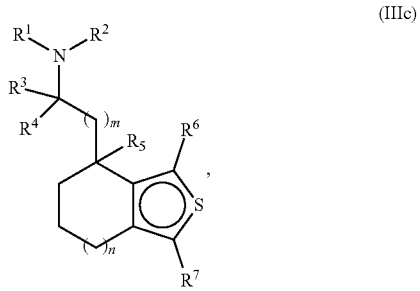
(IIIc)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, provided herein is a compound of formula (IVa):

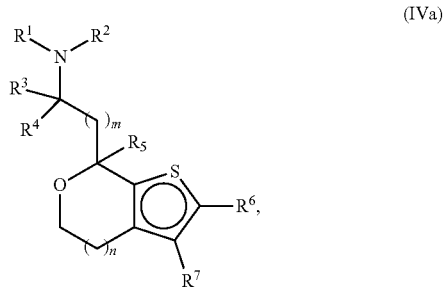
(IVa)

or a pharmaceutically acceptable salt or stereoisomer thereof, wherein $R^1$, $R^2$, $R^3$, $R^4$, $R^5$, $R^6$, $R^7$, m and n are as defined herein elsewhere.

In one embodiment, m is 0 or 1. In one embodiment, n is 1 or 2. In one embodiment, m is 0 and n is 1. In one embodiment, n is 0 or 1. In one embodiment, n is 0.

In one embodiment, $R^5$ is hydrogen.

In one embodiment, $R^1$ and $R^2$ are each independently hydrogen, $C_1$-$C_4$ alkyl (e.g., methyl, ethyl, or propyl (e.g., n-propyl or i-propyl)), or $C_3$-$C_6$ cycloalkyl (e.g., cyclopropyl). In one embodiment, $R^1$ and $R^2$ are each independently hydrogen or $C_1$-$C_4$ alkyl (e.g., methyl, ethyl, or propyl (e.g., n-propyl or i-propyl)). In one embodiment, $R^1$ and $R^2$ are each independently $C_1$-$C_4$ alkyl, wherein one or more hydrogen(s) in the alkyl are replaced with deuterium (e.g., $CD_3$).

In one embodiment, $R^3$ and $R^4$ are hydrogen or $C_1$-$C_4$ alkyl (e.g., methyl, ethyl, or propyl (e.g., n-propyl or i-propyl)). In one embodiment, $R^3$ and $R^4$ are hydrogen.

In one embodiment, $R^6$ and $R^7$ are each independently hydrogen, halo (e.g., F or Cl), $C_1$-$C_4$ alkyl (e.g., methyl, ethyl, propyl, or $CF_3$), aryl (e.g., phenyl), heteroaryl (e.g., pyridyl), heterocyclyl (e.g., pyrrolidinyl, piperidinyl, or morpholinyl), alkoxyl (e.g., OMe), or aminoalkyl (e.g., $NMe_2$), each of which is optionally substituted. In one embodiment, $R^6$ and $R^7$ are each independently hydrogen, halo, $C_1$-$C_4$ alkyl, aryl, heteroaryl, heterocyclyl, alkoxyl, or aminoalkyl. In one embodiment, the $C_1$-$C_4$ alkyl is optionally substituted with one or more fluoro. In one embodiment, $R^6$ and $R^7$ are each independently hydrogen, fluoro, chloro, methyl, $CF_3$, ethyl, propyl, isopropyl, phenyl, pyridyl, pyrrolidinyl, piperidinyl, morpholinyl, methoxyl, or dimethylamino.
Specific examples include, but are not limited to, the following compounds:
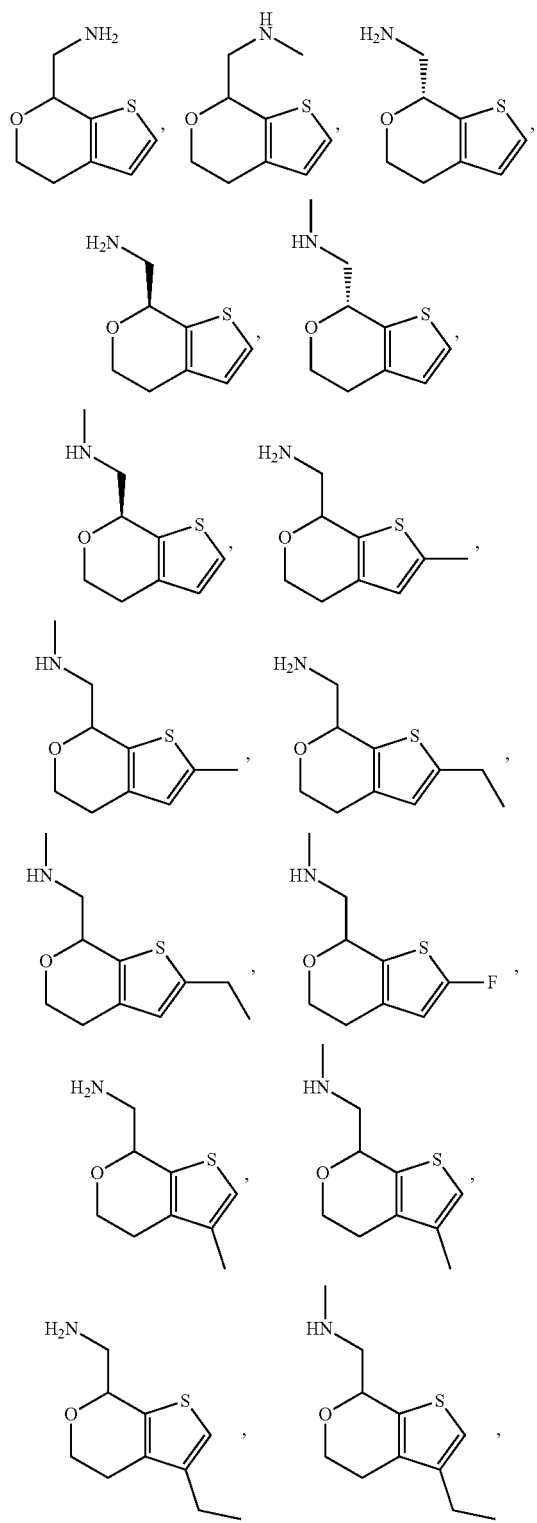
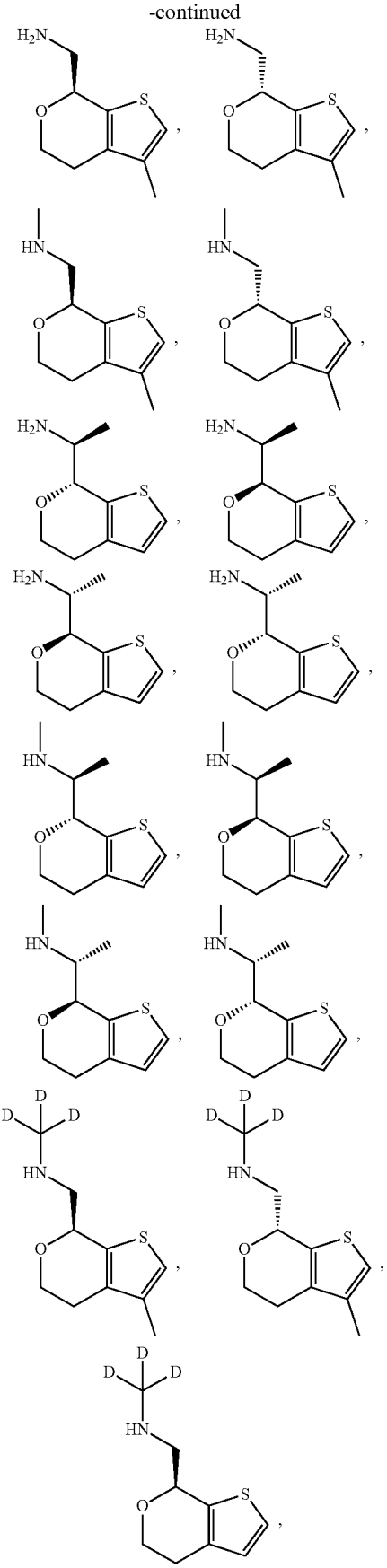

-continued

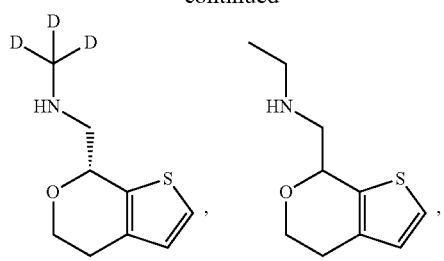
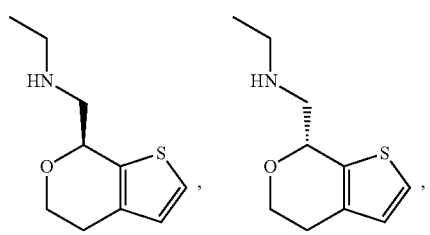
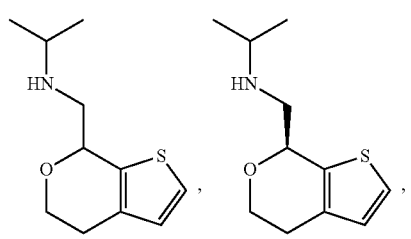
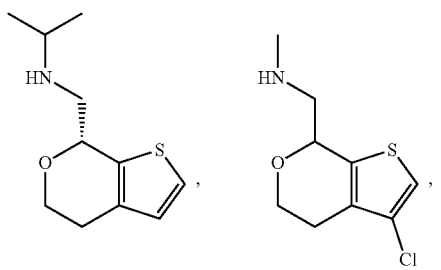
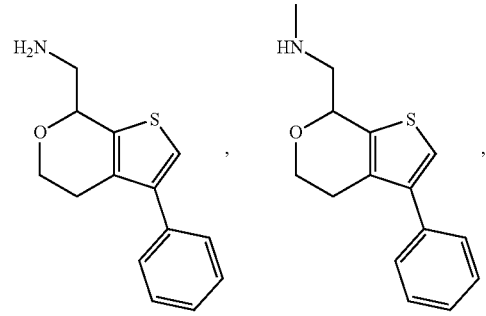
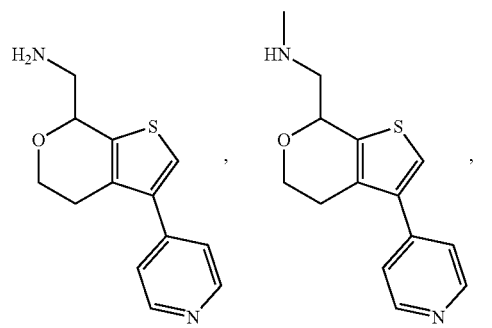

-continued

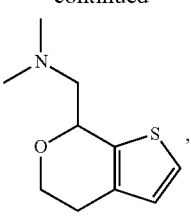

In one embodiment, m is 1. Specific examples include, but are not limited to, the following compounds:

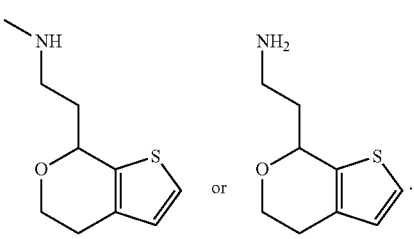

In one embodiment, $R^1$ and $R^2$ together with the nitrogen atom to which they are attached form a heteroaryl or heterocyclyl, each of which is optionally substituted. In one embodiment, $R^1$ and $R^2$ together with the nitrogen atom to which they are attached form an optionally substituted heterocyclyl (e.g., pyrrolidinyl or piperidinyl). Examples include, but are not limited to, azetidinyl, pyrrolidinyl, piperidinyl, azepanyl, morpholinyl, imidazolyl, piperazinyl, and N-methyl-piperazinyl. Specific examples include, but are not limited to, the following compounds:

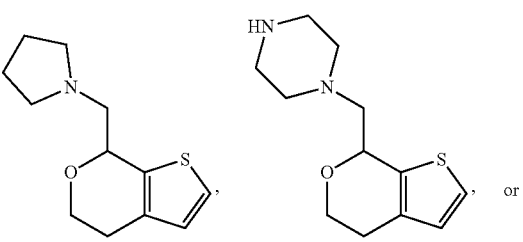

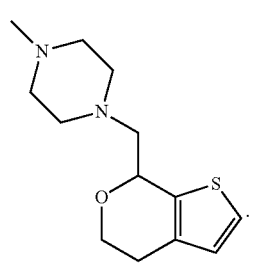

In one embodiment, $R^1$ and $R^3$ together with the atoms to which they are attached form an optionally substituted heterocyclyl ring (e.g., pyrrolidine, including, e.g., unsubstituted pyrrolidine and N-methyl-pyrrolidine). Specific examples include, but are not limited to, the following compounds:

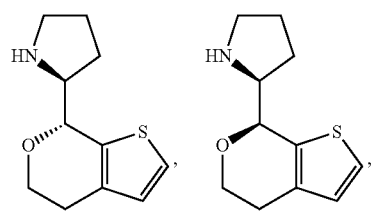

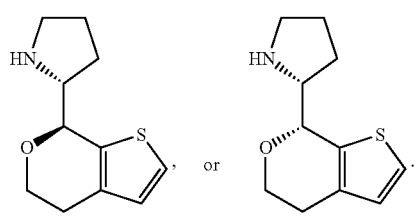

In one embodiment, $R^1$ and $R^5$ together with the atoms to which they are attached form an optionally substituted heterocyclyl. Examples include, but are not limited to, pyrrolidinyl and piperidinyl. Specific examples include, but are not limited to, the following compounds:

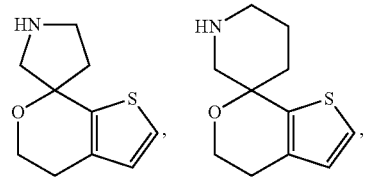

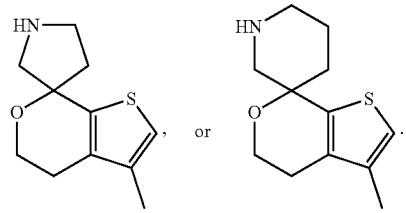

In one embodiment, $R^6$ and $R^7$ together with the atoms to which they are attached form an aryl (e.g., phenyl) or cycloalkyl (e.g., 5-, 6-, or 7-membered) ring, each of which is optionally substituted (e.g., by one or more halo or phenyl). In one embodiment, $R^6$ and $R^7$ together with the atoms to which they are attached form an optionally substituted aryl. Examples include, but are not limited to, phenyl, cyclopentenyl, cyclohexenyl, and cycloheptenyl. Specific examples include, but are not limited to, the following compounds:

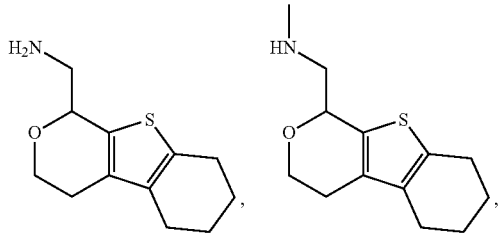

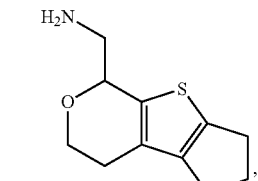 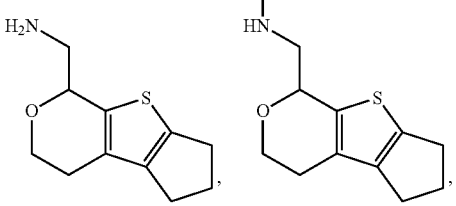

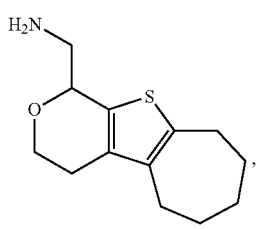 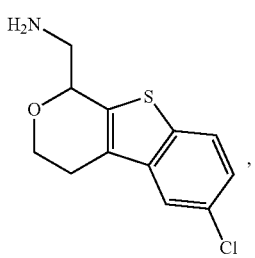

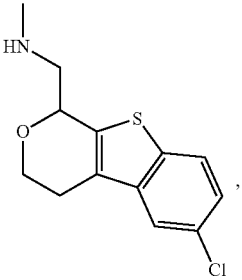 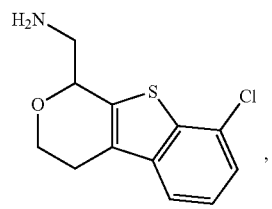

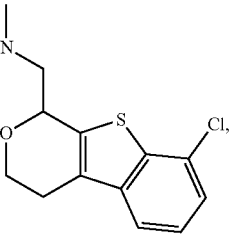 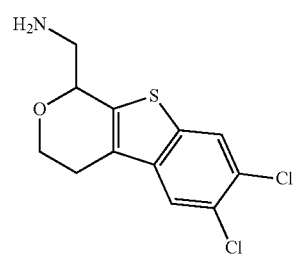

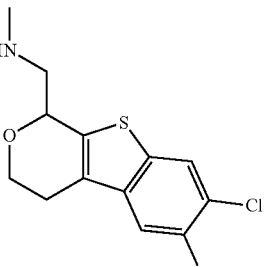 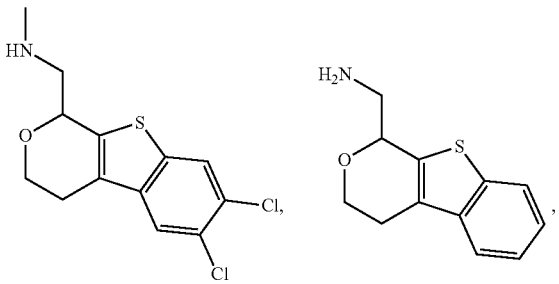

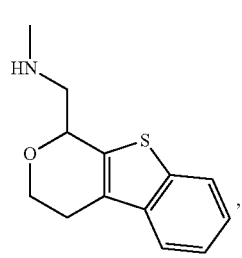 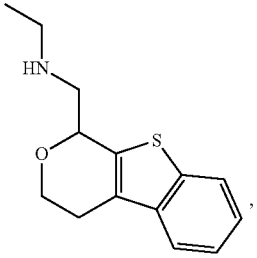

-continued

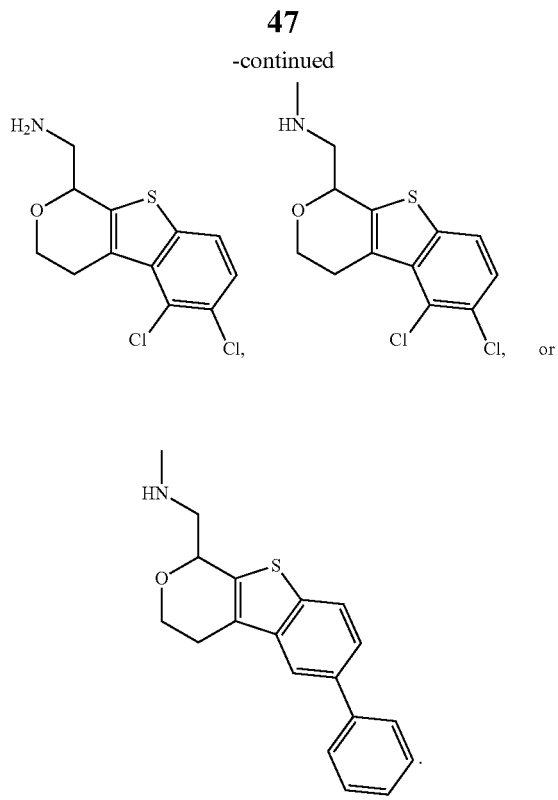

In one embodiment, R$^1$ and R$^5$ together with the atoms to which they are attached form an optionally substituted heterocyclyl (e.g., pyrrolidinyl) and R$^6$ and R$^7$ together with the atoms to which they are attached form an optionally substituted aryl (e.g., phenyl). Specific examples include, but are not limited to, the following compound:

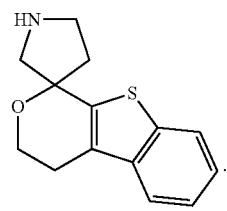 [SMILES: c1ccc2c3c(sc2c1)C1(CCNC1)OCC3]

In one embodiment, m is 0 and R$^3$ and R$^4$ are combined together to form a double bond and together with R$^1$ and/or R$^2$ and the atoms to which they are attached form an optionally substituted heteroaryl. In one embodiment, the heteroaryl contains one or more heteroatoms selected from N, O, and S. Examples include, but are not limited to, imidazolyl, pyrazolyl, or thiazolyl. Specific examples include, but are not limited to, the following compounds:

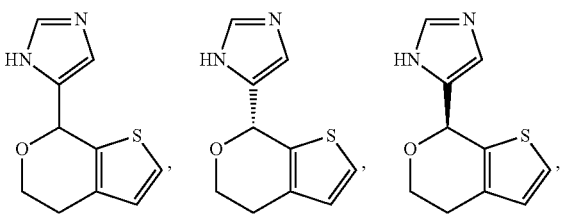

-continued

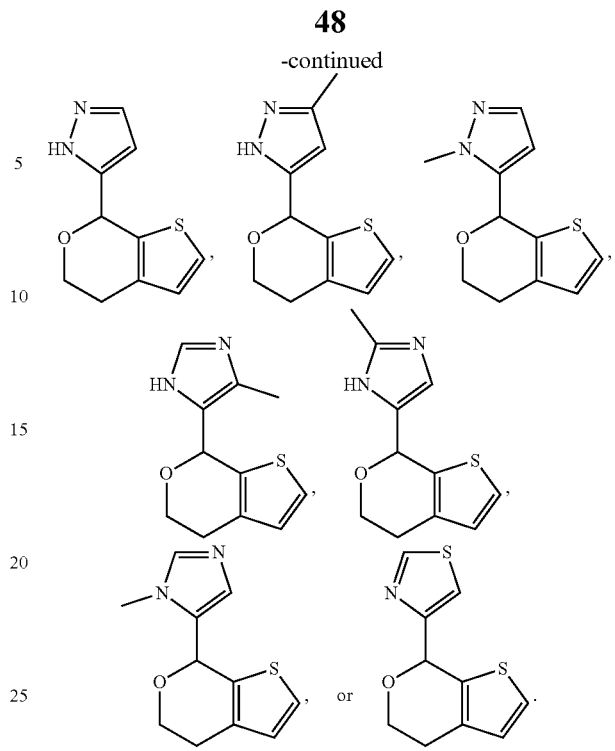

In one embodiment, provided herein is a compound of formula (IVb):

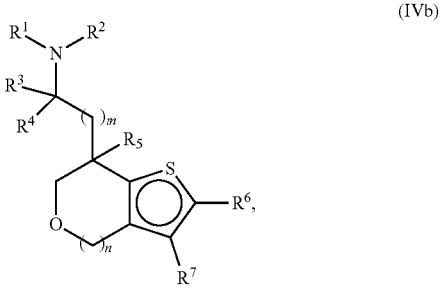

(IVb)

or a pharmaceutically acceptable salt or stereoisomer thereof, wherein R$^1$, R$^2$, R$^3$, R$^4$, R$^5$, R$^6$, R$^7$, m and n are as defined herein elsewhere.

In one embodiment, provided herein is a compound of formula (IVc):

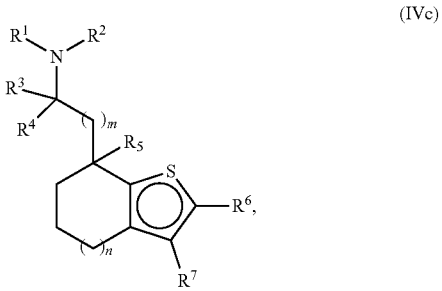

(IVc)

or a pharmaceutically acceptable salt or stereoisomer thereof, wherein R$^1$, R$^2$, R$^3$, R$^4$, R$^5$, R$^6$, R$^7$, m and n are as defined herein elsewhere.

In one embodiment, n is 0. In one embodiment, $R^1$ and $R^2$ are each independently hydrogen or optionally substituted $C_1$-$C_4$ alkyl (e.g., methyl or ethyl). In one embodiment, $R^6$ and $R^7$ are each independently hydrogen, halo (e.g., F or Cl), or optionally substituted $C_1$-$C_4$ alkyl (e.g., methyl or ethyl). Specific examples include, but are not limited to, the following compounds:

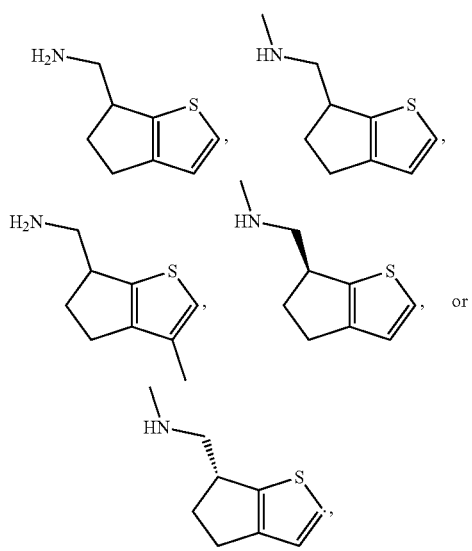

In one embodiment, n is 1. In one embodiment, $R^1$ and $R^2$ are each independently hydrogen or optionally substituted $C_1$-$C_4$ alkyl (e.g., methyl or ethyl). In one embodiment, $R^1$ and $R^2$ together with the atom to which they are attached form an optionally substituted heterocyclyl (e.g., piperidinyl). In one embodiment, $R^6$ and $R^7$ are each independently hydrogen or optionally substituted $C_1$-$C_4$ alkyl (e.g., methyl or ethyl). Specific examples include, but are not limited to, the following compounds:

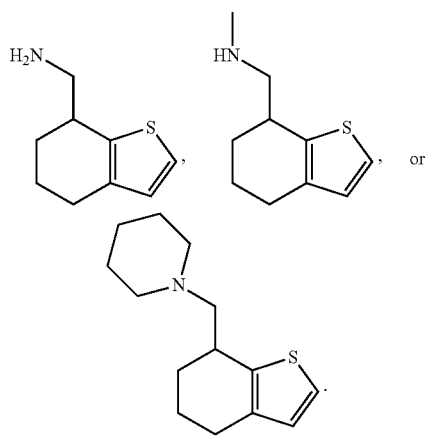

In one embodiment, $R^6$ and $R^7$ together with the atoms to which they are attached form an aryl (e.g., phenyl) or cycloalkyl (e.g., 5-, 6-, or 7-membered) ring, each of which is optionally substituted (e.g., by one or more halo or phenyl). In one embodiment, $R^6$ and $R^7$ together with the atoms to which they are attached form an optionally substituted aryl. Examples include, but are not limited to, phenyl, cyclopentenyl, cyclohexenyl, and cycloheptenyl. Specific examples include, but are not limited to, the following compounds:

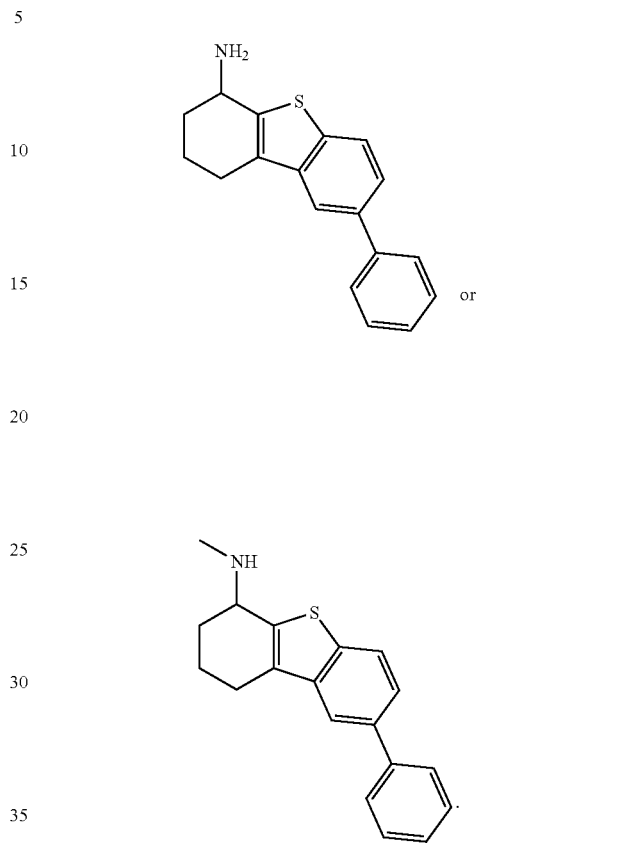

In one embodiment, provided herein is a compound of formula (V):

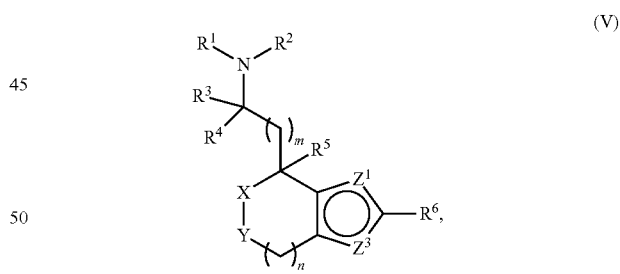

or a pharmaceutically acceptable salt or stereoisomer thereof, wherein $R^1$, $R^2$, $R^3$, $R^4$, $R^5$, $R^6$, $Z^1$, $Z^3$, X, Y, m and n are as defined herein elsewhere. In one embodiment, $Z^1$ is N and $Z^3$ is S. In one embodiment, $Z^1$ is S and $Z^3$ is N. In one embodiment, X and Y is $CH_2$. In one embodiment, m is 0 and n is 1. In one embodiment, $R^1$ and $R^2$ are each independently hydrogen or optionally substituted $C_1$-$C_4$ alkyl (e.g., methyl or ethyl). In one embodiment, $R^3$, $R^4$, and $R^5$ are hydrogen. In one embodiment, $R^6$ is hydrogen, halo (e.g., F or Cl), optionally substituted $C_1$-$C_4$ alkyl (e.g., methyl or ethyl), or optionally substituted amino (e.g., aminoalkyl, such as methylamino). Specific examples include, but are not limited to, the following compounds:

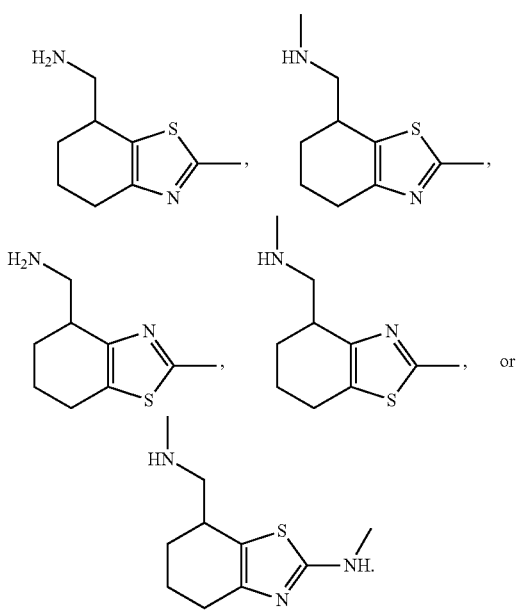

In one embodiment, provided herein is a compound of formula (VI):

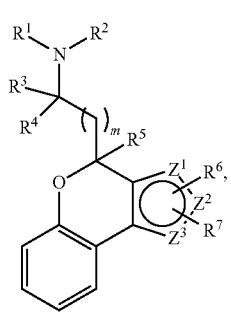
(VI)

or a pharmaceutically acceptable salt or stereoisomer thereof, wherein two of $Z^1$, $Z^2$, and $Z^3$ are C, and one of $Z^1$, $Z^2$, and $Z^3$ is S;

$R^1$ and $R^2$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —(CH$_2$)$_p$—R$^8$, wherein R$^8$ is SO$_2$alkyl or SO$_2$aryl, each of which is optionally substituted; or (iii) $R^1$ and $R^2$ together with the nitrogen atom to which they are attached form an optionally substituted heterocyclyl or heteroaryl;

$R^3$ and $R^4$ are each independently (i) hydrogen, alkyl, alkoxyl, aminoalkyl, alkenyl, alkynyl, cycloalkyl, cycloalkylalkyl, aryl, or aralkyl, each of which is optionally substituted; or (ii) —(CH$_2$)$_p$—R$^9$, wherein R$^9$ is CF$_3$, CN, nitro, amino, hydroxyl, or cycloalkoxyl, each of which is optionally substituted; or (iii) $R^3$ and $R^4$ together with the carbon atom to which they are attached form an optionally substituted cycloalkyl or heterocyclyl; or (iv) $R^3$ and $R^1$ together with the atoms to which they are attached form an optionally substituted heterocyclyl, and $R^4$ is (i) or (ii); or (v) $R^3$ and $R^4$ are combined together to form a double bond and together with $R^1$ and/or $R^2$ and the atoms to which they are attached form an optionally substituted heteroaryl;

$R^5$ is (i) hydrogen, alkyl, alkoxyl, aminoalkyl, alkenyl, alkynyl, cycloalkyl, cycloalkylalkyl, aryl, or aralkyl, each of which is optionally substituted; or (ii) —(CH$_2$)—R$^{10}$, wherein R$^{10}$ is CF$_3$, CN, nitro, amino, hydroxyl, or cycloalkoxyl, each of which is optionally substituted; or (iii) $R^5$ and $R^1$ together with the atoms to which they are attached form an optionally substituted heterocyclyl;

$R^6$ and $R^7$ are each independently (i) hydrogen, halo, alkyl, alkoxyl, aminoalkyl, alkenyl, alkynyl, cycloalkyl, cycloalkylalkyl, aryl, or aralkyl, each of which is optionally substituted; or (ii) —(CH$_2$)$_p$—R$^1$, wherein R$^{11}$ is CF$_3$, CN, nitro, amino, hydroxyl, cycloalkoxyl, heteroaryl, or heterocyclyl, each of which is optionally substituted; or (iii) $R^6$ and $R^7$ together with the atoms to which they are attached form an optionally substituted aryl, heteroaryl, cycloalkyl or heterocyclyl ring; and m is 0, 1, or 2;

each occurrence of p is independently 0, 1, or 2.

In one embodiment, $R^1$, $R^2$, $R^3$, $R^4$, $R^5$, $R^6$, $R^7$, $Z^1$, $Z^2$, $Z^3$, and m are as defined herein elsewhere. In one embodiment, $Z^1$ and $Z^2$ are C, and $Z^3$ is S. In one embodiment, $Z^1$ is S, and $Z^2$ and $Z^3$ are C. In one embodiment, m is 0. In one embodiment, $R^1$ and $R^2$ are each independently hydrogen or optionally substituted C$_1$-C$_4$ alkyl (e.g., methyl or ethyl). In one embodiment, $R^3$ and $R^4$ are hydrogen. In one embodiment, $R^5$ is hydrogen. In one embodiment, $R^1$ and $R^5$ together with the atoms to which they are attached form an optionally substituted heterocyclyl (e.g., pyrrolidinyl). In one embodiment, $R^6$ and $R^7$ are each independently hydrogen, halo (e.g., F or Cl), or optionally substituted C$_1$-C$_4$ alkyl (e.g., methyl or ethyl). Specific examples include, but are not limited to, the following compounds:

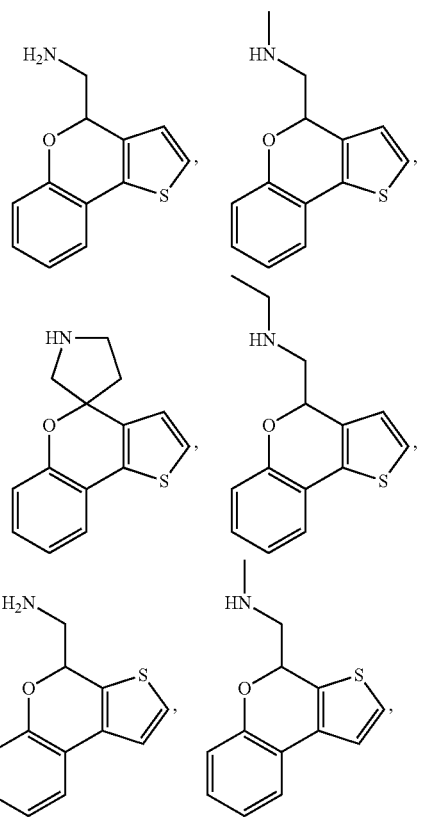

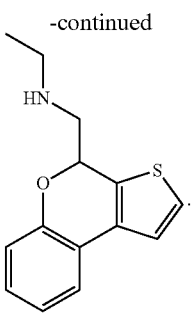

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it or mixtures thereof. Where the compound provided herein contains an alkenyl or alkenylene group, the compound may exist as one of or a mixture of geometric cis/trans (or Z/E) isomers. Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contains, for example, an aromatic moiety. It follows that a single compound may exhibit more than one type of isomerism.

The compounds provided herein may be enantiomerically pure or diastereomerically pure, such as a single enantiomer or a single diastereomer, or be stereoisomeric mixtures, such as a mixture of enantiomers and/or diastereomers, e.g., a racemic or enantioenriched mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers or diastereomers include synthesis from a suitable optically pure precursor, asymmetric synthesis from achiral starting materials, or resolution of a stereomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, aspartic acid, L-aspartic acid, benzenesulfonic acid, benzoic acid, 4-acetamidobenzoic acid, boric acid, camphoric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, gluconic acid, D-gluconic acid, glucuronic acid, D-glucuronic acid, glutamic acid, L-glutamic acid, α-oxoglutaric acid, glycolic acid, hippuric acid, hydrobromic acid, hydrochloric acid, hydroiodic acid, isoethonic acid; (+)-L-lactic acid, (±)-DL-lactic acid, lactobionic acid, lauric acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, pyroglutamic acid, pyroglutamic acid, L-pyroglutamic acid, saccharic acid, salicylic acid, 4-amino-salicylic acid, sebacie acid, stearic acid, succinic acid, sulfuric acid, tannic acid, tartaric acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, potassium carbonate, zinc hydroxide, sodium hydroxide, or ammonia; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Unless otherwise specified, the term "compound" referred to herein, such as, e.g., a compound of formula (I), (IIa), (IIb), (IIc), (IIIa), (IIIb), (IIIc), (IVa), (IVb), (IVc), (V), or (VI) is intended to encompass one or more of the following: a free base of the compound or a salt thereof, a stereoisomer or a mixture of two or more stereoisomers, a solid form (e.g., a crystal form or an amorphous form) or a mixture of two or more solid forms thereof, or a solvate (e.g., a hydrate) thereof. In certain embodiments, the term "compound" referred to herein is intended to encompass a pharmaceutical acceptable form of the compound, including but not limited to, a free base, a pharmaceutically acceptable salt, a stereoisomer or a mixture of two or more stereoisomers, a solid form (e.g., a crystal form or an amorphous form) or a mixture of two or more solid forms, a solvate (e.g., a hydrate), or a cocrystal thereof. In one embodiment, the term "compound" referred to herein, such as, e.g., a compound of formula (I), (IIa), (IIb), (IIc), (IIIa), (IIIb), (IIIc), (IVa), (IVb), (IVc), (V), or (VI) is intended to encompass a solvate (e.g., a hydrate) thereof.

The compound provided herein may also be provided as a prodrug, which is a functional derivative of the compound, for example, of Formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, Drugs 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. Synthetic Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In one embodiment, the compound of formula (I) may be prepared following Schemes 1-3, using suitable starting materials known in the art and/or available from a commercial source. In one embodiment, the hydroxyalkyl thiophene starting material of Schemes 1-3 is known or may be prepared using known methods starting from commercially available compounds. In one embodiment, the amino-aldehyde dimethyl acetal starting material of Schemes 1-3 is known or may be prepared using known methods starting from commercially available compounds. It is understood that other acetals, such as, e.g., diethyl acetals, may also be used as the starting material of the reaction of Schemes 1-3. In one embodiment, the reaction is carried out in an ether solvent, such as, e.g., 1,4-dioxane. In one embodiment, other acids than trifluoromethyl sulfonic acid may be used to facilitate the reaction. In some embodiments, $R^1$, $R^2$, $R^3$, $R^4$, $R^5$, $R^6$, or $R^7$ may be further transformed to suitable functional groups, as described for formula (I), after the ring formation step of Schemes 1-3, using methods known in the art. Specific and non-limiting examples of such transformations are described in the General Procedures in the Examples.

Scheme 1

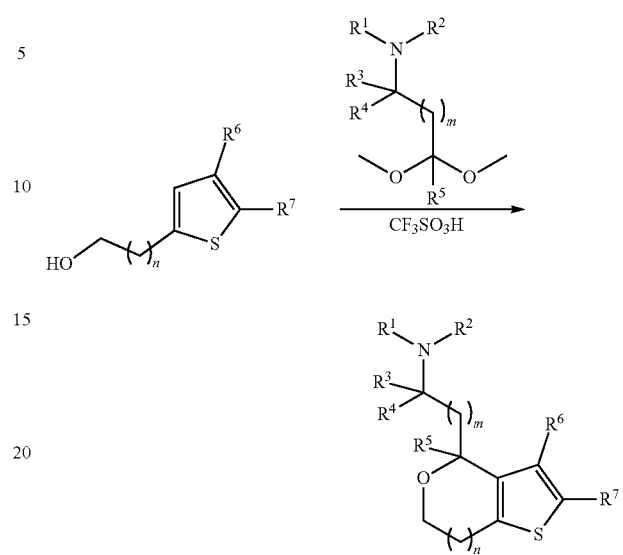

Scheme 2

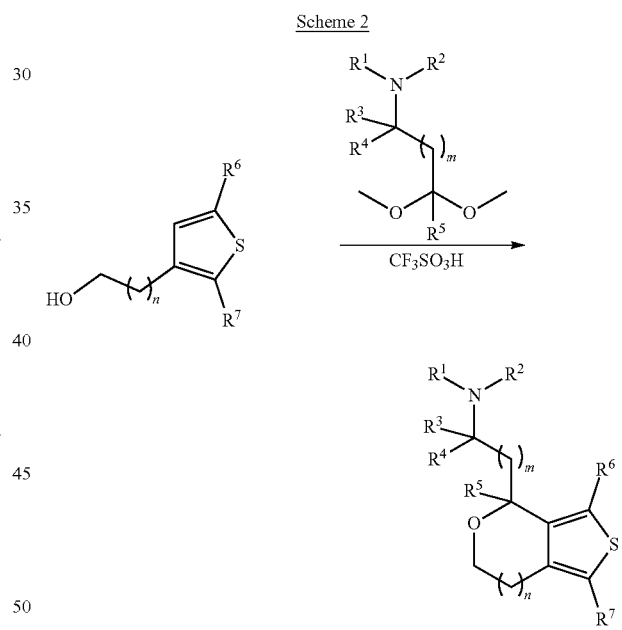

Scheme 3

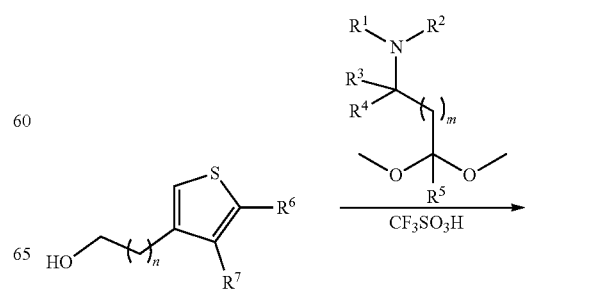

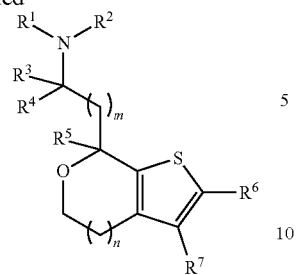

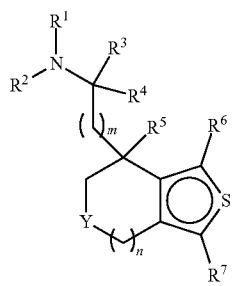

In one embodiment, the compound of formula (I) may be prepared following Schemes 4-6, using suitable nucleophilic starting materials known in the art and/or available from a commercial source. In one embodiment, $R_{12}$ may be cyano, or a suitable alkyl, alkenyl, alkynyl, heteroalkyl, aryl, heteroaryl, cycloalkyl, or heterocyclyl, among others. In one embodiment, the thiophene ketone starting material of Schemes 4-6 is known or may be prepared using known methods starting from commercially available compounds. The hydroxyl compound of Schemes 4-6 may be transformed to a compound of formula (I) using methods known in the art. In some embodiments, $R^1$, $R^2$, $R^3$, $R^4$, $R^5$, $R^6$, or $R^7$ may be further transformed to suitable functional groups, as described for formula (I) using methods known in the art. Specific and non-limiting examples of such transformations are described in the General Procedures in the Examples.

Scheme 4

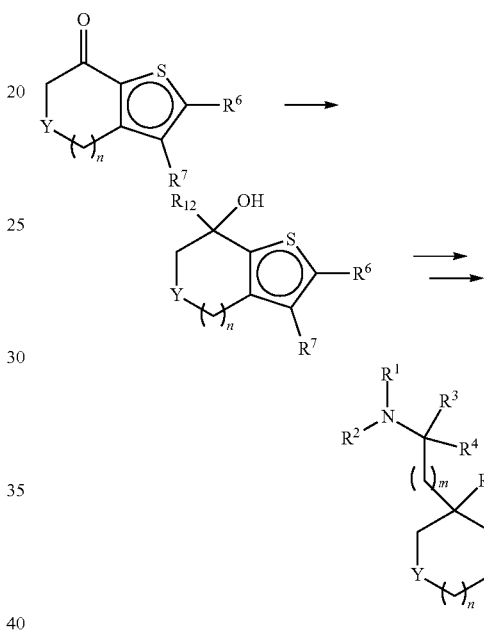

Scheme 6

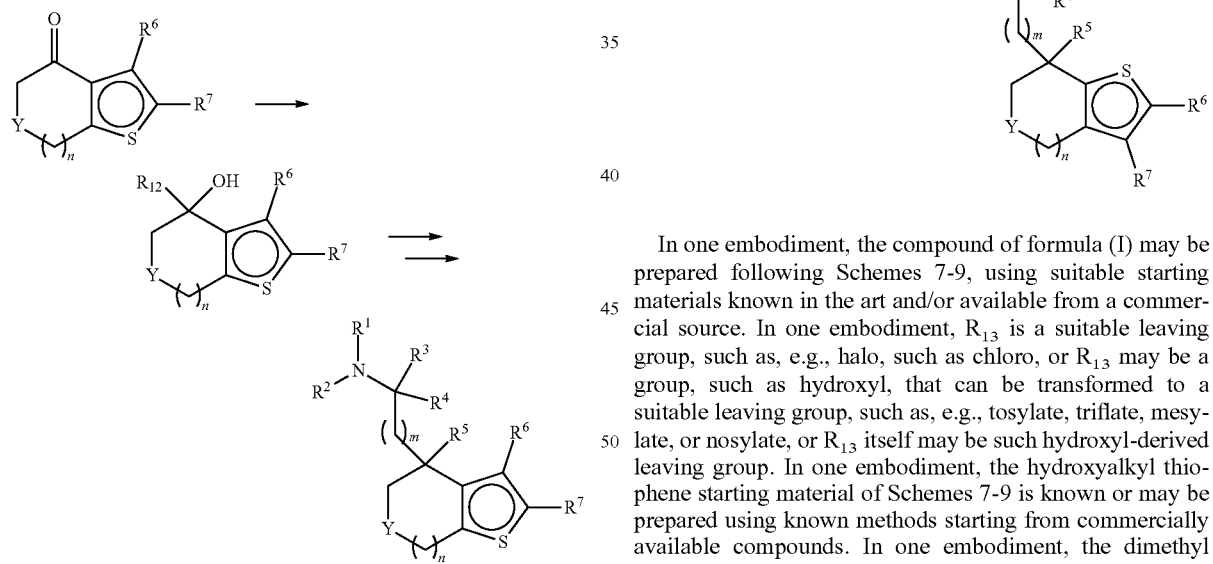

Scheme 5

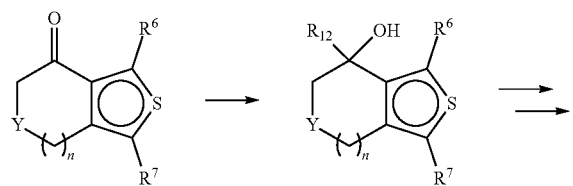

In one embodiment, the compound of formula (I) may be prepared following Schemes 7-9, using suitable starting materials known in the art and/or available from a commercial source. In one embodiment, $R_{13}$ is a suitable leaving group, such as, e.g., halo, such as chloro, or $R_{13}$ may be a group, such as hydroxyl, that can be transformed to a suitable leaving group, such as, e.g., tosylate, triflate, mesylate, or nosylate, or $R_{13}$ itself may be such hydroxyl-derived leaving group. In one embodiment, the hydroxyalkyl thiophene starting material of Schemes 7-9 is known or may be prepared using known methods starting from commercially available compounds. In one embodiment, the dimethyl acetal starting material of Schemes 7-9 is known or may be prepared using known methods starting from commercially available compounds. It is understood that other acetals, such as, e.g., diethyl acetals, may also be used as the starting material of the reaction of Schemes 7-9. In one embodiment, the reaction is carried out in an ether solvent, such as, e.g., 1,4-dioxane. In one embodiment, other acids than trifluoromethyl sulfonic acid may be used to facilitate the reaction. In some embodiments, $R^1$, $R^2$, $R^3$, $R^4$, $R^5$, $R^6$, or $R^7$ may be further transformed to suitable functional groups, as described for formula (I) using methods known in the art. Specific and non-limiting examples of such transformations are described in the General Procedures in the Examples.

Scheme 7

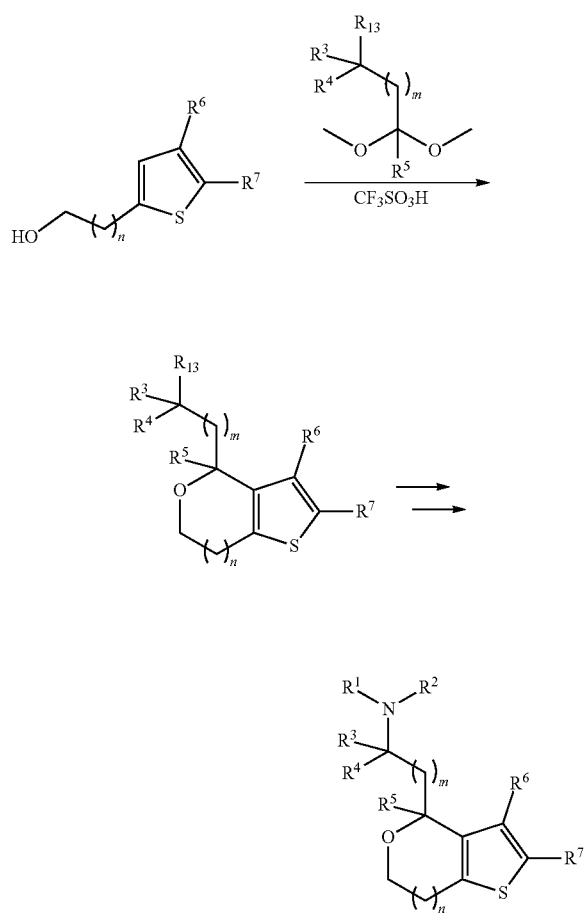

Scheme 8

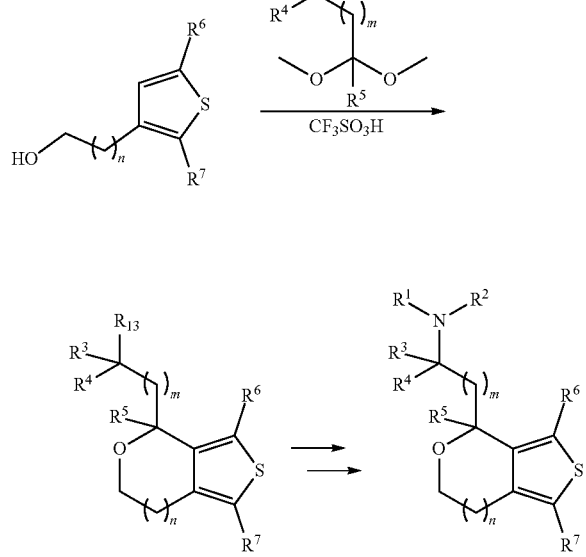

Scheme 9

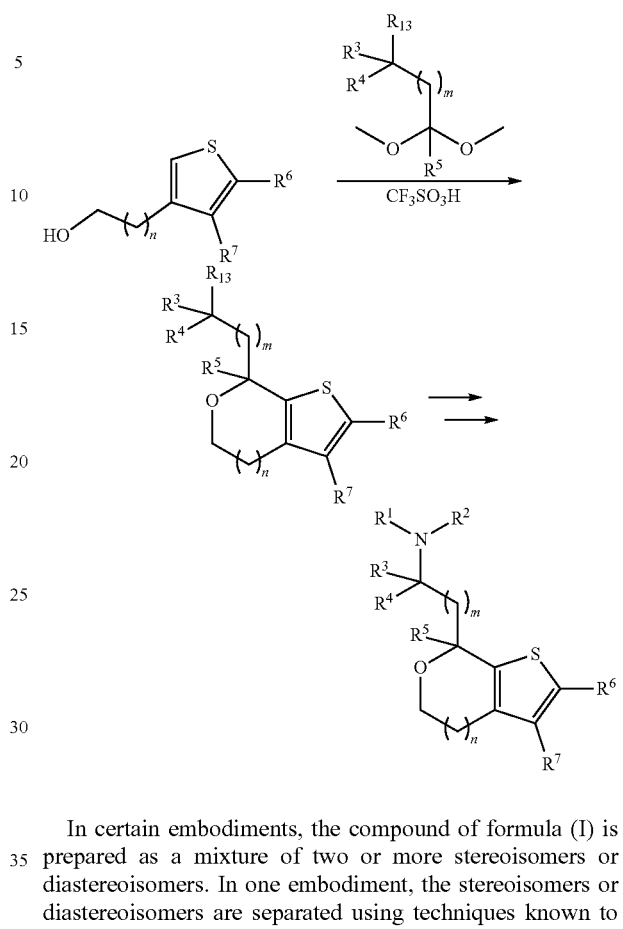

In certain embodiments, the compound of formula (I) is prepared as a mixture of two or more stereoisomers or diastereoisomers. In one embodiment, the stereoisomers or diastereoisomers are separated using techniques known to those skilled in the art, including but not limited to, chiral column chromatography and chiral resolution by forming a salt with a suitable chiral counterion. In certain embodiments, the compound of formula (I) is prepared following one or more stereoselective reaction(s). In some embodiment, the compound of formula (I) is prepared as a substantially pure stereoisomer.

D. Methods of Treatment, Prevention, and/or Management

1. In Vivo Assays

In one embodiment, provided herein is a method of administering a compound provided herein, or a pharmaceutically acceptable salt or stereoisomer thereof, in a disease model that is known in the art. In one embodiment, the disease model is an animal model. In one embodiment, provided herein is a method of administering a compound provided herein, or a pharmaceutically acceptable salt or stereoisomer thereof, in an animal model that is predictive of efficacy in the treatment of certain diseases in human. The method comprises administering a compound provided herein, or a pharmaceutically acceptable salt or stereoisomer thereof, in a subject. In one embodiment, the method comprises administering a therapeutically effective amount of a compound provided herein, or a pharmaceutically acceptable salt or stereoisomer thereof, in a subject. In one embodiment, the method comprises treatment of a test subject (e.g., a mouse or rat) with a compound provided herein, or a pharmaceutically acceptable salt or stereoisomer thereof. In one embodiment, the method comprises treatment of a test subject (e.g., a mouse or rat) with a compound provided herein, or a pharmaceutically acceptable salt or stereoisomer thereof, as well as a reference compound, either in separate animal groups (e.g., administer a reference compound in a control group and administer a compound provided herein in a test group) or in the same animal group (e.g., as combination therapy). In one embodiment, the in vivo activity of the compound provided herein is dose dependent.

In one embodiment, the compounds provided herein are active in animal models of psychosis such as Pre-Pulse Inhibition (PPI) and PCP-induced hyperlocomotion. These two models have been used in the development of several antipsychotics, including olanzapine (ZYPREXA) (Bakshi and Geyer, *Psychopharmacology* 1995, 122, 198-201) and quetapine (SEROQUEL) (Swedlow et al., *J. Pharm. Exp. Ther.*, 1996, 279, 1290-99), and are predictive of efficacy in human psychotic patients. In one embodiment, compounds that are active in in vivo models of psychosis are further optimized to improve the potency in the in vivo assays and drug-like properties such as, e.g., solubility and lipophilicity. Given the exact molecular basis of certain diseases such as schizophrenia are poorly understood, this approach allows the use of predictive and well-validated animal models to develop compounds with established efficacy without focusing on specific molecular targets that may or may not translate to human efficacy in the clinic.

2. Treatment, Prevention, and/or Management

In one embodiment, provided herein is a method of treating, preventing, and/or managing various disorders, including, but not limited to, neurological disorders. In one embodiment, provided herein is a method of treating, preventing, and/or managing one or more symptoms of a neurological disorder. In one embodiment, the method comprises administering to a subject (e.g., human) a therapeutically or prophylactically effective amount of a composition or a compound provided herein or a pharmaceutically acceptable salt or stereoisomer thereof. In one embodiment, the subject is a human. In one embodiment, the subject is an animal. In one embodiment, the compounds provided herein are highly brain penetrable in the subject. In certain embodiments, the efficacious concentration of a compound provided herein is less than 10 nM, less than 100 nM, less than 1 µM, less than 10 µM, less than 100 µM, or less than 1 mM. In one embodiment, a compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of antipsychotic activity in humans. The phenotypic approach to develop antipsychotics has been used in psychopharmacology, with the antipsychotic chlorpromazine developed in this way. The phenotypic approach may also offer advantages over compounds developed by traditional in vitro based drug discovery approach, because the compounds developed using the phenotypic approach have established pharmaceutical properties and in vivo activity, rather than activity toward a given molecular target, which may be less predictive and lead to attrition at later stages of, for example, clinical development.

In one embodiment, provided herein is a method of treating, preventing, and/or managing a neurological disorder, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., biopolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, Huntington's chorea, and premenstrual dysphoria, comprising administering to a subject an effective amount of a compound provided herein, or a pharmaceutically acceptable salt or stereoisomer thereof.

In one embodiment, provided herein is a method of treating, preventing, and/or managing a disorder related to psychosis, schizophrenia, ADHD, mood disorder or affective disorder such as depression and anxiety, comprising administering to a subject an effective amount of a compound provided herein. For example, without being limited by a particular theory, the compounds provided herein may improve the gating deficits of DBA/2 mice seen in the pre-pulse inhibition (PPI) test and reverse the methamphetamine-induced hyperlocomotor activity. Without being limited to a particular theory, the compounds provided herein may: 1) reverse the amphetamine-induced hyper-locomotor activity; 2) be useful as antipsychotic agents and dosed sparing; 3) improve attention and modulate impulsively; 4) improve learning parameters in ADHD; 5) enhance learning ability and reduce anxiety in behavioral tests; and/or 6) have an anti-depressant effect.

In another embodiment, provided herein is a method of treating, preventing, and/or managing a disorder related to cognitive impairments, such as Alzheimer's disease, Parkinson's disease, schizophrenia, and attention deficit hyperactivity disorder (ADHD), and the like, comprising administering to a subject an effective amount of a compound provided herein. For example, without being limited by a particular theory, the compounds provided herein may have pro-cognitive effects, such as passive avoidance, novel object recognition, social recognition, and attention-set shifting. Further, without being limited by a particular theory, the compounds provided herein may improve social memory, increase the acquisition of an environment, and reverse scopolamine-induced deficits. The compounds provided herein may also reverse scopolamine-induced deficits in a passive avoidance memory test.

In another embodiment, provided herein is a method of treating, preventing, and/or managing a disorder associated with excessive daytime sleepiness, such as, narcolepsy, Parkinson's disease, multiple sclerosis, shift workers, jet lag, relief of side effects of other medications, and the like, comprising administering to a subject an effective amount of a compound provided herein. For example, without being limited by a particular theory, the compounds provided herein may have wake promoting effects.

In another embodiment, provided herein is a method of treating, preventing, and/or managing a sleeping disorder, such as insomnia, comprising administering to a subject an effective amount of a compound provided herein. For example, without being limited by a particular theory, the compounds provided herein may improve wakefulness and lead to an improved sleep pattern, and therefore the compounds provided herein may be useful in treating insomnia.

In another embodiment, provided herein is a method of treating, preventing, and/or managing substance abuse, comprising administering to a subject an effective amount of a compound provided herein. For example, without being limited by a particular theory, the compounds provided herein may alter methamphetamine self-administration in rats, and therefore the compounds provided herein may ameliorate the craving for addictive drugs.

In another embodiment, provided herein is a method of using the compounds provided herein as psycho-stimulants, which may lack the abuse liabilities generally associated with other classes of psycho-stimulants. Without being limited by a particular theory, the compounds provided herein may increase the levels of histamine, dopamine, norepinephrine, and/or acetylcholine in the prefrontal cortical area, which is consistent with their pro-cognitive effects and their wake promoting effects seen in animal models. For example, the compounds provided herein may increase dopamine in the frontal cortex but not the striatum. The compounds provided herein may not induce increased locomotor activity or sensitization that is associated with other psycho-stimulus.

In another embodiment, provided herein is a method of treating, preventing, and/or managing a disorder such as seizure, epilepsy, vertigo, and pain, comprising administering to a subject an effective amount of a compound provided herein. For example, without being limited by a particular theory, the compounds provided herein may be protective against pentylene-tetrazole (PTZ) and electrical-induced seizures. The compounds provided herein may increase the seizure threshold in humans. The compounds provided herein may decrease electrical discharge from afferent neurons in an inner ear preparation. Further, without being limited by a particular theory, the compounds provided herein may increase the threshold for neuropathic pain, which is shown in models such as the chronic constriction injure (CCI) model, herpes virus-induced model, and capsaicin-induced allodynia model. Therefore, in some embodiments, the compounds provided herein are employed for their analgesic effects to treat, prevent, and/or manage disorders involving pain and the sensitization that accompanies many neuropathic pain disorders.

In another embodiment, provided herein is a method of treating, preventing, and/or managing a movement disorder, such as Parkinson's disease, restless leg syndrome (RLS), and Huntington's disease, comprising administering to a subject an effective amount of a compound provided herein.

In some embodiments, a compound provided herein is active in at least one model, which can be used to measure the activity of the compound and estimate the efficacy in treating a neurological disorder. For example, when the model is for psychosis (e.g., PCP Hyperactivity Model or Prepulse Inhibition of Startle Model), a compound is active when the compound reduces PCP induced hyperactivity in mice by a statistically signicant amount compared to a vehicle, or when the compound reverses the disruption of prepulse inhibition (PPI) induced by PCP in mice.

In other embodiments, provided herein is a method of effecting a therapeutic effect as described herein elsewhere. The method comprises administering to a subject (e.g., a mammal) a therapeutically effective amount of a compound or composition provided herein. The particular therapeutic effects may be measured using any model system known in the art and described herein, such as those involving an animal model of a disease.

In some embodiments, the neurological disorder is: depression (e.g., major depressive disorder or dysthymia); bipolar disorder, seasonal affective disorder; cognitive deficit; fibromyalgia; pain (e.g., neuropathic pain); sleep related disorder (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; post-traumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, epilepsy, disturbances of consciousness, coma, lowering of attention, speech disorder, Lennox syndrome, autism, and hyperkinetic syndrome.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In one embodiment, the neurological disorder is excessive daytime sleepiness. In another embodiment, the neurological disorder is a cognitive impairment. In another embodiment, the neurological disorder is a mood disorder. In another embodiment, the neurological disorder is an affective disorder. In another embodiment, the neurological disorder is a movement disorder. In another embodiment, the neurological disorder is schizophrenia. In another embodiment, the neurological disorder is an attention disorder. In another embodiment, the neurological disorder is an anxiety disorder. In another embodiment, the neurological disorder is seizure. In another embodiment, the neurological disorder is psychosis. In another embodiment, the neurological disorder is epilepsy. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the compounds described herein treat, prevent, and/or manage a neurological disorder of the central nervous system, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In some embodiments, the compounds disclosed herein may be used in combination with one or more second active agents to treat, prevent, and/or manage disorders described herein.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and/or magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles &Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise a second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy,* 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific example of a binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's The Science and Practice of Pharmacy,* 21st Ed., Lippincott Williams & Wilkins (2005); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's The Science and Practice of Pharmacy,* 21st Ed., Lippincott Williams & Wilkins (2005).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

VI. EXAMPLES

Certain embodiments are illustrated by the following non-limiting examples.

A. General Procedures for Compound Synthesis

In the examples below, unless otherwise indicated, all temperatures are set forth in degrees Celsius and all parts and percentages are by weight. Reagents may be purchased from commercial suppliers, such as Sigma-Aldrich® Chemical Company, and may be used without further purification unless otherwise indicated. Reagents may also be prepared following standard literature procedures known to those skilled in the art. Solvents may be purchased from Sigma-Aldrich® in Sure-Seal® bottles and used as received. All solvents may be purified using standard methods known to those skilled in the art, unless otherwise indicated.

The reactions set forth below were done generally at ambient temperature, unless otherwise indicated. Unless otherwise specified, generally the reaction flasks were fitted with rubber septa for introduction of substrates and reagents via syringe. Analytical thin layer chromatography (TLC) was performed using glass-backed silica gel pre-coated plates and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (see, e.g., Still et al., J. Org. Chem., 43: 2923 (1978)) was performed using, for example, silica gel 60 or various MPLC systems (such as Biotage® or ISCO® separation systems).

The compound structures in the examples below were confirmed by one or more of the following methods: proton nuclear magnetic resonance spectroscopy, mass spectroscopy, elemental microanalysis, and melting point. Proton nuclear magnetic resonance ($^1$H NMR) spectra were determined using a NMR spectrometer operating at a certain field strength. Chemical shifts are reported in parts per million (ppm, δ) downfield from an internal standard, such as TMS. Alternatively, $^1$H NMR spectra were referenced to signals from residual protons in deuterated solvents, for example, as follows: $CDCl_3$=7.25 ppm; DMSO-$d_6$=2.49 ppm; $C_6D_6$=7.16 ppm; $CD_3OD$=3.30 ppm. Peak multiplicities are designated, for example, as follows: s, singlet; d, doublet; dd, doublet of doublets; t, triplet; dt, doublet of triplets; q, quartet; br, broadened; and n, multiplet. Coupling constants are given in Hertz (Hz). Mass spectra (MS) data were obtained using a mass spectrometer with APCI or ESI ionization.

1. General Procedure A

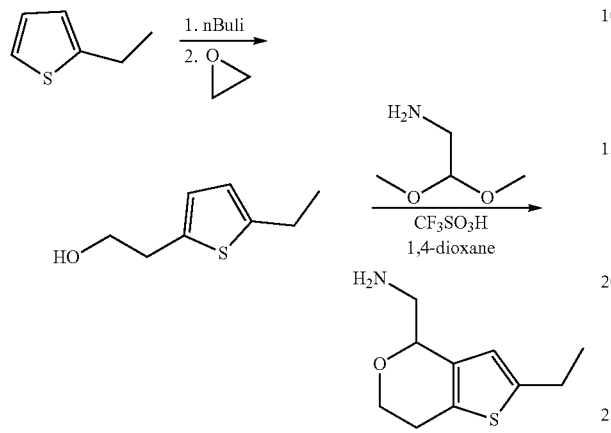

(a) Synthesis of 2-(5-ethylthiophen-2-yl)ethanol

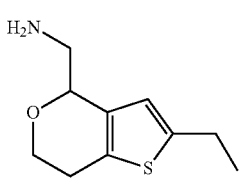

To a solution of 2-ethylthiophene (2 g, 17.85 mmol, 1 eq) in anhydrous diethyl ether at 0° C. was added n-BuLi (8.6 mL, 21.4 mmol, 2.5 M in hexanes, 1.2 eq) over 15 minutes. The mixture was stirred at room temperature for 30 minutes. After cooling to 0° C., a solution of ethylene oxide (1.1 mL, 21.4 mmol, 1.2 eq) in anhydrous ether was added. After stirring at 0° C. for 3 hr, the reaction mixture was quenched with water and extracted with diethyl ether. The organic layer was dried over Na$_2$SO$_4$ and concentrated to give a crude product. The crude product was purified by column chromatography.

(b) Synthesis of (2-ethyl-6,7-dihydro-4H-thieno[3,2-c]pyran-4-yl)methanamine

To a solution of 2-(5-ethylthiophen-2-yl)ethanol (1 g, 6.4 mmol, 1.1 eq) and aminoacetaldehyde dimethylacetal (612 mg, 5.83 mmol, 1 eq) was added CF$_3$SO$_3$H (2.7 g, 17.5 mmol, 3 eq) dropwise at 0° C. After stirring at room temperature overnight, the reaction mixture was diluted with water, adjusted pH to ~8 with Na$_2$CO$_3$, and extracted with EtOAc. The organic layer was dried over Na$_2$SO$_4$, and concentrated. The crude product was purified by column chromatography.

(c) Synthesis of the HCl salt of (2-ethyl-6,7-dihydro-4H-thieno[3,2-c]pyran-4-yl)methanamine

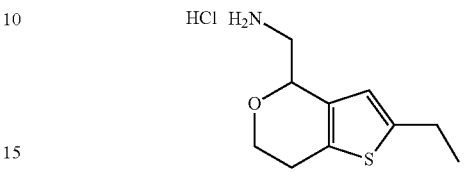

A solution of (2-ethyl-6,7-dihydro-4H-thieno[3,2-c]pyran-4-yl)methanamine in MTBE was treated with gaseous HCl at 0° C. for 10 minutes. The precipitated product was collected by vacuum filtration and dried to give the desired product.

2. General Procedure B

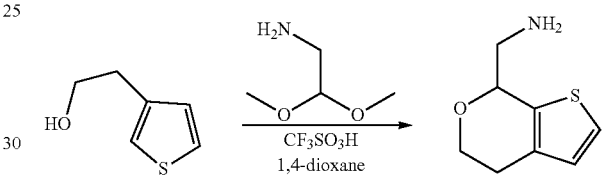

2-(Thiophen-3-yl)ethanol (7.5 mmol), amino acetal (11.25 mmol) and triflic acid (1.70 mL, 15 mmol) were combined in 7.5 mL 1,4-dioxane (anhydrous). The blackish solution was stirred at room temperature for 2 hr, and then poured slowly into saturated aqueous K$_2$CO$_3$ solution. The solution was washed with EtOAc (3×50 mL) and the combined EtOAc washes were washed with brine, dried (Na$_2$SO$_4$), filtered and concentrated. The crude product was dissolved in MeOH and 4M HCl in dioxane (10 mL) was added. The solution was concentrated to 4 mL and MTBE was added (30 mL). The solution was sonicated and the tan precipitate was filtered, washed with MTBE and dried in vacuo.

3. General Procedure C

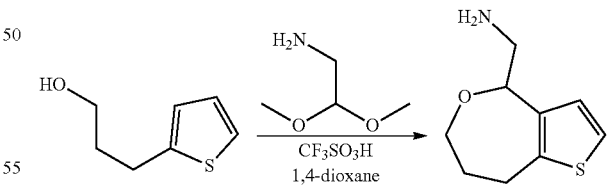

To 3-(thiophen-2-yl)propan-1-ol (1 g, 7.0 mmol) and amino acetal (0.84 g, 7.0 mmol) in 1,4-dioxane in a microwave vial was added CF$_3$SO$_3$H (0.8 mL, 7.0 mmol). The reaction vessel was sealed and heated in a microwave reactor at 110° C. for 15 min at which time the mixture was cooled, made basic with 10% KOH (aq.) and the aqueous layer was extracted with EtOAc (3×50 mL). The combined organic layers were washed with brine, dried over Na$_2$SO$_4$, filtered and the solvent removed in vacuo to afford the crude product mixed with uncyclized side-product. The combined brown liquid was Boc-protected following standard protocols and purified by flash column chromatography (0-50% EtOAc in hexanes) to afford a mixture of uncyclized and cyclized product. The desired 7-membered ring compound was isolated by RP-HPLC (0.1% aqueous $NH_4HCO_3$ in acetonitrile).

4. General Procedure D

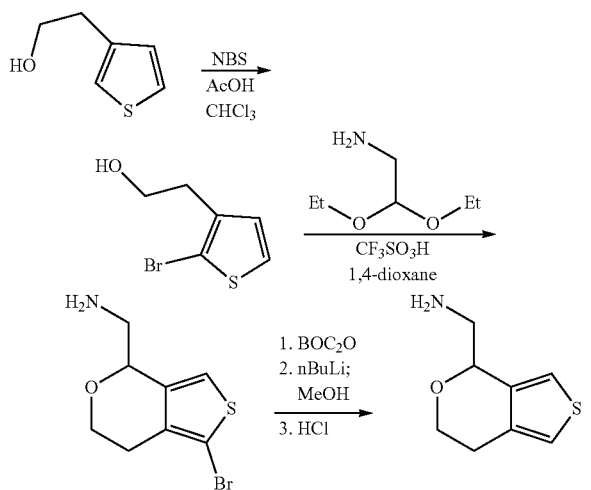

(a) Synthesis of 2-(2-bromothiophen-3-yl)ethanol

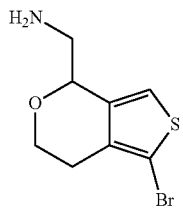

NBS (0.58 g, 3.3 mmol) was added to 2-(thiophen-3-yl)ethanol (0.4 g, 3.1 mmol) in $CHCl_3$:AcOH (1:1 v/v; 9 mL) at 0° C. and the resulting mixture was stirred at 0° C. for 1 hr at which time the reaction mixture was diluted with $NaHCO_3$ (sat. aq.) and extracted with EtOAc (3×50 mL). The combined organic fractions were washed with brine, dried over $Na_2SO_4$, filtered, and the solvent was removed in vacuo. The residue was purified by flash column chromatography (0-50% EtOAc in hexanes) to afford regiopure bromothiophene.

(b) Synthesis of (1-bromo-6,7-dihydro-4H-thieno[3,4-c]pyran-4-yl)methanamine

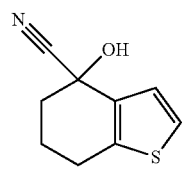 [SMILES: N#CC1(O)CCCc2sccc21]

Bromothiophene (0.31 g, 1.5 mmol) and aminoacetaldehyde diethyl acetal (0.3 g, 2.25 mmol) were combined with 1,4-dioxane (2 mL). $CF_3SO_3H$ (0.45 g, 3.0 mmol) was added and the reaction mixture was stirred at 22° C. for 2 hr at which time the mixture was made basic with 10% KOH (aq.) and the aqueous layer was extracted with EtOAc (3×50 mL). The combined organic layers were washed with brine, dried over $Na_2SO_4$, filtered and the solvent removed in vacuo to afford the crude amine product.

Boc-protection was performed following standard protocols.

(c) Synthesis of (6,7-dihydro-4H-thieno[3,4-c]pyran-4-yl)methanamine

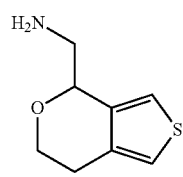

To the purified Boc-protected bromothiophene (0.16 g, 0.45 mmol) in THF (16 mL) at −78° C. was added n-BuLi (2.5 M in hexanes, 0.4 mL, 1.0 mmol) and the resulting mixture was stirred at −78° C. for 2 hr at which time MeOH (2 mL) was added and the reaction was allowed to warm to about 22° C. The solvent was removed and then the residue was redissolved in MeOH for purification by RP-HPLC (0.1% aqueous $NH_4HCO_3$ in acetonitrile). The Boc-protected material was then deprotected using HCl (4.0 M in 1,4-dioxane, 5 mL) and the resulting HCl salt was precipitated with MTBE (50 mL) filtered and isolated as a white powder.

5. General Procedure E

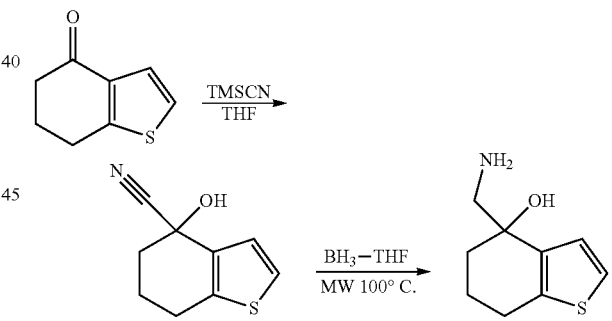

(a) Synthesis of 4-hydroxy-4,5,6,7-tetrahydrobenzo[b]thiophene-4-carbonitrile

To 6,7-dihydrobenzo[b]thiophen-4(5H)-one (0.5 g, 3.3 mmol) and trimethylamine N-oxide (0.074 g, 0.99 mmol) in $CH_2C_2$ (4 mL) was added TMSCN dropwise. The resulting mixture was stirred at 22° C. for 16 hr at which time the entire mixture was deposited on a silica gel column. Purification with flash column chromatography (0-50% EtOAc in hexanes) afforded the desired cyanohydrin compound.

(b) Synthesis of 4-(aminomethyl)-4,5,6,7-tetrahydrobenzo[b]thiophen-4-ol

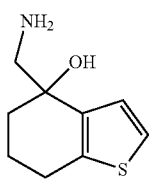 [SMILES: NCC1(O)CCCc2sccc21]

To the cyanohydrin compound (0.59 g, 3.3 mmol) in THF (6.5 mL) at 0° C. was added LAH (1.0 M THF, 6.5 mL). The resulting mixture was stirred at 0° C. for 2 hr at which time the reaction mixture was poured into a saturated aqueous solution of $K_2CO_3$ and extracted with EtOAc (3×50 mL). The combined organic layers were washed with brine, dried over $Na_2SO_4$, filtered and the solvent removed in vacuo to afford the desired amino alcohol which was further purified by RP-HPLC (0.1% aqueous formic acid in acetonitrile). The solvent was removed in vacuo to afford the formic acid salt.

6. General Procedure F

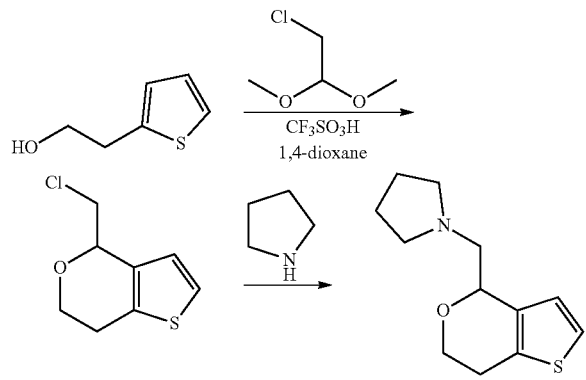

(a) Synthesis of 4-(chloromethyl)-6,7-dihydro-4H-thieno[3,2-c]pyran

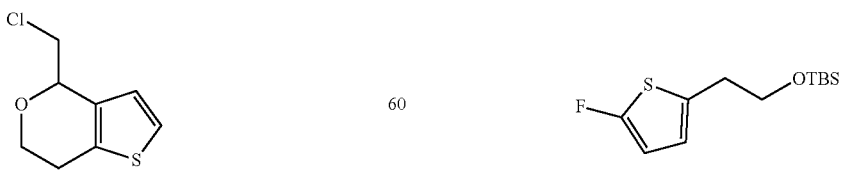

The title compound was synthesized from 2-(thiophen-2-yl) ethanol and chloroacetaldehyde diethyl acetal according to General Procedure A.

(b) Synthesis of 1-((6,7-dihydro-4H-thieno[3,2-c]pyran-4-yl)methyl)pyrrolidine

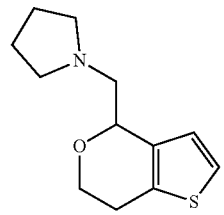 [SMILES: c1cc2c(s1)CCOC2CN1CCCC1]

A mixture of 4-(chloromethyl)-6,7-dihydro-4H-thieno[3,2-c]pyran (1 g, 5.305 mmol, 1 eq), pyrrolidine (11.3 g, 159.1 mmol, 30 eq) and NaI (50 mg) in DMF (50 mL) in a sealed tube was stirred at 130° C. for 6 hr. The reaction mixture was cooled and poured into $H_2O$ and the pH was adjusted to 2 with 2N HCl. The resulting solution was washed with EtOAc. The aqueous layer was then adjusted to pH 9-10 and extracted with EtOAc. The EtOAc layers were washed with brine, dried over $Na_2SO_4$, filtered, and concentrated. The resulting crude product was purified by preparative HPLC. After removal of organic volatiles of the collected HPLC fractions, the pH of remaining aqueous phase was adjusted to ~8 with saturated $Na_2CO_3$ solution. The aqueous solution was extracted with EtOAc (3 times). The combined EtOAc extract was washed with brine, dried with $Na_2SO_4$, and concentrated to give the desired product.

7. General Procedure G

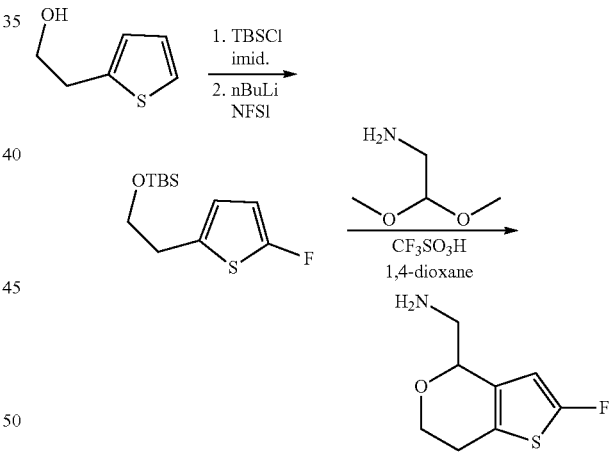

(a) Synthesis of tert-butyl(2-(5-fluorothiophen-2-yl)ethoxy)dimethylsilane

To 2-thiophene-2-ethanol (1.28 g, 10 mmol) in $CH_2Cl_2$ (12 mL) was added TBSCl (1.66 g, 11 mmol) followed by imidazole (1.36 g, 20 mmol) and the resulting cloudy mixture was stirred for 1 hr at 22° C. Upon reaction completion, the mixture was diluted with NH$_4$Cl (sat. aq.) and the aqueous phase was extracted with EtOAc (3×50 mL). The combined organic layers were washed with NaHCO$_3$ (sat. aq.), brine, dried over Na$_2$SO$_4$, filtered and the solvent removed in vacuo to afford the crude protected alcohol which was used in the next step without further purification.

(b) Synthesis of (2-fluoro-6,7-dihydro-4H-thieno[3,2-c]pyran-4-yl)methanamine

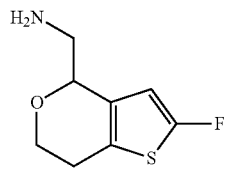 [SMILES: NCC1OCCc2sc(F)cc21]

To the silyl protected 2-(thiophen-2-yl)ethanol (0.96 g, 4.0 mmol) in dry Et$_2$O (20 mL) at −78° C. was added n-BuLi (2.5 M in hexanes, 2.38 mL) and the resulting yellow solution was stirred at −78° C. for 3 hr at which time NFSI (2.5 g, 7.9 mmol) was added and the mixture was allowed to warm to 22° C. over 3 hr. The product formation was monitored by GC-MS. When no more product was formed, the reaction was quenched with MeOH and the solvent removed in vacuo. Purification by flash column chromatography (0 to 50% EtOAc in hexanes) afforded a mixture of the fluorinated and non-fluorinated TBS-protected ethanols which were taken on to the next step without further purification.

Cyclization in the presence of CF$_3$SO$_3$H was performed following the General Procedure A. Upon isolation of the fluorinated and non-fluorinated mixture of amino pyrans, the amine functionality was protected with Boc$_2$O in the presence of 10% NEt$_3$ in methanol. Purification by flash column chromatography (0 to 30% EtOAc in hexanes) afforded a mixture of the fluorinated and non-fluorinated products which were submitted to further purification by RP-HPLC (0.1% aqueous formic acid in acetonitrile) to provide the pure fluorinated analog. The Boc-protecting group on the purified fluorinated analog was removed using standard procedure to give the corresponding amine.

8. General Procedure H

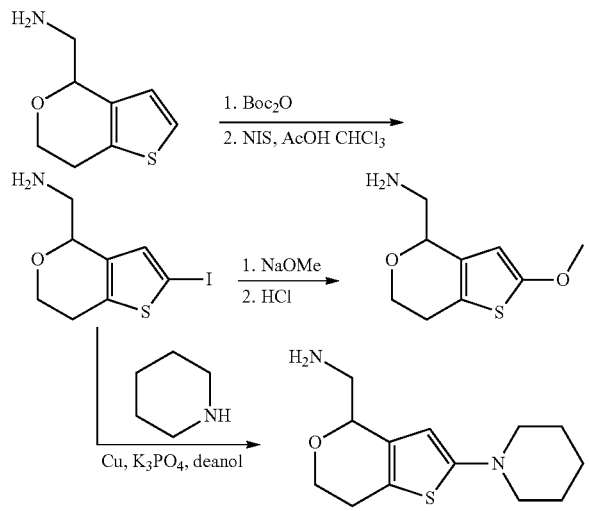

(a) Synthesis of tert-butyl (6,7-dihydro-4H-thieno[3,2-c]pyran-4-yl)methylcarbamate

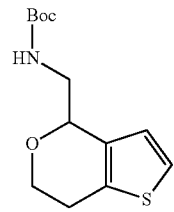

A solution of (6,7-dihydro-4H-thieno[3,2-c]pyran-4-yl)methanamine (6.3 g, 37.3 mmol, 1 eq), Boc$_2$O (8.9 g, 40.8 mmol, 1.1 eq), and DMAP (10 mg) in THF (50 mL) was stirred at room temperature for 1 hr. The mixture was concentrated and purified by column chromatography to give the desired product.

(b) Synthesis of tert-butyl (2-iodo-6,7-dihydro-4H-thieno[3,2-c]pyran-4-yl)methylcarbamate

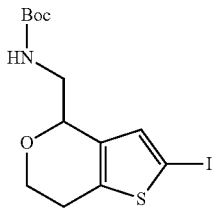 [SMILES: CC(C)(C)OC(=O)NCC1OCCc2sc(I)cc21]

A solution of tert-butyl (6,7-dihydro-4H-thieno[3,2-c]pyran-4-yl)methylcarbamate (2.9 g, 1.3 mmol, 1 eq), NIS (5.2 g, 2.2 mmol, 2 eq), and AcOH (3 mL) in CHCl$_3$ (50 mL) was stirred at room temperature for 7 hr. The reaction mixture was neutralized with triethyl amine, concentrated, and diluted with water. The mixture was extracted with n-hexane. The organic phase was dried over Na$_2$SO$_4$, concentrated, and purified by column chromatography to give the desired product (3 g).

(c) Synthesis of (2-(piperidin-1-yl)-6,7-dihydro-4H-thieno[3,2-c]pyran-4-yl)methanamine

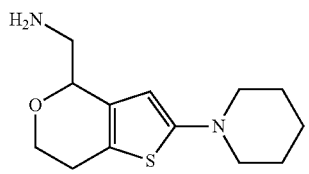 [SMILES: NCC1OCCc2sc(N3CCCCC3)cc21]

A mixture of tert-butyl (2-iodo-6,7-dihydro-4H-thieno[3,2-c]pyran-4-yl)-methylcarbamate (400 mg, 1.0 mmol, 1 eq), piperidine (2 mL), Cu metal (6.4 mg, 1 mmol, 0.1 eq), and K$_3$PO$_4$·3H$_2$O (539.3 mg, 2.34 mmol, 2.3 eq) in 2-dimethylamino-ethanol (deanol) (5 mL) was stirred at 85° C. in a sealed tube for 28 hr. After cooling to room temperature, the reaction mixture was diluted with water, extracted with ethyl acetate, washed with brine, dried over Na$_2$SO$_4$, concentrated and purified by Al$_2$O$_3$ column chromatography. The Boc protecting group was removed with HCl under standard conditions to give the product (2-(piperidin-1-yl)-6,7-dihydro-4H-thieno[3,2-c]pyran-4-yl)methanamine.

9. General Procedure I

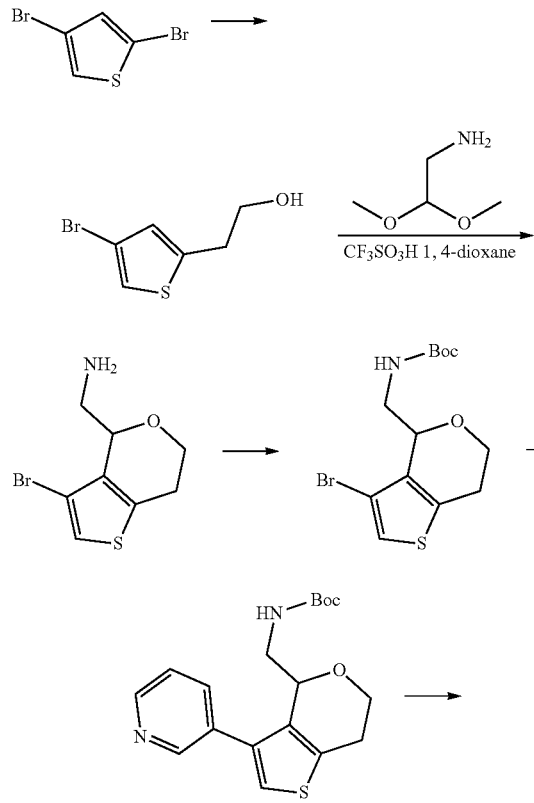

(a) Synthesis of 2-(4-bromothiophen-2-yl)ethanol

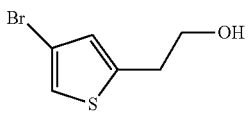

To a solution of 2,4-dibromothiophene (1 g, 4.13 mmol) in anhydrous ether was added n-BuLi (1.66 mL, 4.13 mmol) at −78° C. dropwise. After stirring at −78° C. for 0.5 hr, oxirane (0.32 mL, 19.28 mmol/mL in ether) was added to the reaction mixture quickly. After stirring at 0° C. for 1.5 hr, the reaction mixture was quenched with aqueous NH$_4$Cl solution, extracted with EtOAc, concentrated and purified to give the desired product.

(b) Synthesis of (3-bromo-6,7-dihydro-4H-thieno[3,2-c]pyran-4-yl)methanamine

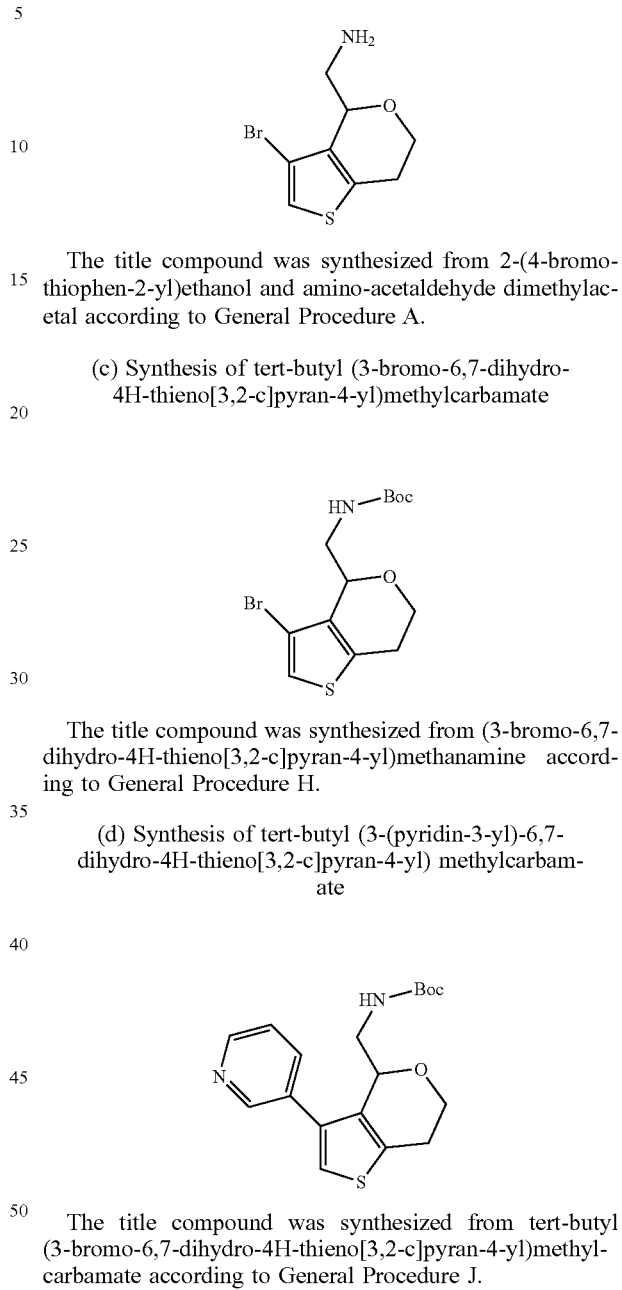

The title compound was synthesized from 2-(4-bromothiophen-2-yl)ethanol and amino-acetaldehyde dimethylacetal according to General Procedure A.

(c) Synthesis of tert-butyl (3-bromo-6,7-dihydro-4H-thieno[3,2-c]pyran-4-yl)methylcarbamate The title compound was synthesized from (3-bromo-6,7-dihydro-4H-thieno[3,2-c]pyran-4-yl)methanamine according to General Procedure H.

(d) Synthesis of tert-butyl (3-(pyridin-3-yl)-6,7-dihydro-4H-thieno[3,2-c]pyran-4-yl) methylcarbamate The title compound was synthesized from tert-butyl (3-bromo-6,7-dihydro-4H-thieno[3,2-c]pyran-4-yl)methylcarbamate according to General Procedure J.

(e) Synthesis of HCl salt of (3-(pyridin-3-yl)-6,7-dihydro-4H-thieno[3,2-c]pyran-4-yl)methanamine

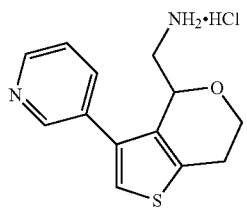

83

The title compound was synthesized from tert-butyl (3-(pyridin-3-yl)-6,7-dihydro-4H-thieno[3,2-c]pyran-4-yl)methylcarbamate according to General Procedure J(e).

10. General Procedure J

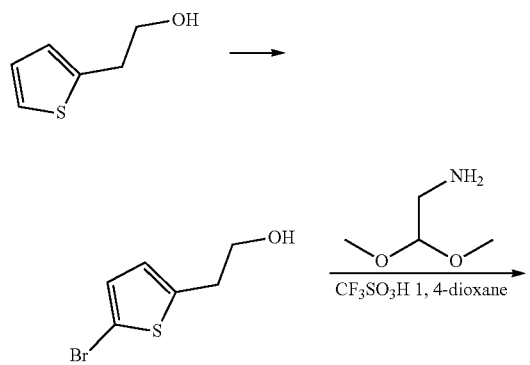

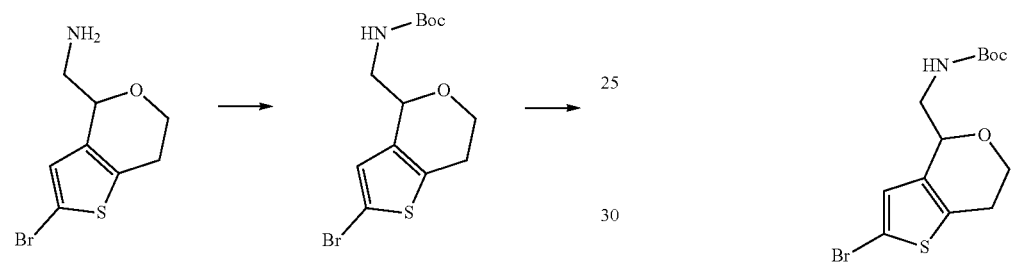

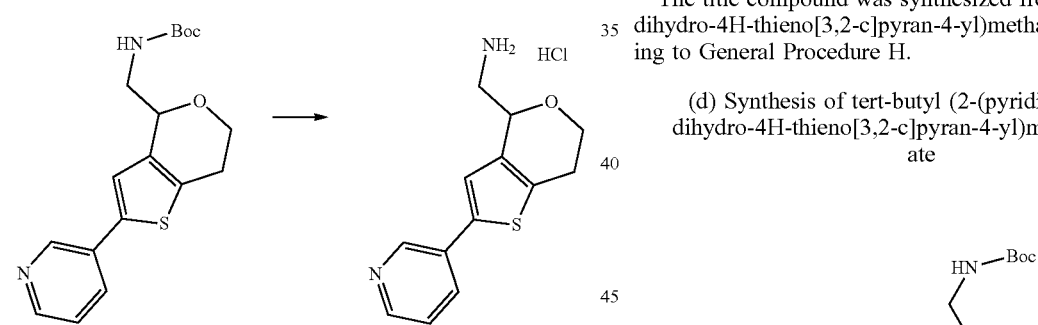

(a) Synthesis of 2-(5-bromothiophen-2-yl)ethanol

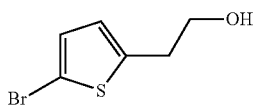

To a solution of 2-(thiophen-2-yl)ethanol (3 g, 23.4 mmol, 1 eq) and HOAc (5 mL) in CHCl₃ was added NBS in portions at room temperature. After stirring at room temperature overnight, the reaction mixture was poured into water and extracted with CHCl₃ twice. The combined organic layer was dried over Na₂SO₄, concentrated and purified by column chromatography to give the desired product.

84

(b) Synthesis of (2-bromo-6,7-dihydro-4H-thieno[3,2-c]pyran-4-yl)methanamine

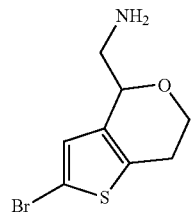

The title compound was synthesized from 2-(5-bromothiophen-2-yl)ethanol and aminoacetaldehyde dimethylacetal according to General Procedure A.

(c) Synthesis of tert-butyl (2-bromo-6,7-dihydro-4H-thieno[3,2-c]pyran-4-yl)methylcarbamate

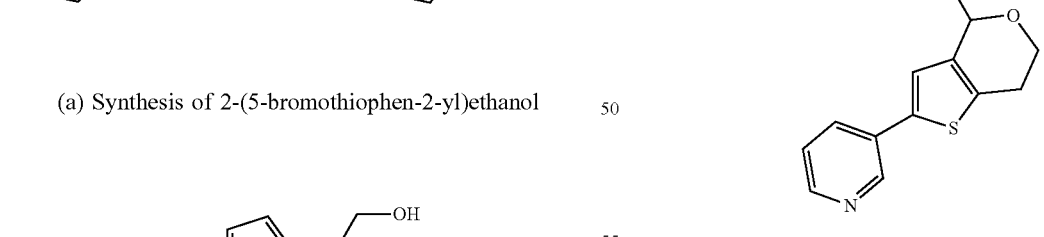

The title compound was synthesized from (2-bromo-6,7-dihydro-4H-thieno[3,2-c]pyran-4-yl)methanamine according to General Procedure H.

(d) Synthesis of tert-butyl (2-(pyridin-3-yl)-6,7-dihydro-4H-thieno[3,2-c]pyran-4-yl)methylcarbamate A mixture of tert-butyl (2-bromo-6,7-dihydro-4H-thieno[3,2-c]pyran-4-yl)methylcarbamate (500 mg, 1.44 mmol), pyridine-3-boronic acid (351 mg, 2.88 mmol), Pd(OAc)₂ (33 mg), PPh₃ (170 mg, 0.65 mmol) in 1,4-dioxane was purged with nitrogen. After stirring at room temperature for 0.5 hr, 457 mg of Na₂CO₃ in 3 mL of H₂O was added. The reaction mixture was stirred at 100° C. for 2 hr. After cooling to room temperature, the reaction mixture was poured into 100 mL of water and extracted with EtOAc twice. The combined organic layers were washed with brine, dried over Na₂SO₄, concentrated and purified by column chromatography to give the desired product.

(e) Synthesis of the HCl salt of (2-(pyridin-3-yl)-6,7-dihydro-4H-thieno[3,2-c]pyran-4-yl)methanamine

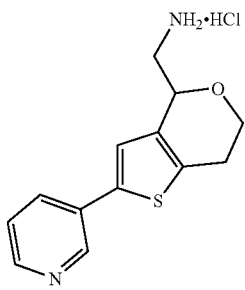

To a solution of tert-butyl (2-(pyridin-3-yl)-6,7-dihydro-4H-thieno[3,2-c]pyran-4-yl)methylcarbamate in MeOH was added an HCl solution (10 mL, 5 N in MeOH). The mixture was stirred at room temperature for 0.5 h, and a solid precipitated. The solid was collected by vacuum filtration and washed with EtOAc to give the desired product.

11. General Procedure K

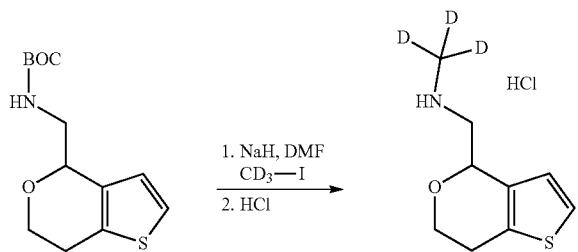 [SMILES: CC(C)(C)OC(=O)NCC1OCCc2sccc21 ; [2H]C([2H])([2H])I ; [2H]C([2H])([2H])NCC1OCCc2sccc21 ; Cl]

tert-Butyl(6,7-dihydro-4H-thieno[3,2-c]pyran-4-yl)methylcarbamate (1.96 mmol) was dissolved in anhydrous DMF (20 mL) and cooled to 0° C. NaH (60% dispersion in mineral oil, 86 mg, 2.15 mmol) was added in one portion and the resulting orange suspension was stirred for 30 min. Deuterated methyl iodide (133 μL, 2.15 mmol) was added and the resulting mixture was stirred over the two to three days. After about 65 hr, the mixture was poured into H$_2$O (30 mL) and washed with Et$_2$O (2×30 mL). The aqueous phase was extracted with EtOAc (1×20 mL) and the organic phases were combined, washed with brine, dried (Na$_2$SO$_4$), filtered, and concentrated. The crude material was purified by flash column chromatography on a Biotage system (eluting with 0 to 50% EtOAc in hexanes gradient) to give the desired Boc-protected material.

The BOC protected material (340 mg, 1.04 mmol) was dissolved in MTBE (10 mL) and HCl in dioxane was added (4 M, 1.5 mL). The resulting solution was stirred for 2 days, then poured into saturated aqueous Na$_2$CO$_3$ (30 mL) and washed with EtOAc (3×40 mL). The combined organic phases were washed with brine, dried (Na$_2$SO$_4$), filtered, and concentrated. The crude N-deutero methyl compound was dissolved in MTBE (10 mL) and HCl in dioxane (4 M, 454 μL, 1.04 eq) was added. The resulting off-white precipitate was collected by filtration, and washed with MTBE, then dried in vacuo to give the pure HCl salt of the deuterated product.

12. General Procedure L

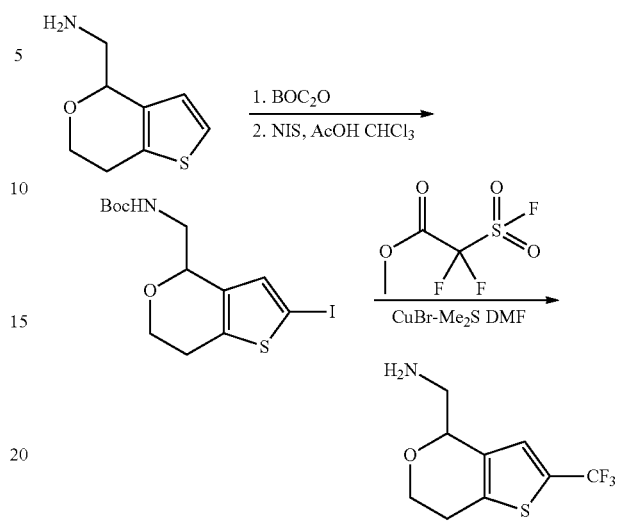

The above iodothienyl compound (0.22 g, 0.55 mmol, prepared using General Procedure H), methyl-2,2-difluoro-2-(fluorosulfonyl)acetate (0.21 g, 1.1 mmol) and CuBr.Me$_2$S (0.023 g, 0.11 mmol) were combined with anhydrous DMF (5 mL) in a sealed microwave vial. The resulting mixture was heated in a microwave reactor for 10 min at 90° C. The reaction was determined by LC-MS to be 5% complete. The reaction mixture was re-subjected to the microwave reactor at 100° C. for 40 min at which time the reaction was determined by LC-MS to be 95% complete. The reaction mixture was diluted with Et$_2$O (50 mL) and the organic layer was washed with NaHCO$_3$ (sat. aq.) and then brine, dried with Na$_2$SO$_4$, filtered, and concentrated in vacuo to afford the crude trifluoromethyl product. Purification with flash column chromatography (0-50% EtOAc in hexanes) afforded pure trifluoromethyl product which was then deprotected using HCl (4 M in 1,4-dioxane, 5 mL), and the resulting HCl salt was precipitated with MTBE (50 mL), filtered, and isolated as a white powder.

13. General Procedure M

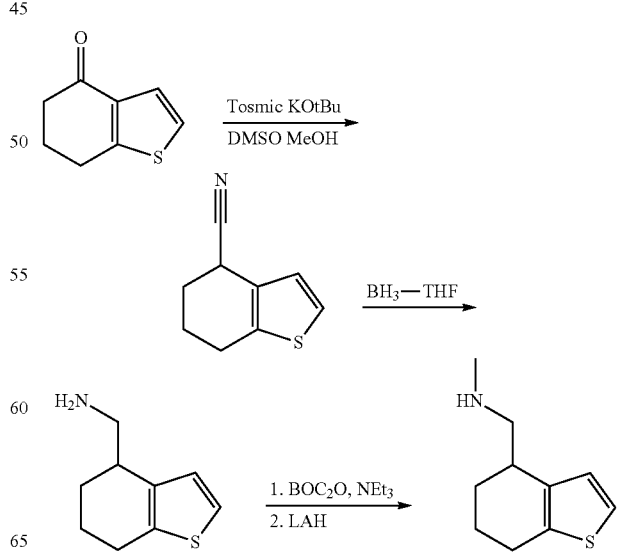

(a) Synthesis of 4,5,6,7-tetrahydrobenzo[b]thiophene-4-carbonitrile

To a solution of the above cyclic ketone (1.0 g, 6.6 mmol) in MeOH (330 mL) and DMSO (10 mL) was added Tosmic (1.7 g, 8.7 mmol) followed by KOtBu (2.5 g, 26.3 mmol) in small portions. The resulting mixture was stirred at 25° C. for 36 hr at which time the bulk of the volatiles were removed in vacuo. The reaction mixture was diluted with EtOAc and H$_2$O. The organics were washed with NH$_4$Cl (sat. aq.), brine, dried over Na$_2$SO$_4$, concentrated and purified by column chromatography (0 to 30% EtOAc in hexanes) to give the desired nitrile compound.

(b) Synthesis of (4,5,6,7-tetrahydrobenzo[b]thiophen-4-yl)methanamine

The resulting nitrile (0.3 g, 1.8 mmol) was reduced to the primary amine using excess BH$_3$.THF (10 mL, 10 mmol) diluted to 20 mL with 10 mL additional THF. The reaction mixture was stirred at 25° C. for 1 hr at which time careful addition of K$_2$CO$_3$ (sat. aq.) was used to quench the reaction. EtOAc was added and the organic layer was washed with NaHCO$_3$ and brine, dried over Na$_2$SO$_4$, and filtered. The resulting yellow oil was further purified by RP-HPLC to afford the primary amine compound.

(c) Synthesis of N-methyl-1-(4,5,6,7-tetrahydrobenzo[b]thiophen-4-yl)methanamine The primary amine was protected with excess BOC$_2$O in a solution of 10% NEt$_3$ in MeOH. The reaction mixture was stirred at 25° C. for 1 hr at which time all volatiles were removed in vacuo. The crude material was taken up in 10 mL THF. 20 mL 1M LAH in THF was added dropwise, and the reaction mixture was stirred at 25° C. for 2 hr at which time careful addition of K$_2$CO$_3$ (sat. aq.) was used to quench the reaction. EtOAc was added and the organic layer was washed with NaHCO$_3$, dried with brine, dried over Na$_2$SO$_4$, and filtered. The resulting yellow oil was further purified by RP-HPLC to afford the secondary amine compound.

14. General Procedure N

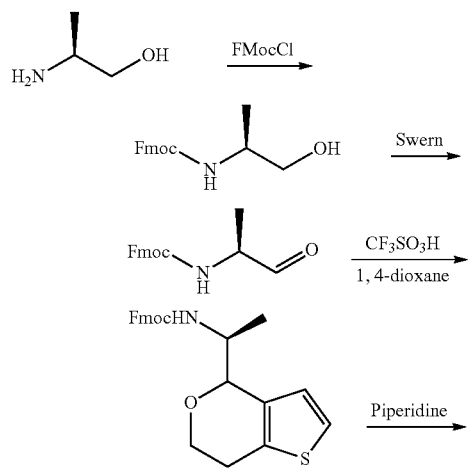

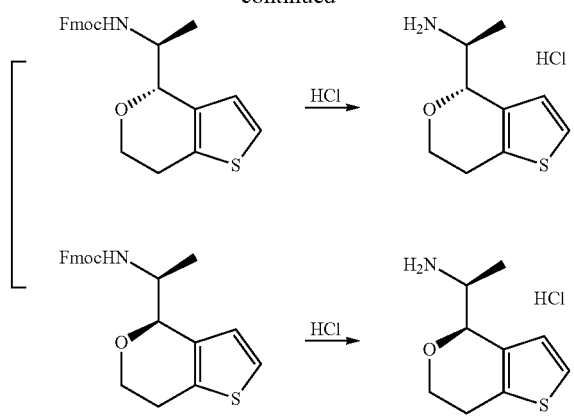

(a) Synthesis of (S)-(9H-fluoren-9-yl)methyl 1-hydroxy-3-methylbutan-2-yl(methyl)carbamate

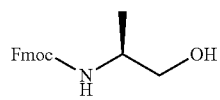

To a mixture of (S)-2-aminopropan-1-ol (2 g, 26.6 mmol) and Na$_2$CO$_3$ (5.6 g, 53.2 mmol) in 1,4-dioxane and water (25 mL/25 mL) at 0° C. was added FmocCl (10.2 g, 39.9 mmol) and the resulting mixture was then warmed to room temperature gradually. After the amine was consumed completely as indicated by TLC, water (25 mL) was added. The mixture was extracted with DCM (3×50 mL). The organic phase was washed with brine (50 mL), and dried over anhydrous Na$_2$SO$_4$. After filtration and concentration, the crude product was purified by column chromatography to give the title compound (7.1 g, 90%).

(b) Synthesis of (S)-(9H-fluoren-9-yl)methyl methyl (3-methyl-1-oxobutan-2-yl)carbamate

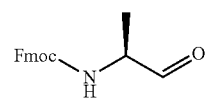

To a solution of oxalyl chloride (1.89 g, 15.0 mmol) in dry DCM (10 mL) at −65° C. was added DMSO (1.2 g, 15.0 mmol) in dry DCM (10 mL) dropwise. After stirring for 30 min, N-Fmoc (S)-2-aminopropan-1-ol (3.0 g, 10.0 mmol) in dry DCM (20 mL) was added dropwise. After stirring for 2 hr, Et$_3$N (3.0 g, 30 mmol) was added dropwise and the mixture was then warmed to room temperature gradually. The reaction mixture was treated with water, extracted with DCM (3×100 mL). The organic extract was washed with brine, and dried over anhydrous Na$_2$SO$_4$. After filtration, the solvent was removed under reduced pressure to give the title compound (2.8 g, 94.9%).

(c) Synthesis of (S)-(9H-fluoren-9-yl)methyl 1-(6,7-dihydro-4H-thieno[3,2-c]pyran-4-yl)-2-methylpropyl (methyl)carbamate

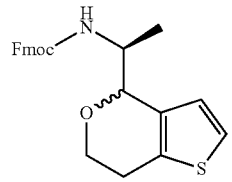

The title compound was synthesized from (S)-(9H-fluoren-9-yl)methyl methyl(3-methyl-1-oxobutan-2-yl)carbamate according to General Procedure A. Diastereomeric products were separated by RP-HPLC at this stage.

(d) Synthesis of (S)-1-((S)-6,7-dihydro-4H-thieno[3,2-c]pyran-4-yl)ethanamine

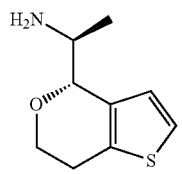

To a solution of (9H-fluoren-9-yl)methyl (S)-1-((S)-6,7-dihydro-4H-thieno[3,2-c]pyran-4-yl)ethylcarbamate (885 mg, 3.0 mmol) in CH₃CN (10 mL) at 0° C. was added piperidine (382 mg, 4.5 mmol) dropwise. After stirring overnight, the reaction solution was concentrated under reduced pressure and the residue was purified by column chromatography to give the title compound (450 mg, 82%).

(e) Synthesis of the HCl salt of (S)-1-((S)-6,7-dihydro-4H-thieno[3,2-c]pyran-4-yl)ethanamine

A solution of (S)-1-((S)-6,7-dihydro-4H-thieno[3,2-c]pyran-4-yl)ethanamine (450 mg, 2.5 mmol) in ether (50 mL) was treated with gaseous HCl at 0° C. for 10 minutes. The precipitated solid was collected by vacuum filtration and dried to give the title product (460 mg, 84%).

15. General Procedure O

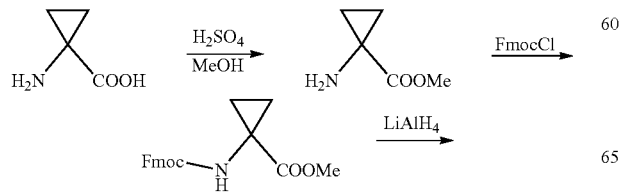

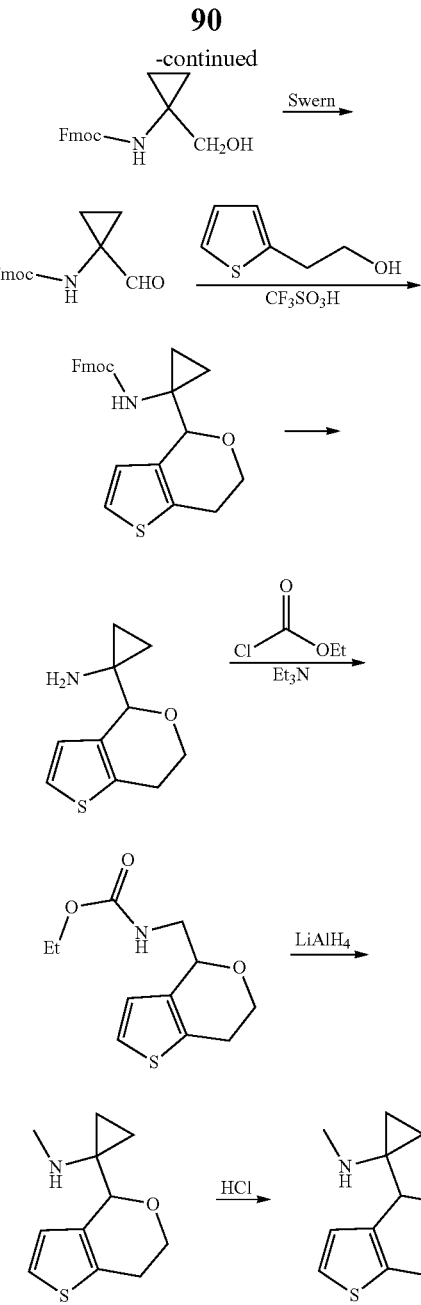

(a) Synthesis of methyl 1-aminocyclohexanecarboxylate

To MeOH (50 mL) was added SOCl₂ (8.8 g, 75.1 mmol) dropwise at 0° C., followed by the addition of 1-aminocyclopropanecarboxylic acid (5.0 g, 49.8 mmol) in one portion. The resulting mixture was refluxed for 1 to 3 h. The reaction solution was concentrated under reduced pressure to give a salt of the title compound (5.8 g, 100%).

(b) Synthesis of methyl 1-(((9H-fluoren-9-yl)methoxy)carbonylamino)cyclohexanecarboxylate

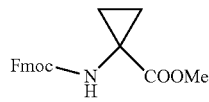

To a mixture of methyl 1-aminocyclopropanecarboxylate (5.8 g, 50.4 mmol) and $Na_2CO_3$ (8.0 g, 74.6 mmol) in 1,4-dioxane (50 mL) and water (50 mL) at 0° C. was added FmocCl (19.4 g, 75.2 mmol). The resulting mixture was warmed gradually to room temperature. After the amine was consumed completely as indicated by TLC, water (50 mL) was added and the mixture was extracted with DCM (3×60 mL). The DCM extract was washed with brine, and dried over anhydrous $Na_2SO_4$. After filtration and concentration, the crude product was purified by column chromatography to give the title compound (15 g, 88%).

Synthesis of (9H-fluoren-9-yl)meth 1-(hydroxymethyl)cyclohexylcarbamate

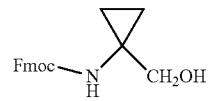

To a solution of (9H-fluoren-9-yl)methyl 1-(methoxycarbonyl)-cyclopropylcarbamate (15 g, 44.5 mmol) in THF (100 mL) at −5° C. was added $LiAlH_4$ (1.0 g, 26.3 mmol) in portions. After stirring at room temperature for 3 h, water (10 mL) was added to quench the reaction. The mixture was filtered and the filtrate was extracted with EtOAc (3×100 mL). The organic extract was washed with brine, and dried over anhydrous $Na_2SO_4$. After filtration and concentration, the crude product was purified by column chromatography to give the title compound (12.3 g, 90%).

(c) Synthesis of (9H-fluoren-9-yl)methyl 1-formylcyclohexylcarbamate

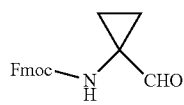

The title compound was synthesized according to General Procedure N.

(d) Synthesis of (9H-fluoren-9-yl)methyl 1-(6,7-dihydro-4H-thieno[3,2-c]pyran-4-yl)cyclohexylcarbamate

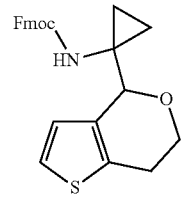

The title compound was synthesized according to General Procedure A(b).

(e) Synthesis of 1-(6,7-dihydro-4H-thieno[3,2-c]pyran-4-yl)cyclohexanamine

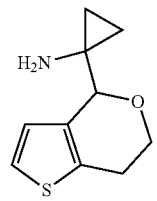 [SMILES: NC1(C2OCCc3sccc32)CC1]

The title compound was synthesized according to General Procedure N(d).

(f) Synthesis of ethyl 1-(6,7-dihydro-4H-thieno[3,2-c]pyran-4-yl)cyclohexylcarbamate

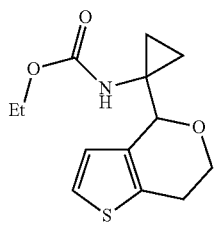 [SMILES: CCOC(=O)NC1(C2OCCc3sccc32)CC1]

To a solution of 1-(6,7-dihydro-4H-thieno[3,2-c]pyran-4-yl)-cyclopropanamine (1 g, 5.1 mmol) and $Et_3N$ (0.8 g, 7.5 mmol) in dry DCM (20 mL) at 0° C. was added ethyl chloroformate (0.8 g, 7.5 mmol) dropwise. After stirring at 0° C. for 4 h, water (20 mL) was added to quench the reaction. The mixture was extracted with DCM (3×50 mL) and the organic extract was dried over anhydrous $Na_2SO_4$. After filtration and concentration, the crude product was purified by column chromatography to give the title compound (1.1 g, 83%).

93

(g) Synthesis of 1-(6,7-dihydro-4H-thieno[3,2-c]pyran-4-yl)-N-methylcyclohexanamine

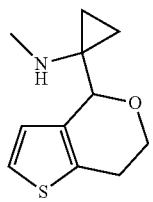

To a solution of ethyl 1-(6,7-dihydro-4H-thieno[3,2-c]pyran-4-yl)cyclopropylcarbamate (1.1 g, 4.1 mmol) in dry THF (20 mL) at 0° C. under $N_2$ was added LiAlH$_4$ (152 mg, 4.0 mmol) in one portion. The resulting mixture was refluxed for 2 h and then cooled to room temperature. Water (5 mL) was added to quench the reaction. The reaction mixture was filtered and the filtrate was extracted with EtOAc (3×75 mL). The combined extract was washed with brine, and dried over anhydrous Na$_2$SO$_4$. After filtration and concentration, the crude product was purified by column chromatography to give the title compound (700 mg, 84%).

(h) Synthesis of the HCl salt of 1-(6,7-dihydro-4H-thieno[3,2-c]pyran-4-yl)-N-methylcyclohexanamine

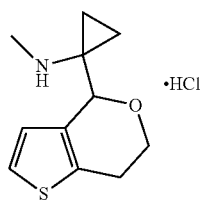

The title compound was synthesized according to General Procedure N.

16. General Procedure P

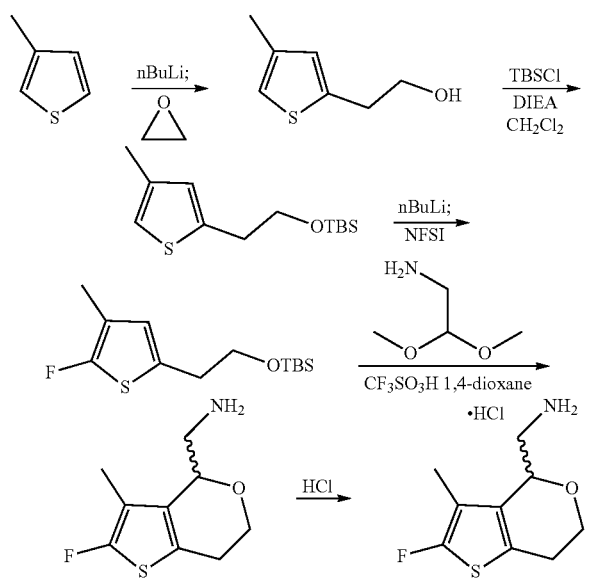

94

(a) Synthesis of 2-(4-methylthiophen-2-yl)ethanol

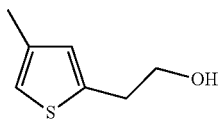

To a solution of 3-methylthiophene (5 g, 51.0 mmol) in dry ether (250 mL) at −65° C. was added n-BuLi (25 mL, 2.5 N in THF) dropwise. After stirring for 1 h, oxirane (2.7 g, 61.3 mmol) was added in one portion. The resulting reaction mixture was warmed to room temperature and stirred overnight. The reaction was then quenched with water. After separation of layers, the organic layer was washed with brine, and dried over anhydrous Na$_2$SO$_4$. After filtration and concentration, the crude product was purified by column chromatography to give the title compound (6.2 g, 86%).

(b) Synthesis of tert-butyldimethyl(2-(4-methylthiophen-2-yl)ethoxy)silane

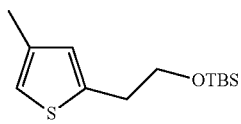 [SMILES: Cc1csc(CCO[Si](C)(C)C(C)(C)C)c1]

To a solution of 2-(4-methylthiophen-2-yl)ethanol (3.0 g, 21.1 mmol) and diisopropylethylamine (4.1 g, 31.7 mmol) in dry DCM (50 mL) at 0° C. was added TBSCl (4.8 g, 32.0 mmol) in dry DCM (20 mL) dropwise and the mixture was then warmed to room temperature gradually. After the alcohol was consumed completely, water (10 mL) was added. The resulting mixture was extracted with DCM (3×100 mL), washed with brine, and dried over anhydrous Na$_2$SO$_4$. After filtration and concentration, the crude product was purified by column chromatography to give the title compound (5.1 g, 94%).

(c) Synthesis of tert-butyl(2-(5-fluoro-4-methylthiophen-2-yl)ethoxy)dimethylsilane

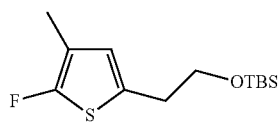 [SMILES: Cc1cc(CCO[Si](C)(C)C(C)(C)C)sc1F]

To a solution of (2-(4-methylthiophen-2-yl)ethoxy)(tert-butyl)dimethylsilane (5.1 g, 19.9 mmol) in dry THF (30 mL) at −5° C. was added LDA (20 mL in THF, 30 mmol) dropwise. After stirring for 1 h, NFSI (9.4 g, 29.8 mmol) in dry THF (10 mL) was added dropwise and the resulting mixture was stirred for another 2 h. The reaction was quenched with water (15 mL) and the resulting mixture was extracted with EtOAc (3×100 mL), washed with brine, and dried over anhydrous Na$_2$SO$_4$. After filtration and concentration, the crude product was purified by column chromatography to give the title compound (3.7 g, 68%).

(d) Synthesis of (2-fluoro-3-methyl-6,7-dihydro-4H-thieno[3,2-c]pyran-4-yl)methanamine

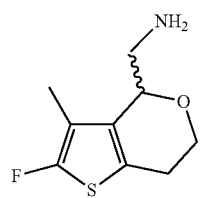

The title compound was synthesized according to General Procedure A.

(e) Synthesis of the HCl salt of (2-fluoro-3-methyl-6,7-dihydro-4H-thieno[3,2-c]pyran-4-yl)methanamine

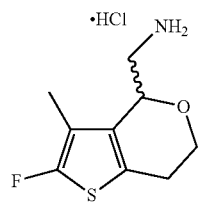

The title compound was synthesized according to General Procedure N.

17. General Procedure Q

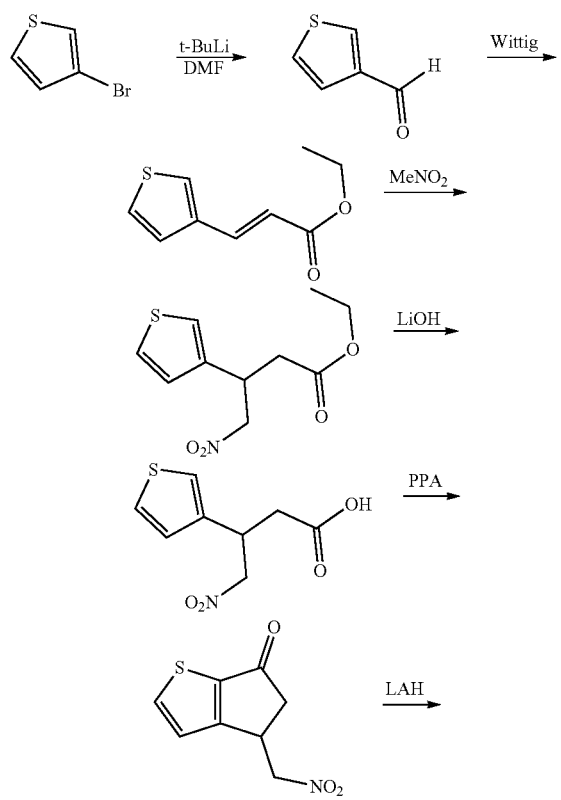

(a) Synthesis of thiophene-3-carboxaldehyde

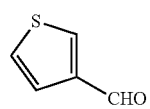

To a solution of 3-bromothiophene (0.65 g, 4.0 mmol) in anhydrous THF (20 mL) at −65° C. was added t-BuLi (3.5 mL, 8.8 mmol, 2.5 M in hexane) over 15 minutes. After stirring at −65° C. for 30 minutes, DMF (0.32 g, 4.4 mmol) was added dropwise and the reaction was stirred at −65° C. for 2 h. The reaction mixture was quenched with water and the mixture was extracted with diethyl ether. The organic layer was dried over $Na_2SO_4$ and concentrated to give a crude product. The crude product was purified by column chromatography to provide the title compound.

(b) Synthesis of ethyl 3-(thiophen-3-yl)acrylate

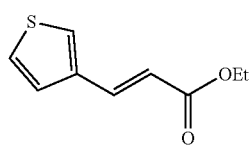 [SMILES: CCOC(=O)/C=C/c1ccsc1]

To a solution of thiophene-3-carbaldehyde (10 g, 89.3 mmol) in THF (500 mL) at 0° C. was added ethyl (triphenylphosphoranylidene)acetate (35 g, 100.5 mmol) in portions. After stirring overnight, the reaction mixture was concentrated and purified by column chromatography to give the title compound (13.6 g, 83%).

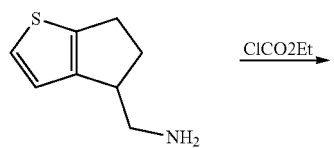
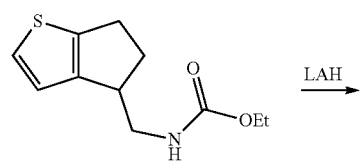
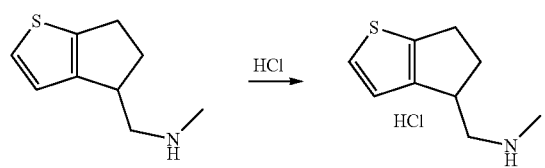

(c) Synthesis of ethyl 4-nitro-3-(thiophen-3-yl)butanoate

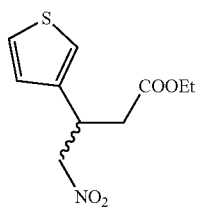 [SMILES: CCOC(=O)CC(C[N+](=O)[O-])c1ccsc1]

To a solution of ethyl 3-(thiophen-3-yl)acrylate (5 g, 27.5 mmol) in CH$_3$NO$_2$ (20 mL) was added Triton B (5 mL) under N$_2$ and the resulting reaction mixture was refluxed overnight. The reaction mixture was concentrated and then diluted with water. The mixture was extracted with EtOAc, washed with brine, and dried over anhydrous Na$_2$SO$_4$. After filtration and concentration, the crude product was purified by column chromatography to give the title compound (4.3 g, 65%).

(d) Synthesis of 4-nitro-3-(thiophen-3-yl)butanoic acid

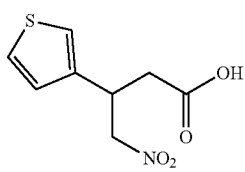 [SMILES: O=C(O)CC(C[N+](=O)[O-])c1ccsc1]

To a solution of ethyl 4-nitro-3-(thiophen-3-yl)butanoate (4.3 g, 18.2 mmol) in MeOH (40 mL) at 0° C. was added 3 N aqueous NaOH (10 mL). The resulting mixture was stirred at room temperature overnight. 2 N HCl was then added to adjust pH to 3 4 followed by extraction with DCM. The organic extract was washed with brine and dried over anhydrous Na$_2$SO$_4$. After filtration, the solution was concentrated to give the title compound (3.4 g, 87%).

(e) Synthesis of 4,5-dihydro-4-(nitromethyl)cyclopenta[b]thiophen-6-one

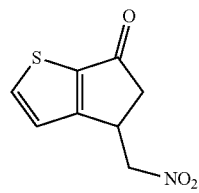 [SMILES: O=C1CC(C[N+](=O)[O-])c2ccsc21]

To a solution of 4-nitro-3-(thiophen-3-yl)butanoic acid (3.4 g, 15.9 mmol) in DCE (20 mL) was added PPA (20 g) and the resulting mixture was refluxed overnight. After concentration, the reaction mixture was treated with solid NaOH, followed by addition of water. After stirring for 30 minutes, the mixture was extracted with DCM. The DCM extract was washed with brine and dried over anhydrous Na$_2$SO$_4$. After filtration and concentration, the crude product was purified by column chromatography to give the title compound (2.3 g, 74%).

(f) Synthesis of (5,6-dihydro-4H-cyclopenta[b]thiophen-4-yl)methanamine

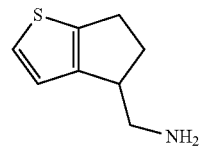

To a solution of 4,5-dihydro-4-(nitromethyl)cyclopenta[b]thiophen-6-one (2.3 g, 11.7 mmol) in dry THF (30 mL) at 0° C. was added LiAlH$_4$ (0.5 g 13.1 mmol) in one portion. The resulting mixture was then refluxed for 4 h. After cooling to room temperature, the reaction was quenched with water and filtered. The filtrate was extracted with EtOAC, washed with brine, and dried over anhydrous Na$_2$SO$_4$. After filtration and concentration, the crude product was purified by column chromatography to give the title compound (1.3 g, 72%).

(g) Synthesis of ethyl (5,6-dihydro-4H-cyclopenta[b]thiophen-4-yl)methylcarbamate

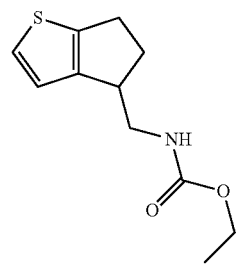

The title compound was synthesized according to General Procedure O(g).

(h) Synthesis of 1-(5,6-dihydro-4H-cyclopenta[b]thiophen-4-yl)-N-methylmethanamine

The title compound was synthesized according to General Procedure O(h).

(i) Synthesis of the HC salt of 1-(5,6-dihydro-4H-cyclopenta[b]thiophen-4-yl)-N-methylmethanamine

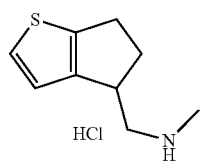

The title compound was synthesized according to General Procedure N(e).

18. General Procedure R

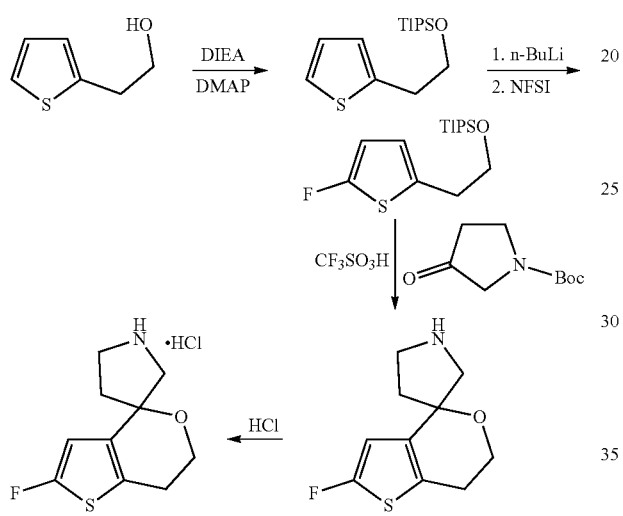

(a) Synthesis of triisopropyl(2-(thiophen-2-yl)ethoxy)silane

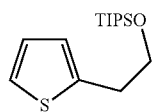

The title compound was synthesized according to General Procedure P.

(b) Synthesis of (2-(5-fluorothiophen-2-yl)ethoxy)triisopropylsilane

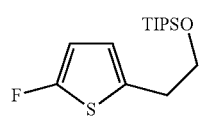

The title compound was synthesized according to General Procedure P.

(c) Synthesis of 2'-fluoro-6',7'-dihydrospiro[pyrrolidine-3,4'-thieno[3,2-c]pyran]

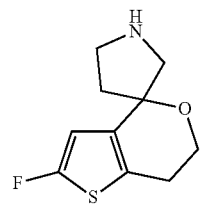 [SMILES: Fc1cc2c(s1)CCOC21CCNC1]

The title compound was synthesized according to General Procedure A.

(d) Synthesis of HC salt of 2'-fluoro-6',7'-dihydrospiro[pyrrolidine-3,4'-thieno[3,2-c]pyran]

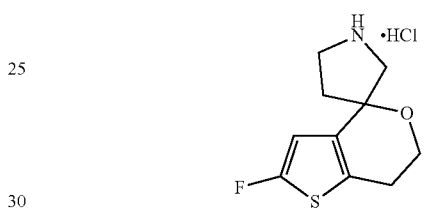

The title compound was synthesized according to General Procedure N.

19. General Procedure S

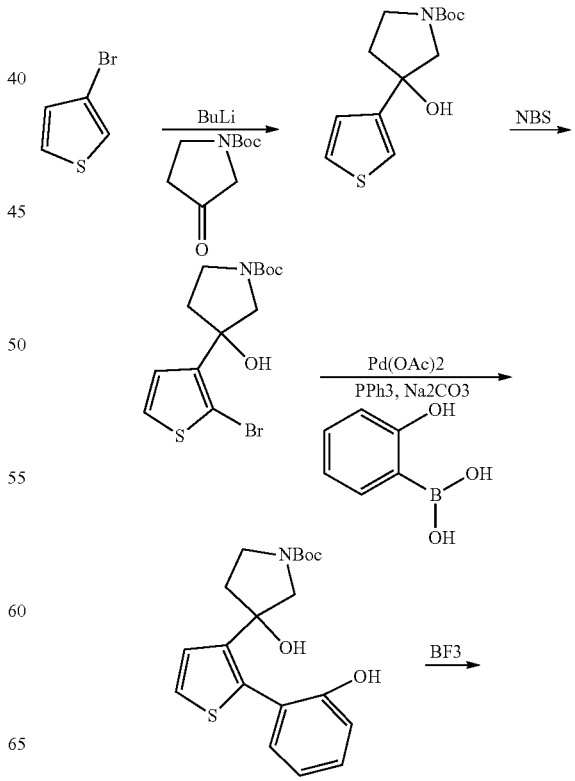

-continued

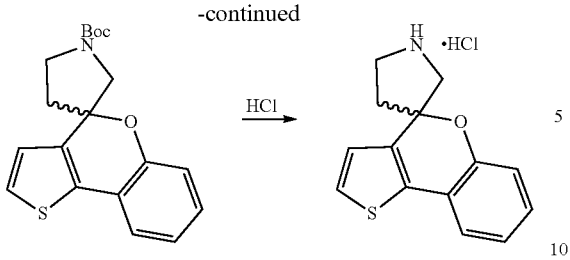

(a) Synthesis of tert-butyl 3-hydroxy-3-(thiophen-3-yl)pyrrolidine-1-carboxylate

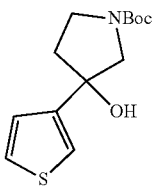

To a solution of 3-bromothiophene (10 g, 61.8 mmol) in dry ether (200 mL) at −65° C. under $N_2$ was added n-BiLi dropwise. After stirring at −65° C. for 1 h, tert-butyl 3-oxopyrrolidine-1-carboxylate (13.7 g, 74.2 mmol) in dry ether (80 mL) was added dropwise. After addition, the reaction mixture was warmed to 0° C. and stirred for 3 h. The reaction was quenched with water and extracted with ether. The combined organic layer was washed with brine, and dried over anhydrous $Na_2SO_4$. After filtration and concentration, the crude product was purified by column chromatography to give the title compound (9.8 g, 59%).

(b) Synthesis of tert-butyl 3-(2-bromothiophen-3-yl)-3-hydroxypyrrolidine-1-carboxylate

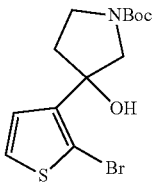

To a solution of tert-butyl 3-hydroxy-3-(thiophen-3-yl)pyrrolidine-1-carboxylate (5 g, 18.6 mmol) in AcOH (10 mL) and $CHCl_3$ (10 mL) at 0° C. was added NBS (5.0 g, 27.9 mmol) in portions. After stirring for 3 h, the reaction mixture was treated with $Na_2SO_3$ and water, followed by extraction with EtOAc. The combined organic layer was washed with brine, and dried over anhydrous $Na_2SO_4$. After filtration and concentration, the crude product was purified by column chromatography to give the title compound (5.4 g, 84%).

(c) Synthesis of tert-butyl 3-hydroxy-3-(2-(2-hydroxyphenyl)thiophen-3-yl)pyrrolidine-1-carboxylate

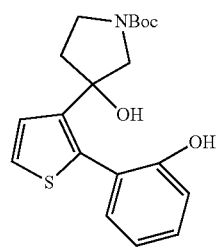 [SMILES: CC(C)(C)OC(=O)N1CCC(O)(c2ccsc2-c2ccccc2O)C1]

A mixture of tert-butyl 3-(2-bromothiophen-3-yl)-3-hydroxypyrrolidine-1-carboxylate (5 g, 13.8 mmol), $Pd(OAc)_2$ (31 mg, 0.14 mmol), $Ph_3P$ (147 mg, 0.42 mmol), 2-hydroxyphenylboronic acid (1.74 g, 27.6 mmol) and $Na_2CO_3$ (2.9 g, 27.6 mmol) in dioxane (10 mL) and water (10 mL) was refluxed under $N_2$ for 3 h. After the reaction was cooled to room temperature, the reaction mixture was extracted with EtOAc several times. The combined organic layers were washed with brine, and dried over anhydrous $Na_2SO_4$. After filtration and concentration, the crude product was purified by column chromatography to give the title compound (4.4 g, 88%).

(d) Synthesis of tert-butyl spiro[pyrrolidine-3,4'-thieno[3,2-c]chromene]-1-carboxylate

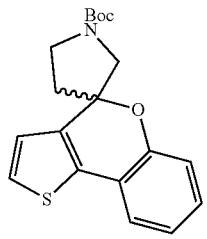 [SMILES: CC(C)(C)OC(=O)N1CCC2(C1)Oc1ccccc1-c1sccc12]

To a solution of tert-butyl 3-hydroxy-3-(2-(2-hydroxyphenyl)thiophen-3-yl)pyrrolidine-1-carboxylate (4.4 g, 12.1 mmol) in DCM (25 mL) at 0° C. was added $BF_3$ (1.6 g, 24.2 mmol) dropwise. After stirring overnight, the reaction mixture was treated with water and extracted with EtOAc several times. The combined organic layer was washed with brine, and dried over anhydrous $Na_2SO_4$. After filtration and concentration, the crude product was purified by column chromatography to give the title compound (3.8 g, 92%).

(e) Synthesis of the HCl salt of tert-butyl spiro[pyrrolidine-3,4'-thieno[3,2-c]chromene]-1-carboxylate

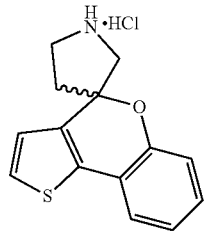 [SMILES: Cl ; c1ccc2c(c1)OC1(CCNC1)c1ccsc1-2]

The title compound was synthesized according to General Procedure N.

20. General Procedure T

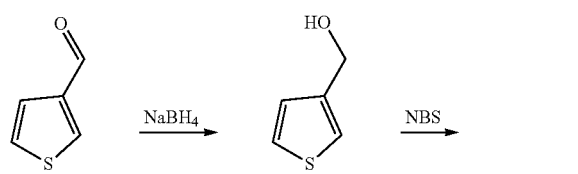

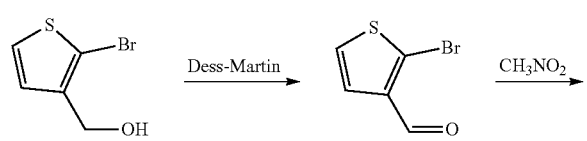

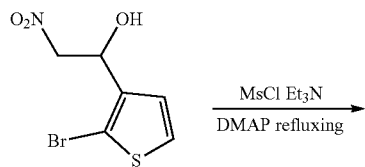

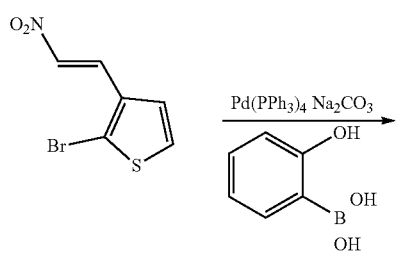

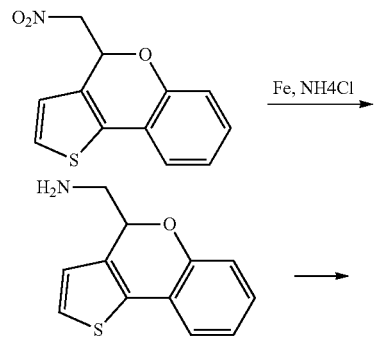

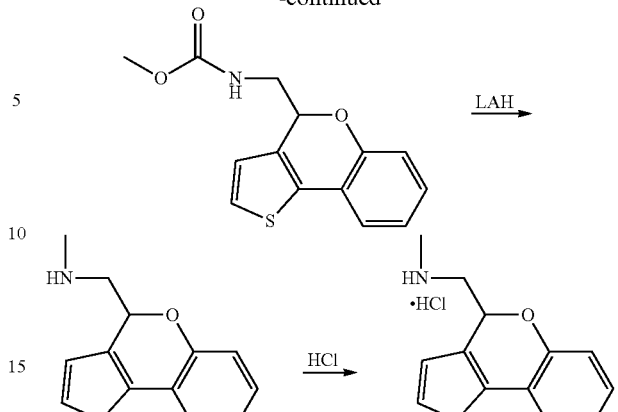

(a) Synthesis of thiophen-3-ylmethanol

To a solution of thiophene-3-carbaldehyde (10 g, 89.3 mmol) in THF (200 mL) at 0° C. was added NaBH$_4$ (1.7 g, 45.0 mmol) in portions. After stirring at 0° C. for 3 h, The reaction was quenched with water and extracted with EtOAc. The combined organic layer was washed with brine, and dried over anhydrous Na$_2$SO$_4$. After filtration and concentration, the crude product was purified by column chromatography to give the title compound (9.7 g, 95%).

(b) Synthesis of (2-bromothiophen-3-yl)methanol

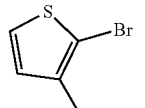

The title compound was synthesized according to General Procedure S.

(c) Synthesis of 2-bromothiophene-3-carbaldehyde

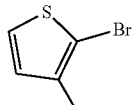

To a solution of (2-bromothiophen-3-yl)methanol (5 g, 26.3 mmol) in THF (60 mL) at 0° C. was added Dess-Martin periodinane (13.4 g, 31.6 mmol) in portions. After stirring at 0° C. for 3 h, water and Na$_2$SO$_3$ were added. The mixture was extracted with DCM, and the combined organic layers were washed with brine and dried over anhydrous Na$_2$SO$_4$.

After filtration and concentration, the crude product was purified by column chromatography to give the title compound (4.1 g, 83%).

(d) Synthesis of 1-(2-bromothiophen-3-yl)-2-nitroethanol

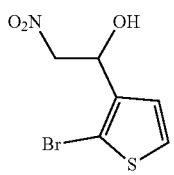 [SMILES: O=[N+]([O-])CC(O)c1ccsc1Br]

The title compound was synthesized according to General Procedure Q.

(e) Synthesis of (E)-2-bromo-3-(2-nitrovinyl)thiophene

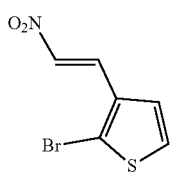

To a solution of 1-(2-bromothiophen-3-yl)-2-nitroethanol (3 g, 12.0 mmol), DMAP (146 mg, 1.2 mmol) and Et$_3$N (2.4 g, 24.0 mmol) in DCM (30 mL) was added MsCl (2.4 g, 24.0 mmol) dropwise. The resulting mixture was then refluxed for 3 h. After cooling, the reaction mixture was diluted with water and extracted with DCM. The combined organic layers were washed with brine and dried over anhydrous Na$_2$SO$_4$. After filtration and concentration, the crude product was purified by column chromatography to give the title compound (2.5 g, 88%).

(f) Synthesis of 4-(nitromethyl)-4H-thieno[3,2-c]chromene

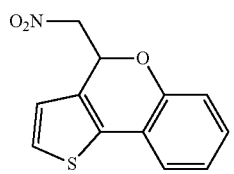 [SMILES: O=[N+]([O-])CC1Oc2ccccc2-c2sccc21]

The title compound was synthesized according to General Procedure S(c).

(g) Synthesis of (4H-thieno[3,2-c]chromen-4-yl)methanamine

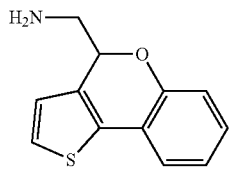

To a solution of 4-(nitromethyl)-4H-thieno[3,2-c]chromene (2.5 g, 10.7 mmol) in AcOH (20 mL) was added NH$_4$Cl (5.4 g, 100 mmol) and Fe (2.8 g, 50 mmol). After stirring overnight, the reaction mixture was filtered. The filtrate was concentrated under reduced pressure and the residue was purified by column chromatography to give the title compound (2.2 g, 96%).

(h) Synthesis of ethyl (4H-thieno[3,2-c]chromen-4-yl)methylcarbamate

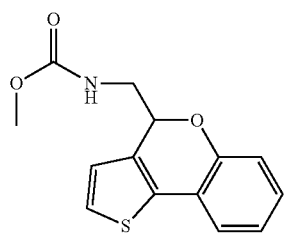 [SMILES: COC(=O)NCC1Oc2ccccc2-c2sccc21]

The title compound was synthesized according to General Procedure O.

(i) Synthesis of N-methyl-1-(4H-thieno[3,2-c]chromen-4-yl)methanamine

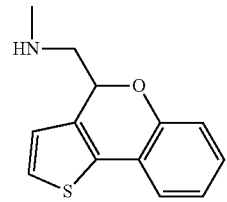 [SMILES: CNCC1Oc2ccccc2-c2sccc21]

The title compound was synthesized according to General Procedure O.

(j) Synthesis of the HCl salt of N-methyl-1-(4H-thieno[3,2-c]chromen-4-yl)methanamine

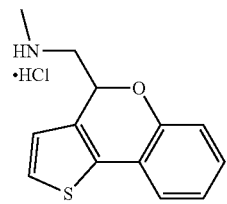 [SMILES: Cl ; CNCC1Oc2ccccc2-c2sccc21]

The title compound was synthesized according to General Procedure N.

21. General Procedure U

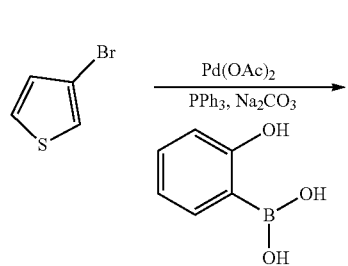

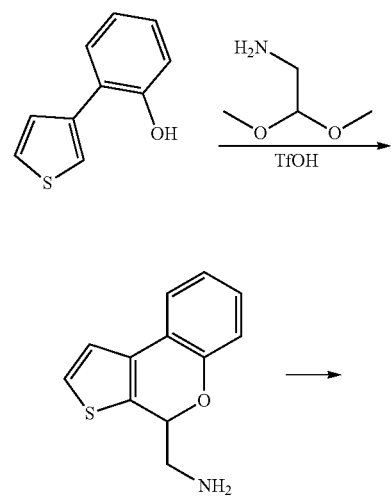

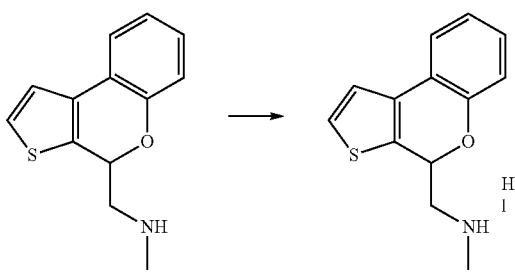

(a) Synthesis of 2-(thiophen-3-yl)phenol

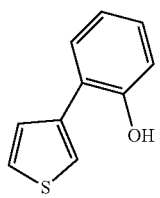 [SMILES: Oc1ccccc1-c1ccsc1]

The title compound was synthesized according to General Procedure S(c).

(b) Synthesis of (4H-thieno[2,3-c]chromen-4-yl)methanamine

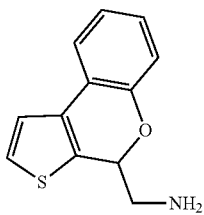 [SMILES: NCC1Oc2ccccc2-c2ccsc21]

The title compound was synthesized according to General Procedure A.

(c) Synthesis of N-methyl-1-(4H-thieno[2,3-c]chromen-4-yl)methanamine

The title compound was synthesized according to General Procedure O.

(d) Synthesis of the HCl salt of N-methyl-1-(4H-thieno[2,3-c]chromen-4-yl)methanamine

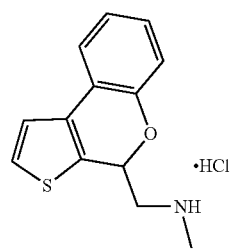 [SMILES: CNCC1Oc2ccccc2-c2ccsc21 ; Cl]

The title compound was synthesized according to General Procedure N.

22. General Procedure V

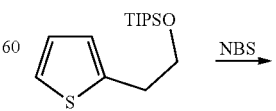

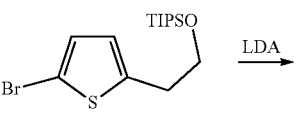

(c) Synthesis of (2-(5-bromo-4-(trifluoromethyl)thiophen-2-yl)ethoxy)triisopropylsilane

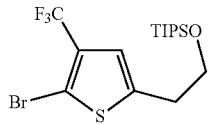

A solution of CuBr (20 mg, 0.15 mmol) and Me$_2$S (10 mg, 0.15 mmol) in DMF (10 mL) was stirred at 80° C. for 0.5 h. (2-(5-bromo-4-iodothiophen-2-yl)ethoxy)triisopropylsilane (0.35 g, 0.71 mmol) and methyl 3,3-difluoro-3-(fluorosulfonyl)propanoate (0.27 g, 1.42 mmol) were added to the reaction mixture. The reaction mixture was heated to 160° C. for 4 h. After that, the mixture was cooled and extracted with hexanes (3×20 mL). The combined organic layers were washed with brine and dried over anhydrous Na$_2$SO$_4$. After filtration and concentration, the crude product was purified by column chromatography to give the title compound.

(d) Synthesis of 1-(2-bromo-3-(trifluoromethyl)-6,7-dihydro-4H-thieno[3,2-c]pyran-4-yl)-N-methylmethanamine

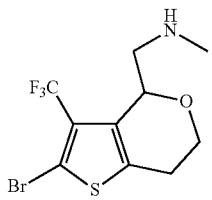 [SMILES: CNCC1OCCc2sc(Br)c(C(F)(F)F)c21]

The title compound was synthesized according to General Procedure P.

(e) Synthesis of N-methyl-1-(3-(trifluoromethyl)-6,7-dihydro-4H-thieno[3,2-c]pyran-4-yl)methanamine

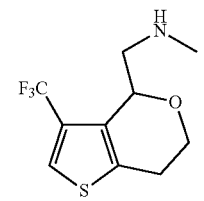

To a solution of 1-(2-bromo-3-(trifluoromethyl)-6,7-dihydro-4H-thieno[3,2-c]pyran-4-yl)-N-methylmethanamine (5 mmol) in MeOH (5 mL) was added a catalytic amount of Pd/C. A vacuum was applied and the reaction vessel was back filled with hydrogen gas three times. The resulting mixture was stirred under atmospheric H$_2$. After the reduction was completed, the reaction mixture was filtered and the filter cake was washed with methanol. The combined filtrate was concentrated and purified by column chromatography to give the desired product.

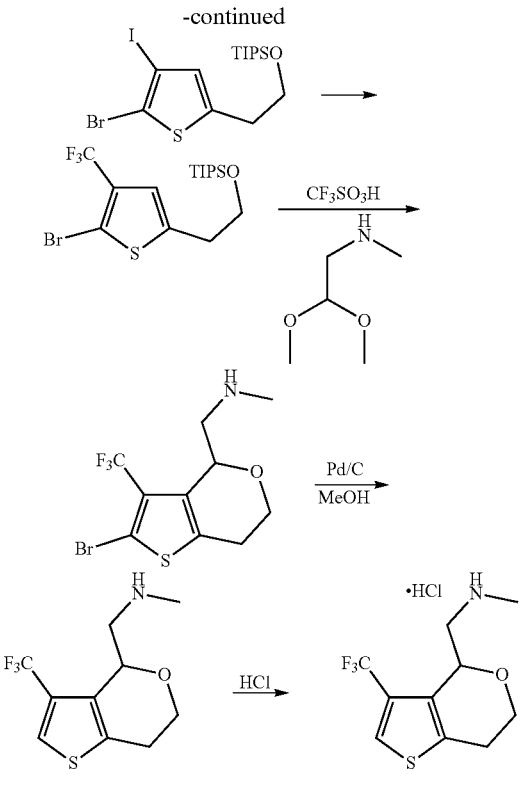

(a) Synthesis of (2-(5-bromothiophen-2-yl)ethoxy)triisopropylsilane

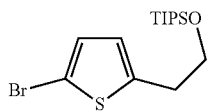

The title compound was synthesized according to General Procedure S.

(b) Synthesis of (2-(5-bromo-4-iodothiophen-2-yl)ethoxy)triisopropylsilane

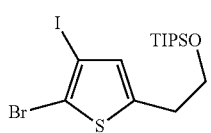

To a solution of (2-(5-bromothiophen-2-yl)ethoxy)triisopropylsilane (7.24 g, 20 mmol) in dry THF (80 mL) at −5° C. was added LDA (20 mL in THF, 30 mmol) dropwise. After stirred for 1 h, NIS (6.75 g, 30 mmol) in dry THF (20 mL) was added dropwise and the resulting mixture was stirred for another 2 h. The reaction was quenched with water (30 mL) and the resulting mixture was extracted with EtOAc (3×150 mL), washed with brine, dried over anhydrous Na$_2$SO$_4$. After filtration and concentration, the crude product was purified by column chromatography to give the title compound (5.9 g, 61%).

(f) Synthesis of the HCl salt of N-methyl-1-(3-(trifluoromethyl)-6,7-dihydro-4H-thieno[3,2-c]pyran-4-yl)methanamine

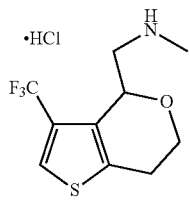

The title compound was synthesized according to General Procedure N.

23. General Procedure W

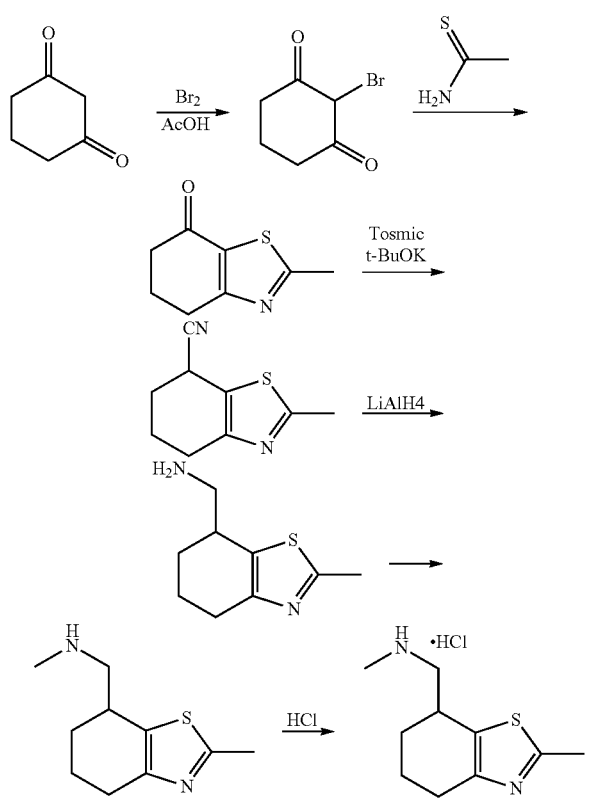

(a) Synthesis of 2-bromocyclohexane-1,3-dione

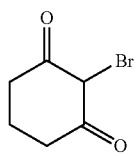

Cyclohexane-1,3-dione (11.2 g, 0.1 mol) was suspended in ice water (70 mL) and bromine (5.16 mL, 0.1 mol) was added dropwise over 5 minutes. The resulting suspension was stirred at room temperature for 3 hours. The suspension was filtered and the solid was stirred in water (200 mL) for 30 minutes. The solid was collected by vacuum filtration, rinsed with water, and dried to render crude product. The crude product was recrystallized from ethanol to produce the title compound.

(b) Synthesis of 2-methyl-5,6-dihydrobenzo[d]thiazol-7(4H)-one

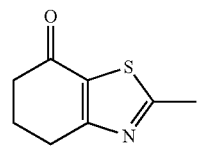

To a solution of ethanethioamide (0.75 g, 10 mmol) in ethanol (20 mL) at room temperature was added 2-bromocyclohexane-1,3-dione (1.9 g, 10 mmol) in portions. The reaction solution was refluxed for 2 hours while stirring. After removal of solvents, the residue was diluted with water and washed with diethyl ether. The separated aqueous layer was basified with sodium carbonate solution. The resulting solid was collected by vacuum filtration, rinsed with water. The solid was suspended in methanol and followed by evaporation to dryness to produce the title compound.

(c) Synthesis of 2-methyl-4,5,6,7-tetrahydrobenzo[d]thiazole-7-carbonitrile

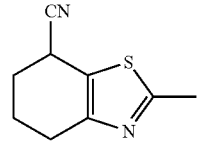

To a stirred and cooled solution of 5,6-dihydro-2-methylbenzo[d]thiazol-7(4H)-one (1.67 g, 10 mmol) and TOSMIC (2.5 g, 13 mmol) in a mixture of DME (25 mL) and absolute ethanol (25 mL) was added solid t-BuOK (2.8 g, 24 mmol) portionwise while keeping the reaction temperature between 5 and 10° C. The resulting mixture was stirred at room temperature for 30 minutes and at 30-45° C. for 30 minutes. The resulting suspension was cooled to room temperature. The precipitate (TosK) was removed by filtration and rinsed with DME. The combined DME solutions were concentrated under reduced pressure to give the crude product, which was purified by column chromatography.

(d) Synthesis of (2-methyl-4,5,6,7-tetrahydrobenzo[d]thiazol-7-yl)methanamine

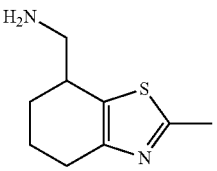

The title compound was synthesized according to General Procedure O(h).

(e) Synthesis of N-methyl-1-(2-methyl-4,5,6,7-tetrahydrobenzo[d]thiazol-7-yl)methanamine

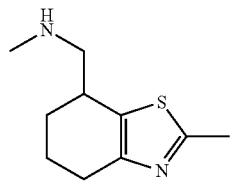

The title compound was synthesized according to General Procedure O.

(f) Synthesis of the HCl salt of N-methyl-1-(2-methyl-4,5,6,7-tetrahydrobenzo[d]thiazol-7-yl)methanamine

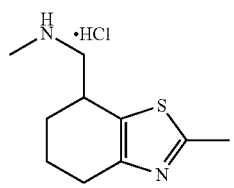

The title compound was synthesized according to General Procedure N.

24. General Procedure X

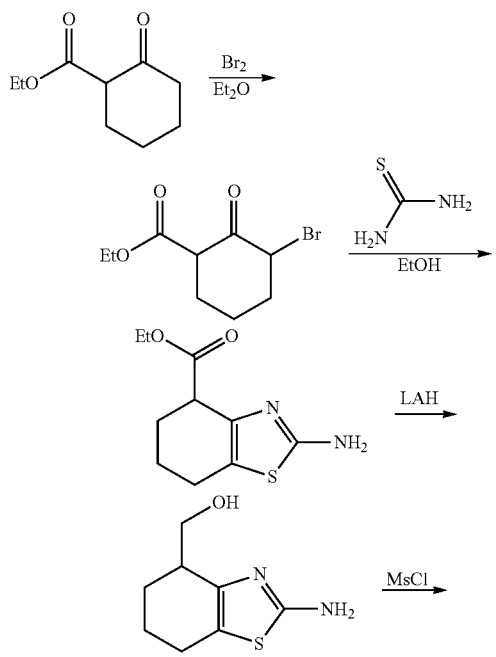

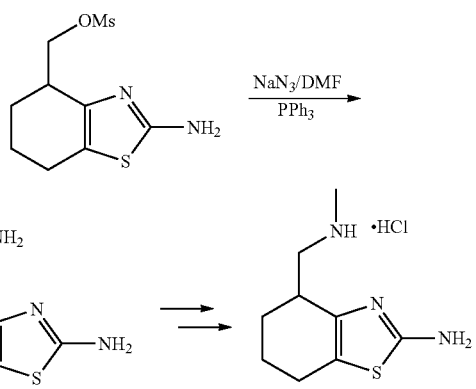

(a) Synthesis of ethyl 3-bromo-2-oxocyclohexanecarboxylate

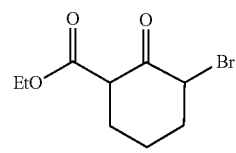

The title compound was synthesized according to General Procedure W.

(b) Synthesis of ethyl 2-amino-4,5,6,7-tetrahydrobenzo[d]thiazole-4-carboxylate

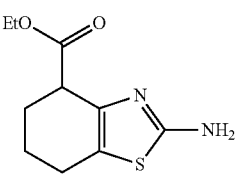 [SMILES: CCOC(=O)C1CCCc2sc(N)nc21]

The title compound was synthesized according to General Procedure W.

(c) Synthesis of (2-amino-4,5,6,7-tetrahydrobenzo[d]thiazol-4-yl)methanol

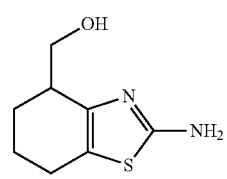 [SMILES: Nc1nc2c(s1)CCCC2CO]

The title compound was synthesized according to General Procedure O(h).

(d) Synthesis of (2-amino-4,5,6,7-tetrahydrobenzo[d]thiazol-4-yl)methyl methanesulfonate

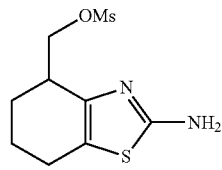 [SMILES: CS(=O)(=O)OCC1CCCc2sc(N)nc21]

To a solution of (2-amino-4,5,6,7-tetrahydrobenzo[d]thiazol-4-yl)methanol (3.3 mmol) and Et$_3$N (1.4 mL, 10 mmol) in THF (10 mL) was added MsCl (0.3 mL, 3.6 mmol) dropwise at room temperature. The resulting mixture was stirred at room temperature for 1 hr. The reaction mixture was diluted with water (200 mL), filtered, and dried to give the crude product, which was used directly in the next step without further purification.

(e) Synthesis of 4-(aminomethyl)-4,5,6,7-tetrahydrobenzo[d]thiazol-2-amine

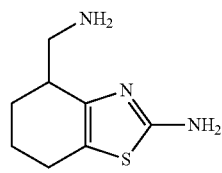

To a solution of (2-amino-4,5,6,7-tetrahydrobenzo[d]thiazol-4-yl)methyl methanesulfonate (3.3 mmol) in DMF (10 mL) was added NaN$_3$ (0.21 g, 3.3 mmol). The resulting mixture was stirred at 85° C. for 30 minutes. The mixture was poured into water (100 mL) and extracted with EtOAc. The organic extract was dried over anhydrous sodium sulfate. After filtration and concentration, the crude product was dissolved in THF (20 mL) and H$_2$O (10 mL), Na$_2$CO$_3$ (0.35 g, 3.3 mmol) and PPh$_3$ (0.8 g, 3 mmol) was added. After stirring overnight, the reaction mixture was diluted with water (100 mL) and then filtered. The filtrate was extracted with EtOAc, and the organic layer was washed with brine and dried over anhydrous sodium sulfate. After filtration and concentration, the crude product was obtained and used directly in the next step without further purification.

(f) Synthesis of N-methyl-4-((methylamino)methyl)-4,5,6,7-tetrahydrobenzo[d]thiazol-2-amine

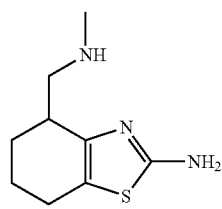

The title compound was synthesized according to General Procedure 0.

(g) Synthesis of the HCl salt of N-methyl-4-((methylamino)methyl)-4,5,6,7-tetrahydrobenzo[d]thiazol-2-amine

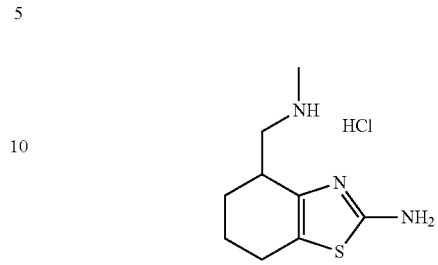

The title compound was synthesized according to General Procedure N.

25. General Procedure Y

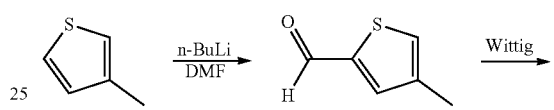

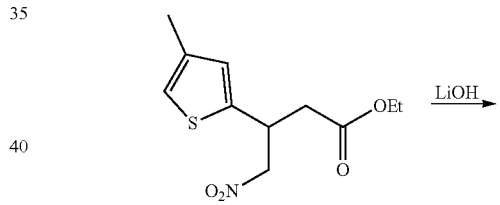

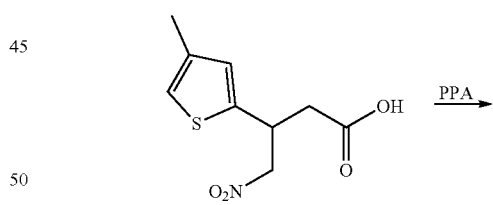

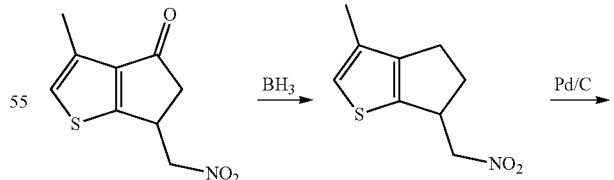

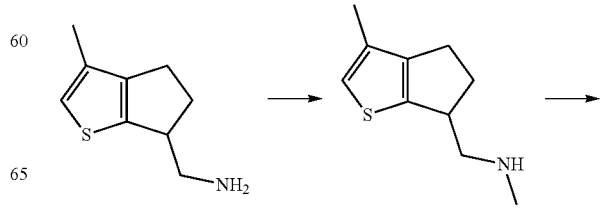

-continued

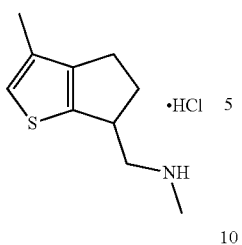

(a) Synthesis of 4-methylthiophene-2-carbaldehyde

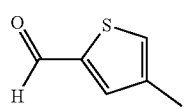

To a solution of 3-methylthiophene (1.89 g, 15.0 mmol) in dry THF (10 mL) at −65° C. was added n-BuLi (15.0 mmol) dropwise. After stirring for 30 min, DMF (3.0 g, 10.0 mmol) in dry THF (3 mL) was added dropwise and the reaction mixture was stirred at −65° C. for 2 h. The reaction was warmed to room temperature and water was added. The resulting mixture was extracted with EtOAc (3×100 mL). The combined extract was washed with brine and dried over anhydrous $Na_2SO_4$. After filtration and concentration, the crude product was purified by column chromatography to give the title compound (7.1 g, 90%).

(b) Synthesis of (E)-ethyl 3-(4-methylthiophen-2-yl) acrylate

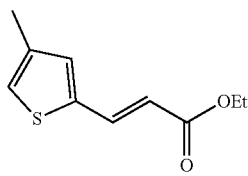

The title compound was synthesized according to General Procedure Q.

(c) Synthesis of ethyl 3-(4-methylthiophen-2-yl)-4-nitrobutanoate

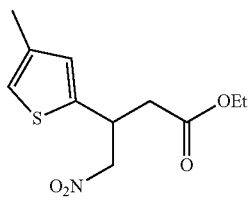 [SMILES: CCOC(=O)CC(C[N+](=O)[O-])c1cc(C)cs1]

The title compound was synthesized according to General Procedure Q.

(d) Synthesis of 3-(4-methylthiophen-2-yl)-4-nitrobutanoic acid

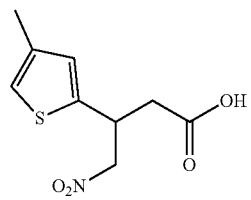

The title compound was synthesized according to General Procedure Q.

(e) Synthesis of 3-methyl-6-(nitromethyl)-5,6-dihydro-4H-cyclopenta[b]thiophen-4-one

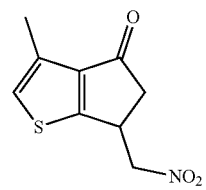

The title compound was synthesized according to General Procedure Q.

(f) Synthesis of 3-methyl-6-(nitromethyl)-5,6-dihydro-4H-cyclopenta[b]thiophene

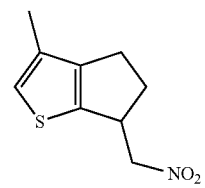

A solution of 3-methyl-6-(nitromethyl)-5,6-dihydro-4H-cyclopenta[b]thiophen-4-one (9.5 g) in $BH_3$-THF (400 mL) was stirred at room temperature overnight. TLC analysis indicated the consumption of starting material. The reaction mixture was acidified to pH 2 with 10% HCl and stirred for 2 h. The mixture was extracted with EtOAc (100 mL×3). The combined organic phase was dried with $Na_2SO_4$, and concentrated in vacuo. The crude product was purified by flash column chromatography to afford 5 g of title compound (yield: 56.4%).

(g) Synthesis of (3-methyl-5,6-dihydro-4H-cyclopenta[b]thiophen-6-yl)methanamine

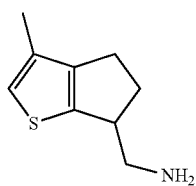

To a solution of 3-methyl-6-(nitromethyl)-5,6-dihydro-4H-cyclopenta[b]thiophene (5 g) in MeOH (100 mL) was added 10% Pd/C and the reaction was placed under a hydrogen atmosphere using a balloon. The mixture was stirred at room temperature overnight. TLC analysis indicated the consumption of starting material and the reaction mixture was filtered through a pad of Celite. The filtrate was concentrated in vacuo. The residue was resolved in Et$_2$O, and treated with gaseous HCl at 0° C. for 10 minutes. The precipitated product was collected by vacuum filtration and dried to give 4.0 g of HCl salt of the title compound.

(h) Synthesis N-methyl-1-(3-methyl-5,6-dihydro-4H-cyclopenta[b]thiophen-6-yl)methanamine

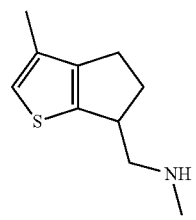

The title compound was synthesized according to General Procedure O.

(i) Synthesis of the HCl salt of N-methyl-1-(3-methyl-5,6-dihydro-4H-cyclopenta[b]thiophen-6-yl)methanamine

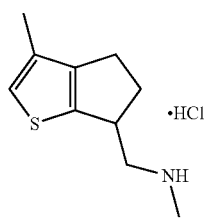

The title compound was synthesized according to General Procedure N(e).

26. General Procedure Z

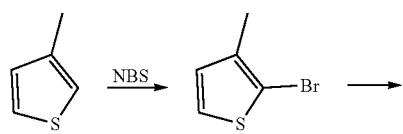

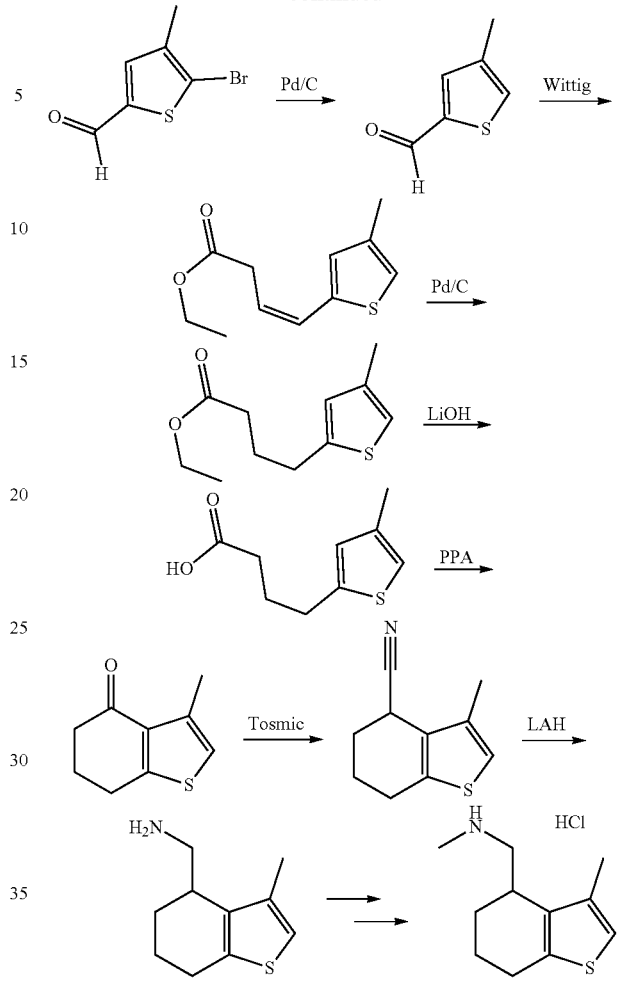

(a) Synthesis of 2-bromo-3-methylthiophene

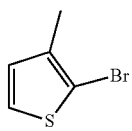

The title compound was synthesized according to General Procedure S.

(b) Synthesis of 5-bromo-4-methylthiophene-2-carbaldehyde

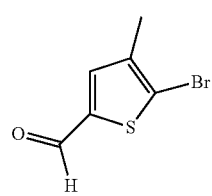

To a solution of 2-bromo-3-methylthiophene (2.66 g, 15.0 mmol) in dry THF (10 mL) at −65° C. was added LDA solution (15.0 mmol) dropwise. After stirring for 30 min, DMF (3.0 g, 10.0 mmol) in dry THF (3 mL) was added dropwise and the reaction was stirred at −65° C. for 2 h. The reaction was warmed to room temperature and water was added. The quenched mixture was extracted with EtOAc (3×100 mL). The combined extract was washed with brine and dried over anhydrous Na$_2$SO$_4$. After filtration and concentration, the crude product was purified by column chromatography to give the title compound.

(c) Synthesis of 4-methylthiophene-2-carbaldehyde

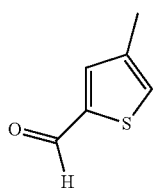

The title compound was synthesized according to General Procedure V(e).

(d) Synthesis of (Z)-ethyl 4-(4-methylthiophen-2-yl)but-3-enoate

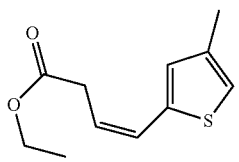

The title compound was synthesized according to General Procedure Q.

(e) Synthesis of ethyl 4-(4-methylthiophen-2-yl)butanoate

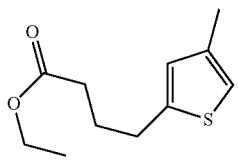

The title compound was synthesized according to General Procedure V(e).

(f) Synthesis of 4-(4-methylthiophen-2-yl)butanoic acid

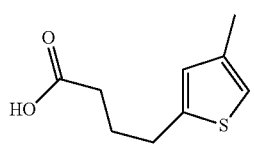

The title compound was synthesized according to General Procedure Q.

(g) Synthesis of 3-methyl-6,7-dihydrobenzo[b]thiophen-4(5H)-one

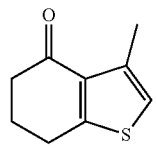

The title compound was synthesized according to General Procedure Q.

(h) Synthesis of 3-methyl-4,5,6,7-tetrahydrobenzo[b]thiophene-4-carbonitrile

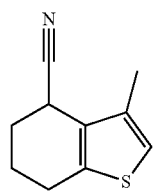

The title compound was synthesized according to General Procedure W.

(i) Synthesis of (3-methyl-4,5,6,7-tetrahydrobenzo[b]thiophen-4-yl)methanamine

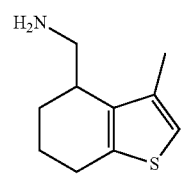

The title compound was synthesized according to General Procedure W.

(j) Synthesis of N-methyl-1-(3-methyl-4,5,6,7-tetrahydrobenzo[b]thiophen-4-yl)methanamine

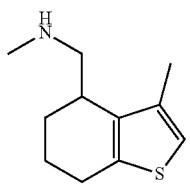

The title compound was synthesized according to General Procedure O.

123

(k) Synthesis of the HCl salt of N-methyl-1-(3-methyl-4,5,6,7-tetrahydrobenzo[b]thiophen-4-yl)methanamine

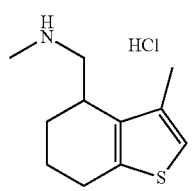

The title compound was synthesized according to General Procedure N.

27. General Procedure AA

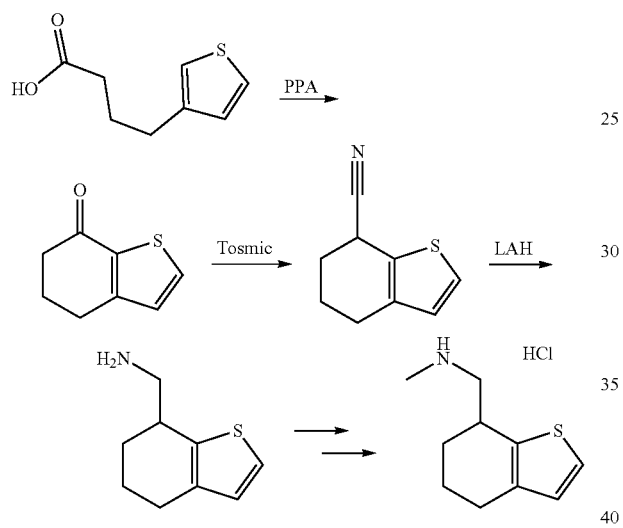

The above compounds, 4-(thiophen-3-yl)butanoic acid, 5,6-dihydrobenzo[b]thiophen-7(4H)-one, 4,5,6,7-tetrahydrobenzo[b]thiophene-7-carbonitrile, (4,5,6,7-tetrahydrobenzo[b]thiophen-7-yl)methanamine, and N-methyl-1-(4,5,6,7-tetrahydrobenzo[b]thiophen-7-yl)methanamine, were synthesized according to General Procedure Z. The HC salt of N-methyl-1-(4,5,6,7-tetrahydrobenzo[b]thiophen-7-yl)methanamine was synthesized according to General Procedure N.

28. General Procedure BB

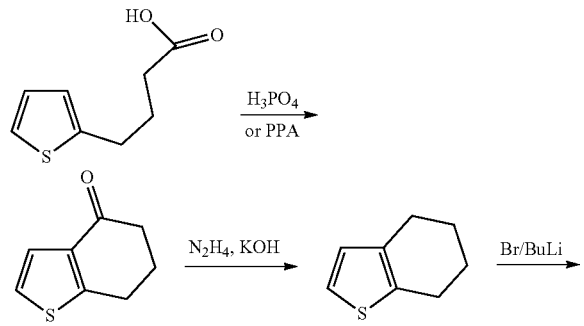

124

-continued

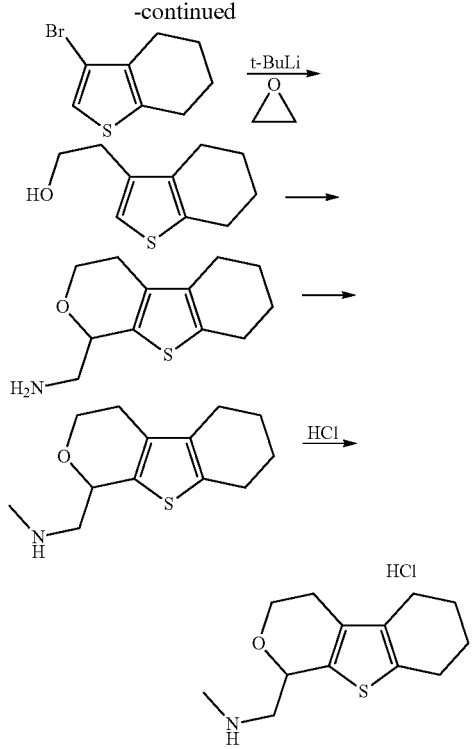

(a) Synthesis of 6,7-dihydrobenzo[b]thiophen-4(5H)-one

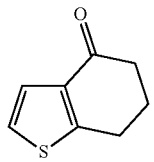

The title compound was synthesized according to General Procedures Q and Z.

(b) Synthesis of 4,5,6,7-tetrahydrobenzo[b]thiophene

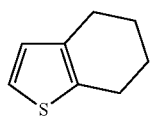

A mixture of the starting material (4.93 mmol), ethylene glycol (3.6 mL), 88% KOH (0.55 g, 9.8 mol), and 85% hydrazine hydrate (0.62 mL) was refluxed for about half an hour. The condenser was then removed to allow the aqueous liquor to evaporate. The temperature of the reaction mixture reached about 200° C. After the reaction mixture refluxed overnight, it was cooled, diluted with water and extracted with ether. The combined ether solution was concentrated under reduced pressure to give the crude product, which was purified by column chromatography.

(c) Synthesis of 3-bromo-4,5,6,7-tetrahydrobenzo[b]thiophene

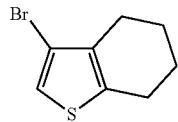

The title compound was synthesized according to General Procedure T.

(d) Synthesis of 2-(4,5,6,7-tetrahydrobenzo[b]thiophen-3-yl)ethanol

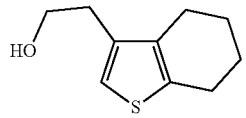

The title compound was synthesized according to General Procedure P.

(e) Synthesis of 4,5,6,7-tetrahydrobenzo[b]thiophene[2,3-c]pyran-7-yl)amine

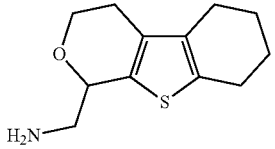

The title compound was synthesized according to General Procedure B.

(f) Synthesis of 4,5,6,7-tetrahydrobenzo[b]thiophene[2,3-c]pyran-7-yl)methanamine

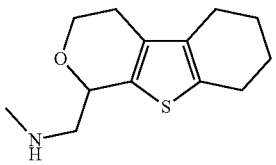 [SMILES: CNCC1OCCc2c1sc1c2CCCC1]

The title compound was synthesized according to General Procedure O(g, h).

(g) Synthesis of 4,5,6,7-tetrahydrobenzo[b]thiophene[2,3-c]pyran-7-yl)methanamine

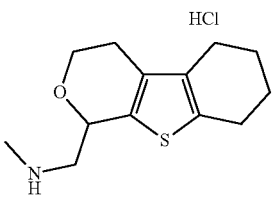 [SMILES: Cl ; CNCC1OCCc2c1sc1c2CCCC1]

The title compound was synthesized according to General Procedure N(e).

29. General Procedure CC

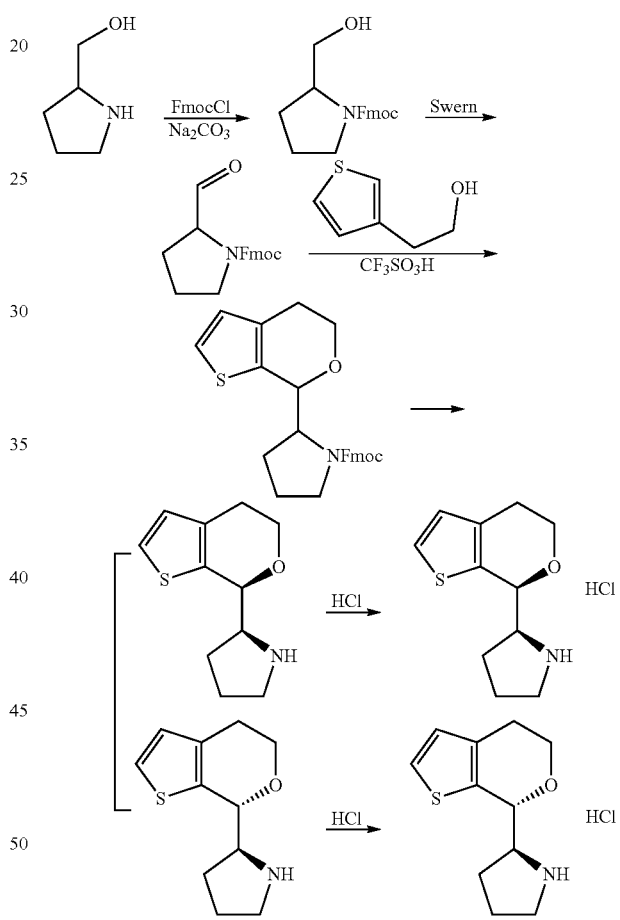

(a) Synthesis of (S)-(9H-fluoren-9-yl)methyl 2-(hydroxymethyl)pyrrolidine-1-carboxylate

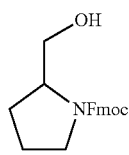

The title compound was synthesized according to General Procedure O using pyrrolidin-2-ylmethanol as starting material.

(b) Synthesis of (S)-(9H-fluoren-9-yl)methyl 2-formylpyrrolidine-1-carboxylate

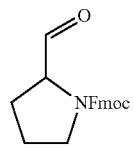

The title compound was synthesized according to General Procedure O.

(c) Synthesis of (S)-(9H-fluoren-9-yl)methyl 2-((R)-5,7-dihydro-4H-thieno[2,3-c]pyran-7-yl)pyrrolidine-1-carboxylate

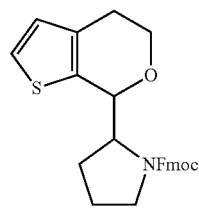

The title compound was synthesized according to General Procedure B. Diasteromeric products were separated at this stage by RP-HPLC.

(d) Synthesis of (S)-2-((R)-5,7-dihydro-4H-thieno[2,3-c]pyran-7-yl)pyrrolidine

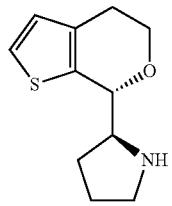 [SMILES: c1cc2c(s1)[C@@H]([C@@H]1CCCN1)OCC2]

The title compound was synthesized according to General Procedure N(d).

(e) Synthesis of the HCl salt of (S)-2-((R)-5,7-dihydro-4H-thieno[2,3-c]pyran-7-yl)pyrrolidine

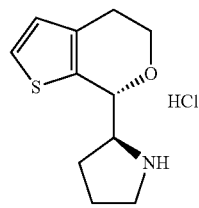 [SMILES: c1cc2c(s1)[C@@H]([C@@H]1CCCN1)OCC2 ; Cl]

The title compound was synthesized according to General Procedure N(d).

30. General Procedure DD

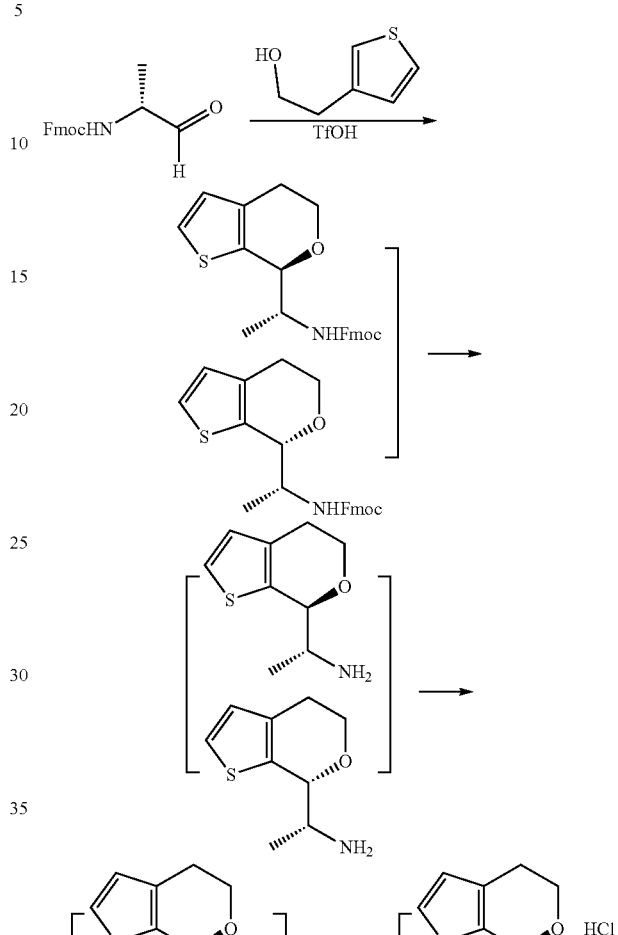

(a) (9H-fluoren-9-yl)methyl (R)-1-((S)-5,7-dihydro-4H-thieno[2,3-c]pyran-7-yl)ethylcarbamate

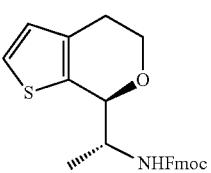

The title compound was synthesized according to General Procedure O.

(b) (R)-1-((S)-5,7-dihydro-4H-thieno[2,3-c]pyran-7-yl)ethanamine

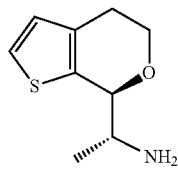

The title compound was synthesized according to General Procedure O.

(c) Synthesis of (R)-1-((S)-5,7-dihydro-4H-thieno[2,3-c]pyran-7-yl)-N-methylethanamine

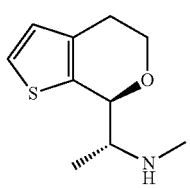

The title compound was synthesized according to General Procedure O.

(d) Synthesis of the HCl salt of (R)-1-((S)-5,7-dihydro-4H-thieno[2,3-c]pyran-7-yl)-N-methylethanamine

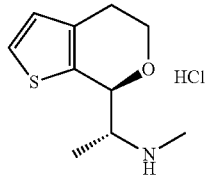

The title compound was synthesized according to General Procedure O.

31. General Procedure EE

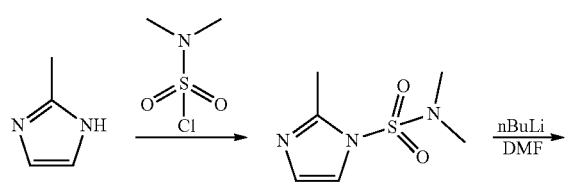

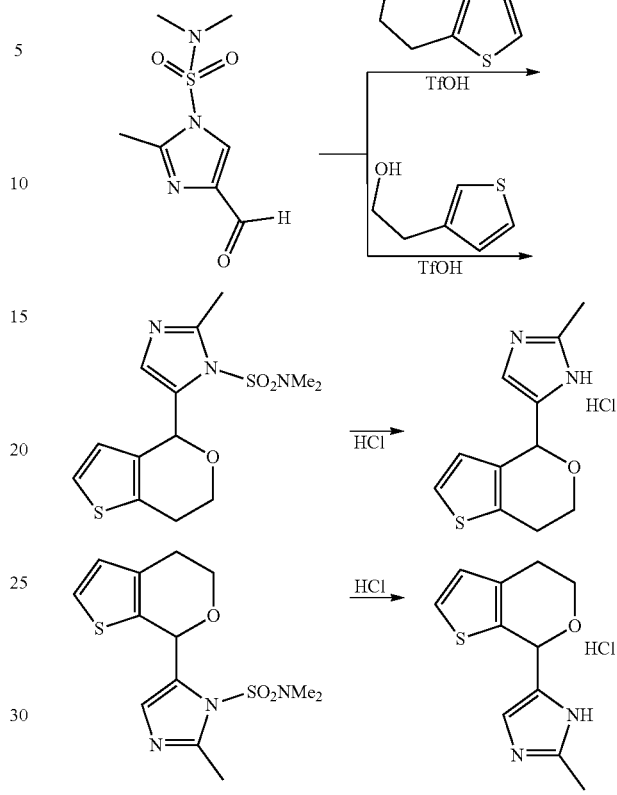

(a) Synthesis of N,N,2-trimethyl-1H-imidazole-1-sulfonamide

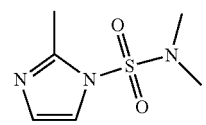

The title compound was synthesized according to *J Org. Chem.* 1989, 54, 1256.

(b) Synthesis of 5-formyl-N,N,2-trimethyl-1H-imidazole-1-sulfonamide

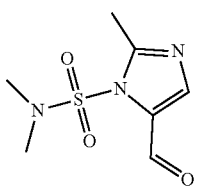

The title compound was synthesized according to General Procedure Y.

(c) Synthesis of 5-(6,7-dihydro-4H-thieno[3,2-c]pyran-4-yl)-N,N,2-trimethyl-1H-imidazole-1-sulfonamide and 5-(5,7-dihydro-4H-thieno[2,3-c]pyran-7-yl)-N,N,2-trimethyl-1H-imidazole-1-sulfonamide

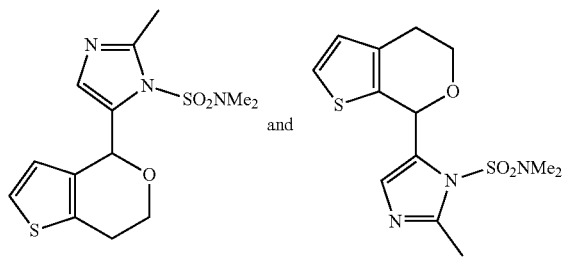

The title compound was synthesized according to General Procedure A and B.

(d) Synthesis of HCl salt of 5-(6,7-dihydro-4H-thieno[3,2-c]pyran-4-yl)-N,N,2-trimethyl-1H-imidazole-1-sulfonamide and 5-(5,7-dihydro-4H-thieno[2,3-c]pyran-7-yl)-N,N,2-trimethyl-1H-imidazole-1-sulfonamide

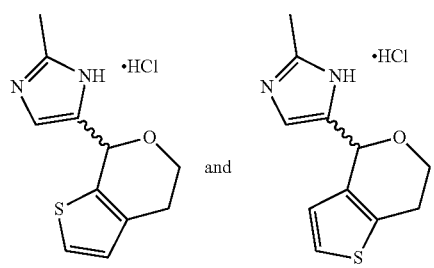

The title compound was synthesized according to General Procedure J(e).

32. General Procedure FF

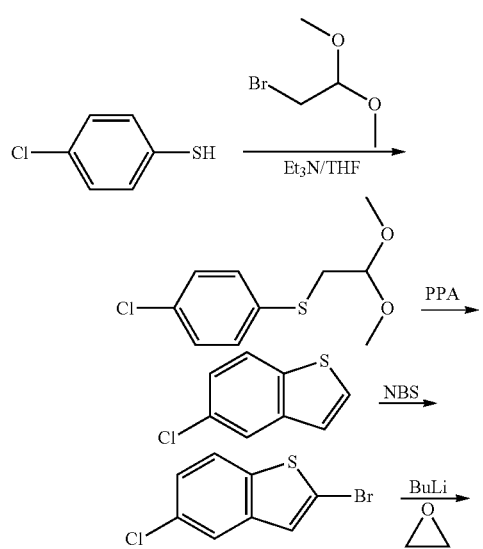

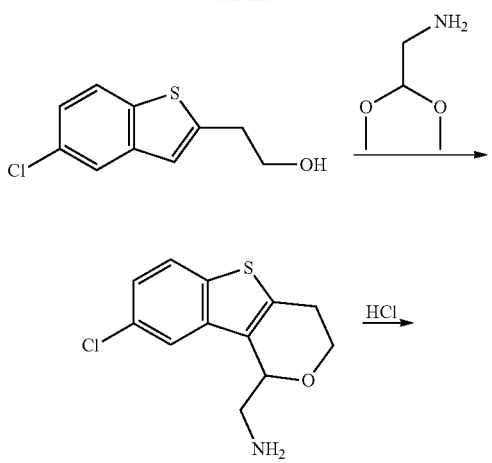

(a) Synthesis of (4-chlorophenyl)(2,2-dimethoxyethyl)sulfane

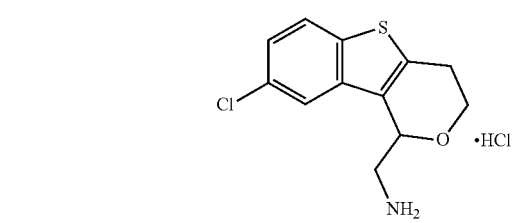

To a solution of 4-chlorobenzenethiol (13 mmol) and Et₃N (1.4 g, 13 mmol) in THF (25 mL) at room temperature was added 2-bromo-1,1-dimethoxyethane (2.36 g, 13 mmol) in THF (5 mL). After stirring at room temperature for 30 minutes, the reaction mixture was poured into water (200 mL) and extracted with diethyl ether (3×150 mL). The combined organic layer was dried over Na₂SO₄. After filtration and concentration, the crude product was purified by column chromatography to give the title compound.

(b) Synthesis of 5-chlorobenzo[b]thiophene

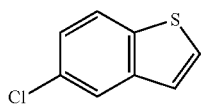

The title compound was synthesized in the presence of PPA according to General Procedure Q(e).

(c) Synthesis of 2-bromo-5-chlorobenzo[b]thiophene

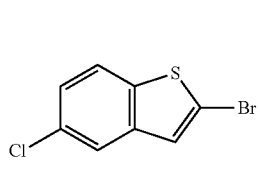 [SMILES: Clc1ccc2sc(Br)cc2c1]

The title compound was synthesized according to General Procedure S.

(d) Synthesis of 2-(5-chlorobenzo[b]thiophen-2-yl)ethanol

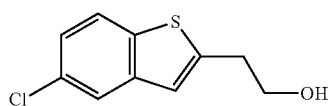 [SMILES: OCCc1cc2cc(Cl)ccc2s1]

The title compound was synthesized according to General Procedure A(a).

(e) Synthesis of 2-(5-chlorobenzo[b]thiophen[3,2-c]pyran-4-yl)methanamine

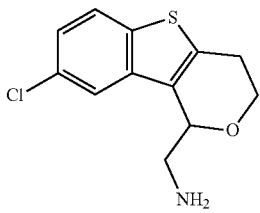 [SMILES: NCC1OCCc2sc3ccc(Cl)cc3c21]

The title compound was synthesized according to General Procedure A(b).

(f) Synthesis of the HCl salt of 2-(5-chlorobenzo[b]thiophen[3,2-c]pyran-4-yl)methanamine

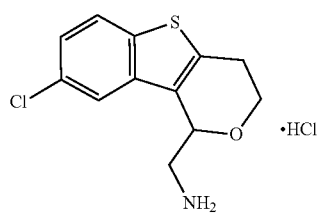 [SMILES: NCC1OCCc2sc3ccc(Cl)cc3c21 ; Cl]

The title compound was synthesized according to General Procedure N.

33. General Procedure GG

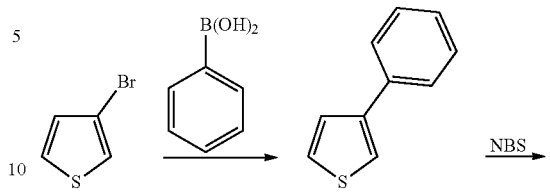

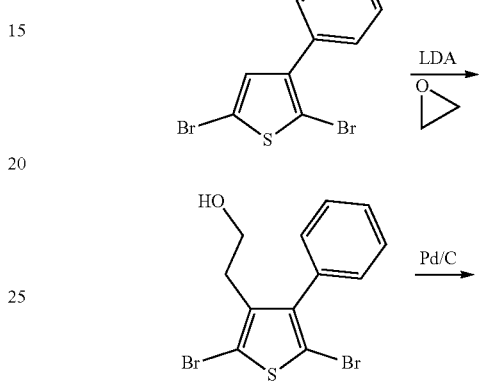

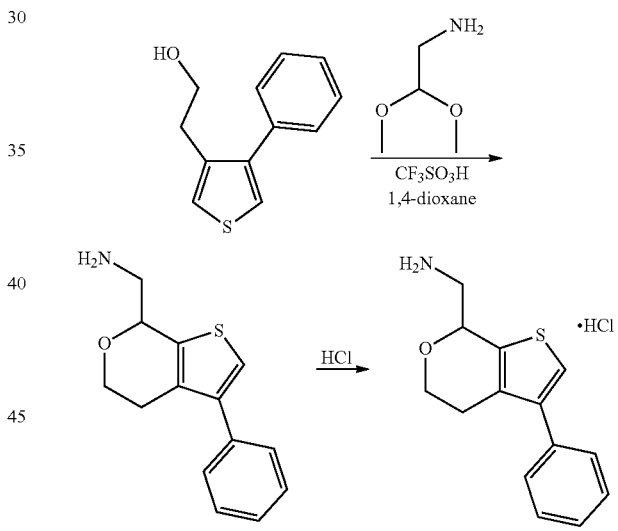

(a) Synthesis of 3-phenylthiophene

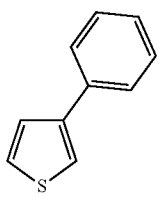 [SMILES: c1ccc(-c2ccsc2)cc1]

The title compound was synthesized according to General Procedure U.

(b) Synthesis of 2,5-dibromo-3-phenylthiophene

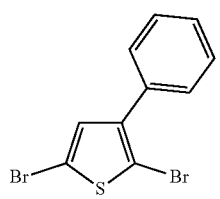 [SMILES: Brc1cc(-c2ccccc2)c(Br)s1]

The title compound was synthesized according to General Procedure S.

(c) Synthesis of 2,5-dibromo-3-ethyl-4-phenylthiophene

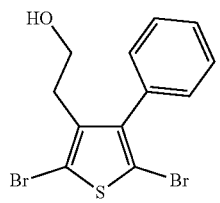 [SMILES: OCCc1c(Br)sc(Br)c1-c1ccccc1]

To a solution of 2,5-dibromo-3-phenylthiophene (2.54 g, 8.0 mmol) in dry THF (30 mL) at −65° C. was added LDA (8.8 mmol) dropwise. After stirring for 30 min at −65° C., oxirane (20.0 mmol) was added and the reaction was stirred for 2 h. The reaction mixture was then warmed to room temperature and water was added. The resulting mixture was extracted with EtOAc (3×100 mL), washed with brine, and dried over anhydrous $Na_2SO_4$. After filtration and concentration, the crude product was purified by column chromatography to give the title compound.

(d) Synthesis of 2-(4-phenylthiophen-3-yl)ethanol

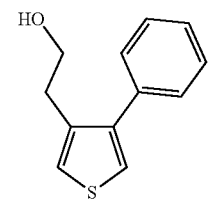 [SMILES: OCCc1cscc1-c1ccccc1]

The title compound was synthesized according to General Procedure V.

(e) Synthesis of N-methyl-1-(3-phenyl-5,7-dihydro-4H-thieno[2,3-c]pyran-7-yl)methanamine

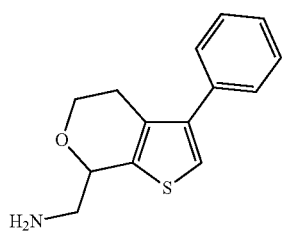 [SMILES: NCC1OCCc2c(-c3ccccc3)csc21]

The title compound was synthesized according to General Procedure B.

(f) Synthesis of the HCl salt of N-methyl-1-(3-phenyl-5,7-dihydro-4H-thieno[2,3-c]pyran-7-yl)methanamine

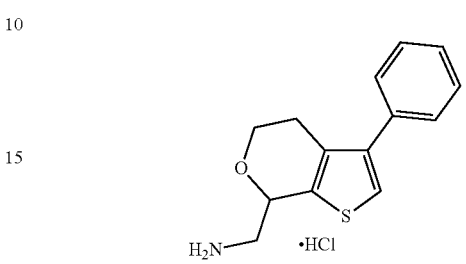

The title compound was synthesized according to General Procedure N.

34. General Procedure HH

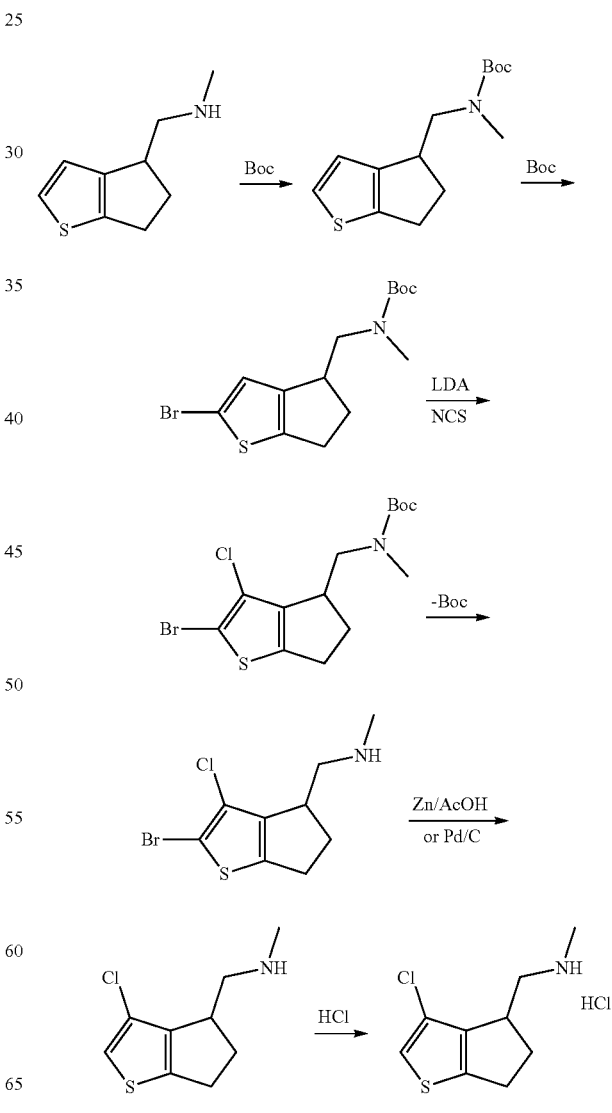

(a) Synthesis of tert-butyl (5,6-dihydro-4H-cyclopenta[b]thiophen-4-yl)methyl(methyl)carbamate

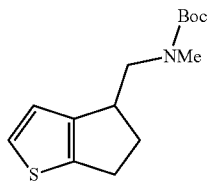 [SMILES: CN(CC1CCc2sccc21)C(=O)OC(C)(C)C]

The title compound was Boc-protected from the appropriate secondary amine according to General Procedure M.

(b) Synthesis of tert-butyl (2-bromo-5,6-dihydro-4H-cyclopenta[b]thiophen-4-yl)methyl(methyl)carbamate

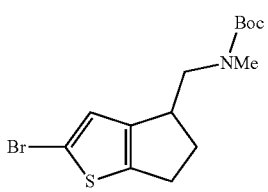 [SMILES: CN(CC1CCc2sc(Br)cc21)C(=O)OC(C)(C)C]

The title compound was synthesized according to General Procedure V.

(c) Synthesis of tert-butyl (2-bromo-3-chloro-5,6-dihydro-4H-cyclopenta[b]thiophen-4-yl)methyl(methyl)carbamate

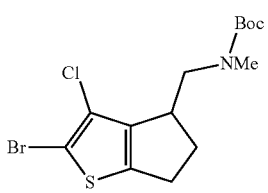

The title compound was synthesized according to General Procedure V.

(d) Synthesis of 1-(2-bromo-3-chloro-5,6-dihydro-4H-cyclopenta[b]thiophen-4-yl)-N-methylmethanamine

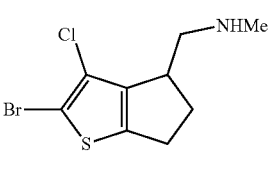 [SMILES: CNCC1CCc2sc(Br)c(Cl)c21]

The title compound was synthesized according to General Procedure J.

(e) Synthesis of 1-(3-chloro-5,6-dihydro-4H-cyclopenta[b]thiophen-4-yl)-N-methylmethanamine

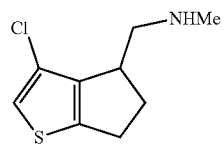 [SMILES: CNCC1CCc2scc(Cl)c21]

The title compound was synthesized according to General Procedure V.

(f) Synthesis of the HCl salt of 1-(3-chloro-5,6-dihydro-4H-cyclopenta[b]thiophen-4-yl)-N-methylmethanamine

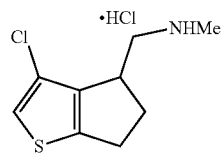 [SMILES: Cl ; CNCC1CCc2scc(Cl)c21]

The title compound was synthesized according to General Procedure N.

35. General Procedure II

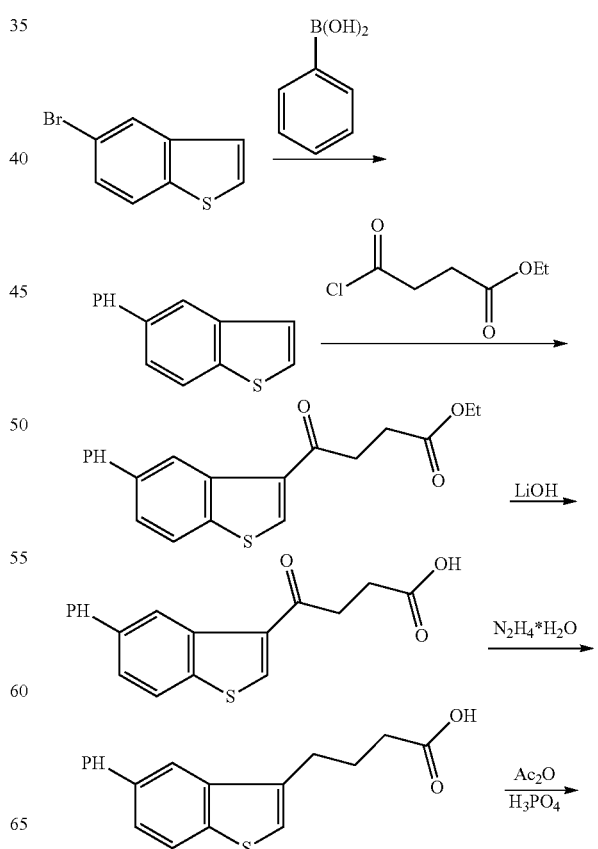

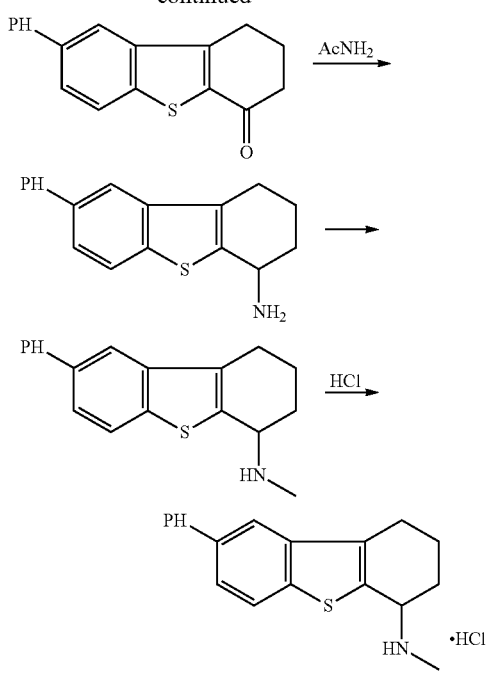

(a) Synthesis of 5-phenylbenzo[b]thiophene

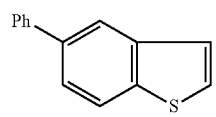

The title compound was synthesized according to General Procedure S(c).

(b) Synthesis of ethyl 4-oxo-4-(5-phenylbenzo[b]thiophen-3-yl)butanoate

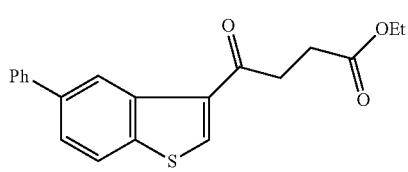 [SMILES: CCOC(=O)CCC(=O)c1csc2ccc(-c3ccccc3)cc12]

To a solution of 5-phenylbenzo[b]thiophene (1.05 g, 5.0 mmol, 1 eq) in DCM (100 mL) at 0° C. was added ethyl 4-chloro-4-oxobutanoate (0.9 g, 21.4 mmol). The resulting mixture was stirred at 0° C. for 30 minutes. SnCl$_4$ (2.3 mL, 6.0 mmol, 1.2 eq) was added and the mixture was stirred at room temperature overnight. The reaction mixture was quenched with aqueous HCl solution (50 mL, 3 M) and extracted with diethyl ether. The combined organic layers were dried over Na$_2$SO$_4$. After filtration and concentration, the crude product was purified by column chromatography to give the title compound.

(c) Synthesis of 4-oxo-4-(5-phenylbenzo[b]thiophen-3-yl)butanoic acid

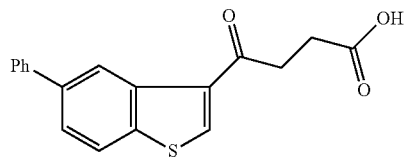 [SMILES: O=C(O)CCC(=O)c1csc2ccc(-c3ccccc3)cc12]

The title compound was synthesized according to General Procedure Q.

(d) Synthesis of 4-(5-phenylbenzo[b]thiophen-3-yl)butanoic acid

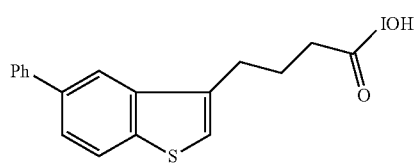

The title compound was synthesized according to General Procedure BB.

(e) Synthesis of 8-phenyl-2,3-dihydrodibenzo[b,d]thiophen-4(1H)-one

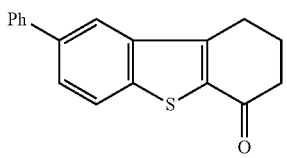 [SMILES: O=C1CCCc2c1sc1ccc(-c3ccccc3)cc21]

The title compound was synthesized according to General Procedure BB.

(f) Synthesis of 8-phenyl-1,2,3,4-tetrahydrodibenzo[b,d]thiophen-4-amine

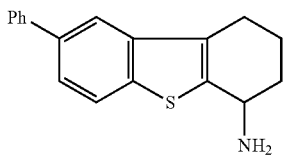 [SMILES: NC1CCCc2c1sc1ccc(-c3ccccc3)cc21]

To a solution of 8-phenyl-2,3-dihydrodibenzo[b,d]thiophen-4(1H)-one (0.28 g, 1.0 mmol, 1 eq), ammonium acetate (0.77 g, 10 eq) in MeOH (20 mL) was added NaBH$_3$CN (160 mg, 2.5 eq) in one portion. The reaction mixture was heated to 50° C. and stirred for 20 h, After that the solvent was removed, diluted with saturated NaHCO$_3$ and extracted with ethyl acetate (3×50 mL). The combined organic layers were dried over Na$_2$SO$_4$. After filtration and concentration, the residue was purified by silica gel chromatography to give the title compound (64 mg, 23%).

(g) Synthesis of N-methyl-8-phenyl-1,2,3,4-tetrahydrodibenzo[b,d]thiophen-4-amine

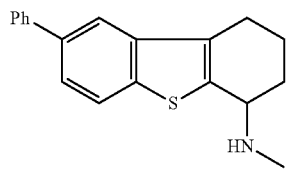 [SMILES: CNC1CCCc2c1sc1ccc(-c3ccccc3)cc21]

The title compound was synthesized according to General Procedure O.

(h) Synthesis of HCl salt of N-methyl-8-phenyl-1,2,3,4-tetrahydrodibenzo[b,d]thiophen-4-amine

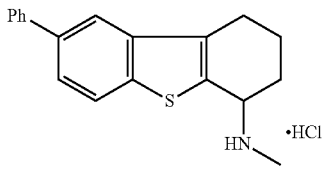 [SMILES: CNC1CCCc2c1sc1ccc(-c3ccccc3)cc21 ; Cl]

The title compound was synthesized according to General Procedure N.

36. General Procedure JJ

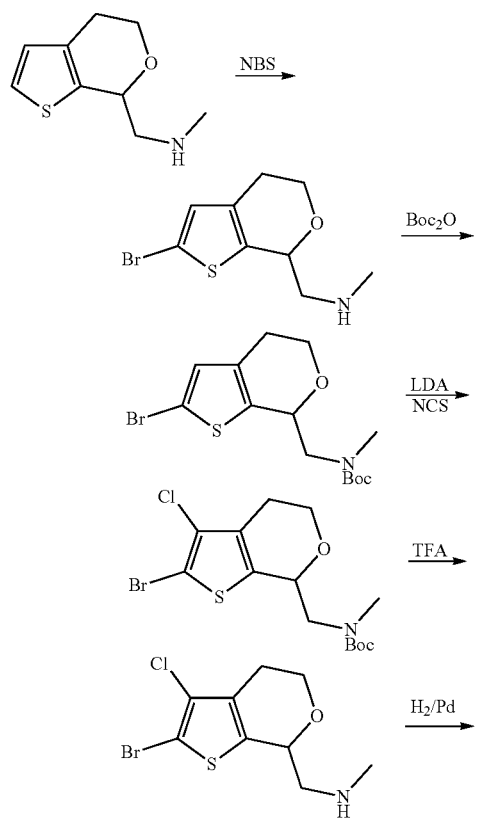

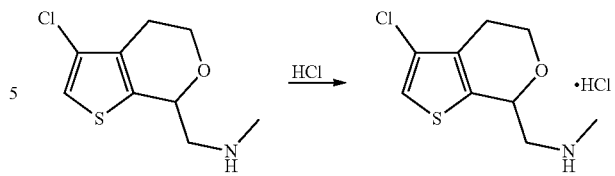

(a) Synthesis of 1-(2-bromo-5,7-dihydro-4H-thieno[2,3-c]pyran-7-yl)-N-methylmethanamine

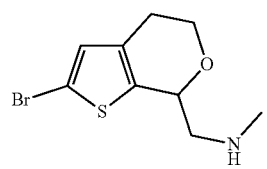

The title compound was synthesized according to General Procedure S.

(b) Synthesis of tert-butyl (2-bromo-5,7-dihydro-4H-thieno[2,3-c]pyran-7-yl)methyl(methyl)carbamate

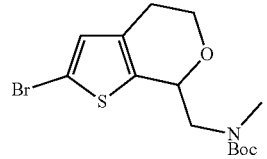 [SMILES: CN(CC1OCCc2cc(Br)sc21)C(=O)OC(C)(C)C]

The title compound was Boc-protected according to General Procedure M.

(c) Synthesis of tert-butyl (2-bromo-3-chloro-5,7-dihydro-4H-thieno[2,3-c]pyran-7-yl)methyl(methyl)carbamate

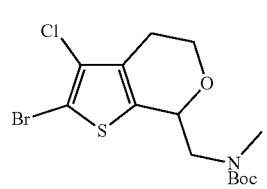 [SMILES: CN(CC1OCCc2c1sc(Br)c2Cl)C(=O)OC(C)(C)C]

The title compound was synthesized according to General Procedure HH.

(d) Synthesis of 1-(2-bromo-3-chloro-5,7-dihydro-4H-thieno[2,3-c]pyran-7-yl)-N-methylmethanamine

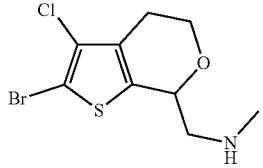

The title compound was synthesized according to General Procedure J(e).

(e) Synthesis of 1-(3-chloro-5,7-dihydro-4H-thieno[2,3-c]pyran-7-yl)-N-methylmethanamine

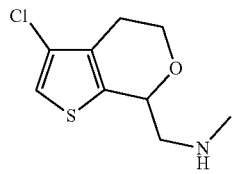

The title compound was synthesized according to General Procedure V(e).

(f) Synthesis of HCl salt of 1-(3-chloro-5,7-dihydro-4H-thieno[2,3-c]pyran-7-yl)-N-methylmethanamine

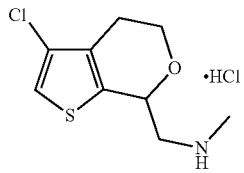

The title compound was synthesized according to General Procedure N.

37. General Procedure KK

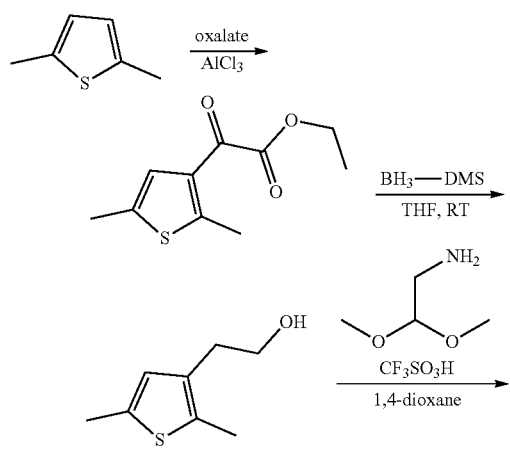

(a) Synthesis of ethyl 2-(2,5-dimethylthiophen-3-yl)-2-oxoacetate

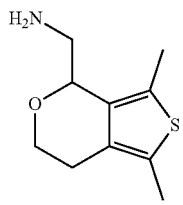

To a solution of AlCl$_3$ (29.5 g, 221 mmol) in CH$_2$Cl$_2$ (150 mL) was added 2,5-dimethyl thiophene (6.2 g, 55 mmol) followed by ethyl 2-chloro-2-oxoacetate (15.1 g, 110 mmol). The resulting mixture was stirred at room temperature for 12 h at which time the reaction mixture was filtered, diluted carefully with H$_2$O and extracted with EtOAc. Removal of volatiles afforded mostly pure crude material, which was used in the next step without further purification.

(b) Synthesis of 2-(2,5-dimethylthiophen-3-yl)ethanol

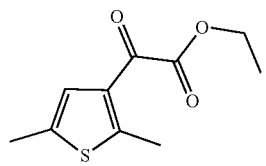

Ethyl 2-(2,5-dimethylthiophen-3-yl)-2-oxoacetate was reduced at ambient temperature using excess BH$_3$-DMS in THF over 18 h. Standard work-up protocols and purification by column chromatography on silica afforded the desired alcohol product.

(c) Synthesis of (1,3-dimethyl-6,7-dihydro-4H-thieno[3,4-c]pyran-4-yl)methanamine

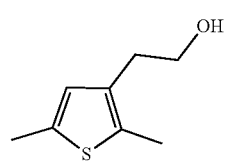

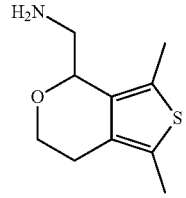

The title compound was synthesized according to General Procedure D.

B. General Procedure CS (Chiral Separation)

Normal phase chiral separation of the racemic compounds disclosed herein was carried out using Chiral Technologies AS, AD, OJ and OD columns and the specified solvent system.

The following abbreviations were used:

IHD 5=5% isopropanol/95% hexanes/0.1% diethylamine;

IHD 10=10% isopropanol/90% hexanes/0.1% diethylamine;

MEHD 5=2.5% Methanol/2.5% ethanol/95% hexanes/0.1% diethylamine; and

MEHD 2.5=1.25% ethanol/1.25% methanol/97.5% hexanes/0.1% diethylamine.

The Faster Moving Enantiomer (FME) was the earlier eluting enantiomer and the Slower Moving Enantiomer (SME) was the later eluting enantiomer. When the free primary or secondary amines disclosed herein were not separable by column chromatography, they were N-BOC or N-TROC protected using standard methods and then separated by column chromatography, which typically improved the separation. Following separation of the protected amines, the protecting groups were removed using standard methods (e.g., HCl for BOC, Zn dust/$NH_4Cl$ for TROC).

SFC (supercritical $CO_2$ fluid chromatography) chiral separation was done using the specified column and co-solvent and $CO_2$ total flows were between 60 to 80 g/minute.

C. Compounds

The following compounds were prepared using the above general procedures.

| Compd. No. | Structure | Salt or FB* | Method of Preparation | Analytical Data |
|---|---|---|---|---|
| 1 | H₂N-CH₂-[pyranothiophene] | HCl | A | $^1$H NMR (CD$_3$OD): 7.29 (d, J = 5.0 Hz, 1H), 6.89 (d, J = 5.0 Hz, 1H), 4.94 (d, J = 8.0 Hz, 1H), 4.29-4.23 (m, 1H), 3.85-3.78 (m, 1H), 3.46 (d, J = 13.0 Hz, 1H), 3.14 (dd, J = 9.5, 11.5 Hz, 1H), 3.05-2.97 (m, 1H), 2.80 (d, J = 16.0 Hz, 1H). |
| 2 | H₂N-CH₂-[pyranothiophene] | HCl | CS; BOC deriv of compound 1 was FME with OD and IHD 5 | $^1$H NMR (CD$_3$OD): 7.29 (d, J = 5.0 Hz, 1H), 6.89 (d, J = 5.0 Hz, 1H), 4.94 (d, J = 8.0 Hz, 1H), 4.29-4.23 (m, 1H), 3.85-3.78 (m, 1H), 3.46 (d, J = 13.0 Hz, 1H), 3.14 (dd, J = 9.5, 11.5 Hz, 1H), 3.05-2.97 (m, 1H), 2.80 (d, J = 16.0 Hz, 1H). |
| 3 | H₂N-CH₂-[pyranothiophene] | HCl | CS; BOC deriv of compound 1 was SME with OD and IHD 5 | $^1$H NMR (CD$_3$OD): 7.29 (d, J = 5.0 Hz, 1H), 6.89 (d, J = 5.0 Hz, 1H), 4.94 (d, J = 8.0 Hz, 1H), 4.29-4.23 (m, 1H), 3.85-3.78 (m, 1H), 3.46 (d, J = 13.0 Hz, 1H), 3.14 (dd, J = 9.5, 11.5 Hz, 1H), 3.05-2.97 (m, 1H), 2.80 (d, J = 16.0 Hz, 1H). |
| 4 | CH₃-HN-CH₂-[pyranothiophene] | HCl | A | LC-MS (6 min method): 0.24 minute, M$^+$ 184 @ 0.26 min; $^1$H NMR (CD$_3$OD): 7.30 (d, J = 5.50 Hz, 1H), 6.90 (d, J = 5.50 Hz, 1H), 5.00 (dd, J = 2.57, 8.80 Hz, 1H), 4.30-4.26 (m, 1H), 3.89-3.80 (m, 1H), 3.57-3.53 (m, 1H), 3.28-3.21 (m, 1H), 3.05-3.01 (m, 1H), 2.84-2.79 (m, 1H), 2.74 (s, 3H). |
| 5 | CH₃-HN-CH₂-[methyl pyranothiophene] | HCl | A | $^1$H NMR (CD$_3$OD): δ 6.54 (s, 1H), 4.91-4.85 (m, 1H), 4.26-4.21 (m, 1H), 3.80 (td, J = 3.5, 10.0 Hz, 1H), 3.47 (dd, J = 3.0, 13.0 Hz, 1H), 3.20 (dd, J = 8.5, 13.0 Hz, 1H), 2.93-2.88 (m, 1H), 2.72 (s, 3H), 2.71-2.66 (m, 1H), 2.42 (s, 3H). |
| 6 | [spiropiperidine-pyranothiophene] | HCl | A | $^1$H NMR (CD$_3$OD): δ 7.22 (d, J = 5.10 Hz, 1H), 6.87 (d, J = 5.10 Hz, 1H), 3.97 (t, J = 5.50 Hz, 2H), 3.40-3.25 (m, 4H), 2.84 (t, J = 5.5 Hz, 2H), 2.22-2.14 (m, 2H), 2.06-2.02 (m, 2H). |

| Compd. No. | Structure | Salt or FB* | Method of Preparation | Analytical Data |
|---|---|---|---|---|
| 7 | (structure) | HCl | A | LC-MS (3.0 min method): 0.98 minute, M$^+$ 220; $^1$H NMR (400 MHz, CD$_3$OD) δ 7.86 (d, J = 7.6 Hz, 1H), 7.68 (d, J = 8.0 Hz, 1H), 7.40 (td, J = 7.2, 0.8 Hz, 1H), 7.34 (t, J = 7.2 Hz, 1H), 5.27 (dd, J = 8.4, 2.0 Hz, 1H), 4.25 (m, 1H), 3.94 (m, 1H), 3.62 (dd, J = 13.2, 2.0 Hz, 1H), 3.35 (m, 1H), 3.00 (m, 2H). |
| 8 | (structure) | HCl | A | LC-MS (3.0 min method): 1.00 minute, M$^+$ 234; $^1$H NMR (400 MHz, CD$_3$OD) δ 7.85 (d, J = 8.0 Hz, 1H), 7.20 (d, J = 8.0 Hz, 1H), 7.40 (t, J = 7.6 Hz, 1H), 7.33 (t, J = 7.6 Hz, 1H), 5.34 (d, J = 8.8 Hz, 1H), 4.26 (m, 1H), 3.94 (m, 1H), 3.68 (dd, J = 13.2, 2.0 Hz, 1H), 3.42 (m, 1H), 2.98 (m, 2H), 2.77 (s, 3H). |
| 9 | (structure) | HCl | A | $^1$H NMR (DMSO-d$^6$): δ 8.22 (br s, 3H), 6.70 (s, 1H), 4.85-4.83 (d, J = 8.01 Hz, 1H), 4.13-4.07 (m, 1H), 3.78-3.70 (m, 1H), 3.29 (s, 1H), 2.91-2.67 (m, 5H), 1.22-1.18 (t, J = 7.50 Hz, 3H). |
| 10 | (structure) | HCl | A | $^1$H NMR (DMSO-d$^6$): δ 9.07 (br s, 1H), 8.67 (br s, 1H), 6.60 (s, 1H), 4.94-4.92 (d, J = 8.0 Hz, 1H), 4.15-4.08 (m, 1H), 3.80-3.72 (m, 1H), 3.46-3.42 (d, J = 12.3 Hz, 1H), 3.13-3.09 (m, 1H), 2.87-2.68 (m, 4H), 2.57 (s, 3H), 1.24-1.19 (t, J = 7.5 Hz, 3H). |
| 11 | (structure) | HCl | A | $^1$H NMR (DMSO-d$^6$ + D$_2$O): δ 7.02 (s, 1H), 4.81-4.78 (dd, J$_1$ = 2.1 Hz, J$_2$ = 6.5 Hz, 1H), 4.15-4.08 (m, 1H), 3.80-3.72 (m, 1H), 3.35-3.29 (dd, J$_1$ = 2.9 Hz, J$_2$ = 13.3 Hz, 1H), 3.02-2.95 (m, 1H), 2.81-2.72 (m, 2H). |
| 12 | (structure) | HCl | A | $^1$H NMR (DMSO-d$^6$): δ 9.26 (br s, 1H), 8.80 (br s, 1H), 7.04 (s, 1H), 4.98-4.94 (dd, J$_1$ = 1.8 Hz, J$_2$ = 9.2 Hz, 1H), 4.16-4.09 (m, 1H), 3.82-3.74 (m, 1H), 3.47-3.36 (d, J = 29.1 Hz, 1H), 3.13 (m, m1H), 2.87-2.69 (m, 2H), 2.56 (s, 3H). |
| 13 | (structure) | HCl | F | GC-MS m/z 139 (M$^+$); $^1$H NMR (DMSO-d$^6$): δ 9.02 (s, 1H), 8.65 (s, 1H), 7.41-7.40 (d, J = 5.19 Hz, 1H), 6.99-6.97 (d, J = 5.19 Hz, 1H), 5.03-5.00 (d, J = 8.13 Hz, 1H), 4.21-4.12 (m, 1H), 3.83-3.75 (m, 1H), 3.52-3.48 (d, J = 12.43 Hz, 1H), 3.13-2.72 (m, 5H), 1.25-1.20 (t, J = 7.26 Hz, 3H). |
| 14 | (structure) | FB | F | GC-MS m/z 211 (M$^+$); $^1$H NMR (CDCl$_3$): δ 7.12-7.11 (d, J = 5.13 Hz, 1H), 6.79-6.78 (d, J = 5.13 Hz, 1H), 4.85-4.82 (dd, J$_1$ = 2.04 Hz, J$_2$ = 8.82 Hz, 1H), 4.26-4.20 (m, 1H), 3.84-3.75 (m, 1H), 3.06-2.95 (m, 2H), 2.90-2.83 (m, 1H), 2.79-2.72 (m, 1H), 2.69-2.58 (m, 2H), 1.61-1.50 (m, 2H), 0.97-0.92 (t, J = 14.80 Hz, 3H). |

-continued

| Compd. No. | Structure | Salt or FB* | Method of Preparation | Analytical Data |
|---|---|---|---|---|
| 15 | 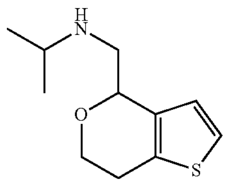 | FB | F | $^1$H NMR (CDCl$_3$): δ 7.12-7.10 (d, J = 5.16 Hz, 1H), 6.79-6.78 (d, J = 5.16 Hz, 1H), 4.82-4.79 (dd, J$_1$ = 2.34 Hz, J$_2$ = 9.18 Hz, 1H), 4.25-4.19 (m, 1H), 3.83-3.75 (m, 1H), 3.08-2.99 (m, 2H), 2.87-2.73 (m, 3H), 1.11 (s, 3H), 1.09 (s, 3H). |
| 16 | 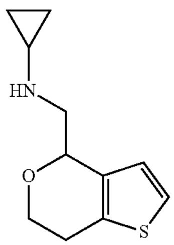 [SMILES: c1cc2c(s1)CCOC2CNC1CC1] | HCl | F | GC-MS m/z 209 (M$^+$); $^1$H NMR (DMSO-d$^6$): δ 9.35 (br s, 1H), 9.03 (br s, 9.03, 1H), 7.41-7.40 (d, J = 5.20 Hz, 1H), 7.04-7.02 (d, J = 5.20 Hz, 1H), 5.08-5.05 (d, J = 8.49 Hz, 1H), 4.18-4.12 (m, 1H), 3.82-3.74 (m, 1H), 3.62-3.58 (d, J = 12.82 Hz, 1H), 3.220-3.14 (t, J = 11.65 Hz, 1H), 2.96-2.72 (m, 3H), 0.99-0.82 (m, 2H), 0.79-0.72 (m, 2H). |
| 17 | 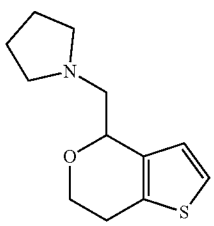 [SMILES: c1cc2c(s1)CCOC2CN1CCCC1] | FB | F | GC-MS m/z 223 (M$^+$); $^1$H NMR (CDCl$_3$): δ 7.10-7.08 (d, J = 4.95 Hz, 1H), 6.86-6.84 (d, J = 4.95 Hz, 1H), 4.87-4.82 (m, 1H), 4.28-4.22 (m, 1H), 3.82-3.74 (m, 1H), 3.04-2.94 (m, 1H), 2.85-2.70 (m, 3H), 2.67-2.56 (m, 4H), 1.89-1.76 (m, 4H). |
| 18 | 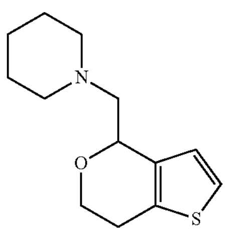 [SMILES: c1cc2c(s1)CCOC2CN1CCCCC1] | FB | F | $^1$H NMR (CDCl$_3$): δ 7.10-7.09 (d, J = 5.1 Hz, 1H), 6.91-6.89 (d, J = 5.1 Hz, 1H), 4.90-4.84 (m, 1H), 4.27-4.21 (m, 1H), 3.81-3.73 (m, 1H), 3.04-2.94 (m, 1H), 2.78-2.70 (m, 1H), 2.67-2.62 (m, 2H), 2.55-2.52 (m, 4H), 1.69-1.59 (m, 4H), 1.50-1.43 (m, 2H). |
| 19 | 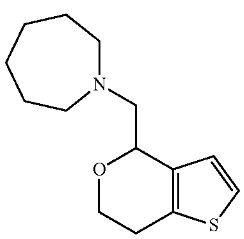 [SMILES: c1cc2c(s1)CCOC2CN1CCCCCC1] | FB | F | GC-MS m/z 251 (M$^+$); $^1$H NMR (DMSO-d$^6$): δ 7.28-7.27 (d, J = 5.16 Hz, 1H), 7.03-7.02 (d, J = 5.16 Hz, 1H), 4.68-4.64 (t, J = 5.82 Hz, 1H), 4.11-4.04 (m, 1H), 3.70-3.61 (m, 1H), 2.83-2.64 (m, 8H), 1.55 (s, 8H). |
| 20 | 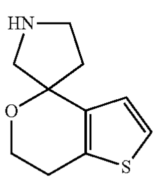 [SMILES: c1cc2c(s1)CCOC21CCNC1] | HCl | A | $^1$H NMR (CD$_3$OD): δ 7.26 (d, J = 5.1, Hz, 1H), 6.96 (d, J = 5.1 Hz, 1H), 4.01-3.97 (m, 2H), 3.59-3.53 (m, 3H), 3.38 (d, J = 6.8 Hz, 1H), 2.89 (brs, 2H), 2.38-2.36 (m, 2H). |
| 21 | 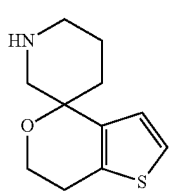 [SMILES: c1cc2c(s1)CCOC21CCCNC1] | HCl | A | $^1$H NMR (CD$_3$OD): δ 7.26 (d, J = 5.0 Hz, 1H), 6.94 (d, J = 5.0 Hz, 1H), 4.00 (t, J = 5.1 Hz, 2H), 3.33-3.21 (m, 3H), 3.08 (apt, J = 2.8 Hz, 1H), 2.87 (t, J = 5.1 Hz, 2H), 2.18-2.11 (m, 1H), 2.04-1.97 (m, 2H), 1.84-1.80 (m, 1H). |

| Compd. No. | Structure | Salt or FB* | Method of Preparation | Analytical Data |
|---|---|---|---|---|
| 22 | 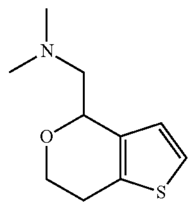 | formate | A | $^1$H NMR (CD$_3$OD): δ 7.29 (d, J = 5.0 Hz, 1H), 6.88 (d, J = 5.0 Hz, 1H), 5.14 (apd, J = 6.0 Hz, 1H), 4.27 (m, 1H), 3.85 (dr, J = 11.0, 3.0 Hz, 1H), 3.67 (m, 1H), 3.38-3.25 (m, 1H), 3.04-2.77 (m, 2H), 3.00 (s, 3H), 2.92 (s, 3H). |
| 23 | 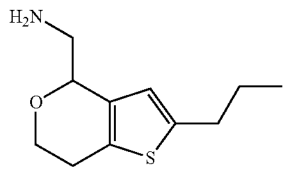 | HCl | A | $^1$H NMR (DMSO-d$^6$): δ 8.18 (br s, 3H), 6.69 (s, 1H), 4.84-4.82 (d, J = 7.5 Hz, 1H), 4.14-4.07 (m, 1H), 3.78-3.70 (m, 1H), 3.29 (s, 1H), 2.95-2.66 (m, 5H), 1.65-1.53 (m, 2H), 1.04-0.92 (t, J = 7.32 Hz, 3H). |
| 24 | 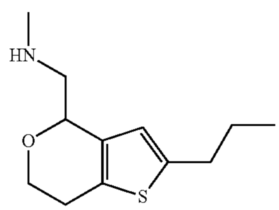 | HCl | A | $^1$H NMR (DMSO-d$^6$): δ 9.11 (br s, 1H), 9.69 (br, s, 1H), 6.65 (s, 1H), 4.95-4.92 (d, J = 7.9 Hz, 1H), 4.15-4.08 (m, 1H), 3.80-3.72 (m, 1H), 3.4 (m, 1H), 3.1 (m, 1H), 2.87-2.78 (m, 1H), 2.73-2.67 (m, 3H), 2.57 (s, 3H), 1.66-1.53 (m, 2H), 0.94-0.89 (m, 3H). |
| 25 | 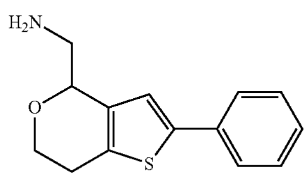 [SMILES: NCC1OCCc2sc(-c3ccccc3)cc21] | HCl | A | $^1$H NMR (DMSO-d$^6$ + D$_2$O): δ 7.59-7.57 (d, J = 7.5 Hz, 2H), 7.43-7.38 (t, 3H), 7.32-7.27 (t, 1H), 4.90-4.87 (d, J = 7.1 Hz, 1H), 4.19-4.15 (m, 1H), 3.82-3.79 (m, 1H), 3.45-3.40 (dd, J$_1$ = 2.8 Hz, J$_2$ = 13.3 Hz, 1H), 3.09-3.02 (m, 1H), 2.92-2.82 (m, 2H). |
| 26 | 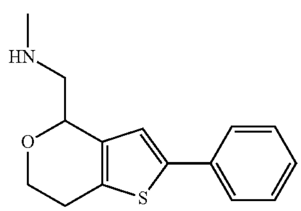 [SMILES: CNCC1OCCc2sc(-c3ccccc3)cc21] | HCl | A | $^1$H NMR (DMSO-d$^6$): δ 9.01 (br s, 1H), 8.69 (br, s, 1H), 7.60-7.58 (d, J = 7.2 Hz, 2H), 7.45-7.38 (m, 3H), 7.33-7.28 (t, J = 7.20 Hz, 1H), 5.03-5.00 (d, J = 7.7 Hz, 1H), 4.22-4.09 (m, 1H), 3.86-3.78 (m, 1H), 3.59-3.52 (m, 1H), 3.29-3.17 (m, 1H), 2.93-2.79 (m, 2H), 2.53-2.48 (t, J = 5.31 Hz, 3H). |
| 27 | 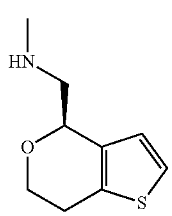 | HCl | CS; FME of SFC separation of BOC protected Compound 4, using isocratic 10% [(1:1:2, MeOH:EtOH:Hexanes (1% isopropylamine))] in CO$_2$ on a LUX-2 5 μ in and flow of 60 g/min | LC-MS (6 min method on lab 209 instrument): 0.24 minute, M$^+$ 184 @ 0.26 min.; $^1$H NMR (CD$_3$OD): δ 7.30 (d, J = 5.50 Hz, 1H), 6.90 (d, J = 5.50 Hz, 1H), 5.00 (dd, J = 2.57, 8.80 Hz, 1H), 4.30-4.26 (m, 1H), 3.89-3.80 (m, 1H), 3.57-3.53 (m, 1H), 3.28-3.21 (m, 1H), 3.05-3.01 (m, 1H), 2.84-2.79 (m, 1H), 2.74 (s, 3H). |
| 28 | 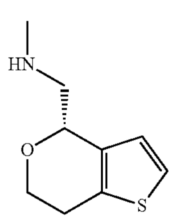 | HCl | CS; SME of SFC separation of BOC protected Compound 4, using isocratic 10% [(1:1:2, MeOH:EtOH:Hexanes (1% isopropylamine))] in CO$_2$ on a LUX-2 5 μ in and flow of 60 g/min | LC-MS (6 min method): 0.24 minute, M$^+$ 184 @ 0.26 min.; $^1$H NMR (CD$_3$OD): δ 7.30 (d, J = 5.50 Hz, 1H), 6.90 (d, J = 5.50 Hz, 1H), 5.00 (dd, J = 2.57, 8.80 Hz, 1H), 4.30-4.26 (m, 1H), 3.89-3.80 (m, 1H), 3.57-3.53 (m, 1H), 3.28-3.21 (m, 1H), 3.05-3.01 (m, 1H), 2.84-2.79 (m, 1H), 2.74 (s, 3H). |

-continued

| Compd. No. | Structure | Salt or FB* | Method of Preparation | Analytical Data |
|---|---|---|---|---|
| 29 | 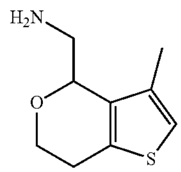 | HCl | A | $^1$H NMR (DMSO-d$^6$): δ 8.14 (br s, 3H), 7.00 (s, 1H), 4.97-4.90 (m, 1H), 4.02-3.94 (m, 1H), 3.85-3.78 (m, 1H), 3.11-3.08 (t, J = 10.66 Hz, 2H), 2.88-2.73 (m, 2H), 2.13-2.12 (d, J = 0.8 Hz, 3H). |
| 30 | 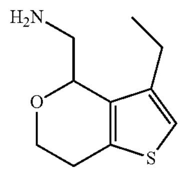 | HCl | A | $^1$H NMR (DMSO-d$^6$): δ 8.06 (br s, 3H), 7.02 (s, 1H), 4.97-4.93 (dd, J$_1$ = 3.5 Hz, J$_2$ = 9.1 Hz, 1H), 4.03-3.95 (m, 1H), 3.86-3.79 (m, 1H), 3.09 (br s, 2H), 2.84-2.73 (m, 2H), 2.47-2.37 (m, 2H), 1.21-1.17 (t, J = 7.41 Hz, 3H). |
| 31 | 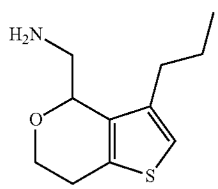 | HCl | A | $^1$H NMR (DMSO-d$^6$): δ 7.96 (br s, 3H), 7.02 (s, 1H), 4.92-4.90 (d, J = 6.75 Hz, 1H), 4.03-3.95 (m, 1H), 3.86-3.79 (m, 1H), 3.09-3.08 (d, J = 3.96 Hz, 2H), 2.89-2.78 (m, 2H), 2.43-2.38 (t, J = 6.84 Hz, 2H), 1.70-1.54 (m, 2H), 0.97-0.92 (t, J = 7.31 Hz, 3H). |
| 32 | 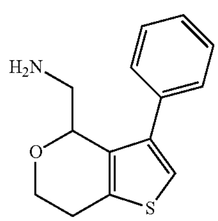 [SMILES: NCC1OCCc2scc(-c3ccccc3)c21] | HCl | A | $^1$H NMR (DMSO-d$^6$ + D$_2$O): δ 7.46-7.35 (m, 5H), 7.30 (s, 1H), 5.27-5.24 (d, J = 8.49 Hz, 1H), 4.05-3.98 (m, 1H), 3.88-3.82 (m, 1H), 2.88 (s, 2H), 2.71-2.64 (m, 1H), 2.47-2.46 (d, J = 2.85 Hz, 1H). |
| 33 | 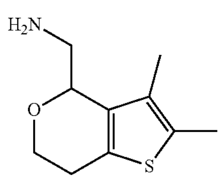 | HCl | A | GC-MS m/z 197 (M$^+$); $^1$H NMR (D$_2$O): δ 4.95-4.91 (t, J = 5.1 Hz, 1H), 4.04-3.97 (m, 1H), 3.85-2.78 (m, 1H), 3.30-3.28 (d, J = 5.01 Hz, 2H), 2.76-2.72 (t, J = 5.33 Hz, 2H), 2.21 (s, 3H), 1.92 (s, 3H). |
| 34 | 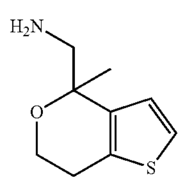 | HCl | A | LC-MS (6 min method): 0.48 minute, M$^+$ 184 @ 0.48 min.; $^1$H NMR (CD$_3$OD): δ 7.28 (d, J = 5.0 Hz, 1H), 6.90 (d, J = 5.0 Hz, 1H), 4.11-4.07 (m, 1H), 3.97-3.91 (m, 1H), 3.33-3.00 (m, 1H), 3.16 (d, J = 13.0 Hz, 1H), 3.02-2.94 (m, 1H), 2.76 (d, J = 6.1 Hz, 1H), 1.50 (s, 3H). |
| 35 | 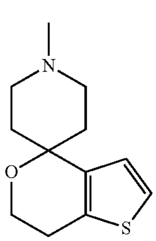 | HCl | A | $^1$H NMR (CD$_3$OD): δ 7.23 (d, J = 5.0 Hz, 1H), 6.84 (d, J = 5.0 Hz, 1H), 3.97 (t, J = 5.0 Hz, 2H), 3.39 (brs, 4H), 2.92 (s, 3H), 2.84 (t, J = 5.0 Hz, 2H), 2.17-1.18 (m, 4H). |
| 36 | 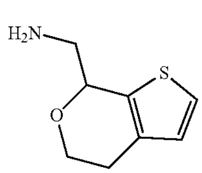 [SMILES: NCC1OCCc2ccsc21] | HCl | B | $^1$H NMR (CD$_3$OD): δ 7.36 (d, J = 4.4 Hz, 1H), 6.91 (d, J = 4.77 Hz. 1H), 5.08 (d, J = 7.7 Hz, 1H), 4.27-4.23 (m, 1H), 3.84-3.78 (m, 1H), 3.42-3.38 (m, 1H), 3.17-3.12 (m, 1H), 2.91-2.83 (m, 1H), 2.70-2.65 (m, 1H). |

-continued

| Compd. No. | Structure | Salt or FB* | Method of Preparation | Analytical Data |
|---|---|---|---|---|
| 37 | (H₂N-CH₂ substituted 4-hydroxy-4,5,6,7-tetrahydrobenzothiophene) | formate | E | ¹H NMR (CD₃OD): δ 7.20 (d, J = 5.1 Hz, 1H), 7.08 (d, J = 5.1 Hz, 1H), 3.25 (d, J = 13.0 Hz, 1H), 3.07 (d, J = 13.0 Hz, 1H), 2.83-2.79 (m, 2H), 2.04-1.88 (m, 4H). |
| 38 | (H₂N-CH₂ substituted 2-CF₃-pyranothiophene) | HCl | L | ¹H NMR (CD₃OD): δ 7.44 (s, 1H), 4.96-4.92 (m, 1H), 4.32-4.28 (m, 1H), 3.86 (dt, J = 13.0, 3.5 Hz, 1H), 3.51 (d, J = 13.0 Hz, 1H), 3.20-3.15 (m, 1H), 3.10-3.04 (m, 1H), 2.90-2.86 (m, 1H). |
| 39 | (MeHN-CH₂ substituted 2-CF₃-pyranothiophene) | HCl | L | ¹H NMR (CD₃OD): δ 7.42 (s, 1H), 5.00-4.98 (m, 1H), 4.32-4.28 (m, 1H), 3.94 (t, J = 13.0, 1H), 3.57 (d, J = 13.0 Hz, 1H), 3.30-3.20 (m, 1H), 3.09-3.02 (m, 1H), 2.91-2.86 (m, 1H), 2.74 (s, 3H). |
| 40 | (spiro-piperidine benzothiophene pyran) | HCl | A | ¹H NMR (CD₃OD): δ 7.91 (d, J = 8.0 Hz, 1H), 7.85 (d, J = 8.0 Hz, 1H), 7.41 (dt, J = 1.0, 7.5 Hz, 1H), 7.33 (dt, J = 1.0, 7.5 Hz, 1H), 4.08 (dt, J = 1.5, 5.5 Hz, 2H), 3.74 (d, J = 13.0 Hz, 1H), 3.42-3.30 (m, 3H), 3.00 (dt, J = 1.5, 5.5 Hz, 2H), 2.52-2.44 (m, 1H), 2.27 (tq, J = 4.0, 14.0 Hz, 1H), 2.08 (dd, J = 2.0, 14.0 Hz, 1H), 1.89 (d, J = 14.0 Hz, 1H). |
| 41 | (H₂N-CH₂ benzothiophene pyran, one enantiomer) | HCl | CS: FME of separation of Compound 7, on AD with IHD 10 | ¹H NMR (CD₃OD): δ 7.86 (d, J = 7.5 Hz, 1H), 7.67 (d, J = 7.5 Hz, 1H), 7.40 (dt, J = 1.0, 7.5 Hz, 1H), 7.34 (dt, J = 1.0, 7.5 Hz, 1H), 5.29-5.25 (m, 1H), 4.28-4.22 (m, 1H), 3.96-3.90 (m, 1H), 3.61 (dd, J = 1.5, 13.5 Hz, 1H), 3.37-3.30 (m, 1H), 3.09-2.91 (m, 2H). |
| 42 | (H₂N-CH₂ benzothiophene pyran, other enantiomer) | HCl | CS: SME of separation of Compound 7, on AD with IHD 10 | ¹H NMR (CD₃OD): δ 7.86 (d, J = 7.5 Hz, 1H), 7.67 (d, J = 7.5 Hz, 1H), 7.40 (dt, J = 1.0, 7.5 Hz, 1H), 7.34 (dt, J = 1.0, 7.5 Hz, 1H), 5.29-5.25 (m, 1H), 4.28-4.22 (m, 1H), 3.96-3.90 (m, 1H), 3.61 (dd, J = 1.5, 13.5 Hz, 1H), 3.37-3.30 (m, 1H), 3.09-2.91 (m, 2H). |
| 43 | (spiro-pyrrolidine thienopyran) | HCl | CS; FME of Compound 20 on AD with MEHD 5 | ¹H NMR (CD₃OD): δ 7.26 (d, J = 5.1, Hz, 1H), 6.96 (d, J = 5.1 Hz, 1H), 4.01-3.97 (m, 2H), 3.59-3.53 (m, 3H), 3.38 (d, J = 6.8 Hz, 1H), 2.89 (brs, 2H), 2.38-2.36 (m, 2H). |
| 44 | (H₂N-CH₂ 2-methyl thienopyran) | HCl | CS: FME of N-Troc deriv. on OD with IHD 5 | ¹H NMR (CD₃OD): δ 6.53 (s, 1H), 4.86 (s, 1H), 4.25-4.20 (m, 1H), 3.82-3.76 (m, 1H), 3.39 (dd, J = 2.93, 13.2 Hz, 1H), 3.08 (dd, J = 8.06, 13.2 Hz, 1H), 2.96-2.88 (m, 1H), 2.70-2.66 (m, 1H), 2.42 (s, 3H). |

-continued

| Compd. No. | Structure | Salt or FB* | Method of Preparation | Analytical Data |
|---|---|---|---|---|
| 45 | 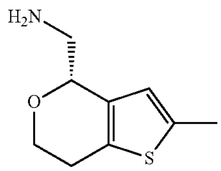 | HCl | CS: SME of N-Troc deriv. on OD with IHD 5 | $^1$H NMR (CD$_3$OD): δ 6.53 (s, 1H), 4.86 (s, 1H), 4.25-4.20 (m, 1H), 3.82-3.76 (m, 1H), 3.39 (dd, J = 2.93, 13.2 Hz, 1H), 3.08 (dd, J = 8.06, 13.2 Hz, 1H), 2.96-2.88 (m, 1H), 2.70-2.66 (m, 1H), 2.42 (s, 3H). |
| 46 | 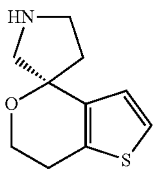 [SMILES: c1cc2c(s1)CCO[C@@]21CCNC1] | HCl | CS; SME of Compound 20 on AD with MEHD 5 | $^1$H NMR (CD$_3$OD): δ 7.26 (d, J = 5.1, Hz, 1H), 6.96 (d, J = 5.1 Hz, 1H), 4.01-3.97 (m, 2H), 3.59-3.53 (m, 3H), 3.38 (d, J = =6.8 Hz, 1H), 2.89 (brs, 2H), 2.38-2.36 (m, 2H). |
| 47 | 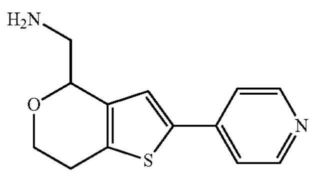 [SMILES: NCC1OCCc2sc(-c3ccncc3)cc21] | HCl | J | LC-MS m/z 247.2 (MH$^+$); $^1$H NMR (DMSO-d$^6$): δ 8.83-8.81 (d, J = 6.78 Hz, 2H), 8.38 (s, 3H), 8.25 (s, 1H), 8.17-8.14 (d, J = 6.78 Hz, 2H), 5.02-5.00 (d, J = 7.65 Hz, 1H), 4.23-4.17 (m, 1H), 3.94-3.87 (m, 1H), 3.47-3.46 (m, 1H), 3.11-2.90 (m, 3H). |
| 48 | 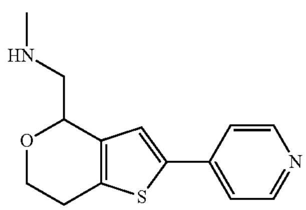 [SMILES: CNCC1OCCc2sc(-c3ccncc3)cc21] | HCl | J | LC-MS m/z 261.3 (MH$^+$); $^1$H NMR (DMSO-d$^6$): δ 9.61 (br s, 1H), 8.00 (br s, 1H), 8.84-8.82 (d, J = 6.75 Hz, 1H), 8.23 (s, 1H), 8.16-8.13 (d, J = 6.75 Hz, 1H), 5.16-5.13 (d, J = 8.25 Hz, m1H), 4.30-4.17 (m, 1H), 3.88-3.80 (m, 1H), 3.59-3.53 (m, 1H), 3.27-3.16 (m, 1H), 3.08-2.88 (m, 2H), 2.61-2.58 (t, J = 5.19 Hz, 3H). |
| 49 | 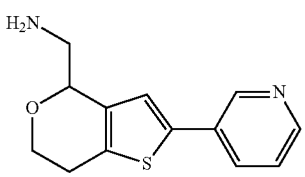 [SMILES: NCC1OCCc2sc(-c3cccnc3)cc21] | HCl | J | LC-MS m/z 247.2 (MH$^+$); $^1$H NMR (DMSO-d$^6$): δ 9.11 (br s, 1H), 8.98-8.95 (d, J = 4.83 Hz, 1H), 8.51-8.48 (d, J = 8.25 Hz, 1H), 8.35 (br s, 3H), 7.94-7.86 (m, 2H), 4.99-4.97 (d, J = 7.74 Hz, 1H), 4.22-4.15 (m, 1H), 3.85-3.77 (m, 1H), 3.42-3.39 (m, 1H), 3.08-2.89 (m, 3H). |
| 50 | 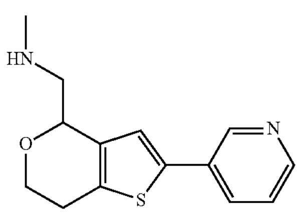 [SMILES: CNCC1OCCc2sc(-c3cccnc3)cc21] | HCl | J | LC-MS m/z 261.2 (MH$^+$); $^1$H NMR (DMSO-d$^6$): δ 9.37 (br s, 1H), 9.03 (s, 1H), 8.85 (s, 1H), 8.67-8.65 (d, J = 5.01 Hz, 1H), 8.38-8.36 (d, J = 7.86 Hz, 1H), 7.81-7.77 (m, 2H), 5.10-5.08 (d, J = 7.98 Hz, 1H), 4.23-4.16 (m, 1H), 3.87-3.79 (m, 1H), 3.55-3.48 (m, 1H), 3.26-3.17 (m, 1H), 3.03-2.85 (m, 2H), 2.61-2.58 (t, J = 5.31 Hz, 3H). |
| 51 | 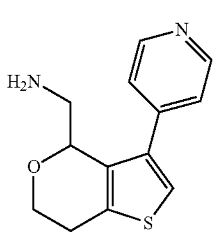 [SMILES: NCC1OCCc2scc(-c3ccncc3)c21] | HCl | I | LC-MS m/z 247.2 (MH$^+$); $^1$H NMR (DMSO-d$^6$): δ 8.87-8.85 (d, J = 6.69 Hz, 2H), 8.22 (br s, 3H), 8.09-8.07 (d, J = 6.69 Hz, 2H), 8.05 (s, 1H), 5.62-5.60 (d, J = 8.64 Hz, 1H), 4.10-4.02 (m, 1H), 3.93-3.86 (m, 1H), 3.00-2.92 (m, 2H), 2.89-2.77 (m, 1H), 2.57-2.51 (m, 1H). |

-continued

| Compd. No. | Structure | Salt or FB* | Method of Preparation | Analytical Data |
|---|---|---|---|---|
| 52 | 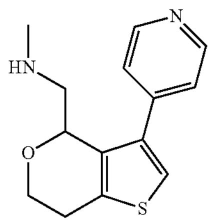 [SMILES: CNCC1OCCc2scc(-c3ccncc3)c21] | HCl | I | LC-MS m/z 261.3 (MH+); $^1$H NMR (DMSO-d$^6$): δ 9.72 (br s, 1H), 8.88-8.86 (d, J = 6.75 Hz, 2H), 8.69 (br s, 1H), 8.17-8.15 (d, J = 6.75 Hz, 2H), 8.11 (s, 1H), 5.77-5.73 (d, J = 9.24 Hz, 1H), 4.14-4.04 (m, 1H), 3.94-3.87 (m, 1H), 3.06-2.94 (m, 3H), 2.66-2.60 (m, 1H), 2.42-2.41 (t, J = 5.28 Hz, 3H). |
| 53 | 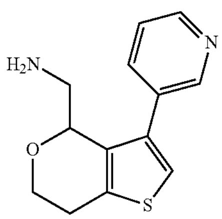 [SMILES: NCC1OCCc2scc(-c3cccnc3)c21] | HCl | I | LC-MS m/z 247.2 (MH+); $^1$H NMR (DMSO-d$^6$): δ 8.97-8.96 (d, J = 1.77 Hz, 1H), 8.84-8.83 (d, J = 4.53 Hz, 1H), 8.54-8.51 (d, J = 8.22 Hz, 1H), 8.17 (s, 3H), 8.07-7.95 (dd, J$_1$ = 5.49 Hz, J$_2$ = 8.01 Hz, 1H), 7.76 (s, 1H), 5.50-5.47 (d, J = 8.85 Hz, 1H), 4.07-4.01 (m, 1H), 3.91-3.84 (m, 1H), 2.95-2.93 (m, 2H), 2.83-2.74 (m, 1H), 2.45-2.35 (m, 1H). |
| 54 | 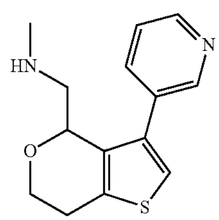 [SMILES: CNCC1OCCc2scc(-c3cccnc3)c21] | HCl | I | LC-MS m/z 261.3 (MH+); $^1$H NMR (DMSO-d$^6$): δ 9.26 (br s, 1H), 8.90-8.89 (d, J = 1.92 Hz, 1H), 8.79-8.77 (dd, J$_1$ = 1.22 Hz, J$_2$ = 5.27 Hz, 1H), 8.59 (br s, 1H), 8.39-8.36 (d, J = 7.62 Hz, 1H), 7.87-7.83 (dd, J$_1$ = 5.43 Hz, J$_2$ = 7.83 Hz, 1H), 7.71 (s, 1H), 5.59-5.56 (d, J = 3.94-3.85 (m, 1H), 3.05-2.93 (m, 3H), 2.65-2.60 (m, 1H), 2.39-2.35 (t, J = 5.28 Hz, 3H). |
| 55 | 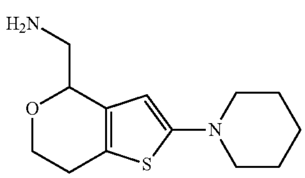 [SMILES: NCC1OCCc2sc(N3CCCCC3)cc21] | HCl | H | LC-MS m/z 253.3 (MH+); $^1$H NMR (DMSO-d$^6$ + D$_2$O): δ 4.69-4.67 (d, J = 7.68 Hz, 1H), 4.09-4.06 (m, 1H), 3.73-3.71 (m, 2H), 3.28-3.22 (dd, J$_1$ = 2.52 Hz, J$_2$ = 13.30 Hz, 1H), 2.99-2.90 (m, 4H), 2.78-2.68 (m, 1H), 2.56 (s, 1H), 1.56 (s, 5H), 1.47-1.46 (m, 2H). |
| 56 | 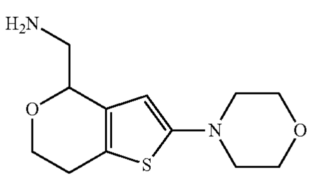 [SMILES: NCC1OCCc2sc(N3CCOCC3)cc21] | HCl | H | LC-MS m/z 277.3 (M + Na+); $^1$H NMR (DMSO-d$^6$): δ 8.01 (s, 3H), 6.05 (s, 1H), 4.74-4.72 (d, J = 7.44 Hz, 1H), 4.14-4.08 (m, 1H), 3.78-3.69 (m, 5H), 3.35-3.29 (m, 1H), 3.00-2.97 (m, 5H), 2.77-2.70 (m, 1H), 2.62-2.56 (m, 1H). |
| 57 | 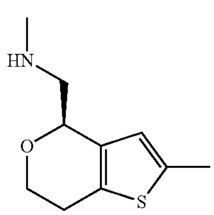 | HCl | CS; FME of SFC separation of Compound 5, using isocratic 25% [(75:25 MeOH:iPrOH (2% isopropylamine))] in CO$_2$ on a ChiralPak AD-H and flow of 60 g/min | $^1$H NMR (CD$_3$OD): δ 6.54 (s, 1H), 4.91-4.85 (m, 1H), 4.26-4.21 (m, 1H), 3.80 (td, J = 3.5, 10.0 Hz, 1H), 3.47 (dd, J = 3.0, 13.0 Hz, 1H), 3.20 (dd, J = 8.5, 13.0 Hz, 1H), 2.93-2.88 (m, 1H), 2.72 (s, 3H), 2.71-2.66 (m 1H), 2.42 (s, 3H). |
| 58 | 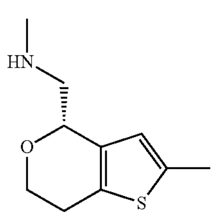 | HCl | CS; SME of SFC separation of Compound 5, using isocratic 25% [(75:25 MeOH:iPrOH (2% isopropylamine))] in CO$_2$ on a ChiralPak AD-H and flow of 60 g/min | $^1$H NMR (CD$_3$OD): δ 6.54 (s, 1H), 4.91-4.85 (m, 1H), 4.26-4.21 (m, 1H), 3.80 (td, J = 3.5, 10.0 Hz, 1H), 3.47 (dd, J = 3.0, 13.0 Hz, 1H), 3.20 (dd, J = 8.5, 13.0 Hz, 1H), 2.93-2.88 (m, 1H), 2.72 (s, 3H), 2.71-2.66 (m, 1H), 2.42 (s, 3H). |

-continued

| Compd. No. | Structure | Salt or FB* | Method of Preparation | Analytical Data |
|---|---|---|---|---|
| 59 | 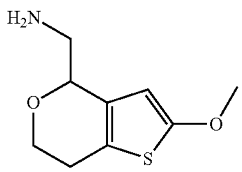 | HCl | H | LC-MS m/z 200.3 (MH+); $^1$H NMR (DMSO-d$^6$): δ 8.11 (s, 3H), 6.21 (s, 1H), 4.76-4.73 (d, J = 7.14 Hz, 1H), 4.15-4.08 (m, 1H), 3.79-3.72 (m, 4H), 3.31-3.26 (m, 1H), 2.98-2.89 (m, 1H), 2.78-2.68 (m, 1H), 2.60-2.54 (m, 1H). |
| 60 | 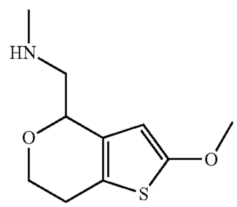 | HCl | H | LC-MS m/z 214.3 (MH+); $^1$H NMR (DMSO-d$^6$): δ 9.09 (br s, 1H), 8.67 (br s, 1H), 6.15 (s, 1H), 4.87-4.85 (d, J = 7.7 Hz, 1H), 4.15-4.08 (m, 1H), 3.80-3.73 (m, 4H), 3.34 (s, 1H), 3.15-3.05 (m, 1H), 2.77-2.68 (m, 1H), 2.61-2.55 (m, 4H). |
| 61 | 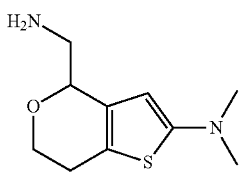 | HCl | H | LC-MS m/z 213.3 (MH+); $^1$H NMR (DMSO-d$^6$ + D$_2$O): δ 5.74 (s, 1H), 4.71-4.68 (d, J = 7.03 Hz, 1H), 4.12-4.05 (m, 1H), 3.79-3.68 (m, 1H), 3.33-3.25 (m, 1H), 2.95-2.88 (m, 1H), 2.78 (s, 6H), 2.71-2.67 (m, 1H), 2.59-2.58 (m, 1H). |
| 62 | 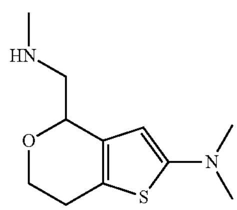 | HCl | H | LC-MS m/z 227.3 (MH+); $^1$H NMR (DMSO-d$^6$): δ 9.11 (br s, 1H), 8.65 (br s, 1H), 5.73 (s, 1H), 4.87-4.83 (d, J = 9.54 Hz, 1H), 4.13-4.07 (m, 1H), 3.78-3.72 (m, 1H), 3.43-3.39 (m, 1H), 3.16-3.06 (m, 1H), 2.79-2.71 (m, 7H), 2.58-2.55 (m, 4H). |
| 63 | 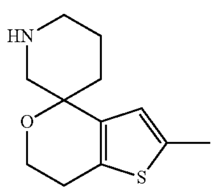 | HCl | A | $^1$H NMR (CD$_3$OD): δ 6.59 (s, 1H), 3.97 (t, J = 5.0 Hz, 2H), 3.33-3.24 (m, 3H), 3.05 (dt, J = 3.0, 13.0 Hz, 1H), 2.77 (t, J = 5.0 Hz, 2H), 2.41 (s, 3H), 2.16-2.08 (m, 1H), 2.00-1.88 (m, 2H), 1.80 (d, J = 14.0 Hz. 1H). |
| 64 | 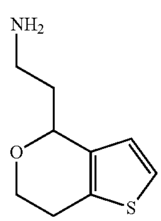 [SMILES: NCCC1OCCc2sccc21] | HCl | A | LC-MS m/z 184.3 (MH+); $^1$H NMR (DMSO-d$^6$): δ 8.04 (s, 3H), 7.36-7.34 (d, J = 5.07 Hz, 1H), 6.85-6.84 (d, J = 5.07 Hz, 1H), 4.76-4.74 (d, J = 7.38 Hz, 1H), 4.14-4.09 (m, 1H), 3.71-3.64 (m, 1), 2.87-2.69 (m, 4H), 2.24-2.15 (m, 1H), 2.00-1.88 (m, 1H). |
| 65 | 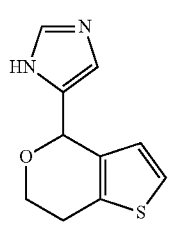 [SMILES: c1ncc(C2OCCc3sccc32)[nH]1] | HCl | A | LC-MS m/z 207.3 (MH+); $^1$H NMR (DMSO-d$^6$): δ 14.65 (s, 2H), 9.12 (s, 1H), 7.50 (s, 1H), 7.40-7.38 (d, J = 5.20 Hz, 1H), 6.74-6.72 (d, J = 5.20 Hz, 1H), 5.95 (s, 1H), 4.03-3.85 (m, 2H), 2.98-2.84 (m, 2H). |

-continued

| Compd. No. | Structure | Salt or FB* | Method of Preparation | Analytical Data |
|---|---|---|---|---|
| 66 | 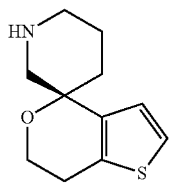 [SMILES: c1cc2c(s1)CCO[C@]21CCCNC1] | HCl | CS; FME of separation of Compound 21 on OJ with 2.5% MEHD | ¹H NMR (CD₃OD): δ 7.26 (d, J = 5.0 Hz, 1H), 6.94 (d, J = 5.0 Hz, 1H), 4.00 (t, J = 5.1 Hz, 2H), 3.33-3.21 (m, 3H), 3.08 (apt, J = 2.8 Hz, 1H), 2.87 (t, J = 5.1 Hz, 2H), 2.18-2.11 (m, 1H), 2.04-1.97 (m, 2H), 1.84-1.80 (m, 1H). |
| 67 | 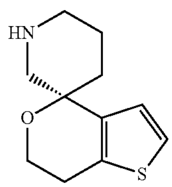 [SMILES: c1cc2c(s1)CCO[C@@]21CCCNC1] | HCl | CS; SME of separation of Compound 21 on OJ with 2.5% MEHD | ¹H NMR (CD₃OD): δ 7.26 (d, J = 5.0 Hz, 1H), 6.94 (d, J = 5.0 Hz, 1H), 4.00 (t, J = 5.1 Hz, 2H), 3.33-3.21 (m, 3H), 3.08 (apt, J = 2.8 Hz, 1H), 2.87 (t, J = 5.1 Hz, 2H), 2.18-2.11 (m, 1H), 2.04-1.97 (m, 2H), 1.84-1.80 (m, 1H). |
| 68 | 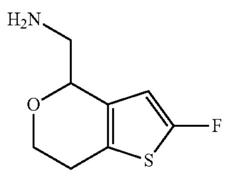 [SMILES: NCC1OCCc2sc(F)cc21] | HCl | G | ¹H NMR (CD₃OD): δ 6.40 (d, J = 2.0 Hz, 1H), 4.80 (dd, J = 3.0, 5.5 Hz, 1H), 4.27-4.22 (m, 1H), 3.89-3.83 (m, 1H), 3.37 (dd, J = 3.0, 13.0 Hz, 1H), 3.11 (dd, J = 8.0, 13.0 Hz, 1H), 2.93-2.85 (m, 1H), 2.61 (dd, J = 2.0 16.0 Hz, 1H). |
| 69 | 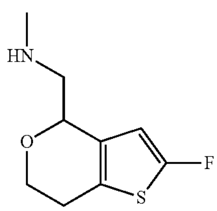 | HCl | G | ¹H NMR (CD₃OD): δ 6.40 (d, J = 2.0 Hz, 1H), 4.86 (m, 1H), 4.28-4.23 (m, 1H), 3.90-3.84 (m, 1H), 3.45 (dd, J = 2.5, 13.0 Hz, 1H), 3.23 (dd, J = 8.5, 13.0 Hz, 1H), 2.93-2.85 (m, 1H), 2.73 (s, 3H), 2.63 (dd, J = 2.0, 6.0 Hz, 1H). |
| 70 | 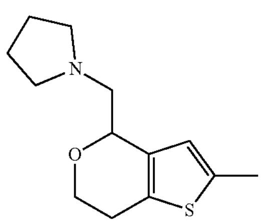 [SMILES: Cc1cc2c(s1)CCOC2CN1CCCC1] | HCl | F | LC-MS m/z 238.3 (MH⁺); ¹H NMR (CD₃OD): δ 6.57 (s, 1H), 5.03-5.00 (d, J = 9.62 Hz, 1H), 4.30-4.23 (mm 1H), 3.89-3.55 (m, 4H), 3.46-3.38 (m, 1H), 3.28-3.08 (m, 2H), 2.99-2.89 (m, 1H), 2.75-2.70 (d, J = 16.44 Hz, 1H), 2.43 (s, 3H), 2.25-2.01 (m, 4H). |
| 71 | 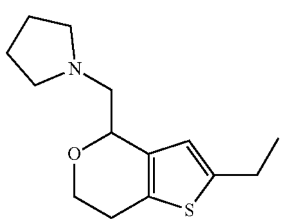 [SMILES: CCc1cc2c(s1)CCOC2CN1CCCC1] | HCl | F | LC-MS m/z 252.3 (MH⁺); ¹H NMR (DMSO-d⁶): δ 10.36 (s, 1H), 6.68 (s, 1H), 5.07-5.04 (d, J = 8.61 Hz, 1H), 4.15-4.08 (m, 1H), 3.82-3.66 (m, 2H), 3.57-3.55 (m, 2H), 3.40-3.30 (m, 1H), 3.17-3.01 (m, 2H), 2.86-2.68 (m, 4H), 2.00-1.88 (m, 4H), 1.23-1.18 (t, J = 7.49 Hz, 3H). |
| 72 | 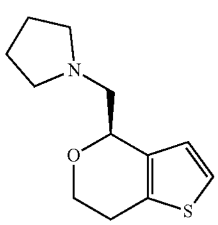 [SMILES: c1cc2c(s1)CCO[C@H]2CN1CCCC1] | HCl | CS: FME of separation of Compound 17, on OJ with IHD 5 | LC-MS (6 min method): broad peak at 0.23-0.67 minute, M⁺ 224 @ 0.56 min.; ¹H NMR (CD₃OD): δ 7.28 (d, J = 5.13 Hz, 1H), 6.94 (d, J = 5.13 Hz, 1H), 5.15-5.12 (m, 1H), 4.30-4.26 (m, 1H), 3.89-3.74 (m, 3H), 3.68-3.63 (m, 1H), 3.44 (dd, J = 9.90, 12.8 Hz, 1H), 3.34-3.29 (m, 1H), 3.19-3.12 (m, 1H), 3.04-2.99 (m, 1H), 2.84-2.79 (m, 1H), 2.24-2.03 (m, 4H). |

-continued

| Compd. No. | Structure | Salt or FB* | Method of Preparation | Analytical Data |
|---|---|---|---|---|
| 73 | 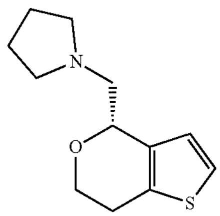 [SMILES: c1cc2c(s1)CCO[C@@H]2CN1CCCC1] | HCl | CS: SME of separation of Compound 17, on OJ with IHD 5 | LC-MS (6 min method on lab 209 instrument): broad peak at 0.23- 0.67 minute, M+ 224 @ 0.56 min.; $^1$H NMR (CD$_3$OD): δ 7.28 (d, J = 5.13 Hz, 1H), 6.94 (d, J = 5.13 Hz, 1H), 5.15-5.12 (m, 1H), 4.30-4.26 (m, 1H), 3.89-3.74 (m, 3H), 3.68-3.63 (m, 1H), 3.44 (dd, J = 9.90, 12.8 Hz, 1H), 3.34-3.29 (m, 1H), 3.19-3.12 (m, 1H), 3.04-2.99 (m, 1H), 2.84-2.79 (m, 1H), 2.24-2.03 (m, 4H). |
| 74 | 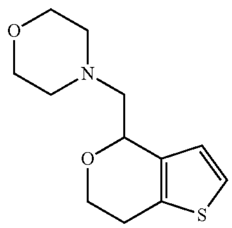 [SMILES: c1cc2c(s1)CCOC2CN1CCOCC1] | HCl | F | LC-MS (6 min method): 2.24 minute, M+ 240 @ 2.25 min.; $^1$H NMR (CD$_3$OD): δ 7.30 (d, J = 5.13 Hz, 1H), 6.90 (d, J = 5.13 Hz, 1H), 5.24 (dd, J = 2.57, 10.3 Hz, 1H), 4.31-4.27 (m, 1H), 4.12-4.03 (m, 2H), 3.89-3.81 (m, 4H), 3.75 (dd, J = 2.93, 1.32 Hz, 1H), 3.70-3.66 (d, J = 13.2 Hz, 1H), 3.55 (d, J = 12.5 Hz, 1H), 3.41-3.35 (m, 1H), 3.26-3.22 (m, 1H), 3.06-2.98 (m, 1H), 2.86-2.82 (m, 1H). |
| 75 | 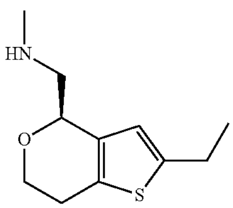 | HCl | CS; FME of SFC separation of Compound 10, using isocratic 18% [(25:75 MeOH:iPrOH (0.5% isopropylamine))] in CO$_2$ on a RegisPack 5 μ and flow of 80 g/min | LC-MS (6 min method): 1.6 min, M+ 212 @ 1.71 min; $^1$H NMR (CD$_3$OD): δ 6.59 (s, 1H), 4.91 (d, J = 8.43 Hz, 1H), 4.27-4.22 (m, 1H), 3.84-3.78 (m, 1H), 3.50 (dd, J = 2.93, 12.8 Hz, 1H), 3.24-3.19 (m, 1H), 2.98-2.92 (m, 1H), 2.79 (q, 2H), 2.80-2.68 (m, 1H), 2.73 (s, 3H), 1.27 (t, 3H). |
| 76 | 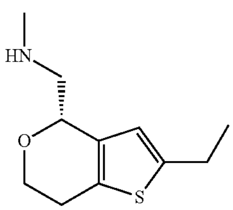 | HCl | CS; SME of SFC separation of Compound 10, using isocratic 18% [(25:75 MeOH:iPrOH (0.5% isopropylamine))] in CO$_2$ on a RegisPack 5 μ and flow of 80 g/min | LC-MS (6 min method): 1.6 min, M+ 212 @ 1.71 min; $^1$H NMR (CD$_3$OD): δ 6.59 (s, 1H), 4.91 (d, J = 8.43 Hz, 1H), 4.27-4.22 (m, 1H), 3.84-3.78 (m, 1H), 3.50 (dd, J = 2.93, 12.8 Hz, 1H), 3.24-3.19 (m, 1H), 2.98-2.92 (m, 1H), 2.79 (q, 2H), 2.80-2.68 (m, 1H), 2.73 (s, 3H), 1.27 (t, 3H). |
| 77 | 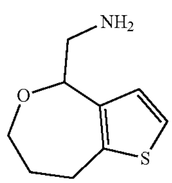 [SMILES: NCC1OCCCc2sccc21] | HCl | C | $^1$H NMR (CD$_3$OD): δ 7.10 (d, J = 5.5 Hz, 1H), 6.83 (d, J = 5.5 Hz, 1H), 4.73 (dd, J = 3.5, 10.0 Hz, 1H), 4.33 (dt, J = 5.0, 12.5 Hz, 1H), 3.92-3.85 (m, 1H), 3.52 (dd, J = 3.0, 13.0 Hz, 1H), 3.25-3.19 (m, 1H), 3.15-3.08 (m, 1H), 3.00-2.93 (m, 1H), 1.99-1.88 (m, 2H). |
| 78 | 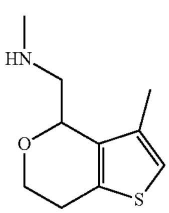 | HCl | A | LC-MS m/z 198.3 (MH+); $^1$H NMR (DMSO-d$^6$): δ 9.11 (br s, 1H), 8.59 (br s, 1H), 7.00 (s, 1H), 5.05-5.03 (d, J = 6.63 Hz, 1H), 4.04-3.96 (m, 1H), 3.87-3.80 (m, 1H), 3.28-3.21 (m, 2H), 2.83-2.74 (m, 2H), 2.61-2.59 (d, J = 1.68 Hz, 3H), 2.13 (s, 3H). |
| 79 | 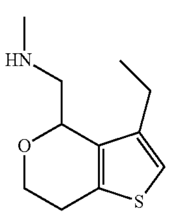 | HCl | A | LC-MS m/z 212.3 (MH+); $^1$H NMR (DMSO-d$^6$): δ 9.16 (br s, 1H), 8.58 (s, 1H), 7.02 (s, 1H), 5.07-5.05 (d, J = 8.07 Hz, 1H), 4.05-3.97 (m, 1H), 3.87-3.80 (m, 1H), 3.27-3.15 (m, 2H), 2.90-2.73 (m, 2H), 2.60 (s, 3H), 2.47-2.41 (m, 2H), 1.22-1.17 (t, J = 7.40 Hz, 3H). |

-continued

| Compd. No. | Structure | Salt or FB* | Method of Preparation | Analytical Data |
|---|---|---|---|---|
| 80 | 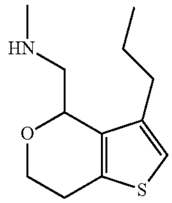 | HCl | A | LC-MS m/z 226.0 (MH+); 1H NMR (DMSO-d6): δ 8.99 (br s, 1H), 8.54 (br s, 1H), 7.02 (s, 1H), 5.04-5.01 (d, J = 8.85 Hz, 1H), 4.05-3.97 (m, 1H), 3.87-3.80 (m, 1H), 3.18 (s, 2H), 2.90-2.72 (m, 2H), 2.61 (s, 3H), 2.46-2.40 (t, J = 7.80 Hz, 2H), 1.67-1.55 (m, 2H), 0.97-0.92 (t, J = 7.31 Hz, 3H). |
| 81 | 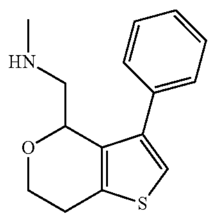 [SMILES: CNCC1OCCc2scc(-c3ccccc3)c21] | HCl | A | LC-MS m/z 260.3 (MH+); 1H NMR (CD3OD): δ 7.55-7.39 (m, 5H), 7.23 (s, 1H), 5.41-5.38 (m, 1H), 4.28-4.21 (m, 1H), 3.98-3.90 (m, 1H), 3.11-3.01 (m, 1H), 2.96-2.92 (m, 2H), 2.80-2.75 (dd, J1 = 3.3 Hz, J2 = 12.9 Hz, 1H), 2.47 (s, 3H). |
| 82 | 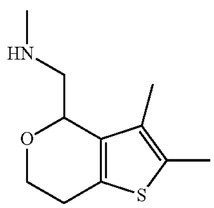 | HCl | A | LC-MS m/z 212.3 (MH+); 1H NMR (DMSO-d6): δ 9.10 (br s, 1H), 8.57 (br s, 1H), 4.98-4.95 (d, J = 8.28 Hz, 1H), 4.03-3.95 (m, 1H), 3.85-3.78 (m, 1H), 3.21-3.17 (m, 2H), 2.79-2.65 (m, 2H), 2.60 (s, 3H), 2.25 (s, 3H), 1.99 (s, 3H). |
| 83 | 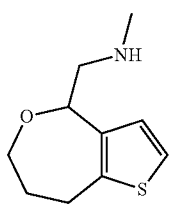 | HCl | C | 1H NMR (CD3OD): δ 7.10 (d, J = 5.0 Hz, 1H), 6.84 (d, J = 5.0 Hz, 1H), 4.82 (dd, J = 3.0, 10.5 Hz, 1H), 4.33 (dt, J = 4.5, 12.5 Hz, 1H), 3.93-3.86 (m, 1H), 3.59 (dd, J = 2.5, 12.5 Hz, 1H), 3.39-3.33 (m, 1H), 3.15-3.08 (m, 1H), 3.01-2.80 (m, 1H), 2.78 (s, 3H), 1.99-1.88 (m, 2H). |
| 84 | 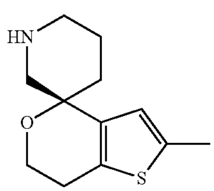 | HCl | CS; FME of separation of Compound 63 on AS with IHD 10 | 1H NMR (CD3OD): δ 6.59 (s, 1H), 3.97 (t, J = 5.0 Hz, 2H), 3.33-3.24 (m, 3H), 3.05 (dt, J = 3.0, 13.0 Hz, 1H), 2.77 (t, J = 5.0 Hz, 2H), 2.41 (s, 3H), 2.16-2.08 (m, 1H), 2.00-1.88 (m, 2H), 1.80 (d, J = 14.0 Hz, 1H). |
| 85 | 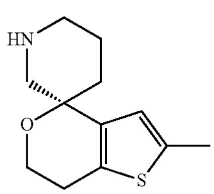 | HCl | CS; SME of separation of Compound 63 on AS with IHD 10 | 1H NMR (CD3OD): δ 6.59 (s, 1H), 3.97 (t, J = 5.0 Hz, 2H), 3.33-3.24 (m, 3H), 3.05 (dt, J = 3.0, 13.0 Hz, 1H), 2.77 (t, J = 5.0 Hz, 2H), 2.41 (s, 3H), 2.16-2.08 (m, 1H), 2.00-1.88 (m, 2H), 1.80 (d, J = 14.0 Hz, 1H). |
| 86 | 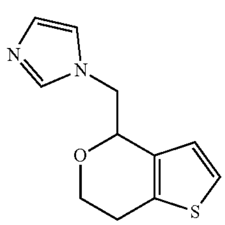 [SMILES: c1cn(CC2OCCc3sccc32)cn1] | HCl | F | LC-MS (6 min method): 1.85 min, M+ 221 @ 1.83 min; 1H NMR (CD3OD): δ 8.91 (s, 1H), 7.57 (s, 1H), 7.49 (s, 1H), 7.29 (d, J = 5.13 Hz, 1H), 7.09 (d, J = 5.50 Hz, 1H), 5.13-5.10 (m, 1H), 4.80 (dd, J = 2.57, 14.3 Hz, 1H), 4.60 (dd, J = 6.60, 14.3 Hz, 1H), 4.26-4.22 (m, 1H), 3.79-3.73 (m, 1H), 2.87-2.79 (m, 1H), 2.74-2.70 (m, 1H). |

-continued

| Compd. No. | Structure | Salt or FB* | Method of Preparation | Analytical Data |
|---|---|---|---|---|
| 87 | 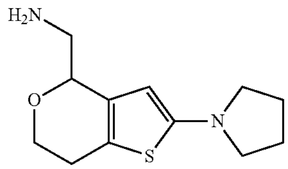 [SMILES: NCC1OCCc2sc(N3CCCC3)cc21] | HCl | H | ¹H NMR (CD₃OD): δ 4.64 (dd, J = 3.0, 9.5 Hz, 1H), 4.23 (dd, J = 3.5, 11.5 Hz, 1H), 4.16-4.08 (m, 2H), 3.87 (td, J = 1.5, 12.0 Hz, 1H), 3.82-3.78 (m, 2H), 3.68 (dd, J = 2.5, 13.0 Hz, 1H), 3.40 (dd, J = 9.5, 13.0 Hz, 1H), 3.30 (bs, 1H), 2.74 (d, J = 13.0 Hz, 1H), 2.29-2.20 (m, 4H), 1.96-1.89 (td, J = 5.0, 12.5 Hz, 1H). |
| 88 | 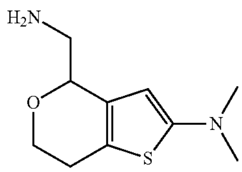 | HCl | H | LC-MS (6 min method): 0.28 minute, M⁺ 213 @ 0.33 min.; ¹H NMR (CD₃OD): δ 4.61 (dd, J = 3.0, 10.0 Hz, 1H), 4.26-4.20 (m, 1H), 3.86 (td, J = 2.0, 12.5 Hz, 1H), 3.69 (s, 3H), 3.66 (d, J = 2.0 Hz, 1H), 3.57 (s, 3H), 3.45-3.35 (m, 1H), 3.13-2.97 (m, 1H), 2.74 (d, J = 13.0 Hz, 1H), 1.92 (td, J = 4.0, 13.0 Hz, 1H). |
| 89 | 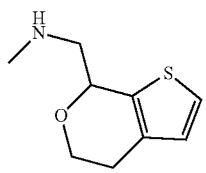 | HCl | B | LC-MS (6 min method): 0.27-0.45 min, M⁺ 184 @ 0.38 min; ¹H NMR (CD₃OD): δ 7.36 (d, J = 4.76 Hz, 1H), 6.90 (d, J = 5.13 Hz, 1H), 5.16 (d, J = 8.06 Hz, 1H), 4.28-4.23 (m, 1H), 3.85-3.79 (m, 1H), 3.51-3.47 (m, 1H), 3.26-3.23 (m, 1H), 2.86-2.82 (m, 1H), 2.75 (s, 3H), 2.71-2.66 (m, 1H). |
| 90 | 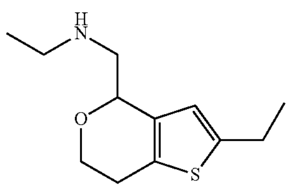 | HCl | F | LC-MS (6 min method): 1.37 min, M⁺ 226 @ 1.44 min; ¹H NMR (CD₃OD): δ 6.60 (s, 1H), 4.94-4.91 (m, 1H), 4.26-4.21 (m, 1H), 3.84-3.78 (m, 1H), 3.50 (dd, J = 2.2, 1′2.8 Hz, 1H), 3.19-3.09 (m, 3H), 2.93-2.89 (m, 1H), 2.81-2.69 (m, 3H), 1.33 (t, 3H), 1.27 (t, 3H). |
| 91 | 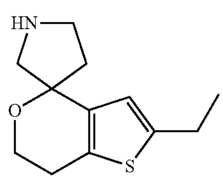 | HCl | A | LC-MS m/z 224.3 (MH⁺); ¹H NMR (DMSO-d⁶ + D₂O): δ 6.75 (s, 1H), 3.90-3.85 (m, 2H), 3.45-3.41 (m, 2H), 3.26-3.22 (m, 2H), 2.77-2.69 (m, 4H), 2.23-2.18 (m, 2H), 1.22-1.17 (t, J = 7.52 Hz, 3H). |
| 92 | 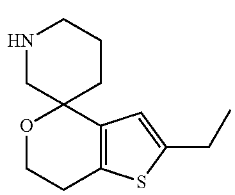 [SMILES: CCc1cc2c(s1)CCOC21CCCNC1] | HCl | A | LC-MS m/z 238.3 (MH⁺); ¹H NMR (DMSO-d⁶): δ 9.04 (br s, 1H), 8.31 (s, 1H), 6.76 (s, 1H), 3.93-3.89 (t, J = 5.10 Hz, 2H), 3.25-3.15 (m, 3H), 2.93-2.90 (m, 1H), 2.81-2.70 (m, 4H), 1.94-1.80 (m, 3H), 1.69-1.67 (m, 1H), 1.24-1.19 (t, J = 7.52 Hz, 3H). |
| 93 | 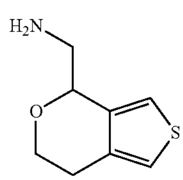 [SMILES: NCC1OCCc2cscc21] | HCl | D | ¹H NMR (CD₃OD): δ 7.23 (d, J = 2.0 Hz, 1H), 7.14 (d, J = 2.5 Hz, 1H), 4.93 (d, J = 7.0 Hz, 1H), 4.24-4.19 (m, 1H), 3.71 (td, J = 4.0, 11.0 Hz, 1H), 3.52 (dd, J = 2.5, 13.0 Hzs, 1H), 3.19 (dd, J = 7.5, 13.0 Hz, 1H), 2.96-2.87 (m, 1H), 2.81-2.75 (m, 1H). |
| 94 | 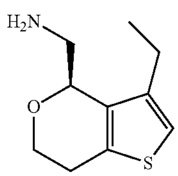 | HCl | CS; FME of separation of Compound 30, on AD column with MEHD 5 | LC-MS (6 min method): 0.49-1.01 min, M⁺ 198 @ 0.73 min; ¹H NMR (DMSO-d⁶): δ 8.06 (br s, 1H), 7.02 (s, 1H), 4.97-4.93 (dd, J₁ = 3.5 Hz, J₂ = 9.1 Hz, 1H), 4.03-3.95 (m, 1H), 3.86-3.79 (m, 1H), 3.09 (br s, 2H), 2.84-2.73 (m, 2H), 2.47-2.37 (m, 2H), 1.21-1.17 (t, J = 7.41 H, 3H). |

-continued

| Compd. No. | Structure | Salt or FB* | Method of Preparation | Analytical Data |
|---|---|---|---|---|
| 95 | 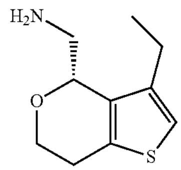 | HCl | CS; SME of separation of Compound 30, on AD column with MEHD 5 | LC-MS (6 min method): 0.49-1.01 min, M+ 198 @ 0.73 min; $^1$H NMR (DMSO-d$^6$): δ 8.06 (br s, 1H), 7.02 (s, 1H), 4.97-4.93 (dd, $J_1$ = 43.5 Hz, $J_2$ = 9.1 Hz, 1H), 4.03-3.95 (m, 1H), 3.86-3.79 (m, 1H), 3.09 (br s, 2H), 2.84-2.73 (m, 2H), 2.47-2.37 (m, 2H), 1.21-1.17 (t, J = 7.41 Hz, 3H). |
| 96 | 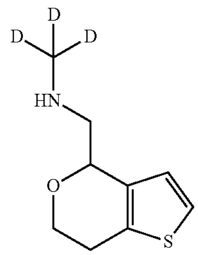 [SMILES: [2H]C([2H])([2H])NCC1OCCc2sccc21] | HCl | K | LC-MS (6 min method): 0.37 min, M+ 187 @ 0.35 min.; $^1$H NMR (CD$_3$OD): δ 7.27 (d, J = 5.13 Hz, 1H), 6.87 (d, J = 5.13 Hz, 1H), 4.98 (d, J = 8.43 Hz, 1H), 4.28-4.23 (m, 1H), 3.84-3.78 (m, 1H), 3.54-3.51 (m, 1H), 3.22 (dd, J = 8.43, 12.8 Hz, 1H), 3.03-2.95 (m, 1H), 2.80 (d, J = 16.1 Hz, 1H). |
| 97 | 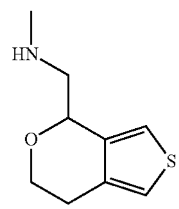 | HCl | D | $^1$H NMR (CD$_3$OD): δ 7.20 (d, J = 2.0 Hz, 1H), 7.13 (d, J = 2.5 Hz, 1H), 4.96 (d, J = 7.0 Hz, 1H), 4.23-4.19 (m, 1H), 3.70 (td, J = 4.0, 11.0 Hz, 1H), 3.49 (dd, J = 3.0, 13.0 Hz, 1H), 3.22 (dd, J = 8.5, 13.0 Hz, 1H), 2.936-2.86 (m, 1H), 2.81-2.75 (m, 1H), 2.69 (s, 3H). |
| 98 | 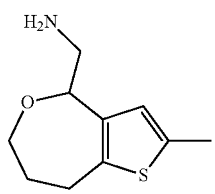 | HCl | C | $^1$H NMR (CD$_3$OD): δ 6.50 (s, 1H), 4.66 (dd, J = 2.5, 0.7 Hz, 1H), 4.30 (dt, J = 2.5, 1.2 Hz, 1H), 3.85 (ddd, J = 3.0, 2.5, 1.2 Hz, 1H), 3.46 (dd, J = 3.0, 0.7 Hz, 1H), 3.33-3.29 (m, 1H), 3.17 (dd, J = 3.0, 2.5 Hz, 1H), 3.00 (ddd, J = 4.0, 2.0, 0.7 Hz, 1H), 2.86 (ddd, J = 4.0, 2.0, 0.7 Hz, 1H), 2.37 (s, 3H), 1.96-1.86 (m, 2H). |
| 99 | 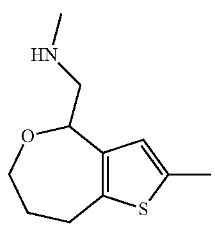 | HCl | C | $^1$H NMR (CD$_3$OD): δ 6.51 (s, 1H), 4.74 (dd, J = 2.5, 0.8 Hz, 1H), 4.30 (dt, J = 3.0, 1.5 Hz, 1H), 3.86 (ddd, J = 3.0, 2.0, 1.0 Hz, 1H), 3.53 (dd, J = 3.0, 1.0 Hz, 1H), 3.01 (ddd, J = 4.0, 2.0, 1.0 Hz, 1H), 2.87 (ddd, J = 4.0, 2.0, 1.0 Hz, 1H), 2.76 (s, 3H), 2.37 (s, 3H), 1.98-1.85 (m, 2H). |
| 100 | 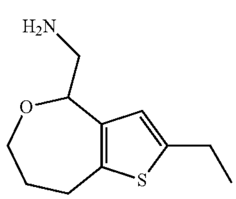 | HCl | C | $^1$H NMR (CD$_3$OD): δ 6.53 (s, 1H), 4.66 (dd, J = 2.5, 0.7 Hz, 1H), 4.30 (dt, J = 3.0, 1.2 Hz, 1H), 3.85 (ddd, J = 3.2, 2.7, 1.2 Hz, 1H), 3.48 (dd, J = 3.2, 0.7 Hz, 1H), 3.17 (dd, J = 3.2, 2.7 Hz, 1H), 3.03 (ddd, J = 4.0, 2.0, 1.0 Hz, 1H), 2.88 (ddd, J = 4.0, 2.0, 1.0 Hz, 1H), 2.74 (q, J = 1.9 Hz, 2H), 1.96-1.88 (m, 2H), 1.24 (t, J = 3H). |
| 101 | 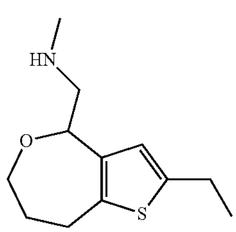 | HCl | C | $^1$H NMR (CD$_3$OD): δ 6.54 (s, 1H), 4.75 (dd, J = 2.5, 0.7 Hz, 1H), 4.31 (dt, J = 3.0, 1.2 Hz, 1H), 3.86 (ddd, J = 3.2, 2.2, 1.0 Hz, 1H), 3.55 (dd, J = 3.0, 0.7 Hz, 1H), 3.34-3.28 (m, 1H), 3.02 (ddd, J = 4.0, 2.0, 1.0 Hz, 1H), 2.89 (ddd, J = 4.0, 2.0, 1.0 Hz, 1H), 2.77 (s, 3H), 2.74 (q, J = 1.9 Hz, 2H), 1.98-1.86 (m, 2H), 1.25 (t, J = 1.9 Hz, 3H). |

-continued

| Compd. No. | Structure | Salt or FB* | Method of Preparation | Analytical Data |
|---|---|---|---|---|
| 102 | 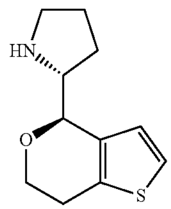 [SMILES: c1cc2c(s1)CCO[C@H]2[C@H]1CCCN1] | HCl | N | LC-MS: m/z 210 (MH$^+$); $^1$H NMR (DMSO-d$_6$): δ 10.05 (s, 1H), 8.79 (s, 1H), 7.41-7.39 (d, J = 5.19 Hz, 1H), 6.99-6.98 (d, J = 5.22 Hz, 1H), 5.06-5.05 (d, J = 2.10 Hz, 1H), 4.28-4.17 (m, 2H), 3.75-3.67 (m, 1H), 3.22-3.05 (m, 2H), 2.96-2.90 (m, 1H), 2.79-2.73 (m, 1H), 1.91-1.74 (m, 2H), 1.65-1.55 (m, 2H). |
| 103 | 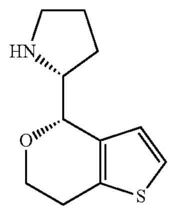 [SMILES: c1cc2c(s1)CCO[C@@H]2[C@H]1CCCN1] | HCl | N | LC-MS: m/z 210 (MH$^+$); $^1$H NMR (DMSO-d$_6$): δ 9.69 (s, 1H), 8.51 (s, 1H), 7.41-7.40 (d, J = 4.50 Hz, 1H), 6.97-6.96 (d, J = 4.20 Hz, 1H), 4.89-4.88 (d, J = 4.20 Hz, 1H), 4.19-4.15 (m, 1H), 3.92-3.90 (m, 1H), 3.76 (s, 1H), 3.10-2.95 (m, 3H), 2.80-2.75 (m, 1H), 2.14-1.84 (m, 4H). |
| 104 | 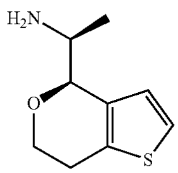 | HCl | N | LC-MS: m/z 184 (MH$^+$); $^1$H NMR (DMSO-d$_6$): δ 8.39 (s, 3H), 7.40-7.38 (d, J = 5.16 Hz, 1H), 6.99-6.98 (d, J = 5.22 Hz, 1H), 4.99-4.98 (d, J = 1.78 Hz, 1H), 4.27-4.22 (dd, J = 11.24 Hz, 5.12 Hz, 1H), 3.82 (s, 1H), 3.70-3.62 (m, 1H), 2.98-2.87 (m, 1H), 2.77-2.71 (m, 1H), 0.91-0.89 (d, J = 6.69 Hz, 3H). |
| 105 | 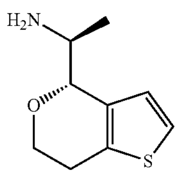 | HCl | N | LC-MS: m/z 184 (MH$^+$); $^1$H NMR (DMSO-d$_6$): δ 7.84 (s, 3H), 7.41-7.40 (d, J = 5.10 Hz, 1H), 7.00-6.98 (d, J = 5.10 Hz, 1H), 4.71-4.70 (d, J = 2.11 Hz, 1H), 4.20-4.13 (m, 1H), 3.77-3.69 (m, 2H), 2.95-2.76 (m, 2H), 1.36-1.34 (d, J = 6.6 Hz, 3H). |
| 106 | 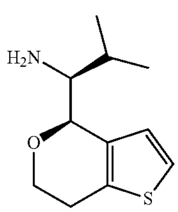 | HCl | N | LC-MS: m/z 212 (MH$^+$); $^1$H NMR (DMSO-d$_6$): δ 7.59 (s, 3H), 7.43-7.41 (d, J = 5.40 Hz, 1H), 7.01-6.99 (d, J = 5.10 Hz, 1H), 4.95 (s, 1H), 4.24-4.18 (m, 1H), 3.77-3.68 (m, 1H), 2.95-2.91 (m, 1H), 2.77-2.72 (m, 1H), 2.12-2.05 (m, 1H), 1.06-1.03 (m, 6H). |
| 107 | 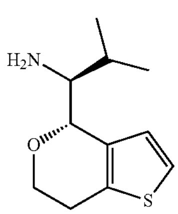 | HCl | N | LC-MS: m/z 212 (MH$^+$); $^1$H NMR (CD$_3$OD): δ 7.33-7.31 (d, J = 5.40 Hz, 1H), 6.93-6.91 (d, J = 7.56 Hz, 1H), 5.08-5.06 (m, m1H), 4.39-4.33 (m, 1H), 3.76-3.67 (m, 1H), 3.53-3.51 (m, 1H), 3.10-3.07 (m, 1H), 2.81-2.75 (m, 1H), 2.08-2.01 (m, 1H), 1.04-0.97 (m, 6H). |
| 108 | 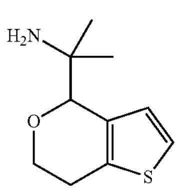 | HCl | O | LC-MS: m/z 198 (MH$^+$); $^1$H NMR (DMSO-d$_6$): δ 8.16 (s, 3H), 7.41-7.40 (d, J = 5.28 Hz, 1H), 6.98-6.97 (d, J = 5.22 Hz, 1H), 4.80 (s, 1H), 4.25-4.20 (m, 1H), 3.58-3.50 (dd, J = 10.85 Hz, 3.20 Hz, 1H), 2.96-2.74 (m, 2H), 1.48 (s, 3H), 1.01 (s, 3H). |

-continued

| Compd. No. | Structure | Salt or FB* | Method of Preparation | Analytical Data |
|---|---|---|---|---|
| 109 | 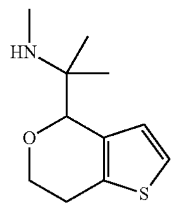 | HCl | O | LC-MS: m/z 212 (MH$^+$); $^1$H NMR (CD$_3$OD): δ 7.34-7.32 (dd, J = 5.03 Hz, 5.03 Hz, 1H), 6.98-6.96 (d, J = 5.34 Hz, 1H), 4.98-4.97 (m, 1H), 4.38-4.32 (m, 1H), 3.71-3.62 (td, J = 11.13 Hz, 2.94 Hz, 1H), 3.03-2.97 (m, 1H), 2.84-2.78 (m, 1H), 2.69 (s, 3H), 1.59 (s, 3H), 1.14 (s, 3H). |
| 110 | 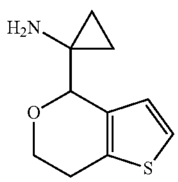 [SMILES: NC1(C2OCCc3sccc32)CC1] | HCl | O | LC-MS: m/z 196 (MH$^+$); $^1$H NMR (DMSO-d$_6$): δ 8.25-8.21 (brs, 3H), 7.40-7.39 (d, J = 5.10 Hz, 1H), 7.25-7.23 (d, J = 5.40 Hz, 1H), 4.10-4.03 (m, 2H), 3.90-3.82 (m, 1H), 2.93-2.73 (m, 2H), 2.29-2.21 (m, 2H), 2.18-2.02 (m, 2H). |
| 111 | 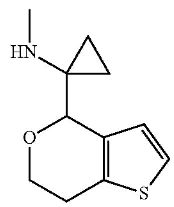 | HCl | O | LC-MS: m/z 210 (MH$^+$); $^1$H NMR (DMSO-d$_6$): δ 9.03 (s, 2H), 7.41-7.40 (d, J = 4.51 Hz, 1H), 7.22-7.20 (d, J = 3.92 Hz, 1H), 4.13-4.04 (m, 2H), 3.86-3.79 (m, 1H), 2.96-2.91 (m, 1H), 2.78-2.73 (m, 1H), 2.31 (s, 3H), 2.26-2.01 (m, 4H). |
| 112 | 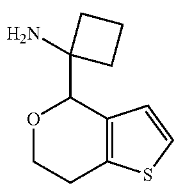 [SMILES: NC1(C2OCCc3sccc32)CCC1] | HCl | O | LC-MS: m/z 210 (MH$^+$); $^1$H NMR (DMSO-d$_6$): δ 7.86 (s, 3H), 7.37-7.36 (d, J = 5.10 Hz, 1H), 7.05-7.04 (d, J = 5.31 Hz, 1H), 4.10-4.05 (dd, J = 11.49 Hz, 4.71 Hz, 1H), 3.81-3.71 (m, 2H), 2.98-2.87 (m, 1H), 2.89-2.87 (m, 1H), 2.17-2.10 (m, 2H), 1.88-1.82 (m, 4H). |
| 113 | 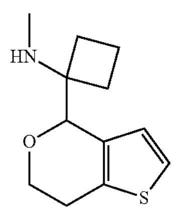 | HCl | O | LC-MS: m/z 224 (MH$^+$); $^1$H NMR (DMSO-d$_6$): δ 9.20 (s, 1H), 8.17 (s, 1H), 7.40-7.38 (d, J = 5.1 Hz, 1H), 7.06-7.05 (d, J = 5.4 Hz, 1H), 4.13-4.07 (m, 1H), 3.84-3.70 (m, 2H), 3.02-2.89 (m, 1H), 2.77-2.71 (m, 1H), 2.26-2.16 (m, 5H), 1.89-1.80 (m, 4H). |
| 114 | 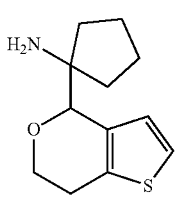 [SMILES: NC1(C2OCCc3sccc32)CCCC1] | HCl | O | LC-MS: m/z 224 (MH$^+$); $^1$H NMR (DMSO-d$_6$): δ 7.85 (s, 3H), 7.41-7.39 (d, J = 4.82 Hz, 1H), 7.00-6.98 (d, J = 4.83 Hz, 1H), 4.85 (s, 1H), 4.23-4.17 (m, 1H), 3.61-3.54 (t, J = 10.24 Hz, 1H), 3.01-2.92 (m, 1H), 2.79-2.74 (m, 1H), 2.17-2.12 (m, 1H), 1.87-1.77 (m, 5H), 1.54 (s, 2H). |
| 115 | 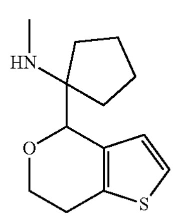 | HCl | O | LC-MS: m/z 238 (MH$^+$); $^1$H NMR (DMSO-d$_6$): δ 8.66 (s, 2H), 7.41-7.40 (d, J = 3.95 Hz, 1H), 7.00-9.99 (d, J = 3.96 Hz, 1H), 5.03 (s, 1H), 4.20-4.17 (m, 1H), 3.62-3.55 (m, 1H), 2.93-2.82 (m, 1H), 2.76-2.74 (m, 1H), 2.50 (s, 3H), 2.20-2.15 (m, 1H), 1.96-1.89 (m, 1H), 1.74-1.61 (m, 4H), 1.49-1.38 (m, 2H). |

-continued

| Compd. No. | Structure | Salt or FB* | Method of Preparation | Analytical Data |
|---|---|---|---|---|
| 116 | 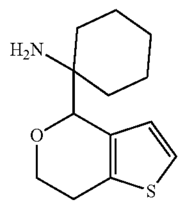 [SMILES: NC1(C2OCCc3sccc32)CCCCC1] | HCl | O | LC-MS: m/z 238 (MH+); 1H NMR (DMSO-d6): δ 7.73 (s, 3H), 7.43-7.41 (d, J = 4.84 Hz, 1H), 6.97-6.95 (d, J = 4.85 Hz, 1H), 4.94 (s, 1H), 4.22-4.19 (m, 1H), 3.57-3.51 (m, 1H), 2.98-2.90 (m, 1H), 2.78-2.74 (m, 1H), 1.94-1.91 (m, 1H), 1.77-1.42 (m, 8H), 1.26 (s, 1H). |
| 117 | 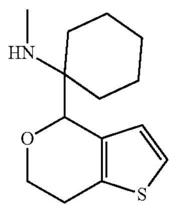 [SMILES: CNC1(C2OCCc3sccc32)CCCCC1] | HCl | O | LC-MS: m/z 252 (MH+); 1H NMR (DMSO-d6): δ 8.47 (s, 1H), 8.36 (s, 1H), 7.45-7.44 (d, J = 4.88 Hz, 1H), 6.99-6.97 (d, J = 1.86 Hz, 1H), 5.05 (s, 1H), 4.24-4.19 (m, 1H), 3.58-3.51 (m, 1H), 2.97-2.90 (m, 1H), 2.80-2.75 (m, 1H), 2.34 (s, 3H), 1.95-1.32 (m, 10H). |
| 118 | 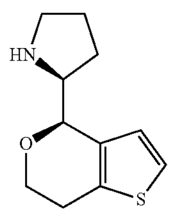 [SMILES: c1cc2c(s1)CCO[C@H]2[C@@H]1CCCN1] | HCl | N | LC-MS: m/z 210 (MH+); 1H NMR (DMSO-d6): δ 9.48-9.47 (d, J = 2.07 Hz, 1H), 8.40-8.39 (d, J = 3.54 Hz, 1H), 7.42-7.40 (d, J = 3.54 Hz, 1H), 6.98-6.96 (d, J = 5.22 Hz, 1H), 4.89-4.87 (d, J = 5.31 Hz, 1H), 4.22-4.15 (m, 1H), 3.95-3.89 (m, 1H), 3.80-3.72 (m, 1H), 3.13-3.06 (m, 2H), 2.97-2.75 (m, 1H), 2.50-2.49 (m, 1H), 2.13-1.84 (m, 4H). |
| 119 | 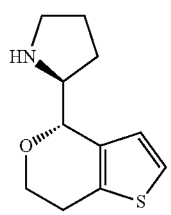 [SMILES: c1cc2c(s1)CCO[C@@H]2[C@@H]1CCCN1] | HCl | N | LC-MS: m/z 210 (MH+); 1H NMR (DMSO-d6): δ 9.94 (s, 1H), 8.76-8.75 (d, J = 4.20 Hz, 1H), 7.41-7.39 (d, J = 5.19 Hz, 1H), 6.99-6.98 (d, J = 5.22 Hz, 1H), 5.05-5.04 (d, J = 2.07 Hz, 1H), 4.28-4.15 (m, 2H), 3.75-3.70 (m, 1H), 3.20-3.10 (m, 2H), 2.96-2.92 (m, 1H), 2.79-2.73 (m, 1H), 1.90-1.56 (m, 4H). |
| 120 | 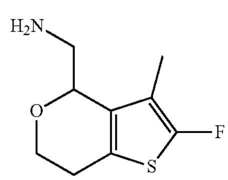 | HCl | P | LC-MS: m/z 202 (MH+); 1H NMR (DMSO-d6): δ 8.19 (s, 3H), 4.89-4.86 (d, J = 7.25 Hz, 1H), 4.06-4.00 (m, 1H), 3.98-3.79 (m, 1H), 3.16-3.06 (m, 2H), 2.76-2.62 (m, 2H), 1.99-1.98 (d, J = 2.14 Hz, 3H). |
| 121 | 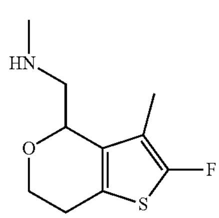 | HCl | P | LC-MS: m/z 216 (MH+); 1H NMR (DMSO-d6): δ 9.25 (s, 1H), 8.67 (s, 1H), 5.00-4.97 (d, J = 8.10 Hz, 1H), 4.08-4.00 (m, 1H), 3.88-3.79 (m, 1H), 3.41-3.14 (m, 2H), 2.77-2.65 (m, 5H), 2.01-2.00 (d, J = 2.10 Hz, 3H). |
| 122 | 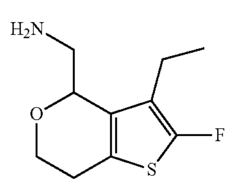 | HCl | P | LC-MS: m/z 216 (MH+); 1H NMR (CD3OD): δ 4.91-4.85 (m, 1H), 4.20-4.12 (m, 1H), 3.91-3.84 (m, 1H), 3.29-3.17 (m, 2H), 2.79-2.72 (m, 2H), 2.57-2.43 (m, 2H), 1.22-1.15 (m, 3H). |

-continued

| Compd. No. | Structure | Salt or FB* | Method of Preparation | Analytical Data |
|---|---|---|---|---|
| 123 | 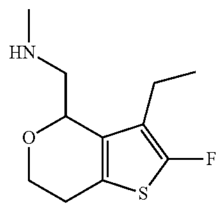 | HCl | P | LC-MS: m/z 230 (MH+); 1H NMR (CD3OD): δ 4.98-4.94 (m, 1H), 4.22-4.14 (m, 1H), 3.92-3.84 (m, 1H), 3.36-3.33 (m, 2H), 2.80-2.69 (m, 5H), 2.62-2.51 (m, 1H), 2.50-2.35 (m, 1H), 1.22-1.17 (t, J = 7.55 Hz, 3H). |
| 124 | 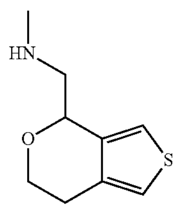 | HCl | D | 1H NMR (CD3OD): δ 7.20 (d, J = 2.0 Hz, 1H), 7.13 (d, J = 2.5 Hz, 1H), 4.96 (d, J = 7.0 Hz, 1H), 4.23-4.19 (m, 1H), 3.70 (td, J = 4.0, 11.0 Hz, 1H), 3.49 (dd, J = 3.0, 13.0 Hz, 1H), 3.22 (dd, J = 8.5, 13.0 Hz, 1H), 2.94-2.86 (m, 1H), 2.81-2.75 (m, 1H) 2.69 (s, 3H). |
| 125 | 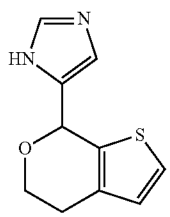 [SMILES: c1ncc(C2OCCc3ccsc32)[nH]1] | HCl | A | LC-MS (6 minute method): 1.17 min, M+ 207 @ 1.1 min; 1H NMR (CD3OD-d4): δ 7.61 (s, 1H), 7.16 (d, J = 4.76 Hz, 1H), 7.03 (s, 1H), 6.81 (d, J = 5.13 Hz, 1H), 5.94 (s, 1H), 4.16-4.12 (m, 1H), 3.93-3.86 (m, 1H), 2.87-2.80 (m, 1H), 2.74-2.68 (m, 1H). |
| 126 | 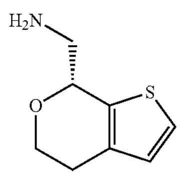 [SMILES: NC[C@H]1OCCc2ccsc21] | HCl | CS; FME from SFC separation of Compound 36, using isocratic 15% Methanol in CO2 on a 4.6 × 100 mm LUX Cellulose 2 from Phenomenex and flow of 4 mL/min | 1H NMR (CD3OD): δ 7.34 (d, J = 5.13 Hz, 1H), 6.89 (d, J = 5.13 Hz, 1H), 5.06 (s, 1H), 4.25-4.22 (m, 1H), 3.83-3.77 (m, 1H), 3.38 (d, J = 13.2 Hz, 1H), 3.16-3.12 (m, 1H), 2.85-2.83 (m, 1H), 2.68-2.65 (m, 1H). |
| 127 | 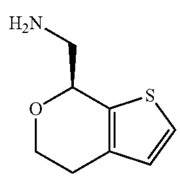 [SMILES: NC[C@@H]1OCCc2ccsc21] | HCl | CS; SME from SFC separation of Compound 36, using isocratic 15% Methanol in CO2 on a 4.6 × 100 mm LUX Cellulose 2 from Phenomenex and flow of 4 mL/min | 1H NMR (CD3OD): δ 7.34 (d, J = 5.13 Hz, 1H), 6.89 (d, J = 5.13 Hz, 1H), 5.06 (s, 1H), 4.25-4.22 (m, 1H), 3.83-3.77 (m, 1H), 3.38 (d, J = 13.2 Hz, 1H), 3.16-3.12 (m, 1H), 2.85-2.83 (m, 1H), 2.68-2.65 (m, 1H). |
| 128 | 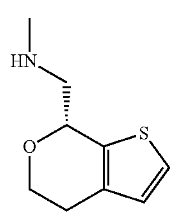 | HCl | CS; FME from SFC separation of Boc-protected Compound 89, using isocratic 15% isopropanol in CO2 on a 4.6 × 100 mm LUX Cellulose 2 from Phenomenex and flow of 80 g/min | 1H NMR (CD3OD): δ 7.36 (d, J = 5.13 Hz, 1H), 6.89 (d, J = 4.76 Hz, 1H), 5.14-5.11 (m, 1H), 4.27-4.22 (m, 1H), 3.84-3.77 (m, 1H), 3.49-3.45 (m, 1H), 3.26-3.23 (m, 1H), 2.89-2.81 (m, 1H), 2.73 (s, 3H), 2.70-2.64 (m, 1H). |
| 129 | 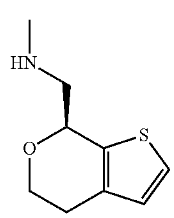 | HCl | CS; SME from SFC separation of Boc-protected Compound 89, using isocratic 15% isopropanol in CO2 on a 4.6 × 100 mm LUX Cellulose 2 from Phenomenex and flow of 80 g/min | 1H NMR (CD3OD): δ 7.36 (d, J = 5.13 Hz, 1H), 6.89 (d, J = 4.76 Hz, 1H), 5.14-5.11 (m, 1H), 4.27-4.22 (m, 1H), 3.84-3.77 (m, 1H), 3.49-3.45 (m, 1H), 3.26-3.23 (m, 1H), 2.89-2.81 (m, 1H), 2.73 (s, 3H), 2.70-2.64 (m, 1H). |

| Compd. No. | Structure | Salt or FB* | Method of Preparation | Analytical Data |
|---|---|---|---|---|
| 130 | 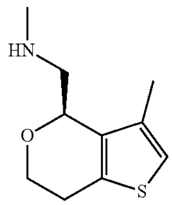 | HCl | CS; FME from SFC separation of Boc-protected Compound 78, using isocratic 43% (hexane:isopropanol 99:1) in CO₂ on a 4.6 × 100 mm Whelk-O1 from Regis and flow of 80 g/min | $^1$H NMR (DMSO-d$^6$): δ 9.11 (br s, 1H), 8.59 (br s, 1H), 7.00 (s, 1H), 5.05-5.03 (d, J = 6.63 Hz, 1H), 4.04-3.96 (m, 1H), 3.87-3.80 (m, 1H), 3.28-3.21 (m, 2H), 2.83-2.74 (m, 2H), 2.61-2.59 (d, J = 1.68 Hz, 3H), 2.13 (s, 3H). |
| 131 | 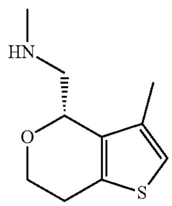 | HCl | CS; SME from SFC separation of Boc-protected Compound 78, using isocratic 43% (hexane:isopropanol 99:1) in CO₂ on a 4.6 × 100 mm Whelk-O1 from Regis and flow of 80 g/min | $^1$H NMR (DMSO-d$^6$): δ 9.11 (br s, 1H), 8.59 (br s, 1H), 7.00 (s, 1H), 5.05-5.03 (d, J = 6.63 Hz, 1H), 4.04-3.96 (m, 1H), 3.87-3.80 (m, 1H), 3.28-3.21 (m, 2H), 2.83-2.74 (m, 2H), 2.61-2.59 (d, J = 1.68 Hz, 3H), 2.13 (s, 3H). |
| 132 | 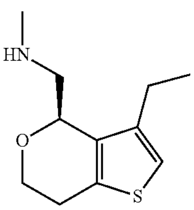 | HCl | CS; FME from SFC separation of Compound 79, using isocratic 10% Hexane:Isopropanol (1:1) in CO₂ on a 4.6 × 100 mm LUX Cellulose 2 from Phenomenex and flow of 4 mL/min | $^1$H NMR (DMSO-d$^6$): δ 9.16 (br s, 1H), 8.58 (s, 1H), 7.02 (s, 1H), 5.07-5.05 (d, J = 8.07 Hz, 1H), 4.05-3.97 (m, 1H), 3.87-3.80 (m, 1H), 3.27-3.15 (m, 2H), 2.90-2.73 (m, 2H), 2.60 (s, 3H), 2.47-2.41 (m, 2H), 1.22-1.17 (t, J = 7.40 Hz, 3H). |
| 133 | 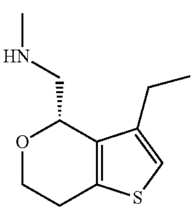 | HCl | CS; SME from SFC separation of Compound 79, using isocratic 10% Hexane:Isopropanol (1:1) in CO₂ on a 4.6 × 100 mm LUX Cellulose 2 from Phenomenex and flow of 4 mL/min | $^1$H NMR (DMSO-d$^6$): δ 9.16 (br s, 1H), 8.58 (s, 1H), 7.02 (s, 1H), 5.07-5.05 (d, J = 8.07 Hz, 1H), 4.05-3.97 (m, 1H), 3.87-3.80 (m, 1H), 3.27-3.15 (m, 2H), 2.90-2.73 (m, 2H), 2.60 (s, 3H), 2.47-2.41 (m, 2H), 1.22-1.17 (t, J = 7.40 Hz, 3H). |
| 134 | 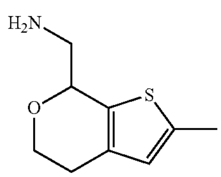 | HCl | B | LC-MS: m/z 184 (MH$^+$); $^1$H NMR (DMSO-d$_6$): δ 8.15 (s, 3H), 6.61 (s, 1H), 4.98-4.96 (d, J = 8.10 Hz, 1H), 4.12-4.03 (m, 1H), 3.77-3.66 (m, 1H), 3.23-3.14 (m, 1H), 2.98 (s, 1H), 2.85-2.62 (m, 2H), 2.40 (s, 3H). |
| 135 | 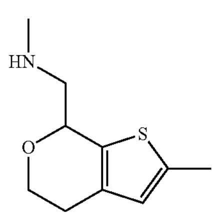 | HCl | B | LC-MS: m/z 198 (MH$^+$); $^1$H NMR (DMSO-d$_6$): δ 9.17 (s, 1H), 8.75 (s, 1H), 66.2-6.61 (d, J = 0.95 Hz, 1H), 4.13-4.06 (m, 1H), 5.09-5.06 (d, J = 9.06 Hz, 1H), 3.78-3.70 (m, 1H), 3.30-3.08 (m, 2H), 2.69-2.52 (m, 5H), 2.40 (s, 3H). |
| 136 | 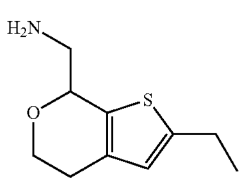 | HCl | B | LC-MS: m/z 198 (MH$^+$); $^1$H NMR (DMSO-d$_6$): δ 8.23 (s, 3H), 6.65 (s, 1H), 5.00-4.97 (d, J = 7.85 Hz, 1H), 4.13-4.06 (m, 1H), 3.77-3.69 (m, 1H), 3.16-3.11 (m, 1H), 3.03-2.93 (m, 1H), 2.79-2.70 (m, 2H), 2.67-2.58 (m, 2H), 1.23-1.18 (t, J = 7.50 Hz, 3H). |

-continued

| Compd. No. | Structure | Salt or FB* | Method of Preparation | Analytical Data |
|---|---|---|---|---|
| 137 | 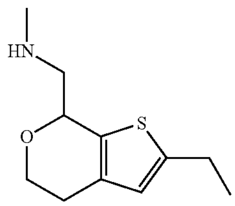 | HCl | B | LC-MS: m/z 212 (MH+); 1H NMR (DMSO-d6 + D2O): δ 6.64 (s, 1H), 5.02-5.00 (d, J = 7.82 Hz, 1H), 4.10-4.05 (m, 1H), 3.77-3.69 (m, 1H), 3.31-3.26 (m, 1H), 3.18-3.11 (m, 1H), 2.78-2.70 (m, 2H), 2.66-2.63 (m, 5H), 1.21-1.16 (t, J = 7.56 Hz, 3H). |
| 138 | 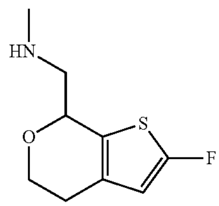 | HCl | B | LC-MS: m/z 202 (MH+); 1H NMR (DMSO-d6): δ 9.31-9.29 (d, J = 6.24 Hz, 1H), 8.85 (s, 1H), 6.59 (s, 1H), 5.06-5.03 (d, J = 8.79 Hz, 1H), 4.13-4.09 (m, 1H), 3.81-3.79 (m, 1H), 3.25-3.20 (m, 2H), 2.72-2.57 (m, 5H). |
| 139 | 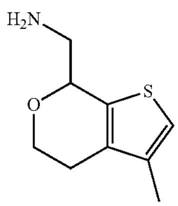 | HCl | B | LC-MS: m/z 184 (MH+); 1H NMR (DMSO-d6): δ 8.06 (s, 3H), 7.10 (s, 1H), 5.02-4.99 (d, J = 8.93 Hz, 1H), 4.19-1.13 (m, 1H), 3.80-3.72 (m, 1H), 3.22-3.14 (m, 1H), 2.99-2.89 (m, 1H), 2.65-2.60 (m, 2H), 2.05 (s, 3H). |
| 140 | 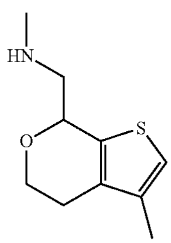 | HCl | B | LC-MS: m/z 198 (MH+); 1H NMR (DMSO-d6): δ 8.87 (s, 2H), 7.11 (s, 1H), 5.11-5.08 (d, J = 9.64 Hz, 1H), 4.02-4.13 (m, 1H), 3.82-3.74 (m, 1H), 3.35 (s, 1H), 3.20-3.12 (m, 1H), 2.60-2.50 (m, 5H), 2.09 (s, 3H). |
| 141 | 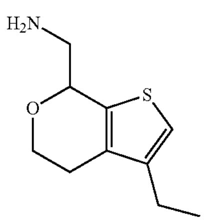 | HCl | B | LC-MS: m/z 198 (MH+); 1H NMR (DMSO-d6): δ 8.21 (s, 3H), 7.10 (s, 1H), 5.03-5.00 (d, J = 8.15 Hz, 1H), 4.18-4.12 (m, 1H), 3.80-3.72 (m, 1H), 3.20-3.18 (m, 1H), 2.99 (s, 1H), 2.68-2.60 (m, 3H), 2.45-2.43 (m, 1H), 1.18-1.14 (t, J = 7.59 Hz, 3H). |
| 142 | 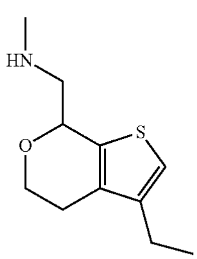 | HCl | B | LC-MS: m/z 212 (MH+); 1H NMR (DMSO-d6 + D2O): δ 7.08 (s, 1H), 5.05 (d, J = 10 Hz, 1H), 4.21-4.11 (m, 1H), 3.80-3.65 (m, 2H), 3.35-3.12 (m, 2H), 2.67-2.35 (m, 6H), 1.19-1.14 (t, J = 7.49 Hz, 3H). |
| 143 | 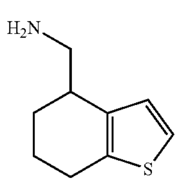 [SMILES: NCC1CCCc2sccc21] | HCl | Z | 1H NMR (CD3OD): δ 7.20 (d, J = 1.5 Hz, 1H), 6.90 (d, J = 1.5 Hz, 1H), 3.33-3.30 (m, 1H), 3.08 (m, 1H), 2.99 (dd, J = 2.5, 3.0 Hz, 1H), 2.80 (apt, J = 1.5 Hz, 2H), 2.02-1.87 (m, 2H), 1.85-1.81 (m, 1H), 1.71-1.64 (m, 1H). |

| Compd. No. | Structure | Salt or FB* | Method of Preparation | Analytical Data |
|---|---|---|---|---|
| 144 | 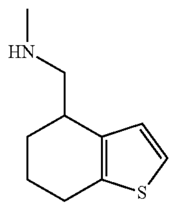 | HCl | Z | $^1$H NMR (CD$_3$OD): δ 7.21 (d, J = 1.5 Hz, 1H), 6.92 (d, J = 1.5 Hz, 1H), 3.36 (dd, J = 3.0, 1.0 Hz, 1H), 3.14 (m, 1H), 3.09 (dd, J = 3.0, 2.5 Hz, 1H), 2.80 (apt, J = 1.5 Hz, 2H), 2.75 (s, 3H), 2.03-1.95 (m, 2H), 1.88-1.81 (m, 1H), 1.72-1.65 (m, 1H). |
| 145 | 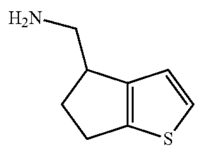 | HCl | Q | LC-MS: m/z 154 (MH$^+$); $^1$H NMR (DMSO-d$_6$): δ 8.10-7.98 (d, J = 9.68 Hz, 2H), 7.39-7.38 (d, J = 3.95 Hz, 1H), 6.98-6.96 (d, J = 5.10 Hz, 1H), 3.35-3.30 (m, 1H), 3.16-3.11 (m, 1H), 2.97-2.79 (m, 3H), 2.70-2.61 (m, 1H), 2.27-2.22 (m, 1H). |
| 146 | 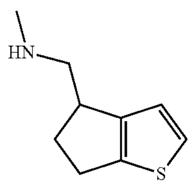 | HCl | Q | LC-MS: m/z 168 (MH$^+$); $^1$H NMR (CD$_3$OD): δ 7.33-7.31 (d, J = 4.20 Hz, 1H), 6.91-6.90 (d, J = 4.52 Hz, 1H), 3.49-3.32 (m, 2H), 3.11-2.80 (m, 4H), 2.76 (s, 3H), 2.35-2.24 (m, 1H). |
| 147 | 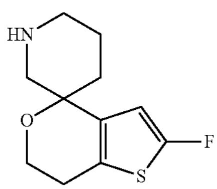 [SMILES: Fc1cc2c(s1)CCOC21CCCNC1] | HCl | R | LC-MS: m/z 228 (MH$^+$); $^1$H NMR (DMSO-d$_6$): δ 9.56-9.53 (d, J = 7.21 Hz, 1H), 8.38-8.29 (m, 1H), 6.75-6.75 (d, J = 5.45 Hz, 2H), 3.33-3.13 (m, 3H), 2.87-2.81 (m, 1H), 2.74-2.62 (m, 2H), 1.93-1.83 (m, 3H), 1.72-1.67 (m, 1H). |
| 148 | 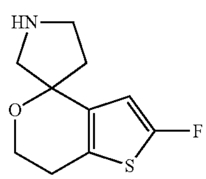 [SMILES: Fc1cc2c(s1)CCOC21CCNC1] | HCl | R | LC-MS: m/z 214 (MH$^+$); $^1$H NMR (CD$_3$OD): δ 9.90 (s, 1H), 9.40 (s, 1H), 6.80-6.79 (d, J = 2.42 Hz, 1H), 3.98-3.86 (t, J = 5.51 Hz, 2H), 3.44-3.39 (m, 2H), 2.30-3.21 (m, 2H), 2.71-2.67 (t, J = 5.01 Hz, 2H), 2.26-2.21 (m, 2H). |
| 149 | 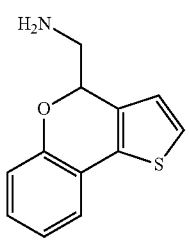 [SMILES: NCC1Oc2ccccc2-c2sccc21] | HCl | T | LC-MS: m/z 218 (MH$^+$); $^1$H NMR (D$_2$O): δ 7.35-7.30 (m, 2H), 7.16-7.11 (m, 1H), 6.97-6.87 (m, 3H), 5.65-5.63 (m, 1H), 3.33-3.31 (m, 3H). |
| 150 | 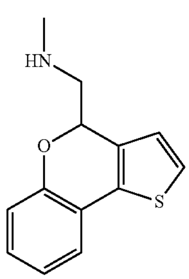 [SMILES: CNCC1Oc2ccccc2-c2sccc21] | HCl | T | LC-MS: m/z 232 (MH$^+$); $^1$H NMR (DMSO-d$_6$): δ 9.25 (s, 1H), 8.99 (s, 1H), 7.70-7.62 (d, J = 5.10 Hz, 1H), 7.12-7.33 (dd, J = 7.47 Hz, 1.50 Hz, 1H), 7.22-7.17 (m, 1H), 7.13-7.10 (m, 2H), 5.85-5.81 (dd, J = 9.36 Hz, 2.75 Hz, 1H), 3.50-3.39 (m, 2H), 2.80 (s, 3H). |

| Compd. No. | Structure | Salt or FB* | Method of Preparation | Analytical Data |
|---|---|---|---|---|
| 151 | 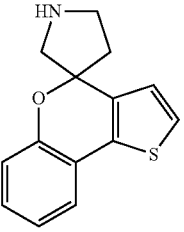 [SMILES: c1ccc2c(c1)OC1(CCNC1)c1ccsc1-2] | HCl | S | LC-MS: m/z 244 (MH$^+$); $^1$H NMR (DMSO-d$_6$): δ 10.16-10.14 (d, J = 3.60 Hz, 1H), 9.97 (s, 1H), 7.66-7.64 (d, J = 5.13 Hz, 1H), 7.41-7.38 (m, 1H), 7.25-7.20 (m, 1H), 7.05-7.01 (m, 2H), 3.76-3.63 (m, 1H), 3.59-3.43 (m, 3H), 2.44-2.33 (m, 2H). |
| 152 | 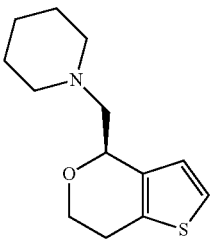 [SMILES: c1cc2c(s1)CCO[C@H]2CN1CCCCC1] | HCl | CS; FME from SFC separation of Compound 18 | LC-MS (6 minute method): 1.17 min, M$^+$ 238 @ 1.21 min, $^1$H NMR (CDCl$_3$): δ 7.10-7.09 (d, J = 5.1 Hz, 1H), 6.91-6.89 (d, J = 5.1 Hz, 1H), 4.90-4.84 (m, 1H), 4.27-4.21 (m, 1H), 3.81-3.73 (m, 1H), 3.04-2.94 (m, 1H), 2.78-2.70 (m, 1H), 2.67-2.62 (m, 2H), 2.55-2.52 (m, 4H), 1.69-1.59 (m, 4H), 1.50-1.43 (m, 2H). |
| 153 | 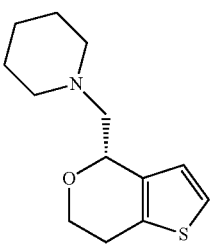 [SMILES: c1cc2c(s1)CCO[C@@H]2CN1CCCCC1] | HCl | CS; SME from SFC separation of Compound 18 | LC-MS (6 minute method): 1.17 min, M$^+$ 238 @ 1.21 min, $^1$H NMR (CDCl$_3$): δ 7.10-7.09 (d, J = 5.1 Hz, 1H), 6.91-6.89 (d, J = 5.1 Hz, 1H), 4.90-4.84 (m, 1H), 4.27-4.21 (m, 1H), 3.81-3.73 (m, 1H), 3.04-2.94 (m, 1H), 2.78-2.70 (m, 1H), 2.67-2.62 (m, 2H), 2.55-2.52 (m, 4H), 1.69-1.59 (m, 4H), 1.50-1.43 (m, 2H). |
| 154 | 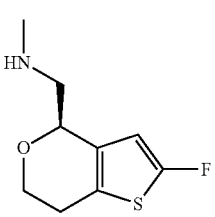 | HCl | CS; FME from SFC separation of Compound 69, using isocratic 10% Methanol in CO$_2$ on a 4.6 × 100 mm ChiralPak AD-H from Chiral Technologies and flow of 4 mL/min | $^1$H NMR (CD$_3$OD): δ 6.40 (d, J = 2.0 Hz, 1H), 4.86 (m, 1H), 4.28-4.23 (m, 1H), 3.90-3.84 (m, 1H), 3.45 (dd, J = 2.5, 13.0 Hz, 1H), 3.23 (dd, J = 8.5, 13.0 Hz, 1H), 2.93-2.85 (m, 1H), 2.73 (s, 3H), 2.63 (dd, J = 2.0, 6.0 Hz, 1H). |
| 155 | 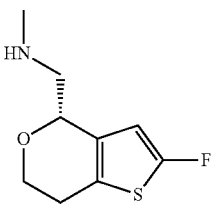 | HCl | CS; SME from SFC separation of Compound 69, using isocratic 10% Methanol in CO$_2$ on a 4.6 × 100 mm ChiralPak AD- H from Chiral Technologies and flow of 4 mL/min | $^1$H NMR (CD$_3$OD): δ 6.40 (d, J = 2.0 Hz, 1H), 4.86 (m, 1H), 4.28-4.23 (m, 1H), 3.90-3.84 (m, 1H), 3.45 (dd, J = 2.5, 13.0 Hz, 1H), 3.23 (dd, J = 8.5, 13.0 Hz, 1H), 2.93-2.85 (m, 1H), 2.73 (s, 3H), 2.63 (dd, J = 2.0, 6.0 Hz, 1H). |
| 156 | 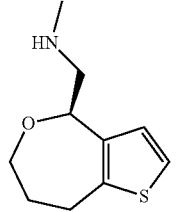 | HCl | CS; FME from SFC separation of Compound 83 | $^1$H NMR (CD$_3$OD): δ 7.10 (d, J = 5.0 Hz, 1H), 6.84 (d, J = 5.0 Hz, 1H), 4.82 (dd, J = 3.0, 10.5 Hz, 1H), 4.33 (dt, J = 4.5, 12.5 Hz, 1H), 3.93-3.86 (m, 1H), 3.59 (dd, J = 2.5, 12.5 Hz, 1H), 3.39-3.33 (m, 1H), 3.15-3.08 (m, 1H), 3.01-2.80 (m, 1H), 2.78 (s, 3H), 1.99-1.88 (m, 2H). |

-continued

| Compd. No. | Structure | Salt or FB* | Method of Preparation | Analytical Data |
|---|---|---|---|---|
| 157 | 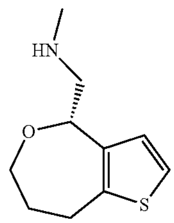 | HCl | CS; SME from SFC separation of Compound 83 | $^1$H NMR (CD$_3$OD): δ 7.10 (d, J = 5.0 Hz, 1H), 6.84 (d, J = 5.0 Hz, 1H), 4.82 (dd, J = 3.0, 10.5 Hz, 1H), 4.33 (dt, J = 4.5, 12.5 Hz, 1H), 3.93-3.86 (m, 1H), 3.59 (dd, J = 2.5, 12.5 Hz, 1H), 3.39-3.33 (m, 1H), 3.15-3.08 (m, 1H), 3.01-2.80 (m, 1H), 2.78 (s, 3H), 1.99-1.88 (m, 2H). |
| 158 | 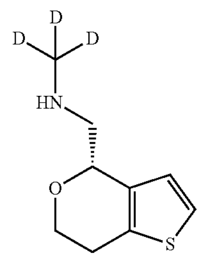 | HCl | K | LC-MS (6 minute method): 0.19 min, M$^+$ 187 @ 0.38 min, $^1$H NMR (CD$_3$OD): δ 7.28 (d, J = 5.13 Hz, 1H), 6.90 (dt, J = 5.13 Hz, 1H), 5.04-5.00 (m, 1H), 4.29-4.24 (m, 1H), 3.85-3.79 (m, 1H), 3.56 (dd, J = 2.57, 12.8 Hz, 1H), 3.31-3.21 (m, 1H), 3.04-2.96 (m, 1H), 2.84-2.78 (m, 1H). |
| 159 | 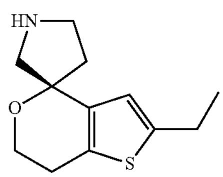 | HCl | CS; FME from SFC separation of Compound 91 | LC-MS (6 minute method): 2.03 min, M$^+$ 224 @ 2.13 min, $^1$H NMR (CD$_3$OD): δ 6.65 (s, 1H), 3.97-3.89 (m, 2H), 3.57-3.47 (m, 3H), 3.34 (d, J = 12.1 Hz, 1H), 2.78-2.73 (m, 4H), 2.32-2.28 (m, 2H), 1.24 (t, J = 7.70 Hz, 3H). |
| 160 | 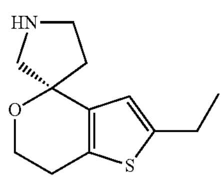 | HCl | CS; SME from SFC separation of Compound 91 | LC-MS (6 minute method): 2.03 min, M$^+$ 224 @ 2.13 min, $^1$H NMR (CD$_3$OD): δ 6.65 (s, 1H), 3.97-3.89 (m, 2H), 3.57-3.47 (m, 3H), 3.34 (d, J = 12.1 Hz, 1H), 2.78-2.73 (m, 4H), 2.32-2.29 (m, 2H), 1.24 (t, J = 7.70 Hz, 3H). |
| 161 | 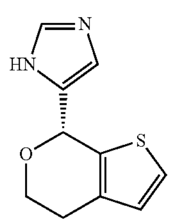 | HCl | CS; FME from SFC separation of Compound 125 | LC-MS (6 minute method): 1.42 min, M$^+$ 207 @ 1.41 min, $^1$H NMR (CD$_3$OD): δ 7.61 (s, 1H), 7.16 (d, J = 4.76 Hz, 1H), 7.03 (s, 1H), 6.81 (d, J = 5.13 Hz, 1H), 5.94 (s, 1H), 4.16-4.12 (m, 1H), 3.93-3.86 (m, 1H), 2.87-2.80 (m, 1H), 2.74-2.68 (m, 1H). |
| 162 | 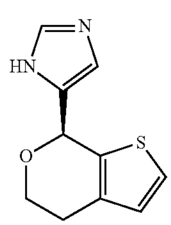 [SMILES: c1ncc([C@@H]2OCCc3ccsc32)[nH]1] | HCl | CS; SME from SFC separation of Compound 125 | LC-MS (6 minute method): 1.42 min, M$^+$ 207 @ 1.41 min, $^1$H NMR (CD$_3$OD): δ 7.61 (s, 1H), 7.16 (d, J = 4.76 Hz, 1H), 7.03 (s, 1H), 6.81 (d, J = 5.13 Hz, 1H), 5.94 (s, 1H), 4.16-4.12 (m, 1H), 3.93-3.86 (m, 1H), 2.87-2.80 (m, 1H), 2.74-2.68 (m, 1H). |
| 163 | 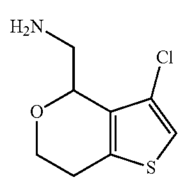 [SMILES: NCC1OCCc2scc(Cl)c21] | HCl | V | LC-MS: m/z 204 (MH$^+$); $^1$H NMR (DMSO-d$_6$): δ 8.06 (s, 3H), 7.08 (s, 1H), 4.82-4.80 (d, J = 6.95 Hz, 1H), 4.15-4.11 (m, 1H), 3.80-3.77 (m, 1H), 3.03-2.96 (m, 1H), 2.88-2.68 (m, 3H). |

-continued

| Compd. No. | Structure | Salt or FB* | Method of Preparation | Analytical Data |
|---|---|---|---|---|
| 164 | 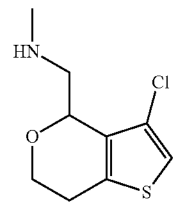 | HCl | V | LC-MS: m/z 218 (MH+); $^1$H NMR (CD$_3$OD): δ 6.84 (s, 1H), 4.94-4.91 (m, 1H), 4.31-4.24 (m, 1H), 3.91-3.82 (m, 1H), 3.52-3.48 (m, 1H), 3.29-3.22 (m, 2H), 3.00-2.89 (m, 1H), 2.75 (s, 3H) |
| 165 | 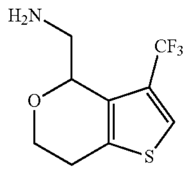 [SMILES: NCC1OCCc2scc(C(F)(F)F)c21] | HCl | V | LC-MS: m/z 238 (MH+); $^1$H NMR (CD$_3$OD): δ 7.45 (s, 1H), 4.97-4.94 (m, 1H), 4.35-4.28 (m, 1H), 3.92-3.83 (m, 1H), 3.56-3.51 (dd, J = 13.12 Hz, 2.68 Hz, 1H), 3.23-3.02 (dd, J = 13.10 Hz, 18.16 Hz, 1H), 3.07-3.04 (m, 1H), 2.92-2.86 (m, 1H). |
| 166 | 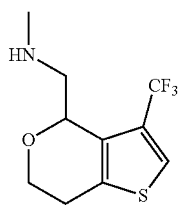 [SMILES: CNCC1OCCc2scc(C(F)(F)F)c21] | HCl | V | LC-MS: m/z 252 (MH+); $^1$H NMR (CDCl$_3$): δ 9.43 (s, 1H), 8.89 (s, 1H), 5.35-5.33 (d, J = 8.46 Hz, 1H), 4.27-4.23 (m, 1H), 3.94-3.86 (m, 1H), 3.55-3.52 (d, J = 9.27 Hz, 1H), 3.17-3.12 (m, 2H), 3.09-3.03 (m, 1H), 2.85 (s, 3H), 2.80 (s, 1H). |
| 167 | 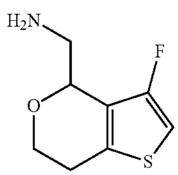 | HCl | V | LC-MS: m/z 188 (MH+); $^1$H NMR (D$_2$O): δ 6.27-6.26 (d, J = 2.15 Hz, 1H), 4.85-4.84 (m, 1H), 4.15-4.09 (m, 1H), 3.84-3.76 (m, 1H), 3.34-3.18 (m, 2H), 2.82-2.72 (m, 1H), 2.64-2.50 (m, 1H). |
| 168 | 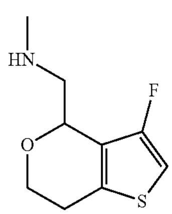 | HCl | V | LC-MS: m/z 202 (MH+); $^1$H NMR (DMSO-d$_6$): δ 9.28 (brs, 1H), 8.73 (brs, 1H), 6.64-6.63 (d, J = 2.11 Hz, 1H), 4.93-4.90 (m, 1H), 4.17-4.10 (m, 1H), 3.85-3.77 (m, 1H), 3.17-3.06 (m, 1H), 2.83-2.73 (m, 3H), 2.62-2.51 (m, 3H). |
| 169 | 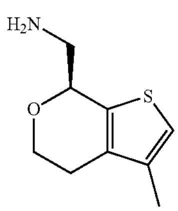 | HCl | CS; FME from SFC separation of Compound 139 | LC-MS: m/z 184 (MH+); $^1$H NMR (DMSO-d$_6$): δ 8.06 (s, 3H), 7.10 (s, 1H), 5.02-4.99 (d, J = 8.93 Hz, 1H), 4.19-1.13 (m, 1H), 3.80-3.72 (m, 1H), 3.22-3.14 (m, 1H), 2.99-2.89 (m, 1H), 2.65-2.60 (m, 2H), 2.05 (s, 3H). |
| 170 | 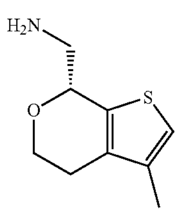 | HCl | CS; SME from SFC separation of Compound 139 | LC-MS: m/z 184 (MH+); $^1$H NMR (DMSO-d$_6$): δ 8.06 (s, 3H), 7.10 (s, 1H), 5.02-4.909 (d, J = 8.93 Hz, 1H), 4.19-1.13 (m, 1H), 3.80-3.72 (m, 1H), 3.22-3.14 (m, 1H), 2.99-2.89 (m, 1H), 2.65-2.60 (m, 2H), 2.05 (s, 3H). |

-continued

| Compd. No. | Structure | Salt or FB* | Method of Preparation | Analytical Data |
|---|---|---|---|---|
| 171 | 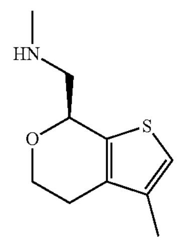 | HCl | CS; FME from SFC separation of Compound 140, using isocratic 10% Methanol:Isopropanol (1:1) w/0.1% Diethylamine in CO₂ on a 4.6 × 100 mm Lux Cellulose-2, Phenomenex and flow of 4 mL/min | LC-MS (6 minute method): 0.46 min, M⁺ 198 @ 0.48 min, ¹H NMR (CD₃OD): δ 6.99 (s, 1H), 5.12-5.09 (m, 1H), 4.32-4.27 (m, 1H), 3.86-3.80 (m, 1H), 3.49-3.45 (m, 1H), 3.25 (dd, J = 8.43, 12.83 Hz, 1H), 2.74 (s, 3H), 2.73-2.68 (m, 1H), 2.58-2.52 (m, 1H), 2.15 (s, 3H). |
| 172 | 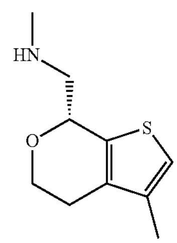 | HCl | CS; SME from SFC separation of Compound 140, using isocratic 10% Methanol: Isopropanol (1:1) w/0.1% Diethylamine in CO₂ on a 4.6 × 100 mm Lux Cellulose-2, Phenomenex and flow of 4 mL/min | LC-MS (6 minute method): 0.46 min, M⁺ 198 @ 0.48 min, ¹H NMR (CD₃OD): δ 6.99 (s, 1H), 5.12-5.09 (m, 1H), 4.32-4.27 (m, 1H), 3.86-3.80 (m, 1H), 3.49-3.45 (m, 1H), 3.25 (dd, J = 8.43, 12.83 Hz, 1H), 2.74 (s, 3H), 2.73-2.68 (m, 1H), 2.58-2.52 (m, 1H), 2.15 (s, 3H). |
| 173 | 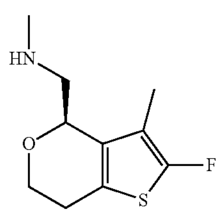 | HCl | CS; FME from SFC separation of Compound 121, using isocratic 3% Hexane:Ethanol (1:1) in CO₂ on a 4.6 × 100 mm (S,S) Whelk0-1 from Regisand flow of 4 mL/min | LC-MS: m/z 216 (MH⁺); ¹H NMR (DMSO-d₆): δ 9.25 (s, 1H), 8.67 (s, 1H), 5.00-4.97 (d, J = 8.10 Hz, 1H), 4.08-4.00 (m, 1H), 3.88-3.79 (m, 1H), 3.41-3.14 (m, 2H), 2.77-2.65 (m, 5H), 2.01-2.00 (d, J = 2.10 Hz, 3H). |
| 174 | 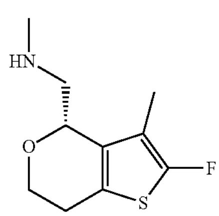 | HCl | CS; SME from SFC separation of Compound 121, using isocratic 3% Hexane:Ethanol (1:1) in CO2 on a 4.6 × 100 mm (S,S) Whelk0-1 from Regisand flow of 4 mL/min | LC-MS: m/z 216 (MH⁺); ¹H NMR (DMSO-d₆): δ 9.25 (s, 1H), 8.67 (s, 1H), 5.00-4.97 (d, J = 8.10 Hz, 1H), 4.08-4.00 (m, 1H), 3.88-3.79 (m, 1H), 3.41-3.14 (m, 2H), 2.77-2.65 (m, 5H), 2.01-2.00 (d, J = 2.10 Hz, 3H). |
| 175 | 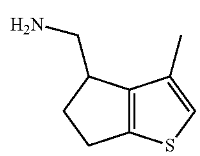 | HCl | Q | LC-MS: m/z 168 (MH⁺); ¹H NMR (DMSO-d₆): δ 8.11 (s, 3H), 6.96 (s, 1H), 3.31-3.25 (m, 1H), 3.08-3.02 (m, 1H), 2.97-2.94 (m, 1H), 2.80-2.65 (m, 2H), 2.61-2.53 (m, 1H), 2.43-2.34 (m, 1H), 2.13-2.13 (d, J = 0.84 Hz, 3H). |
| 176 | 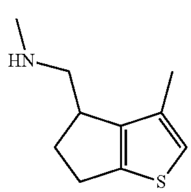 | HCl | Q | LC-MS: m/z 182 (MH⁺); ¹H NMR (CD₃OD): δ 6.89 (s, 1H), 3.33-3.32 (m, 1H), 3.31-3.28 (m, 1H), 3.09-2.97 (m, 2H), 2.93-2.83 (m, 1H), 2.81-2.68 (m, 4H), 2.44-2.22 (m, 1H), 2.22 (s, 3H). |
| 177 | 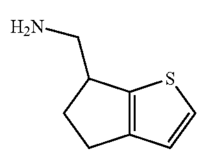 | HCl | Y | LC-MS: m/z 154 (MH⁺); ¹H NMR (DMSO-d₆): δ 8.23 (s, 3H), 7.44-7.43 (d, J = 4.50 Hz, 1H), 6.87-6.86 (d, J = 4.85 Hz, 1H), 3.51 (s, 1H), 3.05 (s, 1H), 2.79-2.56 (m, 4H), 2.35-2.24 (m, 1H). |

| Compd. No. | Structure | Salt or FB* | Method of Preparation | Analytical Data |
|---|---|---|---|---|
| 178 | (structure) | HCl | Y | LC-MS: m/z 168 (MH$^+$); $^1$H NMR (DMSO-d$_6$): δ 9.07-9.06 (m, 2H), 7.45-7.44 (d, J = 4.88 Hz, 1H), 6.88-6.86 (d, J = 4.86 Hz, 1H), 3.60-3.58 (d, J = 3.39 Hz, 1H), 3.20-3.13 (m, 1H), 2.97-2.86 (m, 1H), 2.81-2.60 (m, 3H), 2.57-2.53 (m, 3H), 2.43-2.31 (m, 1H). |
| 179 | (structure) | HCl | Y | LC-MS: m/z 168 (MH$^+$); $^1$H NMR (DMSO-d$_6$): δ 8.10 (s, 3H), 7.02 (s, 1H), 3.09-3.01 (m, 2H), 2.84-2.75 (m, 2H), 2.69-2.54 (m, 3H), 2.33-2.21 m, 1H), 2.09-2.08 (d, J = 0.93 Hz, 3H). |
| 180 | (structure) | HCl | Z | LC-MS: m/z 236 (MH$^+$); $^1$H NMR (DMSO-d$_6$): δ 7.27-7.26 (d, J = 3.99 Hz, 1H), 6.97-6.96 (d, J = 4.23 Hz, 1H), 3.62-3.57 (m, 1H), 3.34-3.21 (m, 3H), 3.10-3.02 (m, 1H), 2.91 (s, 2H), 2.68 (s, 2H), 1.77-1.72 (m, 9H), 1.38 (s, 1H). |
| 181 | (structure) | HCl | AA | LC-MS: m/z 168 (MH$^+$); $^1$H NMR (CDCl$_3$): δ 7.11-7.10 (d, J = 5.07 Hz, 1H), 6.80-6.78 (d, J = 5.10 Hz, 1H), 2.99-2.89 (m, 3H), 2.70-2.60 (m, 2H), 2.05-1.71 (m, 1H), 1.77-1.59 (m, 1H), 1.44 (s, 2H). |
| 182 | (structure) | HCl | AA | LC-MS: m/z 182 (MH$^+$); $^1$H NMR (CD$_3$OD): δ 7.26-7.24 (d, J = 5.10 Hz, 1H), 6.82-6.81 (d, J = 5.10 Hz, 1H), 3.42-3.23 (m, 2H), 3.14-3.06 (m, 1H), 2.74 (s, 3H), 2.69-2.65 (m, 2H), 2.320-2.07 (m, 1H), 2.03-1.96 (m, 1H), 1.82-1.67 (m, 2H). |
| 183 | (structure) | HCl | AA | LC-MS: m/z 236 (MH$^+$); $^1$H NMR (CD$_3$OD): δ 7.15-7.14 (d, J = 5.15 Hz, 1H), 6.76-6.74 (d, J = 5.17 Hz, 1H), 4.09-4.05 (t, J = 12.90 Hz, 2H), 3.59-3.55 (t, J = 12.90 Hz, 2H), 3.43-3.36 (m, 1H), 3.19-3.17 (m, 1H), 3.12-3.01 (m, 1H), 2.64-2.61 (m, 2H), 1.96-1.90 (m, 2H), 1.72-1.51 (m, 6H), 1.50-1.43 (m, 2H). |
| 184 | (structure) | HCl | Z | LC-MS: m/z 182 (MH$^+$); $^1$H NMR (CD$_3$OD): δ 6.84 (s, 1H), 3.09-2.96 (m, 2H), 2.80-2.73 (m, 2H), 2.18 (s, 3H), 2.05-2.02 (m, 1H), 2.00-1.85 (m, 4H). |

-continued

| Compd. No. | Structure | Salt or FB* | Method of Preparation | Analytical Data |
|---|---|---|---|---|
| 185 | (structure) | HCl | Z | LC-MS: m/z 196 (MH+); 1H NMR (CD3OD): δ 6.74 (s, 1H), 2.95 (d, J = 11.86 Hz, 1H), 2.83-2.76 (m, 1H), 2.74-2.68 (m, 2H), 2.65-2.60 (m, 1H), 2.52-2.45 (dd, J = 12.55 Hz, 6.96 Hz, 1H), 2.41 (s, 1H), 2.30-2.26 (d, J = 13.27 Hz, 1H), 2.21-2.20 (m, 1H), 2.182-2.179 (m, 3H), 1.89-1.81 (m, 2H), 1.67-1.58 (m, 1H). |
| 186 | (structure) | HCl | Z | LC-MS: m/z 250 (MH+); 1H NMR (CD3OD): δ 6.72 (s, 1H), 3.01-2.97 (d, J = 10.96 Hz, 1H), 2.82-2.62 (m, 3H), 2.52-2.45 (m, 3H), 2.30-2.20 (m, 2H), 2.17 (s, 3H), 1.91-1.81 (m, 2H), 1.72-1.49 (m, 8H). |
| 187 | (structure) | HCl | B | LC-MS: m/z 195 (MH+); 1H NMR (CD3OD): δ 7.42-7.40 (d, J = 5.1 Hz, 1H), 6.90-6.89 (d, J = 5.1 Hz, 1H), 4.05-3.95 (m, 2H), 3.71-3.70 (m, 1H), 3.67-3.55 (m, 2H), 3.39-3.35 (m, 1H), 2.80-2.79 (m, 2H), 2.55-2.48 (m, 1H), 2.39-2.84 (m, 1H). |
| 188 | (structure) | HCl | B | LC-MS: m/z 209 (MH+); 1H NMR (DMSO-d6): δ 9.26-9.23 (d, J = 8.75 Hz, 1H), 8.41-8.32 (m, 1H), 7.49-7.44 (dd, J = 8.75 Hz, 5.10 Hz, 1H), 6.91-6.88 (m, 1H), 3.94-3.90 (m, 2H), 3.94-3.92 (m, 1H), 3.19-3.15 (m, 2H), 3.07-2.99 (m, 1H), 2.73-2.61 (m, 2H), 2.01-1.80 (m, 3H), 1.71-1.67 (m, 1H). |
| 189 | (structure) | HCl | B | LC-MS: m/z 209 (MH+); 1H NMR (D2O): δ 6.94 (s, 1H), 3.99-3.92 (m, 1H), 3.88-3.79 (m, 1H), 3.63-3.58 (m, 1H), 3.55-3.38 (m, 2H), 3.30-3.26 (m, 1H), 2.57-2.44 (m, 2H), 2.38-2.20 (m, 2H), 1.98 (s, 3H). |
| 190 | (structure) | HCl | B | LC-MS: m/z 223 (MH+); 1H NMR (D2O): δ 6.89 (s, 1H), 3.96-3.92 (m, 1H), 3.87-3.83 (m, 1H), 3.44-3.39 (d, J = 13.56 Hz, 1H), 3.24-3.20 (d, J = 12.30 Hz, 1H), 3.07-3.03 (d, J = 13.44 Hz, 1H), 2.89-2.81 (m, 1H), 2.48-2.47 (m, 2H), 1.96 (s, 3H), 1.90-1.78 (m, 3H), 1.72-1.67 (m, 1H). |
| 191 | (structure) | HCl | BB | LC-MS: m/z 224 (MH+); 1H NMR (DMSO-d6): δ 8.22-8.16 (d, J = 13.20 Hz, 3H), 4.90-4.86 (t, J = 12.15 Hz, 1H), 4.01-3.94 (m, 1H), 3.82-3.75 (m, 1H), 3.05 (s, 2H), 2.72-2.66 (m, 4H), 2.41-2.32 (m, 2H), 1.86-1.83 (m, 2H), 1.71-1.53 (m, 2H). |

-continued

| Compd. No. | Structure | Salt or FB* | Method of Preparation | Analytical Data |
|---|---|---|---|---|
| 192 | 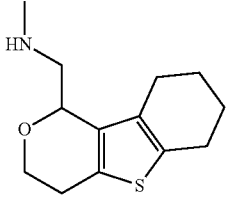 [SMILES: CNCC1OCCc2sc3c(c21)CCCC3] | HCl | BB | LC-MS: m/z 238 (MH$^+$); $^1$H NMR (DMSO-d$_6$): δ 9.39-9.36 (d, J = 11.15 Hz, 1H), 8.70-8.64 (m, 1H), 5.01-4.98 (m, 1H), 4.03-3.95 (m, 1H), 3.83-3.76 (m, 1H), 3.17-3.02 (m, 2H), 2.79-2.57 (m, 7H), 2.50-2.42 (m, 2H), 1.85-1.82 (m, 2H), 1.70-1.51 (m, 2H). |
| 193 | 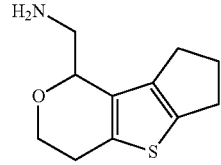 [SMILES: NCC1OCCc2sc3c(c21)CCC3] | HCl | BB | LC-MS: m/z 210 (MH$^+$); $^1$H NMR (DMSO-d$_6$): δ 8.23 (s, 3H), 4.91-4.88 (d, J = 7.80 Hz, 1H), 4.10-4.03 (m, 1H), 3.79-3.71 (m, 1H), 3.15-3.10 (m, 1H), 3.01-2.92 (m, 1H), 2.88-2.70 (m, 4H), 2.62-2.58 (m, 2H), 2.39-2.31 (m, 2H). |
| 194 | 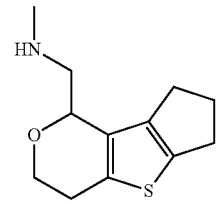 | HCl | BB | LC-MS: m/z 224 (MH$^+$); $^1$H NMR (DMSO-d$_6$): δ 9.40 (s, 1H), 8.75 (s, 1H), 5.02-4.99 (d, J = 9.05 Hz, 1H), 4.10-4.03 (m, 1H), 3.81-3.73 (m, 1H), 3.24-3.01 (m, 2H), 2.86-2.71 (m, 4H), 2.68-2.50 (m, 5H), 2.42-2.35 (m, 2H). |
| 195 | 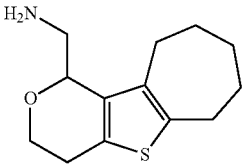 [SMILES: NCC1OCCc2sc3c(c21)CCCCC3] | HCl | BB | LC-MS: m/z 238 (MH$^+$); $^1$H NMR (DMSO-d$_6$): δ 8.09 (s, 3H), 4.88-4.85 (d, J = 9.81 Hz, 1H), 3.97-3.78 (m, 2H), 3.55 (s, 2H), 3.12-3.06 (m, 1H), 2.91-2.70 (m, 1H), 2.68-2.56 (m, 4H), 1.91-1.73 (m 2H), 1.56-1.47 (m, 4H). |
| 196 | 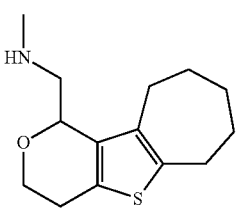 | HCl | BB | LC-MS: m/z 252 (MH$^+$); $^1$H NMR (D$_2$O): δ 4.91-4.89 (d, J = 7.82 Hz, 1H), 3.88-3.87 (d, J = 4.74 Hz, 1H), 3.74-3.70 (m, 1H), 3.28-3.21 (m, 1H), 3.13-3.08 (m, 1H), 2.63-2.52 (m, 7H), 2.33 (s, 2H), 1.68 (s, 2H), 1.43 (s, 4H). |
| 197 | 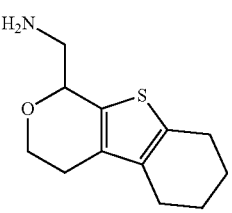 [SMILES: NCC1OCCc2c1sc1c2CCCC1] | HCl | BB | LC-MS: m/z 224 (MH$^+$); $^1$H NMR (D$_2$O): δ 5.02-5.00 (d, J = 5.72 Hz, 1H), 4.13-4.06 (m, 1H), 3.77-3.69 (m, 1H), 3.36-3.30 (m, 1H), 3.19-3.12 (m, 1H), 2.65-2.42 (m, 3H), 2.36-1.68 (m, 3H), 1.66 (s, 4H). |
| 198 | 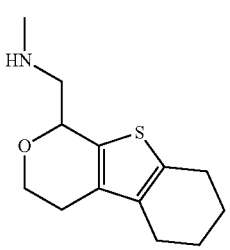 | HCl | BB | LC-MS: m/z 238 (MH$^+$); $^1$H NMR (D$_2$O): δ 5.06 (s, 1H), 4.12-4.09 (m, 1H), 3.74 (s, 1H), 3.40-3.36 (m, 1H), 3.27-3.21 (m, 1H), 2.67 (s, 3H), 2.61-2.51 (m, 3H), 2.43-2.33 (m, 3H), 1.68 (m, 4H). |

| Compd. No. | Structure | Salt or FB* | Method of Preparation | Analytical Data |
|---|---|---|---|---|
| 199 | 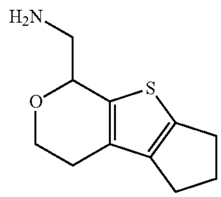 [SMILES: NCC1OCCc2c1sc1c2CCC1] | HCl | BB | LC-MS: m/z 210 (MH$^+$); $^1$H NMR (DMSO-d$_6$): δ 8.14 (s, 3H), 4.98-4.95 (d, J = 8.71 Hz, 1H), 4.15-4.08 (m, 1H), 3.77-3.69 (m, 1H), 3.16-3.12 (m, 1H), 3.03-2.93 (m, 1H), 2.84-2.79 (m, 2H), 2.67-2.52 (m, 4H), 2.42-2.33 (m, 2H). |
| 200 | 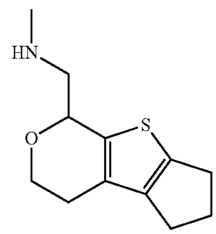 | HCl | BB | LC-MS: m/z 224 (MH$^+$); $^1$H NMR (DMSO-d$_6$): δ 9.13 (s, 1H), 8.74-8.72 (d, J = 6.00 Hz, 1H), 5.09-5.05 (d, J = 9.20 Hz, 1H), 4.15-4.03 (m, 4H), 3.79-3.70 (m, 1H), 3.39-3.10 (m, 2H), 2.84-2.79 (m, 2H), 2.60-2.57 (t, J = 2.57 Hz, 4H), 2.42-2.33 (m, 2H). |
| 201 | 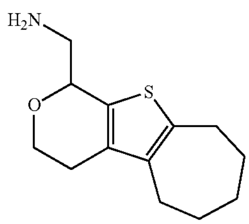 [SMILES: NCC1OCCc2c1sc1c2CCCCC1] | HCl | BB | LC-MS: m/z 238 (MH$^+$); $^1$H NMR (DMSO-d$_6$): δ 8.30 (s, 3H), 4.96-4.93 (d, J = 7.92 Hz, 1H), 4.16-4.09 (m, 1H), 3.78-3.70 (m, 1H), 3.10-3.08 (m, 1H), 3.00-2.91 (m, 1H), 2.76-2.69 (m, 2H), 2.60-2.52 (m, 2H), 2.47-2.42 (m, 2H), 1.83-1.74 (m, 2H), 1.67-1.47 (m, 4H). |
| 202 | 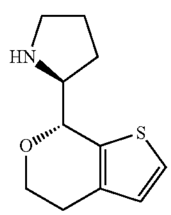 [SMILES: c1cc2c(s1)[C@@H]([C@@H]1CCCN1)OCC2] | HCl | CC | LC-MS: m/z 210 (MH$^+$); $^1$H NMR (DMSO-d$_6$): δ 9.82-9.80 (d, J = 4.11 Hz, 1H), 8.86 (s, 1H), 7.51-7.49 (d, J = 5.04 Hz, 1H), 6.96-6.74 (d, J = 5.04 Hz, 1H), 4.19-4.12 (m, 1H), 3.79-3.71 (m, 2H), 3.13 (s, 2H), 2.86-2.76 (m, 1H), 2.67-2.61 (m, 1H), 2.26-2.22 (m, 1H), 2.04-1.87 (m, 3H). |
| 203 | 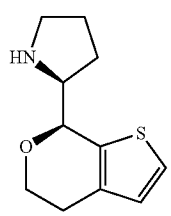 [SMILES: c1cc2c(s1)[C@H]([C@@H]1CCCN1)OCC2] | HCl | CC | LC-MS: m/z 210 (MH$^+$); $^1$H NMR (DMSO-d$_6$): δ 10.19 (s, 1H), 8.90 (brs, 1H), 7.51-7.49 (dd, J = 5.01 Hz, 0.69 Hz, 1H), 6.94-6.93 (d, J = 5.01 Hz, 1H), 5.22-5.21 (d, J = 1.83 Hz, 1H), 4.25-4.20 (dd, J = 11.34 Hz, 5.31 Hz, 1H), 3.95 (s, 1H), 3.75-3.66 (td, J = 11.34 Hz, 3.60 Hz, 1H), 3.19-3.04 (m, 2H), 2.86-2.74 (m, 1H), 2.64-2.59 (m, 1H), 1.90-1.66 (m, 4H). |
| 204 | 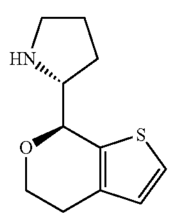 | HCl | CC | LC-MS: m/z 210 (MH$^+$); $^1$H NMR (DMSO-d$_6$): δ 9.82 (s, 1H), 8.87 (s, 1H), 4.51-7.49 (d, J = 5.01 Hz, 1H), 6.96-6.94 (d, J = 5.04 Hz, 1H), 5.03-5.01 (d, J = 7.32 Hz, 1H), 4.19-4.12 (m, 1H), 3.79-3.70 (m, 2H), 3.13 (s, 2H), 2.86-2.76 (m, 1H), 2.67-2.61 (m, 1H), 2.26-2.22 (m, 1H), 2.04-1.87 (m, 3H). |
| 205 | 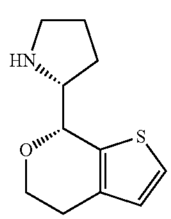 [SMILES: c1cc2c(s1)[C@@H]([C@H]1CCCN1)OCC2] | HCl | CC | LC-MS: m/z 210 (MH$^+$); $^1$H NMR (DMSO-d$_6$): δ 10.23 (s, 1H), 8.90 (s, 1H), 7.51-7.49 (d, J = 5.78 Hz, 1H), 6.94-6.92 (s, J = 5.16 Hz, 1H), 5.22 (s, 1H), 4.25-4.19 (dd, J = 11.24 Hz, 5.45 Hz, 1H), 3.94 (s, 1H), 3.74-3.66 (td, J = 11.31 Hz, 3.57 Hz, 1H), 3.19-3.08 (m, 2H), 2.80-2.75 (m, 1H), 2.64-2.58 (m, 1H), 1.91-1.63 (m, 4H). |

-continued

| Compd. No. | Structure | Salt or FB* | Method of Preparation | Analytical Data |
|---|---|---|---|---|
| 206 | 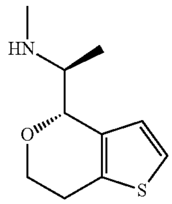 | HCl | N | LC-MS: m/z 198 (MH$^+$); $^1$H NMR (DMSO-d$_6$): δ 9.02-9.00 (d, J = 5.10 Hz, 1H), 8.14 (s, 1H), 7.43-7.41 (d, J = 5.10 Hz, 1H), 7.04-7.02 (d, J = 5.12 Hz, 1H), 4.82-4.81 (d, J = 2.15 Hz, 1H), 4.22-4.15 (m, 1H), 2.79-2.68 (m, 2H), 2.91-2.77 (m, 2H), 2.40-2.37 (m, 3H), 1.39-1.37 (d, J = 6.96 Hz, 3H). |
| 207 | 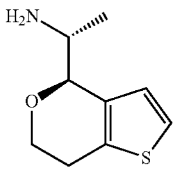 | HCl | N | LC-MS: m/z 184 (MH$^+$); $^1$H NMR (DMSO-d$_6$): δ 7.90 (s, 3H), 7.41-7.39 (d, J = 5.19 Hz, 1H), 7.00-6.98 (d, J = 5.25 Hz, 1H), 4.72-4.71 (d, J = 2.13 Hz, 1H), 4.70-4.12 (m, 1H), 3.77-3.66 (m, 2H), 3.41-3.34 (m, 2H), 1.36-1.34 (d, J = 6.72 Hz, 3H). |
| 208 | 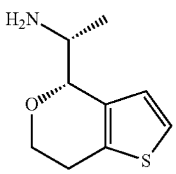 | HCl | N | LC-MS: m/z 184 (MH$^+$); $^1$H NMR (DMSO-d$_6$): δ 8.38 (s, 3H), 7.43-7.39 (d, J = 5.19 Hz, 1H), 6.70-6.98 (d, J = 5.22 Hz, 1H), 4.98 (s, 1H), 4.97-4.22 (m, 1H), 3.82-3.81 (m, 1H), 3.71-3.62 (td, J = 11.13 Hz, J = 3.53 Hz, 1H), 2.97-2.50 (m, 1H), 2.50-2.49 (m, 1H), 0.91-0.88 (d, J = 6.72 Hz, 3H). |
| 209 | 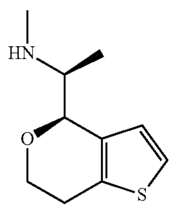 | HCl | N | LC-MS: m/z 198 (MH$^+$); $^1$H NMR (DMSO-d$_6$): δ 9.24-9.14 (m, 2H), 7.42-7.40 (d, J = 5.17 Hz, 1H), 6.94-6.92 (d, J = 5.42 Hz, 1H), 5.17-5.16 (d, J = 1.80 Hz, 1H), 4.27-4.22 (m, 1H), 3.80 (s, 1H), 3.73-3.65 (m, 1H), 2.98-2.88 (m, 1H), 2.77-2.72 (m, 1H), 2.59 (s, 3H), 0.93-0.91 (d, J = 6.62 Hz, 3H). |
| 210 | 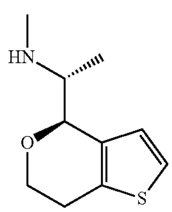 | HCl | N | LC-MS: m/z 198 (MH$^+$); $^1$H NMR (DMSO-d$_6$): δ 8.91 (s, 1H), 8.08 (s, 1H), 7.43-7.41 (d, J = 5.22 Hz, 1H), 7.04-7.02 (d, J = 5.22 Hz, 1H), 4.81-4.80 (m, 1H), 4.22-4.16 (m, 1H), 3.79-3.67 (m, 2H), 2.97-2.77 (m, 2H), 2.41-2.37 (t, J = 5.42 Hz, 3H), 1.39-1.37 (d, J = 6.75 Hz, 3H). |
| 211 | 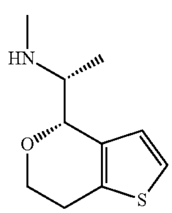 | HCl | N | LC-MS: m/z 198 (MH$^+$); $^1$H NMR (DMSO-d$_6$): δ 9.20-9.10 (m, 2H), 7.42-7.40 (d, J = 5.10 Hz, 1H), 6.94-6.72 (d, J = 5.16 Hz, 1H), 5.15 (s, 1H), 4.27-4.22 (m, 1H), 3.79-3.65 (m, 2H), 3.74-3.65 (td, J = 11.18 Hz, 3.42 Hz, 2H), 2.98-2.88 (m, 1H), 2.77-2.72 (m, 1H), 2.60 (s, 3H), 0.92-0.90 (d, J = 6.66 Hz, 3H). |
| 212 | 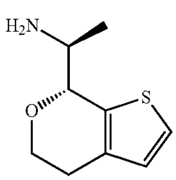 | HCl | DD | LC-MS: m/z 184 (MH$^+$); $^1$H NMR (DMSO-d$_6$): δ 8.03 (s, 3H), 7.52-7.50 (dd, J = 0.58 Hz, J = 5.03 Hz, 1H), 6.96-6.94 (d, J = 5.04 Hz, 1H), 4.83-4.82 (d, J = 5.48 Hz, 1H), 4.17-4.10 (m, 1H), 3.77-3.69 (m, 1H), 3.47 (s, 1H), 2.80-2.61 (m, 2HJ), 1.43-1.40 (d, J = 6.63 Hz, 3H). |
| 213 | 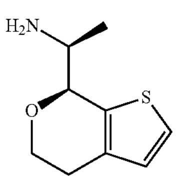 | HCl | DD | LC-MS: m/z 184 (MH$^+$); $^1$H NMR (DMSO-d$_6$): δ 8.42 (s, 3H), 7.51-7.49 (dd, J = 5.11 Hz, J = 0.62 Hz, 1H), 6.94-6.93 (d, J = 5.12 Hz, 1H), 5.14-5.13 (d, J = 1.50 Hz, 1H), 4.25-4.19 (m, 1H), 3.71-3.62 (td, J = 11.12 Hz, 3.64 Hz, 1H), 3.54 (s, 1H), 2.84-2.72 (m, 1H), 2.63-2.57 (m, 1H), 1.01-0.98 (d, J = 6.95 Hz, 3H). |

-continued

| Compd. No. | Structure | Salt or FB* | Method of Preparation | Analytical Data |
|---|---|---|---|---|
| 214 | 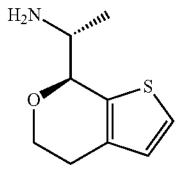 | HCl | DD | LC-MS: m/z 184 (MH$^+$); $^1$H NMR (DMSO-d$_6$): δ 7.87 (s, 3H), 7.53-7.51 (d, J = 4.65 Hz, 1H), 6.97-6.95 (d, J = 5.22 Hz, 1H), 4.82-4.80 (d, J = 5.07 Hz, 1H), 4.18-4.14 (m, 1H), 3.78-3.69 (m, 1H), 3.52-3.44 (m, 1H), 2.78-2.62 (m, 2H), 1.40-1.38 (d, J = 6.57 Hz, 3H). |
| 215 | 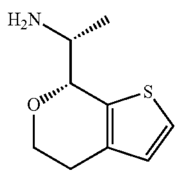 | HCl | DD | LC-MS: m/z 184 (MH$^+$); $^1$H NMR (DMSO-d$_6$): δ 8.32 (s, 3H), 7.512-7.49 (dd, J = 5.01 Hz, J = 0.57 Hz, 1H), 6.95-6.93 (d, J = 5.01 Hz, 1H), 5.11-5.10 (d, J = 1.65 Hz, 1H), 4.25-4.20 (dd, J = 11.34 Hz, 4.98 Hz, 1H), 3.72-3.63 (td, J = 11.27 Hz, 3.51 Hz, 1H), 3.57 (s, 1H), 2.84-2.72 (m, 1H), 2.63-2.58 (m, 1H), 1.01-0.98 (d, J = 6.75 Hz, 3H). |
| 216 | 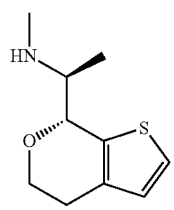 | HCl | DD | LC-MS: m/z 198 (MH$^+$); $^1$H NMR (DMSO-d$_6$): δ 9.09 (s, 1H), 8.35-8.32 (m, 1H), 7.53-7.52 (d, J = 5.12 Hz, 1H), 6.97-6.95 (d, J = 4.80 Hz, 1H), 4.93 (d, J = 1.7 Hz, 1H), 4.19-4.12 (m, 1H), 3.80-3.72 (m, 1H), 3.54-3.51 (m, 1H), 2.77-2.64 (m, 2H), 2.50-2.45 (m, 3H), 1.46-1.43 (d, J = 6.64 Hz, 3H). |
| 217 | 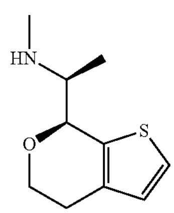 | HCl | DD | LC-MS: m/z 198 (MH$^+$); $^1$H NMR (DMSO-d$_6$): δ 9.42-9.17 (m, 2H), 7.50-7.49 (d, J = 4.85 Hz, 1H), 6.94-6.92 (d, J = 5.18 Hz, 1H), 5.33-5.33 (d, J = 1.27 Hz, 1H), 4.24-4.19 (dd, J = 11.28 Hz, 5.37 Hz, 1H), 3.73-3.64 (td, J = 11.31 Hz, 5.37 Hz, 1H), 3.53 (s, 1H), 2.84-2.72 (m, 1H), 2.63-2.62 (m, 1H), 2.60 (s, 3H), 1.02-1.00 (d, J = 6.9 Hz, 3H). |
| 218 | 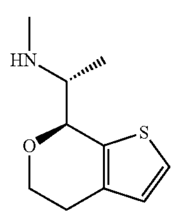 | HCl | DD | LC-MS: m/z 198 (MH$^+$); $^1$H NMR (DMSO-d$_6$): δ 9.07-9.06 (d, J = 5.45 Hz, 1H), 8.31 (s, 1H), 7.53-7.52 (d, J = 5.01 Hz, 1H), 6.97-6.95 (d, J = 5.04 Hz, 1H), 4.94-4.92 (s, J = 5.28 Hz, 1H), 4.19-4.13 (m, 1H), 3.80-3.72 (m, 1H), 3.42-3.49 (m, 1H), 2.82-2.64 (m, 2H), 2.50-2.45 (m, 3H), 1.46-1.43 (d, J = 6.63 Hz, 3H). |
| 219 | 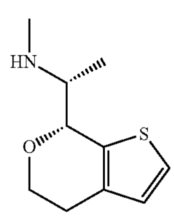 | HCl | DD | LC-MS: m/z 198 (MH$^+$); $^1$H NMR (DMSO-d$_6$): δ 9.39-9.38 (d, J = 1.17 Hz, 1H), 9.16-9.14 (d, J = 4.92 Hz, 1H), 7.51-7.49 (dd, J = 5.01 Hz, 1H), 5.33-5.32 (d, J = 1.49 Hz, 1H), 4.24-4.19 (dd, J = 11.33 Hz, 5.21 Hz, 1H), 3.73-3.64 (td, J = 11.31 Hz, 3.57 Hz, 1H), 3.55-3.53 (m, 1H), 2.84-2.72 (m, 1H), 2.63-2.58 (m, 4H), 1.10-0.99 (d, J = 6.72 Hz, 3H). |
| 220 | 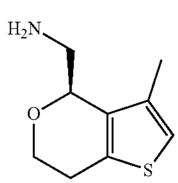 | HCl | CS; FME from SFC separation of Compound 29, using isocratic 10% Hexane:Ethanol (1:1) in CO$_2$ on a 4.6 × 100 mm LUX Cellulose 2 from Phenomenex and flow of 4 mL/min | $^1$H NMR (DMSO-d$^6$): δ 8.14 (br s, 3H), 7.00 (s, 1H), 4.97-4.90 (m, 1H), 4.02-3.94 (m, 1H), 3.85-3.78 (m, 1H), 3.11-3.08 (t, J = 10.66 Hz, 2H), 2.88-2.73 (m, 2H), 2.13-2.12 (d, J = 0.8 Hz, 3H). |

-continued

| Compd. No. | Structure | Salt or FB* | Method of Preparation | Analytical Data |
|---|---|---|---|---|
| 221 | H₂N-CH₂-[(4)-3-methyl-4,6-dihydro-pyrano-thiophene] | HCl | CS; SME from SFC separation of Compound 29, using isocratic 10% Hexane: Ethanol (1:1) in CO₂ on a 4.6 × 100 mm LUX Cellulose 2 from Phenomenex and flow of 4 mL/min | ¹H NMR (DMSO-d⁶): δ 8.14 (br s, 3H), 7.00 (s, 1H), 4.97-4.90 (m, 1H), 4.02-3.94 (m, 1H), 3.85-3.78 (m, 1H), 3.11-3.08 (t, J = 10.66 Hz, 2H), 2.88-2.73 (m, 2H), 2.13-2.12 (d, J = 0.8 Hz, 3H). |
| 222 | CD₃-HN-CH₂-[(S)-3-methyl-4,6-dihydro-pyrano-thiophene] | HCl | K | LC-MS (6 minute method): 0.67 min, M⁺ 201 @ 0.63 min, ¹H NMR (CD₃OD): δ 6.90 (s, 1H), 5.05-5.02 (m, 1H), 4.17-4.12 (m, 1H), 3.86-3.81 (m, 1H), 3.46-3.42 (m, 1H), 3.33-3.28 (m, 1H), 2.92-2.81 (m, 1H), 2.19 (s, 3H). |
| 223 | CD₃-HN-CH₂-[(R)-3-methyl-4,6-dihydro-pyrano-thiophene] | HCl | K | LC-MS (6 minute method): 0.67 min, M⁺ 201 @ 0.63 min, ¹H NMR (CD₃OD): δ 6.90 (s, 1H), 5.05-5.02 (m, 1H), 4.17-4.12 (m, 1H), 3.86-3.81 (m, 1H), 3.46-3.42 (m, 1H), 3.33-3.28 (m, 1H), 2.93-2.81 (m, 1H), 2.19 (s, 3H). |
| 224 | CD₃-HN-CH₂-[(S)-3-methyl-4,6-dihydro-pyrano-thiophene isomer] | HCl | K | LC-MS (6 minute method): 0.70 min, M⁺ 201 @ 0.73 min, ¹H NMR (CD₃OD): δ 6.99 (s, 1H), 5.10 (d, J = 8.07 Hz, 1H), 4.32-4.27 (m, 1H), 3.86-3.80 (m, 1H), 3.48-3.44 (m, 1H), 3.27-3.24 (m, 1H), 2.76-2.68 (m, 1H), 2.57-2.52 (m, 1H), 2.14 (s, 3H). |
| 225 | CD₃-HN-CH₂-[(R)-3-methyl-4,6-dihydro-pyrano-thiophene isomer] | HCl | K | LC-MS (6 minute method): 0.70 min, M⁺ 201 @ 0.73 min, ¹H NMR (CD₃OD): δ 6.99 (s, 1H), 5.10 (d, J = 8.07 Hz, 1H), 4.32-4.27 (m, 1H), 3.86-3.80 (m, 1H), 3.48-3.44 (m, 1H), 3.27-3.24 (m, 1H), 2.76-2.68 (m, 1H), 2.57-2.52 (m, 1H), 2.14 (s, 3H). |
| 226 | CD₃-HN-CH₂-[4,6-dihydro-pyrano-thiophene] | HCl | K | LC-MS (6 minute method): 0.17-0.36 min, M⁺ 187 @ 0.35 min, ¹H NMR (CD₃OD): δ 7.37 (d, J = 2.93 Hz, 1H), 6.90 (d, J = 2.93 Hz, 1H), 5.16 (d, J = 7.33 Hz, 1H), 4.28-4.24 (m, 1H), 3.85-3.80 (m, 1H), 3.50 (d, J = 12.8 Hz, 1H), 3.3-3.25 (m, 1H), 2.89-2.84 (m, 1H), 2.71-2.67 (m, 1H). |

| Compd. No. | Structure | Salt or FB* | Method of Preparation | Analytical Data |
|---|---|---|---|---|
| 227 | 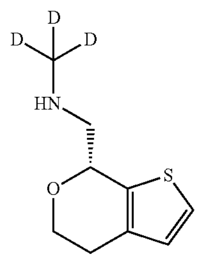 [SMILES: [2H]C([2H])([2H])NC[C@H]1OCCc2ccsc21] | HCl | K | LC-MS (6 minute method): 0.17-0.36 min, M⁺ 187 @ 0.35 min, $^1$H NMR (CD$_3$OD): δ 7.37 (d, J = 2.93 Hz, 1H), 6.90 (d, J = 2.93 Hz, 1H), 5.16 (d, J = 7.33 Hz, 1H), 4.28-4.24 (m, 1H), 3.85-3.80 (m, 1H), 3.50 (d, J = 12.8 Hz, 1H), 3.3-3.25 (m, 1H), 2.89-2.84 (m, 1H), 2.71-2.678 (m, 1H). |
| 228 | 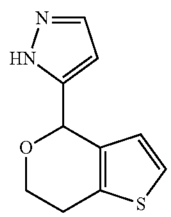 [SMILES: c1cc(C2OCCc3sccc32)[nH]n1] | HCl | EE | LC-MS: m/z 207 (MH⁺); $^1$H NMR (CD$_3$OD): δ 8.20-8.19 (d, J = 2.61 Hz, 1H), 7.30-7.29 (d, J = 5.25 Hz, 1H), 6.79-6.74 (m, 2H), 6.08 (s, 1H), 4.21-4.15 (m, 1H), 4.04-3.96 (m, 1H), 3.11-3.02 (m, 1H), 2.98-2.89 (m, 1H). |
| 229 | 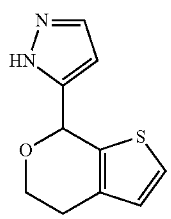 [SMILES: c1cc(C2OCCc3ccsc32)[nH]n1] | HCl | EE | LC-MS: m/z 207 (MH⁺); $^1$H NMR (D$_2$O): δ 7.73 (s, 1H), 7.23-7.22 (d, J = 3.72 Hz, 1H), 6.82 (s, 1H), 6.41 (s, 1H), 6.02 (s, 1H), 4.00-3.95 (m, 1H), 3.85-3.81 (m, 1H), 2.77-2.62 (m, 2H). |
| 230 | 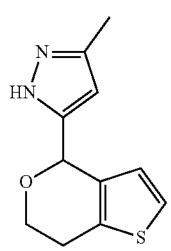 | HCl | EE | LC-MS: m/z 221 (MH⁺); $^1$H NMR (CD$_3$OD): δ 7.31-7.29 (d, J = 5.19 Hz, 1H), 6.81-6.79 (d, J = 5.22 Hz, 1H), 6.56 (s, 1H), 6.09 (s, 1H), 4.21-4.14 (m, 1H), 4.03-3.95 (m, 1H), 3.09-2.90 (m, 2H), 2.46 (s, 3H). |
| 231 | 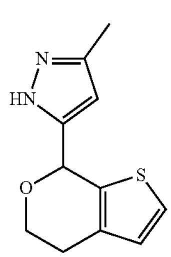 | HCl | EE | LC-MS: m/z 221 (MH⁺); $^1$H NMR (CD$_3$OD): δ 7.41-7.39 (dd, J = 5.09 Hz, 0.71 Hz, 1H), 6.95-6.93 (d, J = 5.07 Hz, 1H), 6.63 (s, 1H), 6.16 (s, 1H), 4.21-4.14 (m, 1H), 4.02-3.94 (m, 1H), 2.97-2.87 (m, 1H), 2.84-2.75 (m, 1H), 1.19 (s, 3H). |
| 232 | 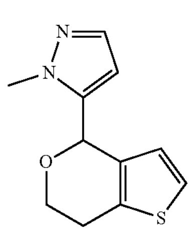 | HCl | EE | LC-MS: m/z 221 (MH⁺); $^1$H NMR (DMSO-d$_6$): δ 9.71-9.66 (d, J = 15.52 Hz, 1H), 7.36-7.33 (m, 2H), 6.62-6.61 (d, J = 5.19 Hz, 1H), 5.98 (s, 1H), 5.91-5.90 (d, J = 1.77 Hz, 1H), 3.93-3.79 (m, 2H), 3.76 (s, 3H), 2.89-2.86 (t, J = 5.27 Hz, 2H). |

-continued

| Compd. No. | Structure | Salt or FB* | Method of Preparation | Analytical Data |
|---|---|---|---|---|
| 233 | 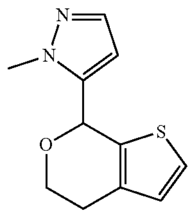 | HCl | EE | LC-MS: m/z 221 (MH+); 1H NMR (CDCl3): δ 12.01 (s, 1H), 7.85-7.84 (d, J = 2.40 Hz, 1H), 7.30-7.28 (m, 1H), 6.91-6.87 (d, J = 5.07 Hz, 1H), 6.50-6.49 (d, J = 2.34 Hz, 1H), 6.08 (s, 1H), 4.20 (s, 3H), 4.07-4.00 (m, 1H), 3.96-3.88 (m, 1H), 2.91-2.88 (m, 2H). |
| 234 | 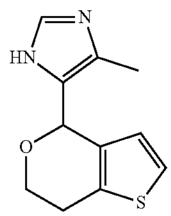 | HCl | EE | LC-MS: m/z 221 (MH+); 1H NMR (CD3OD): δ 8.67 (s, 1H), 7.27-7.25 (d, J = 5.25 Hz, 1H), 6.57-6.56 (d, J = 5.28 Hz, 1H), 5.97-5.96 (m, 1H), 4.25-4.19 (m, 1H), 4.01-3.93 (m, 1H), 3.17-3.07 (m, 1H), 2.92-2.86 (m, 1H), 2.29 (s, 3H). |
| 235 | 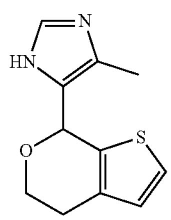 | HCl | EE | LC-MS: m/z 221 (MH+); 1H NMR (CD3OD): δ 8.17 (s, 1H), 7.33-7.31 (dd, J = 5.07 Hz, 0.75 Hz, 1H), 6.92-6.70 (d, J = 5.07 Hz, 1H), 6.02 (s, 1H), 4.27-4.20 (m, 1H), 3.97-3.90 (m, 1H), 3.00-2.92 (m, 1H), 2.78-2.71 (m, 1H), 2.24 (s, 3H). |
| 236 | 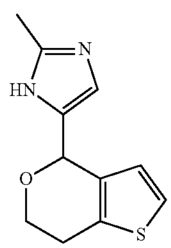 | HCl | EE | LC-MS: m/z 221 (MH+); 1H NMR (CD3OD): δ 7.16-7.14 (d, J = 5.19 Hz, 1H), 6.68-6.67 (d, J = 0.48 Hz, 1H), 6.64-6.62 (d, J = 5.16 Hz, 1H), 5.71 (s, 1H), 4.11-4.04 (m, 1H), 3.91-3.84 (m, 1H), 2.98-2.82 (m, 2H), 2.33 (s, 3H). |
| 237 | 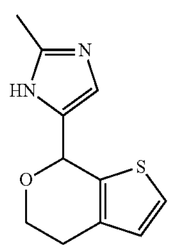 | HCl | EE | LC-MS: m/z 221 (MH+); 1H NMR (CD3OD): δ 7.27-7.25 (dd, J = 5.07 Hz, 0.75 Hz, 1H), 6.87-6.85 (d, J = 5.04 Hz, 1H), 6.84 (s, 1H), 5.82 (s, 1H), 4.17-4.10 (m, 1H), 3.92-3.86 (m, 1H), 2.89-2.81 (m, 1H), 2.76-2.69 (m, 1H), 2.34 (s, 3H). |
| 238 | 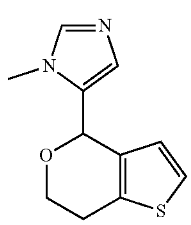 | HCl | EE | LC-MS: m/z 221 (MH+); 1H NMR (CD3OD): δ 8.95 (s, 1H), 7.35-7.33 (d, J = 5.25 Hz, 1H), 7.29 (s, 1H), 6.75-6.73 (d, J = 5.25 Hz, 1H), 6.10 (s, 1H), 4.02-3.97 (m, 2H), 3.89 (s, 3H), 3.00-2.97 (m, 2H). |

-continued

| Compd. No. | Structure | Salt or FB* | Method of Preparation | Analytical Data |
|---|---|---|---|---|
| 239 | 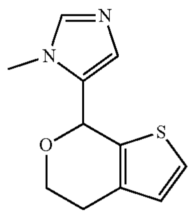 | HCl | EE | LC-MS: m/z 221 (MH+); 1H NMR (CD3OD): δ 8.96 (s, 1H), 7.48-7.47 (d, J = 1.11 Hz, 1H), 7.45-7.44 (dd, J = 5.07 Hz, 0.69 Hz, 1H), 6.98 (d, J = 1.1 Hz, 1H), 6.25 (s, 1H), 4.09-3.92 (m, 2H), 3.88-3.87 (d, J = 0.45 Hz, 3H), 2.89-2.84 (m, 2H). |
| 240 | 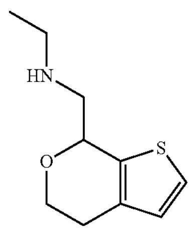 | HCl | B | 1H NMR (CD3OD): δ 7.36 (d, J = 1.5 Hz, 1H), 6.91 (d, J = 1.5 Hz, 1H), 5.13 (d, J = 2.0 Hz, 1H), 4.26 (ddd, J = 3.0, 1.5, 0.7 Hz, 1H), 3.82 (dt, J = 3.0, 1.0 Hz, 1H), 3.46 (dd, J = 3.0, 0.7 Hz, 1H), 3.25 (dd, J = 3.0, 2.0 Hz, 1H), 3.12 (q, J = 1.7 Hz, 2H), 2.91-2.83 (m, 1H), 2.71-2.65 (m, 1H), 1.32 (t, J = 1.7 Hz, 3H). |
| 241 | 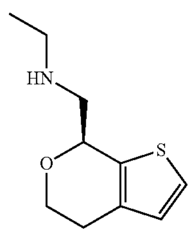 | HCl | CS; FME from SFC separation of Compound 240, using isocratic 8% Hexane: Ethanol (1:1) in CO2 on a 4.6 × 100 mm LUX Cellulose 2 from Phenomenex and flow of 4 mL/min | 1H NMR (CD3OD): δ 7.36 (d, J = 1.5 Hz, 1H), 6.91 (d, J = 1.5 Hz, 1H), 5.13 (d, J = 2.0 Hz, 1H), 4.26 (ddd, J = 3.0, 1.5, 0.7 Hz, 1H), 3.82 (dt, J = 3.0, 1.0 Hz, 1H), 3.46 (dd, J = 3.0, 0.7 Hz, 1H), 3.25 (dd, J = 3.0, 2.0 Hz, 1H), 3.12 (q, J = 1.7 Hz, 2H), 2.91-2.83 (m, 1H), 2.71-2.65 (m, 1H), 1.32 (t, J = 1.7 Hz, 3H). |
| 242 | 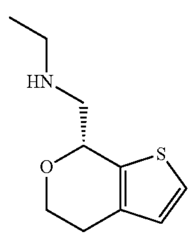 | HCl | CS; SME from SFC separation of Compound 240, using isocratic 8% Hexane: Ethanol (1:1) in CO2 on a 4.6 × 100 mm LUX Cellulose 2 from Phenomenex and flow of 4 mL/min | 1H NMR (CD3OD): δ 7.36 (d, J = 1.5 Hz, 1H), 6.91 (d, J = 1.5 Hz, 1H), 5.13 (d, J = 2.0 Hz, 1H), 4.26 (ddd, J = 3.0, 1.5, 0.7 Hz, 1H), 3.82 (dt, J = 3.0, 1.0 Hz, 1H), 3.46 (dd, J = 3.0, 0.7 Hz, 1H), 3.25 (dd, J = 3.0, 2.0 Hz, 1H), 3.12 (q, J = 1.7 Hz, 2H) 2.91-2.83 (m, 1H), 2.71-2.65 (m, 1H), 1.32 (t, J = 1.7 Hz, 3H). |
| 243 | 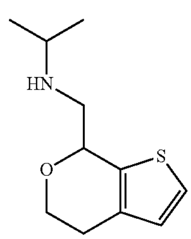 | HCl | B | 1H NMR (CD3OD): δ 7.37 (d, J = 1.2 Hz, 1H), 6.91 (d, J = 1.2 Hz, 1H), 5.12 (apd, J = 1.8 Hz, 1H), 4.26 (ddd, J = 3.0, 1.5, 0.7 Hz, 1H), 3.82 (ddd, J = 3.0, 2.5, 1.0 Hz, 1H), 3.49-3.40 (m, 2H), 3.28-3.21 (m, 1H), 2.92-2.83 (m, 1H), 2.72-2.67 (m, 1H), 1.35 (dd, J = 2.3, 1.6 Hz, 6H). |
| 244 | 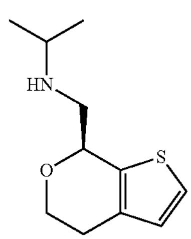 | HCl | CS; FME from SFC separation of Compound 243, using isocratic 8% Hexane: Ethanol (1:1) in CO2 on a 4.6 × 100 mm LUX Cellulose 2 from Phenomenex and flow of 4 mL/min | 1H NMR (CD3OD): δ 7.37 (d, J = 1.2 Hz, 1H), 6.91 (d, J = 1.2 Hz, 1H), 5.12 (apd, J = 1.8 Hz, 1H), 4.26 (ddd, J = 3.0, 1.5, 0.7 Hz, 1H), 3.82 (ddd, J = 3.0, 2.5, 1.0 Hz, 1H), 3.49-3.40 (m, 2H), 3.28-3.21 (m, 1H), 2.92-2.83 (m, 1H), 2.72-2.67 (m, 1H), 1.35 (dd, J = 2.3, 1.6 Hz, 6H). |

-continued

| Compd. No. | Structure | Salt or FB* | Method of Preparation | Analytical Data |
|---|---|---|---|---|
| 245 | 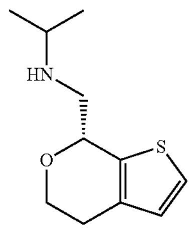 | HCl | CS; SME from SFC separation of Compound 243, using isocratic 8% Hexane: Ethanol (1:1) in CO₂ on a 4.6 × 100 mm LUX Cellulose 2 from Phenomenex and flow of 4 mL/min | $^1$H NMR (CD$_3$OD): δ 7.37 (d, J = 1.2 Hz, 1H), 6.91 (d, J = 1.2 Hz, 1H), 5.12 (apd, J = 1.8 Hz, 1H), 4.26 (ddd, J = 3.0, 1.5, 0.7 Hz, 1H), 3.82 (ddd, J = 3.0, 2.5, 0.7 Hz, 1H), 3.49-3.40 (m, 2H), 3.28-3.21 (m, 1H), 2.92-2.83 (m, 1H), 2.72-2.67 (m, 1H), 1.35 (dd, J = 2.3, 1.6 Hz, 6H). |
| 246 | 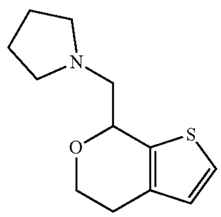 [SMILES: c1cc2c(s1)C(CN1CCCC1)OCC2] | HCl | B | $^1$H NMR (CD$_3$OD): δ 7.36 (d, J = 1.3 Hz, 1H), 6.91 (d, J = 1.3 Hz, 1H), 5.24 (apd, J = 2.5 Hz, 1H), 4.29-4.25 (m, 1H), 3.85 (dt, J = 2.5, 1.0 Hz, 1H), 3.81-3.67 (m, 1H), 3.66-3.63 (m, 2H), 3.50 (dd, J = 3.0, 2.5 Hz, 1H), 3.31-3.12 (m, 2H), 2.91-2.83 (m, 1H), 2.73-2.68 (m, 1H), 2.19-2.00 (m, 4H). |
| 247 | 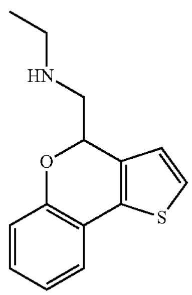 [SMILES: CCNCC1Oc2ccccc2-c2sccc21] | HCl | T | LC-MS: m/z 246 (MH$^+$); $^1$H NMR (DMSO-d$_6$): δ 9.29 (s, 1H), 8.92 (s, 1H), 7.66-7.64 (d, J = 5.10 Hz, 1H), 7.10-7.37 (dd, J = 7.47 Hz, 1.50 Hz, 1H), 7.22-7.21 (m, 1H), 7.13-7.11 (d, J = 5.07 Hz, 1H), 7.07-7.00 (m, 2H), 5.88-5.84 (dd, J = 9.36 Hz, 2.75 Hz, 1H), 3.50-3.39 (m, 2H), 3.07-3.02 (m, 2H), 1.27-1.22 (t, J = 7.23 Hz, 3H). |
| 248 | 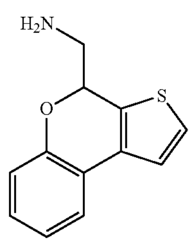 [SMILES: NCC1Oc2ccccc2-c2ccsc21] | HCl | U | LC-MS: m/z 218 (MH$^+$); $^1$H NMR (DMSO-d$_6$): δ 8.40 (s, 3H), 7.71-7.64 (m, 2H), 7.59-7.57 (d, J = 5.10 Hz, 1H), 7.26-7.21 (m, 1H), 7.08-7.03 (m, 2H), 5.87-5.82 (dd, J = 8.90 Hz, 3.23 Hz, 1H), 3.31-3.25 (m, 2H). |
| 249 | 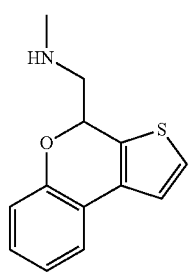 [SMILES: CNCC1Oc2ccccc2-c2ccsc21] | HCl | U | LC-MS: m/z 232 (MH$^+$); $^1$H NMR (DMSO-d$_6$): δ 9.36 (s, 1H), 9.09 (s, 1H), 7.72-7.70 (d, J = 5.10 Hz, 1H), 7.67-7.75 (d, J = 6.27 Hz, 1H), 7.59-7.57 (d, J = 5.13 Hz, 1H), 7.27-7.21 (m, 1H), 7.09-7.03 (m, 2H), 6.01-5.96 (dd, J = 8.18 Hz, J = 4.28 Hz, 1H), 3.37 (s, 2H), 2.65 (s, 3H). |
| 250 | 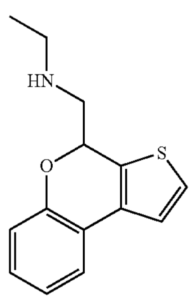 [SMILES: CCNCC1Oc2ccccc2-c2ccsc21] | HCl | U | LC-MS: m/z 246 (MH$^+$); $^1$H NMR (DMSO-d$_6$ + D$_2$O): δ 7.69-7.62 (m, 2H), 7.65-7.55 (d, J = 5.07 Hz, 1H), 7.26-7.21 (m, 1H), 7.09-7.03 (m, 2H), 5.93-5.88 (t, J = 12.3 Hz, 1H), 3.44-3.33 (m, 2H), 3.10-3.03 (m, 2H), 1.24-1.19 (t, J = 7.22 Hz, 3H). |

| Compd. No. | Structure | Salt or FB* | Method of Preparation | Analytical Data |
|---|---|---|---|---|
| 251 | (structure) | HCl | CS; FME from SFC separation of Compound 144, using isocratic 5% isopropyl amine in Methanol:Hexane (1:1) w/3% isopropanol in $CO_2$ on a 4.6 × 100 mm RegisPack from Regis and flow of 4 mL/min | $^1$H NMR ($CD_3OD$): δ 7.21 (d, J = 1.5 Hz, 1H), 6.92 (d, J = 1.5 Hz, 1H), 3.36 (dd, J = 3.0, 1.0 Hz, 1H), 3.14 (m, 1H), 3.09 (dd, J = 3.0, 2.5 Hz, 1H), 2.80 (apt, J = 1.5 Hz, 2H), 2.75 (s, 3H), 2.03-1.95 (m, 2H), 1.88-1.81 (m, 1H), 1.72-1.65 (m, 1H). |
| 252 | (structure) | HCl | CS; SME from SFC separation of Compound 144, using isocratic 5% isopropyl amine in Methanol:Hexane (1:1) w/3% isopropanol in $CO_2$ on a 4.6 × 100 mm RegisPack from Regis and flow of 4 mL/min | $^1$H NMR ($CD_3OD$): δ 7.21 (d, J = 1.5 Hz, 1H), 6.92 (d, J = 1.5 Hz, 1H), 3.36 (dd, J = 3.0, 1.0 Hz, 1H), 3.14 (m, 1H), 3.09 (dd, J = 3.0, 2.5 Hz, 1H), 2.80 (apt, J = 1.5 Hz, 2H), 2.75 (s, 3H), 2.03-1.95 (m, 2H), 1.88-1.81 (m, 1H), 1.72-1.65 (m, 1H). |
| 253 | (structure) | HCl | A | $^1$H NMR ($CD_3OD$): δ 9.85 (d, J = 0.5 Hz, 1H), 7.88 (d, J = 0.5 Hz, 1H), 7.28 (d, J = 1.3, 1H), 6.73 (d, J = 1.3 H, 1H), 6.09 (s, 1H), 4.12-3.95 (m, 2H), 2.99 (ddt, J = 11.0, 4.0, 1.5 Hz, 2H). |
| 254 | (structure) | HCl | A | $^1$H NMR ($CD_3OD$): δ 9.52 (d, J = 0.5 Hz, 1H), 7.82 (d, J = 0.5 Hz, 1H), 7.34 (d, J = 1.3, 1H), 6.91 (d, J = 1.3 H, 1H), 6.17 (s, 1H), 4.15 (dt, J = 2.5, 1.3 Hz, 1H), 3.99-3.92 (m, 1H), 2.96-2.87 (m, 1H), 2.81-2.75 (m, 1H). |
| 255 | (structure) | HCl | FF | LC-MS: m/z 254.4 (MH$^+$); $^1$H NMR ($CD_3OD$): δ 7.89-7.86 (d, J = 8.61 Hz, 1H), 7.76-7.76 (d, J = 1.89 Hz, 1H), 7.37-7.34 (dd, J = 8.60 Hz, 1.97 Hz, 1H), 5.27-5.23 (m, 1H), 4.30-4.22 (m, 1H), 3.99-3.91 (m, 1H), 3.61-3.56 (m, 1H), 3.38-3.26 (m, 1H), 3.13-2.94 (m, 2H). |
| 256 | (structure) | HCl | FF | LC-MS: m/z 268 (MH$^+$); $^1$H NMR (DMSO-$d_6$ + $D_2O$): δ 7.89-7.85 (d, J 8.58 Hz, 1H), 7.77-7.76 (d, J = 1.38 Hz, 1H), 7.37-7.34 (dd, J = 8.80 Hz, 1.70 Hz, 1H), 5.34-5.31 (d, J = 7.77 Hz, 1H), 4.30-4.23 (m, 1H), 4.01-3.94 (m, 1H), 3.66-3.60 (m, 1H), 3.46-3.36 (m, 1H), 3.12-3.00 (m, 2H), 2.80 (s, 3H). |
| 257 | (structure) | HCl | FF | LC-MS: m/z 254 (MH$^+$); $^1$H NMR ($CD_3OD$): δ 7.69-7.66 (dd, J = 6.95 Hz, 1.94 Hz, 1H), 7.47-7.40 (m, 2H), 5.30-5.26 (m, 1H), 4.32-4.25 (m, 1H), 3.40-3.92 (m, 1H), 3.64-3.60 (m, 1H), 3.42-3.35 (dd, J = 13.42 Hz, 8.45 Hz, 1H), 3.10-3.02 (m, 2H). |

-continued

| Compd. No. | Structure | Salt or FB* | Method of Preparation | Analytical Data |
|---|---|---|---|---|
| 258 | 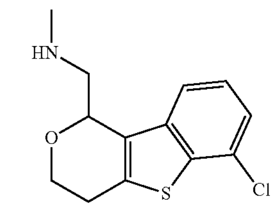 [SMILES: CNCC1OCCc2sc3c(Cl)cccc3c21] | HCl | FF | LC-MS: m/z 268 (MH$^+$); $^1$H NMR (CD$_3$OD): δ 7.72-7.70 (d, J = 1.7 Hz, 1H), 7.48-7.40 (m, 2H), 5.36-5.33 (m, 1H), 4.92-4.26 (m, 1H), 4.01-3.95 )m, 1H), 3.73-3.68 (m, 1H), 3.51-3.44 (m, 1H), 3.10-3.03 (m, 2H), 2.80 (s, 3H). |
| 259 | 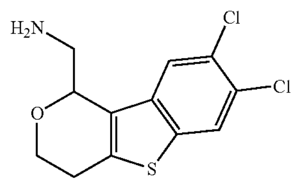 [SMILES: NCC1OCCc2sc3cc(Cl)c(Cl)cc3c21] | HCl | FF | LC-MS: m/z 288 (MH$^+$); $^1$H NMR (CD$_3$OD): δ 8.12 (s, 1H), 7.92 (s, 1H), 5.25-5.22 (d, J = 8.50, 1H), 4.30-4.23 (m, 1H), 3.99-3.91 (m, 1H), 3.61-3.40 (m, 1H), 3.37-3.33 (m, 1H), 3.03-2.94 (m, 2H). |
| 260 | 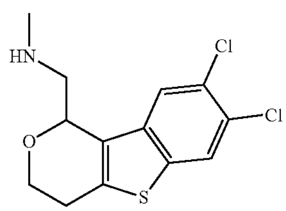 [SMILES: CNCC1OCCc2sc3cc(Cl)c(Cl)cc3c21] | HCl | FF | LC-MS: m/z 302 (MH$^+$); $^1$H NMR (CD$_3$OD): δ 8.12 (s, 1H), 7.97 (s, 1H), 5.33-5.29 (m, 1H), 4.31-4.24 (m, 1H), 3.99-3.92 (m, 1H), 3.71-3.65 (m, 1H), 3.48-3.41 (dd, J = 13.10 Hz, 9.17 Hz, 1H), 3.07-2.99 (m, 2H), 2.80 (s, 3H). |
| 261 | 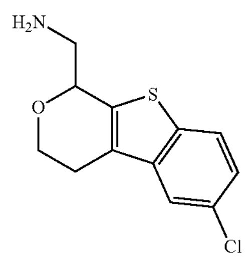 [SMILES: NCC1OCCc2c1sc1ccc(Cl)cc21] | HCl | FF | LC-MS: m/z 254 (MH$^+$); $^1$H NMR (CD$_3$OD): δ 7.88-7.85 (d, J = 8.61 Hz, 1H), 7.74-7.73 (d, J = 1.65 Hz, 1H), 7.38-7.35 (dd, J = 8.57 Hz, 1.79 Hz, 1H), 5.21-8.19 (m, 1H), 4.43-4.37 (m, 1H), 4.01-3.93 (m, 1H), 3.53-3.46 (m, 1H), 3.33-3.23 (m, 1H), 3.04-2.93 (m, 1H), 2.88-2.82 (m, 1H). |
| 262 | 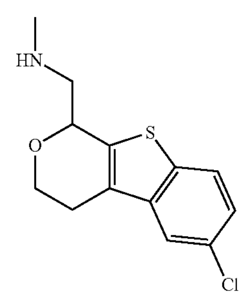 [SMILES: CNCC1OCCc2c1sc1ccc(Cl)cc21] | HCl | FF | LC-MS: m/z 268 (MH$^+$); $^1$H NMR (CD$_3$OD): δ 7.90-7.87 (d, J = 8.55 Hz, 1H), 7.77-7.76 (d, J = 1.98 Hz, 1H), 7.40-7.36 (dd, J = 8.58 Hz, 2.04 Hz, 1H), 5.28-5.24 (m, 1H), 4.44-4.38 (m, 1H), 4.03-3.94 (m, 1H), 3.62-3.56 (m, 1H), 3.43-3.35 (dd, J = 12.95 Hz, 8.42 Hz, 1H), 3.00-2.96 (m, 1H), 2.90-2.79 (m, 1H), 2.79 (s, 3H). |
| 263 | 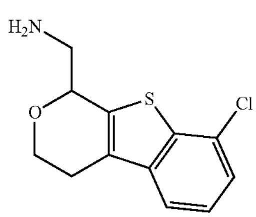 [SMILES: NCC1OCCc2c1sc1c(Cl)cccc21] | HCl | FF | LC-MS: m/z 254 (MH$^+$); $^1$H NMR (DMSO-d$_6$): δ 8.24 (s, 3H), 7.78-7.75 (dd, J = 7.31 Hz, 1.40 Hz, 1H), 7.54-7.46 (m, 2H), 5.21-2.19 (d, J = 6.24 Hz, 1H), 4.30-4.23 (m, 1H), 3.95-3.87 (m, 1H), 3.37 (s, 1H), 3.19-3.17 (m, 1H), 2.90-2.89 (m, 2H). |

-continued

| Compd. No. | Structure | Salt or FB* | Method of Preparation | Analytical Data |
|---|---|---|---|---|
| 264 | 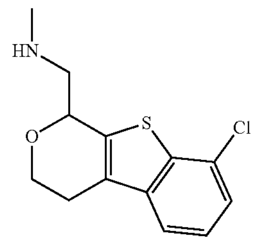 [SMILES: CNCC1OCCc2c1sc1c(Cl)cccc21] | HCl | FF | LC-MS: m/z 268 (MH$^+$); $^1$H NMR (DMSO-d$_6$): δ 9.44-9.38 (m, 1H), 8.93-8.86 (m, 1H), 7.80-7.75 (dd, J = 7.34 Hz, 1.43 Hz, 1H), 7.55-7.46 (m, 2H), 5.34-5.32 (d, J = 7.65 Hz, 1H), 4.30-4.23 (m, 1H), 3.97-3.89 (m, 1H), 3.53-3.46 (m, 1H), 3.36-3.30 (m, 1H), 2.97-2.83 (m, 2H), 2.62-2.59 (t, J = 4.80 Hz, 3H). |
| 265 | 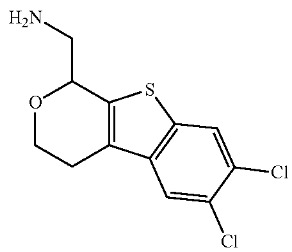 [SMILES: NCC1OCCc2c1sc1cc(Cl)c(Cl)cc21] | HCl | FF | LC-MS: m/z 288 (MH$^+$); $^1$H NMR (MeOD): δ 8.13 (s, 1H), 7.93 (s, 1H), 5.20-5.15 (m, 1H), 4.44-4.37 (m, 1H), 4.01-3.93 (m, 1H), 3.53-3.47 (m, 1H), 3.28-3.26 (m, 1H), 3.00-2.91 (m, 1H), 2.90-2.83 (s, 1H). |
| 266 | 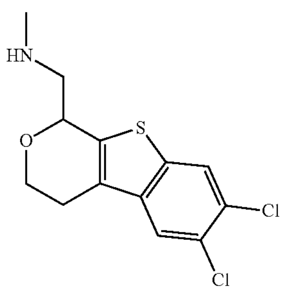 [SMILES: CNCC1OCCc2c1sc1cc(Cl)c(Cl)cc21] | HCl | FF | LC-MS: m/z 302 (MH$^+$); $^1$H NMR (MeOD): δ 8.14 (s, 1H), 7.94 (s, 1H), 5.26-5.22 (dd, J = 8.51 Hz, 2.64 Hz, 1H), 4.43-4.38 (m, 1H), 4.02-3.94 (m, 1H), 3.61-3.56 (m, 1H), 3.43-3.36 (m, 1H), 2.99-2.96 (m, 1H), 2.92-2.90 (m, 1H), 2.79 (s, 3H). |
| 267 | 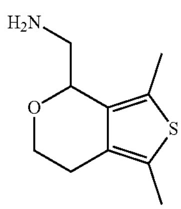 | HCl | KK | $^1$H NMR (CD$_3$OD): δ 4.97 (dd, J = 2.0, 0.7 Hz, 1H), 4.05-3.99 (m, 1H), 3.74-3.68 (m, 1H), 3.34-3.30 (m, 1H), 3.18 (dd, J = 3.3, 2.5 Hz, 1H), 2.64-2.58 (m, 2H), 2.32 (s, 3H), 2.26 (s, 3H). |
| 268 | 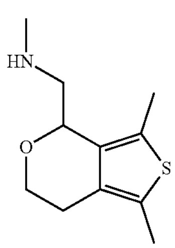 | HCl | KK | $^1$H NMR (CD$_3$OD): δ 5.03 (dd, J = 2.0, 0.7 Hz, 1H), 4.08-4.01 (m, 1H), 3.74-3.67 (m, 1H), 3.39 (dd, J = 3.0, 1.0 Hz, 1H), 3.32-3.26 (m, 1H), 2.75 (s, 3H), 2.69-2.61 (m 2H), 2.33 (s, 3H), 2.26 (s, 3H). |
| 269 | 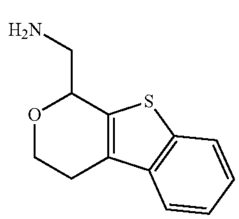 [SMILES: NCC1OCCc2c1sc1ccccc21] | HCl | FF | $^1$H NMR (CD$_3$OD): δ 7.87 (d, J = 2.0 Hz, 1H), 7.72 (d, J = 2.0 Hz, 1H), 7.42 (t, J = 2.0 Hz, 1H), 7.38 (t, J = 2.0 Hz, 1H), 5.19-5.15 (m, 1H), 4.39 (ddd, J = 3.0, 1.5, 0.7 Hz, 1H), 3.97 (ddd, J = 3.0, 2.5, 1.0 Hz, 1H), 3.48 (dd, J = 3.3, 1.0 Hz, 1H), 3.30-3.22 (m, 1H), 3.03-2.96 (m, 1H), 2.91-2.85 (m, 1H). |

-continued

| Compd. No. | Structure | Salt or FB* | Method of Preparation | Analytical Data |
|---|---|---|---|---|
| 270 | 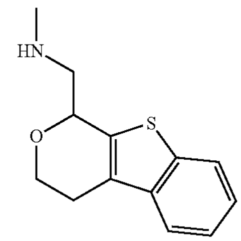 [SMILES: CNCC1OCCc2c1sc1ccccc21] | HCl | FF | ¹H NMR (CD₃OD): δ 7.87 (d, J = 2.0 Hz, 1H), 7.73 (d, J = 2.0 Hz, 1H), 7.42 (t, J = 2.0 Hz, 1H), 7.39 (t, J = 2.0 Hz, 1H), 5.25-5.22 (m, 1H), 4.39 (ddd, J = 3.0, 1.5, 0.7 Hz, 1H), 3.98 (ddd, J = 2.0, 1.7, 1.0 Hz, 1H), 3.57 (dd, J = 3.3, 0.7 Hz, 1H), 3.38 (dd, J = 3.0, 2.0 Hz, 1H), 3.05-2.96 (m, 1H), 2.91-2.86 (m, 1H), 2.77 (s, 3H). |
| 271 | 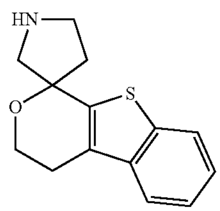 [SMILES: c1ccc2c3c(sc2c1)C1(CCNC1)OCC3] | HCl | FF | ¹H NMR (CD₃OD): δ 7.87 (d, J = 1.7 Hz, 1H), 7.72 (d, J = 1.7 Hz, 1H), 7.43 (t, J = 1.7 Hz, 1H), 7.40 (dt, J = 1.7, 0.7 Hz, 1H), 4.18-3.72 (m, 2H), 3.74 (apd, J = 2.0 Hz, 1H), 3.65-3.58 (m, 2H), 3.47 (d, J = 3.0 Hz, 1H), 2.93 (t, J = 1.0 Hz, 2H), 2.60-2.54 (m, 1H), 2.48-2.39 (m, 1H). |
| 272 | 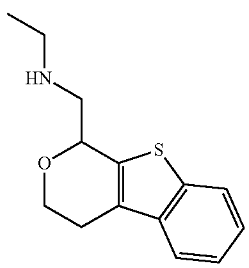 [SMILES: CCNCC1OCCc2c1sc1ccccc21] | HCl | FF | ¹H NMR (CD₃OD): δ 7.87 (d, J = 2.0 Hz, 1H), 7.73 (d, J = 2.0 Hz, 1H), 7.42 (t, J = 2.0 Hz, 1H), 7.38 (dt, J = 2.0, 0.7 Hz, 1H), 5.25-5.22 (m, 1H), 4.40 (ddd, J = 3.0, 1.5, 0.7 Hz, 1H), 3.98 (dt, J = 3.0, 1.0 Hz, 1H), 3.54 (dd, J = 3.3, 1.0 Hz, 1H), 3.36 (dd, J = 3.0, 2.0 Hz, 1H), 3.14 (dq, J = 1.7, 0.7 Hz, 2H), 3.00-2.96 (m, 1H), 2.91-2.87 (m, 1H), 1.34 (t, J = 1.7 Hz, 3H). |
| 273 | 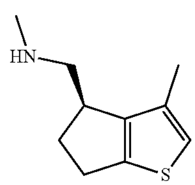 | HCl | CS; FME from SFC separation of Compound 176, using isocratic Isopropanol with 0.1% Isopropylamine in CO₂ on a 4.6 × 100 mm ChiralPak AD-H from Chiral Technologies and flow of 4 mL/min | ¹H NMR (CD₃OD): δ 6.87 (s, 1H), 3.41-3.35 (m, 1H), 3.33-3.25 (m, 1H), 3.05-2.96 (m, 2H), 2.90-2.83 (m, 1H), 2.77-2.70 (m, 1H), 2.75 (s, 3H), 2.39-2.30 (m, 1H), 2.20 (s, 3H). |
| 274 | 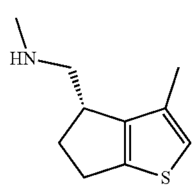 | HCl | CS; SME from SFC separation of Compound 176, using isocratic Isopropanol with 0.1% Isopropylamine in CO₂ on a 4.6 × 100 mm ChiralPak AD-H from Chiral Technologies and flow of 4 mL/min | ¹H NMR (CD₃OD): δ 6.87 (s, 1H), 3.41-3.35 (m, 1H), 3.33-3.25 (m, 1H), 3.05-2.96 (m, 2H), 2.90-2.83 (m, 1H), 2.77-2.70 (m, 1H), 2.75 (s, 3H), 2.39-2.30 (m, 1H), 2.20 (s, 3H). |
| 275 | 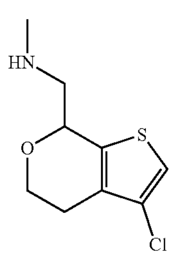 | HCl | JJ | LC-MS: m/z 218 (MH⁺); ¹H NMR (MeOD): δ 6.84 (s, 1H), 5.08-5.03 (m, 1H), 4.28-4.22 (m, 1H), 3.89-3.81 (m, 1H), 3.47-3.42 (m, 1H), 3.29-3.25 (m, 1H), 2.87-2.78 (m, 1H), 2.78 (s, 3H), 2.66-2.58 (m, 1H). |

-continued

| Compd. No. | Structure | Salt or FB* | Method of Preparation | Analytical Data |
|---|---|---|---|---|
| 276 | 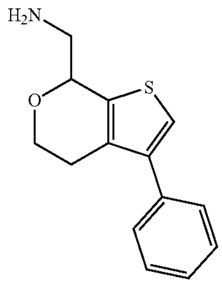 [SMILES: NCC1OCCc2c(-c3ccccc3)csc21] | HCl | GG | LC-MS: m/z 246 (MH$^+$); $^1$H NMR (MeOD): δ 7.49-7.36 (m, 5H), 7.21 (s, 1H), 5.36-5.32 (m, 1H), 4.26-4.17 (m, 1H), 3.97-3.90 (m, 1H), 3.08-3.00 (m, 1H), 2.93-2.88 (m, 1H), 2.81-2.70 (m, 2H). |
| 277 | 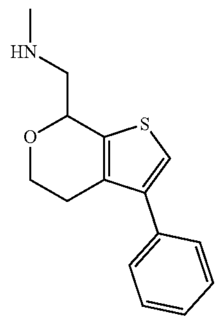 [SMILES: CNCC1OCCc2c(-c3ccccc3)csc21] | HCl | GG | LC-MS: m/z 260 (MH$^+$); $^1$H NMR (MeOD): δ 7.50-7.38 (m, 5H), 7.24 (s, 1H), 5.42-5.38 (m, 1H), 4.27-4.21 (m, 1H), 3.98-3.90 (m, 1H), 2.95-2.93 (m, 1H), 2.92-2.85 (m, 2H), 2.80-2.71 (m, 1H), 2.47 (s, 3H). |
| 278 | 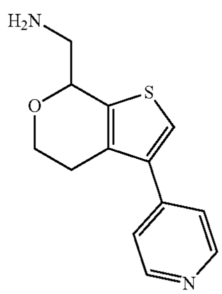 [SMILES: NCC1OCCc2c(-c3ccncc3)csc21] | HCl | GG | LC-MS: m/z 247 (MH$^+$); $^1$H NMR (CD$_3$OD): δ 8.90-8.88 (d, J = 6.87 Hz, 2H), 8.22-8.19 (d, J = 6.87 Hz, 2H), 7.99 (s, 1H), 5.67-5.62 (m, 1H), 4.31-4.24 (m, 1H), 4.03-3.91 (m, 1H), 3.22-2.85 (m, 4H). |
| 279 | 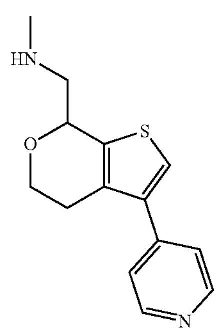 [SMILES: CNCC1OCCc2c(-c3ccncc3)csc21] | HCl | GG | LC-MS: m/z 261 (MH$^+$); $^1$H NMR (MeOD): δ 8.90-8.88 (d, J = 6.87 Hz, 2H), 8.22-8.19 (d, J = 6.87 Hz, 2H), 7.99 (s, 1H), 5.74-5.71 (m, 1H), 4.31-4.24 (m, 1H), 4.03-3.95 (m, 1H), 3.32-2.94 (m, 4H), 2.61 (s, 3H). |
| 280 | 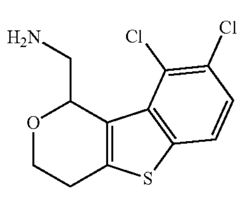 [SMILES: NCC1OCCc2sc3ccc(Cl)c(Cl)c3c21] | HCl | FF | LC-MS: m/z 288 (MH$^+$); $^1$H NMR (MeOD): δ 7.85-7.82 (d, J = 8.40 Hz, 1H), 7.51-7.49 (d, J = 8.40 Hz, 1H), 5.76-5.73 (d, J = 9.92 Hz, 1H), 4.24-4.16 (m, 1H), 4.09-4.00 (m, 1H), 3.67-3.61 (m, 1H), 3.41-3.35 (m, 1H), 3.12-2.99 (m, 2H). |

-continued

| Compd. No. | Structure | Salt or FB* | Method of Preparation | Analytical Data |
|---|---|---|---|---|
| 281 | 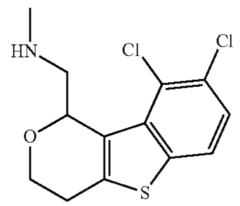 [SMILES: CNCC1OCCc2sc3ccc(Cl)c(Cl)c3c21] | HCl | FF | LC-MS: m/z 302 (MH+); 1H NMR (D2O): δ 7.42-7.41 (d, J = 2.42 Hz, 1H), 7.15 (s, 1H), 5.50 9s, 1H), 4.00 (s, 2H), 3.45 (s, 2H), 2.98-2.85 (m, 2H), 2.70 (s, 3H). |
| 282 | 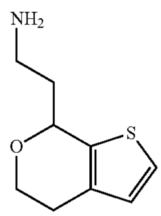 [SMILES: NCCC1OCCc2ccsc21] | HCl | B | LC-MS: m/z 184 (MH+); 1H NMR (MeOD): δ 7.28 (d, J = 1.3 Hz, 1H), 6.85 (d, J = 1.3 Hz, 1H), 5.00-4.96 (m, 1H), 4.24 (ddd, J = 2.8, 1.4, 0.3 Hz, 1H), 3.75 (dt, J = 2.8, 1.0 Hz, 1H), 3.10 (t, J = 1.7 Hz, 2H), 2.90-2.81 (m, 1H), 2.64-2.59 (m, 1H), 2.30-2.22 (m, 1H), 2.09-2.00 (m, 1H). |
| 283 | 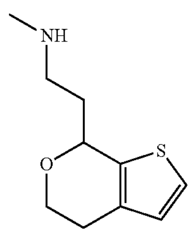 | HCl | B | LC-MS: m/z 198 (MH+); 1H NMR (MeOD): δ 7.29 (d, J = 1.3 Hz, 1H), 6.86 (d, J = 1.3 Hz, 1H), 5.00-4.97 (m, 1H), 4.25 (ddd, J = 2.9, 1.5, 0.4 Hz, 1H), 3.75 (dt, J = 2.9, 0.9 Hz, 1H), 3.23-3.12 (m, 2H), 2.90-2.81 (m, 1H), 2.69 (s, 3H), 2.64-2.59 (m, 1H), 2.33-2.25 (m, 1H), 2.12-2.02 (m, 1H). |
| 284 | 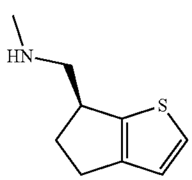 | HCl | CS; FME from SFC separation of Compound 178, using isocratic 7% Hexane: Isopropanol (7:3) in CO2 on a 4.6 × 100 mm (S, S) Whelk0-1 from Regis and flow of 4 mL/min | 1H NMR (CD3OD): δ 7.35 (d, J = 1.3 Hz, 1H), 6.85 (d, J = 1.3 Hz, 1H), 3.62-3.55 (m, 1H), 3.33-3.24 (m, 1'H), 3.11-3.05 (m, 1H), 2.90-2.80 (m, 1H), 2.79-2.65 (m, 2H), 2.75 (s, 3H), 2.33-2.25 (m, 1H). |
| 285 | 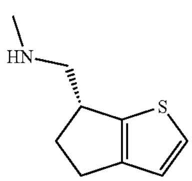 | HCl | CS; SME from SFC separation of Compound 178, using isocratic 7% Hexane: Isopropanol (7:3) in CO2 on a 4.6 × 100 mm (S, S) Whelk0-1 from Regis and flow of 4 mL/min | 1H NMR (CD3OD): δ 7.35 (d, J = 1.3 Hz, 1H), 6.85 (d, J = 1.3 Hz, 1H), 3.62-3.55 (m, 1H), 3.33-3.24 (m, 1H), 3.11-3.05 (m, 1H), 2.90-2.80 (m, 1H), 2.79-2.65 (m, 2H), 2.75 (s, 3H), 2.33-2.25 (m, 1H). |
| 286 | 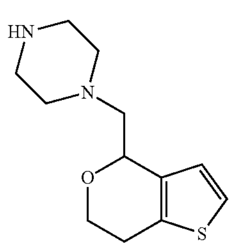 [SMILES: c1cc2c(s1)CCOC2CN1CCNCC1] | HCl | F | 1H NMR (CD3OD): δ 7.30 (d, J = 1.3 Hz, 1H), 6.91 (d, J = 1.3 Hz, 1H), 5.23 (apd, J = 2.3 Hz, 1H), 4.29 (ddd, J = 3.0, 1.5, 0.7 Hz, 1H), 3.88-3.77 (m, 2H), 3.76-3.46 (m, 6H), 3.43-3.29 (m, 2H), 3.25-3.20 (m, 1H), 3.05-2.98 (m, 1H), 2.85-2.80 (m, 1H). |
| 287 | 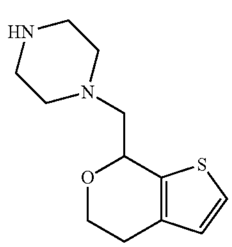 [SMILES: c1cc2c(s1)C(CN1CCNCC1)OCC2] | HCl | B | 1H NMR (CD3OD): δ 7.37 (d, J = 1.3 Hz, 1H), 6.91 (d, J = 1.3 Hz, 1H), 5.40-5.33 (m, 1H), 4.82-4.25 (m, 2H), 3.85 (dt, J = 2.5, 1.0 Hz, 1H), 3.88-3.75 (m, 6H), 3.54-3.44 (m, 1H), 3.28-3.12 (m, 2H), 2.91-2.83 (m, 1H), 2.74-2.67 (m, 1H). |

| Compd. No. | Structure | Salt or FB* | Method of Preparation | Analytical Data |
|---|---|---|---|---|
| 288 | 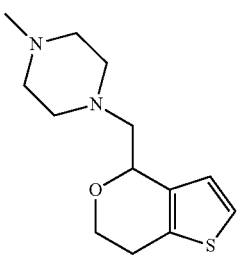 [SMILES: CN1CCN(CC2OCCc3sccc32)CC1] | HCl | F | ¹H NMR (CD₃OD): δ 7.29 (d, J = 0.7 Hz, 1H), 6.91 (d, J = 0.7 Hz, 1H), 5.18 (d, J = 2.0 Hz, 1H), 4.27 (ddd, J = 3.0, 1.5, 0.7 Hz, 1H), 3.87-3.78 (m, 2H), 3.77-3.40 (m, 6H), 3.39-3.12 (m, 3H), 3.11-2.87 (m, 1H), 2.99 (s, 3H), 2.92-2.82 (m, 1H). |
| 289 | 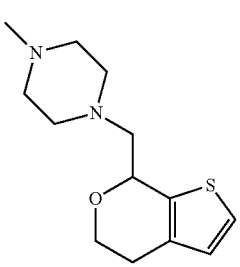 [SMILES: CN1CCN(CC2OCCc3ccsc32)CC1] | HCl | B | ¹H NMR (CD₃OD): δ 7.35 (d, J = 1.3 Hz, 1H), 6.90 (d, J = 1.3 Hz, 1H), 5.29 (brd, J = =2.3 Hz, 1H), 4.26 (ddd, J = 3.0, 1.3, 0.7 Hz, 1H), 3.83 (dt, J = 2.0, 1.0 Hz, 1H), 3.80-3.32 (m, 9H), 3.25 (m, 1H), 3.00 (s, 3H), 2.89-2.82 (m, 1H), 2.72-2.65 (m, 1H). |
| 290 | 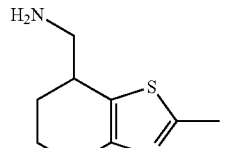 | HCl | W | LC-MS: m/z 183 (MH⁺); ¹H NMR (CD₃OD): δ 3.47-3.42 (m, 2H), 3.21-3.09 (m, 1H), 2.99 (s, 3H), 2.88 (s, 2H), 2.35-2.14 (m, 2H), 1.97-1.92 (m, 2H). |
| 291 | 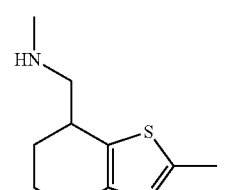 | HCl | W | LC-MS: m/z 197 (MH⁺); ¹H NMR (CD₃OD): δ 3.21 (s, 1H), 3.04-2.94 (m, 1H), 2.91-2.87 (m, 1H), 2.73-2.64 (m, 2H), 2.61 (s, 3H), 2.59 (s, 3H), 2.12-1.99 (m, 2H), 1.84-1.79 (m, 2H), 1.72-1.64 (m, 1H). |
| 292 | 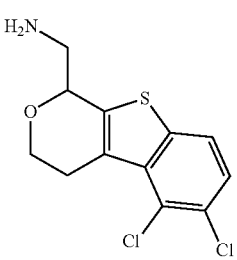 [SMILES: NCC1OCCc2c1sc1ccc(Cl)c(Cl)c21] | HCl | FF | LC-MS: m/z 288 (MH⁺); ¹H NMR (CD₃OD): δ 7.86-7.83 (d, J = 8.61 Hz, 1H), 7.52-7.49 (d, J = 8.58 Hz, 1H), 5.76-5.73 (d, J = 9.90 Hz, 1H), 4.24-4.17 (m, 1H), 4.07-4.00 (m, 1H), 3.66-3.62 (d, J = 11.19 Hz, 1H), 3.42-3.38 (d, J = 9.48 Hz, 1H), 3.17-3.00 (m, 2H). |
| 293 | 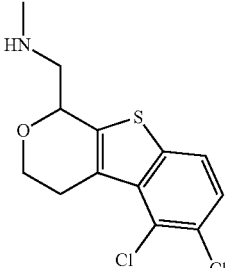 | HCl | FF | LC-MS: m/z 302 (MH⁺); ¹H NMR (CD₃OD): δ 7.85-7.82 (d, J = 8.55, 1H), 7.51-7.49 (d, J = 8.58 Hz, 1H), 5.84-5.81 (d, J = 9.55 Hz, 1H), 4.25-4.19 (m, 1H), 4.08-4.01 (m, 1H), 3.72-3.67 (dd, J = 13.43 Hz, 2.48 Hz, 1H), 3.54-3.47 (m, 1H), 3.12-3.05 (m, 2H), 2.81 (s, 3H). |

-continued

| Compd. No. | Structure | Salt or FB* | Method of Preparation | Analytical Data |
|---|---|---|---|---|
| 294 | 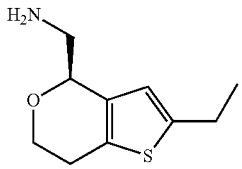 | HCl | CS; FME from SFC separation of Boc-protected Compound 9, using isocratic 10% MeOH in CO$_2$ on a 4.6 × 100 mm LUX Cellulose 2 from Phenomenex and flow of 4 mL/min | $^1$H NMR (DMSO-d$^6$): δ 8.22 (br s, 3H), 6.70 (s, 1H), 4.85-4.83 (d, J = 8.01 Hz, 1H), 4.13-4.07 (m, 1H), 3.78-3.70 (m, 1H), 3.29 (s, 1H), 2.91-2.67 (m, 5H), 1.22-1.18 (t, J = 7.50 Hz, 3H). |
| 295 | 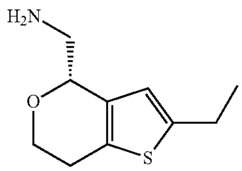 | HCl | CS; SME from SFC separation of Boc-protected Compound 9, using isocratic 10% MeOH in CO$_2$ on a 4.6 × 100 mm LUX Cellulose 2 from Phenomenex and flow of 4 mL/min | $^1$H NMR (DMSO-d$^6$): δ 8.22 (br s, 3H), 6.70 (s, 1H), 4.85-4.83 (d, J = 8.01 Hz, 1H), 4.13-4.07 (m, 1H), 3.78-3.70 (m, 1H), 3.29 (s, 1H), 2.91-2.67 (m, 5H), 1.22-1.18 (t, J = 7.50 Hz, 3H). |
| 296 | 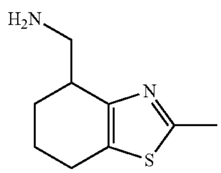 | HCl | X | LC-MS: m/z 183 (MH$^+$); $^1$H NMR (CD$_3$OD): δ 3.46-3.35 (m, 2H), 3.25-3.19 (m, 1H), 2.93 (s, 3H), 2.89-2.85 (t, J = 5.43 Hz, 2H), 2.12-2.01 (m, 2H), 1.96-1.85 (m, 2H). |
| 297 | 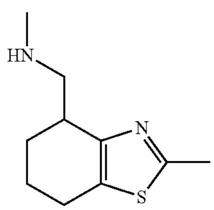 | HCl | X | LC-MS: m/z 197 (MH$^+$); $^1$H NMR (CD$_3$OD): δ 3.51-3.33 (m, 3H), 2.94 (s, 3H), 2.89-2.85 (m, 2H), 2.83 (s, 3H), 2.13-1.90 (m, 4H). |
| 298 | 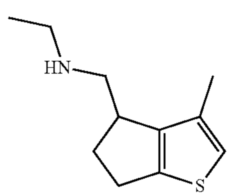 | HCl | Q | LC-MS: m/z 196 (MH$^+$); $^1$H NMR (CD$_3$OD): δ 6.88 (s, 1H), 3.47-3.38 (m, 1H), 3.27-3.26 (m, 1H), 3.18-3.09 (m, 2H), 3.06-2.97 (m, 2H), 2.93-2.83 (m, 1H), 2.80-2.68 (m, 1H), 2.47-2.38 (m, 1H), 8.24-2.22 (m, 3H), 1.39-1.36 (t, J = 7.29 Hz, 3H). |
| 299 | 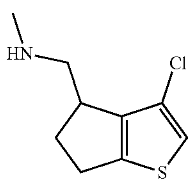 | HCl | HH | LC-MS: m/z 202 (MH$^+$); $^1$H NMR (CD$_3$OD): δ 6.89 (s, 1H), 3.45-3.40 (m, 1H), 3.31-3.29 (m, 1H), 3.09-2.94 (m, 3H), 2.74-2.65 (m, 4H), 2.28-2.17 (m, 1H). |
| 300 | 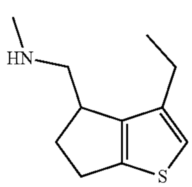 | HCl | Q | LC-MS: m/z 196 (MH$^+$); $^1$H NMR (CD$_3$OD): δ 6.93 (s, 1H), 3.45-3.39 (m, 1H), 3.28-3.24 (m, 1H), 3.08-2.98 (m, 2H), 2.94-2.89 (m, 1H), 2.74-2.68 (m, 4H), 2.64-2.56 (m, 2H), 2.42-2.32 (m, 1H), 1.29-1.24 (t, J = 7.52 Hz, 3H). |
| 301 | 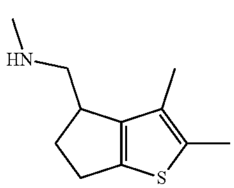 | HCl | Q | LC-MS: m/z 196 (MH$^+$); $^1$H NMR (CD$_3$OD): δ 3.39 (m, 1H), 3.28-3.23 (m, 1H), 3.02-2.93 (m, 2H), 2.87-2.78 (m, 1H), 2.76 (s, 3H), 2.71-2.61 (m, 1H), 2.35-2.22 (m, 1H), 2.31 (s, 3H), 2.10 (s, 3H). |

-continued

| Compd. No. | Structure | Salt or FB* | Method of Preparation | Analytical Data |
|---|---|---|---|---|
| 302 | 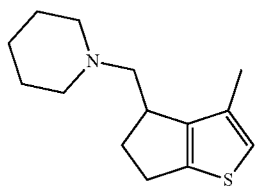 [SMILES: Cc1csc2c1C(CN1CCCCC1)CC2] | HCl | Q | LC-MS: m/z 236 (MH$^+$); $^1$H NMR (CD$_3$OD): δ 6.89 (s, 1H), 3.78-3.75 (m, 1H), 3.58-3.52 (m, 2H), 3.21-3.00 (m, 4H), 2.94-2.72 (m, 3H), 2.50-2.41 (m, 1H), 2.23-2.22 (d, J = 0.96 Hz, 3H), 2.02-1.81 (m, 5H), 1.59 (s, 1H). |
| 303 | 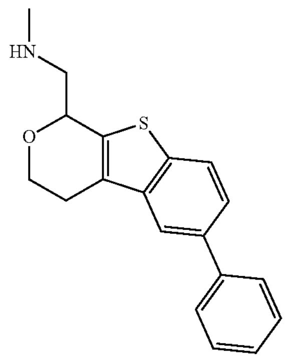 [SMILES: CNCC1OCCc2c1sc1ccc(-c3ccccc3)cc21] | HCl | A | LC-MS: m/z 310 (MH$^+$); $^1$H NMR (CD$_3$OD): δ 7.98-7.75 (m, 2H), 7.72-7.66 (m, 3H), 7.50-7.45 (t, J = 7.47 Hz, 2H), 7.40-7.37 (m, 1H), 5.29-5.26 (m, 1H), 4.47-4.41 (m, 1H), 4.06-4.00 (m, 1H), 3.63-3.58 (m, 1H), 3.45-3.38 (m, 1H), 3.63-3.38 (m, 2H), 2.80 (s, 3H). |
| 304 | 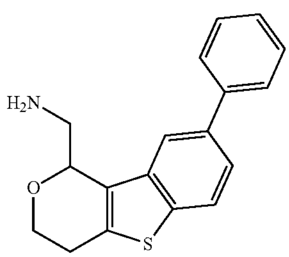 [SMILES: NCC1OCCc2sc3ccc(-c4ccccc4)cc3c21] | HCl | FF | LC-MS: m/z 296 (MH$^+$); $^1$H NMR (CD$_3$OD): δ 7.97-7.94 (d, J = 8.34 Hz, 1H), 7.88-7.87 (d, J = 1.26 Hz, 1H), 7.73-7.70 (m, 2H), 7.65-7.62 (dd, J = 8.37 Hz, 1.65 Hz, 1H), 7.51-7.48 (t, J = 7.47 Hz, 2H), 7.40-7.35 (m, 1H), 5.37-5.34 (d, J = 8.52 Hz, 1H), 4.81-4.25 (m, 1H), 4.02-3.94 (m, 1H), 3.70-3.64 (m, 1H), 3.42-3.37 (m, 1H), 3.31-3.01 (m, 2H). |
| 305 | 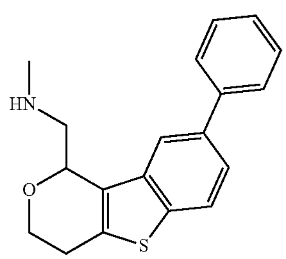 [SMILES: CNCC1OCCc2sc3ccc(-c4ccccc4)cc3c21] | HCl | FF | LC-MS: m/z 310 (MH$^+$); $^1$H NMR (CD$_3$OD): δ 7.96-7.91 (m, 2H), 7.74-7.71 (d, J = 7.11 Hz, 2H), 7.65-7.62 (dd, J = 8.40 Hz, 1.68 Hz, 1H), 7.50-7.48 (t, J = 7.47 Hz, 2H), 7.40-7.37 (m, 1H), 5.43-5.40 (d, J = 6.24 Hz, 1H), 4.84-4.28 (m, 1H), 4.02-3.96 (m, 1H), 3.77-3.72 (dd, J = 13.07 Hz, J = 2.60 Hz, 1H), 3.53-3.33 (m, 1H), 3.32-3.03 (m, 2H), 2.80 (s, 3H). |
| 306 | 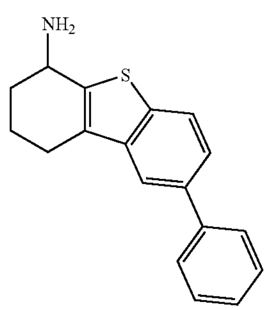 [SMILES: NC1CCCc2c1sc1ccc(-c3ccccc3)cc21] | HCl | II | LC-MS: m/z 280 (MH$^+$); $^1$H NMR (CD$_3$OD): δ 7.87-7.94 (d, J = 8.34 Hz, 2H), 7.58-7.57 (d, J = 1.80 Hz, 3H), 7.39-7.34 (m, 2), 7.28-7.24 (m, 1H), 4.63-4.60 (m, 1H), 2.97-2.88 (m, 2H), 2.30-2.21 (m, 1H), 2.08-1.94 (m, 3H). |

| Compd. No. | Structure | Salt or FB* | Method of Preparation | Analytical Data |
|---|---|---|---|---|
| 307 | 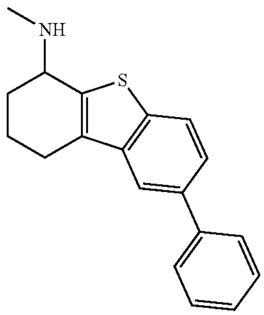 [SMILES: CNC1CCCc2c1sc1ccc(-c3ccccc3)cc21] | HCl | II | LC-MS: m/z 294 (MH+); $^1$H NMR (DMSO-$d_6$): δ 7.99-7.97 (m, 2H), 77.4-7.69 (m, 3H), 7.51-7.46 (t, J = 7.49 Hz, 2H), 7.40-7.38 (m, 1H), 4.67-4.65 (m, 1H), 2.89 (s, 3H), 2.35-2.29 (m, 1H), 2.23-2.18 (m, 1H), 2.13-2.03 (m, 2H), 1.61 (s, 2H). |
| 308 | 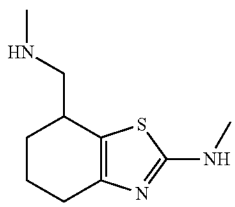 | 2HCl | X | LC-MS: m/z 212 (MH+); $^1$H NMR (CD$_3$OD): δ 3.49-3.43 (m, 1H), 3.31-3.28 (m, 2H), 3.16 (s, 3H), 2.81 (s, 3H), 2.62-2.61 (m, 2H), 1.96-1.74 (m, 4H). |
| 309 | 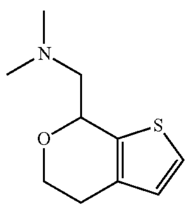 | formate | B | LC-MS: m/z 198 (MH+); $^1$H NMR (CD$_3$OD): δ 7.33 (d, J = 1.2, 0.7 Hz, 1H), 7.15 (brs, 1H), 7.04 (dd, J = 1.2, 0.3 Hz, 1H), 4.82 (t, J =1.2 Hz, 1H), 4.00-3.94 (m, 1H), 3.88-3.82 (m, 1H), 3.25 (d, J = 1.2 Hz, 2H), 2.96 (t, J = 1.6 Hz, 2H), 2.85 (s, 6H). |
| 310 | 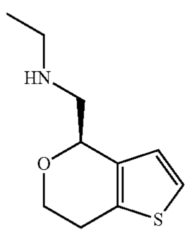 | HCl | CS; FME from SFC separation of Compound 13, using isocratic 10% Hx:MeOH:EtOH (2:1:1) in CO$_2$ on a 4.6 × 100 mm LUX Cellulose 2 from Phenomenex and flow of 4 mL/min | GC-MS m/z 139 (M+); $^1$H NMR (DMSO-$d^6$): δ 9.02 (s, 1H), 8.65 (s, 1H), 7.41-7.40 (d, J = 5.19 Hz, 1H), 6.99-6.97 (d, J = 5.19 Hz, 1H), 5.03-5.00 (d, J = 8.13 Hz, 1H), 4.21-4.12 (m, 1H), 3.83-3.75 (m, 1H), 3.52-3.48 (d, J = 12.43 Hz, 1H), 3.13-2.72 (m, 5H), 1.25-1.20 (t, J = 7.26 Hz, 3H). |
| 311 | 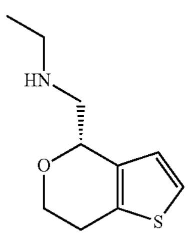 | HCl | CS; SME from SFC separation of Compound 13, using isocratic 10% Hx:MeOH:EtOH (2:1:1) in CO$_2$ on a 4.6 × 100 mm LUX Cellulose 2 from Phenomenex and flow of 4 mL/min | GC-MS m/z 139 (M+); $^1$H NMR (DMSO-$d^6$): δ 9.02 (s, 1H), 8.65 (s, 1H), 7.41-7.40 (d, J = 5.19 Hz, 1H), 6.99-6.97 (d, J = 5.19 Hz, 1H), 5.03-5.00 (d, J = 8.13 Hz, 1H), 4.21-4.12 (m, 1H), 3.83-3.75 (m, 1H), 3.52-3.48 (d, J = 12.43 Hz, 1H), 3.13-2.72 (m, 5H), 1.25-1.20 (t, J = 7.26 Hz, 3H). |

*FB is an abbreviation for "free base".

D. Animal Models

Anti-psychotic like activity of the compounds was evaluated in mice using the PCP hyperactivity and Pre-Pulse Inhibition (PPI) models of schizophrenia.

1. Methods

Animals: Male C57Bl/6J mice from Jackson Laboratories (Bar Harbor, Me.) were used. Upon receipt, mice were assigned unique identification numbers (tail marked) and were group housed with 4 mice per cage in OptiMICE ventilated cages. All animals remained housed in groups of four during the remainder of the study. All mice were acclimated to the colony room for at least two weeks prior to testing. During the period of acclimation, mice were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Chow and water were provided ad libitum for the duration of the study. In each test, animals were randomly assigned across treatment groups.

2. PCP Hyperactivity

Open field (OF) chambers were Plexiglas square chambers (27.3×27.3×20.3 cm; Med Associates Inc., St Albans, Vt.) surrounded by infrared photobeams (16×16×16) to measure horizontal and vertical activity. The analysis was configured to divide the open field into a center and periphery zone. Distance traveled was measured from horizontal beam breaks as the mouse moved whereas rearing activity was measured from vertical beam breaks.

Mice were injected with vehicle, test compound, or clozapine (1 mg/kg; i.p) and placed in the OF chambers for 30 min measurement of baseline activity. Mice were then injected with either water or PCP (5 mg/kg; i.p) and placed back in the OF chambers for a 60-minute session. At the end of each OF test session the OF chambers were thoroughly cleaned.

3. Prepulse Inhibition of Startle

The acoustic startle is an unconditioned reflex response to an external auditory stimulus. Prepulse inhibition of startle (PPI) refers to the reduction in the startle response caused by the presentation of a low-intensity auditory stimulus prior to the startle stimulus. The PPI paradigm is used for the study of schizophrenia and antipsychotic action due to the similarities between the results from human and rodent studies. PPI has been used as a tool for the assessment of deficiencies in sensory-motor gating observed in schizophrenia and to screen for potential antipsychotic drugs. Various psychotomimetic drugs such as PCP can disrupt PP. In mice, antipsychotic drugs such as clozapine can reverse the disruption of PPI induced by PCP.

Mice were placed in the PPI chambers (Med Associates) for a 5 min session of white noise (70 dB) habituation. After the habituation period the test session was initiated. The session started with a habituation block of 6 presentations of the startle stimulus alone, followed by 10 PPI blocks, each of which consisted of 6 different types of trials. Trial types were: 'null' (no stimuli), 'startle' (120 dB), 'startle plus prepulse' (4, 8 and 12 dB over background noise, i.e., 74, 78 or 82 dB) and 'prepulse' (82 dB). Trial types were presented in a random order within each block. Each trial started with a 50 ms stimulus-free period during which baseline movements were recorded. This was followed by a subsequent 20 ms period during which the prepulse stimulus was presented and responses to the prepulse measured. After a further 100 ms period, the startle stimulus was presented for 40 ms and responses recorded for 100 ms from startle onset. Responses were sampled every ms. The inter-trial interval was variable with an average of 15 s (range from 10 to 20 s). In 'startle' trials the basic auditory startle response was measured. The basic startle response was calculated as the mean startle response of all 'startle' trials (i.e., excluding the first habituation block). In 'startle plus prepulse' trials the degree of inhibition of the normal startle was calculated and expressed as a percentage of the basic startle response.

Mice were treated with vehicle, haloperidol (1 mg/kg; i.p) or test compound 30 min prior to PPI test. The PPI enclosures were cleaned following each test.

4. Results

TABLE 1

Effects of Compounds on Pre-pulse Inhibition (PPI) in Mice

| Compound/Doses | Effect |
|---|---|
| Compound 5 | |
| 10 mg/kg | − |
| 30 mg/kg | +++ |
| 100 mg/kg | +++ |

TABLE 1-continued

Effects of Compounds on Pre-pulse Inhibition (PPI) in Mice

| Compound/Doses | Effect |
|---|---|
| Compound 58 | |
| 10 mg/kg | +++ |
| 30 mg/kg | + |
| 100 mg/kg | +++ |
| Compound 57 | |
| 10 mg/kg | − |
| 30 mg/kg | − |
| 100 mg/kg | ++ |
| Compound 4 | |
| 10 mg/kg | +++ |
| 30 mg/kg | − |
| 100 mg/kg | +++ |
| Compound 27 | |
| 10 mg/kg | − |
| 30 mg/kg | − |
| 100 mg/kg | − |
| Compound 28 | |
| 10 mg/kg | − |
| 30 mg/kg | +++ |
| 100 mg/kg | +++ |
| Compound 1 | |
| 10 mg/kg | − |
| 30 mg/kg | +++ |
| 100 mg/kg | +++ |
| Compound 2 | |
| 10 mg/kg | − |
| 30 mg/kg | − |
| 100 mg/kg | +++ |
| Compound 3 | |
| 10 mg/kg | +++ |
| 30 mg/kg | +++ |
| 100 mg/kg | − |
| Compound 10 | |
| 10 mg/kg | +++ |
| 30 mg/kg | +++ |
| 100 mg/kg | +++ |
| Compound 75 | |
| 10 mg/kg | − |
| 30 mg/kg | − |
| 100 mg/kg | − |
| Compound 76 | |
| 10 mg/kg | − |
| 30 mg/kg | − |
| 100 mg/kg | − |
| Compound 13 | |
| 10 mg/kg | − |
| 30 mg/kg | − |
| 100 mg/kg | +++ |
| Compound 140 | |
| 10 mg/kg | − |
| 30 mg/kg | − |
| 100 mg/kg | − |
| Compound 78 | |
| 10 mg/kg | − |
| 30 mg/kg | − |
| 100 mg/kg | − |
| Compound 158 | |
| 3 mg/kg | − |
| 10 mg/kg | − |
| 30 mg/kg | − |
| 100 mg/kg | +++ |

TABLE 1-continued

Effects of Compounds on Pre-pulse Inhibition (PPI) in Mice

| Compound/Doses | Effect |
|---|---|
| Compound 130 | |
| 3 mg/kg | − |
| 10 mg/kg | − |
| 30 mg/kg | − |
| Compound 131 | |
| 3 mg/kg | − |
| 10 mg/kg | − |
| 30 mg/kg | − |
| Compound 171 | |
| 3 mg/kg | − |
| 10 mg/kg | − |
| 30 mg/kg | − |
| 100 mg/kg | +++ |
| Compound 172 | |
| 3 mg/kg | − |
| 10 mg/kg | − |
| 30 mg/kg | − |
| 100 mg/kg | − |
| Compound 129 | |
| 3 mg/kg | +++ |
| 10 mg/kg | +++ |
| 30 mg/kg | +++ |
| Compound 310 | |
| 3 mg/kg | − |
| 10 mg/kg | − |
| 30 mg/kg | +++ |
| Compound 205 | |
| 3 mg/kg | − |
| 10 mg/kg | − |
| 30 mg/kg | +++ |
| Compound 311 | |
| 3 mg/kg | − |
| 10 mg/kg | − |
| 30 mg/kg | +++ |
| Compound 213 | |
| 3 mg/kg | − |
| 10 mg/kg | +++ |
| 30 mg/kg | +++ |
| Compound 170 | |
| 3 mg/kg | − |
| 10 mg/kg | +++ |
| 30 mg/kg | +++ |
| Compound 242 | |
| 3 mg/kg | − |
| 10 mg/kg | − |
| 30 mg/kg | − |
| Compound 127 | |
| 3 mg/kg | +++ |
| 10 mg/kg | − |
| 30 mg/kg | +++ |
| Compound 102 | |
| 3 mg/kg | − |
| 10 mg/kg | − |
| 30 mg/kg | − |

*$P < 0.05$ vs. vehicle
−: No change in PPI
+: Significant increase in PPI at one pre-pulse intensity (P value < 0.05)
++: Significant increase in PPI at two pre-pulse intensities (P value < 0.05)
+++: Significant increase in PPI at three pre-pulse intensities (P value < 0.05)

TABLE 2

Effects of Compounds on PCP-Induced Hyperactivity Responses in Mice

| Compound/Doses | Total Distance Traveled (cm) |
|---|---|
| Compound 4 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 27 | |
| 0.3 mg/kg Compound + PCP | − |
| 1 mg/kg Compound + PCP | − |
| 3 mg/kg Compound + PCP | − |
| 10 mg/kg Compound + PCP | + |
| 30 mg/kg Compound + PCP | + |
| 100 mg/kg Compound + PCP | + |
| Compound 28 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 2 | |
| 10 mg/kg Compound + PCP | + |
| 30 mg/kg Compound + PCP | + |
| 100 mg/kg Compound + PCP | − |
| Compound 3 | |
| 10 mg/kg Compound + PCP | − |
| 30 mg/kg Compound + PCP | − |
| 100 mg/kg Compound + PCP | − |
| Compound 1 | |
| 10 mg/kg Compound + PCP | + |
| 30 mg/kg Compound + PCP | + |
| 100 mg/kg Compound + PCP | − |
| Compound 5 | |
| 10 mg/kg Compound + PCP | + |
| 30 mg/kg Compound + PCP | + |
| 100 mg/kg Compound + PCP | + |
| Compound 57 | |
| 10 mg/kg Compound + PCP | + |
| 30 mg/kg Compound + PCP | + |
| 100 mg/kg Compound + PCP | + |
| Compound 58 | |
| 10 mg/kg Compound + PCP | + |
| 30 mg/kg Compound + PCP | + |
| 100 mg/kg Compound + PCP | + |
| Compound 10 | |
| 10 mg/kg Compound + PCP | + |
| 30 mg/kg Compound + PCP | + |
| 100 mg/kg Compound + PCP | + |
| Compound 75 | |
| 10 mg/kg Compound + PCP | + |
| 30 mg/kg Compound + PCP | − |
| 100 mg/kg Compound + PCP | + |
| Compound 76 | |
| 10 mg/kg Compound + PCP | − |
| 30 mg/kg Compound + PCP | − |
| 100 mg/kg Compound + PCP | + |
| Compound 140 | |
| 10 mg/kg Compound + PCP | − |
| 30 mg/kg Compound + PCP | − |
| 100 mg/kg Compound + PCP | + |

TABLE 2-continued
Effects of Compounds on PCP-Induced Hyperactivity Responses in Mice

| Compound/Doses | Total Distance Traveled (cm) |
|---|---|
| Compound 78 | |
| 10 mg/kg Compound + PCP | + |
| 30 mg/kg Compound + PCP | + |
| 100 mg/kg Compound + PCP | + |
| Compound 129 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 130 | |
| 0.3 mg/kg Compound + PCP | − |
| 1 mg/kg Compound + PCP | − |
| 3 mg/kg Compound + PCP | + |
| 10 mg/kg Compound + PCP | + |
| 30 mg/kg Compound + PCP | + |
| 100 mg/kg Compound + PCP | + |
| Compound 119 | |
| 10 mg/kg Compound + PCP | + |
| 30 mg/kg Compound + PCP | + |
| 100 mg/kg Compound + PCP | + |
| Compound 158 | |
| 1 mg/kg Compound + PCP | + |
| 3 mg/kg Compound + PCP | + |
| 10 mg/kg Compound + PCP | + |
| 30 mg/kg Compound + PCP | + |
| 100 mg/kg Compound + PCP | + |
| Compound 131 | |
| 0.3 mg/kg Compound + PCP | − |
| 1 mg/kg Compound + PCP | + |
| 3 mg/kg Compound + PCP | + |
| Compound 171 | |
| 0.3 mg/kg Compound + PCP | − |
| 1 mg/kg Compound + PCP | − |
| 3 mg/kg Compound + PCP | − |
| 10 mg/kg Compound + PCP | − |
| 30 mg/kg Compound + PCP | + |
| Compound 172 | |
| 0.3 mg/kg Compound + PCP | − |
| 1 mg/kg Compound + PCP | + |
| 3 mg/kg Compound + PCP | + |
| 10 mg/kg Compound + PCP | − |
| 30 mg/kg Compound + PCP | − |
| Compound 127 | |
| 0.3 mg/kg Compound + PCP | − |
| 1 mg/kg Compound + PCP | − |
| 3 mg/kg Compound + PCP | + |
| 10 mg/kg Compound + PCP | + |
| 30 mg/kg Compound + PCP | − |
| Compound 310 | |
| 0.3 mg/kg Compound + PCP | + |
| 1 mg/kg Compound + PCP | − |
| 3 mg/kg Compound + PCP | − |
| 10 mg/kg Compound + PCP | + |
| 30 mg/kg Compound + PCP | + |
| Compound 311 | |
| 0.3 mg/kg Compound + PCP | − |
| 1 mg/kg Compound + PCP | + |
| 3 mg/kg Compound + PCP | + |
| 10 mg/kg Compound + PCP | + |
| 30 mg/kg Compound + PCP | + |
| Compound 205 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| Compound 213 | |
| 0.3 mg/kg Compound + PCP | + |
| 1 mg/kg Compound + PCP | + |
| 3 mg/kg Compound + PCP | + |
| 10 mg/kg Compound + PCP | + |
| 30 mg/kg Compound + PCP | + |
| Compound 170 | |
| 0.3 mg/kg Compound + PCP | − |
| 1 mg/kg Compound + PCP | − |
| 3 mg/kg Compound + PCP | − |
| 10 mg/kg Compound + PCP | − |
| 30 mg/kg Compound + PCP | − |
| Compound 242 | |
| 0.3 mg/kg Compound + PCP | − |
| 1 mg/kg Compound + PCP | + |
| 3 mg/kg Compound + PCP | + |
| 10 mg/kg Compound + PCP | + |
| 30 mg/kg Compound + PCP | + |
| Compound 102 | |
| 0.3 mg/kg Compound + PCP | − |
| 1 mg/kg Compound + PCP | + |
| 3 mg/kg Compound + PCP | + |
| 10 mg/kg Compound + PCP | + |
| 30 mg/kg Compound + PCP | + |

*$P < 0.05$ vs. vehicle + PCP
−: No inhibition of PCP hyperactivity
+: Significant value inhibition of PCP hyperactivity (P value < 0.05)

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated by reference herein in their entireties. Citation or identification of any reference in this application is not an admission that such reference is available as prior art to this application. The full scope of the disclosure is better understood with reference to the appended claims.

What is claimed:
1. A compound of formula:

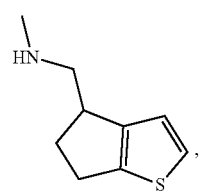

or a pharmaceutically acceptable salt or stereoisomer thereof.

2. A compound of formula:

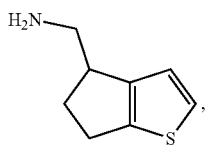

or a pharmaceutically acceptable salt or stereoisomer thereof.

3. A pharmaceutical composition comprising a compound of claim 1, or a pharmaceutically acceptable salt or stereoisomer thereof, and a pharmaceutically acceptable excipient or carrier.

4. A method of treating, or managing a neurological disorder, comprising administering to a subject a therapeutically or prophylactically effective amount of a compound of claim 1, or a pharmaceutically acceptable salt or stereoisomer thereof.

5. The method of claim 4, wherein the neurological disorder is schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis, psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorder, depression, major depressive disorder, dysthymia, bipolar disorder, manic disorder; seasonal affective disorder; attention deficit disorder, attention deficit hyperactivity disorder, obsessive-compulsive disorder, vertigo, epilepsy, pain, neuropathic pain, sensitization accompanying neuropathic pain, inflammatory pain, fibromyalgia, migraine, cognitive impairment, movement disorder, restless leg syndrome, multiple sclerosis, sleep disorder, sleep apnea, narcolepsy, excessive daytime sleepiness, jet lag, drowsy side effect of medications, insomnia, substance abuse or dependency, addiction, eating disorder, sexual dysfunction, hypertension, emesis, Lesche-Nyhane disease, Wilson's disease, autism, Huntington's chorea, or premenstrual dysphoria.

6. The method of claim 5, wherein the disorder is psychosis or schizophrenia.

7. The method of claim 5, wherein the disorder is Parkinson's psychosis.

8. The method of claim 4, wherein the disorder is bipolar disorder, Alzheimer's disease agitation, attention deficit disorder or attention deficit hyperactivity disorder.

9. A pharmaceutical composition comprising a compound of claim 2, or a pharmaceutically acceptable salt or stereoisomer thereof, and a pharmaceutically acceptable excipient or carrier.

10. A method of treating, or managing a neurological disorder, comprising administering to a subject a therapeutically or prophylactically effective amount of a compound of claim 2, or a pharmaceutically acceptable salt or stereoisomer thereof.

11. The method of claim 10, wherein the neurological disorder is schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis, psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorder, depression, major depressive disorder, dysthymia, bipolar disorder, manic disorder; seasonal affective disorder; attention deficit disorder, attention deficit hyperactivity disorder, obsessive-compulsive disorder, vertigo, epilepsy, pain, neuropathic pain, sensitization accompanying neuropathic pain, inflammatory pain, fibromyalgia, migraine, cognitive impairment, movement disorder, restless leg syndrome, multiple sclerosis, sleep disorder, sleep apnea, narcolepsy, excessive daytime sleepiness, jet lag, drowsy side effect of medications, insomnia, substance abuse or dependency, addiction, eating disorder, sexual dysfunction, hypertension, emesis, Lesche-Nyhane disease, Wilson's disease, autism, Huntington's chorea, or premenstrual dysphoria.

12. The method of claim 11, wherein the disorder is psychosis or schizophrenia.

13. The method of claim 11, wherein the disorder is Parkinson's psychosis.

14. The method of claim 10, wherein the disorder is bipolar disorder, Alzheimer's disease agitation, attention deficit disorder or attention deficit hyperactivity disorder.

15. A method of producing N-methyl-1-(5,6-dihydro-4H-cyclopenta[b]thiophen-4-yl)methanamine:

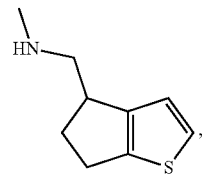

or a pharmaceutically acceptable salt or stereoisomer thereof, by treating (5,6-dihydro-4H-cyclopenta[b]thiophen-4-yl)methanamine with ethyl chloroformate to produce ethyl ((5,6-dihydro-4H-cyclopenta[b]thiophen-4-yl)methyl)carbamate, and reducing said ethyl ((5,6-dihydro-4H-cyclopenta[b]thiophen-4-yl)methyl)carbamate to form N-methyl-1-(5,6-dihydro-4H-cyclopenta[b]thiophen-4-yl)methanamine.

16. The method of claim 15, further comprising treating said N-methyl-1-(5,6-dihydro-4H-cyclopenta[b]thiophen-4-yl)methanamine with HCl to form:

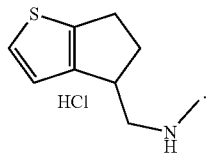

17. The method of claim 15, further comprising reducing 4,5-dihydro-4-(nitromethyl)cyclopenta[b]thiophen-6-one to form (5,6-dihydro-4H-cyclopenta[b]thiophen-4-yl)methanamine.

18. A compound:

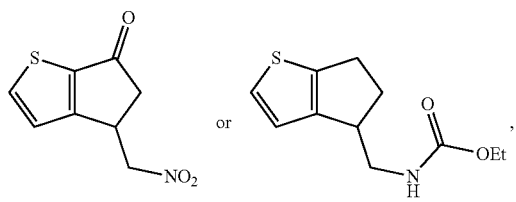 [SMILES: O=C1CC(C[N+](=O)[O-])c2ccsc21 ; CCOC(=O)NCC1CCc2sccc21]

or a pharmaceutically acceptable salt thereof.

19. A compound of formula

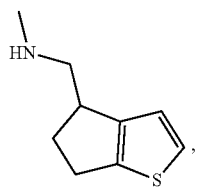

or a pharmaceutically acceptable salt thereof, prepared by the method of claim 15.

20. The compound of claim 19, a pharmaceutically acceptable salt thereof, wherein said method further comprises treating said N-methyl-1-(5,6-dihydro-4H-cyclopenta[b]thiophen-4-yl)methanamine with HCl to form:

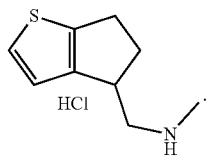

21. The compound of claim 19, or a pharmaceutically acceptable salt thereof, wherein said method further comprises reducing 4,5-dihydro-4-(nitromethyl)cyclopenta[b]thiophen-6-one to form (5,6-dihydro-4H-cyclopenta[b]thiophen-4-yl)methanamine.

* * * * *